(12) United States Patent
Muto et al.

(10) Patent No.: US 8,846,660 B2
(45) Date of Patent: Sep. 30, 2014

(54) SEVEN-MEMBERED RING COMPOUND AND PHARMACEUTICAL USE THEREFOR

(75) Inventors: Tsuyoshi Muto, Kobe (JP); Taisaku Tanaka, Kobe (JP); Junko Futamura, Kobe (JP); Seiichi Imajo, Kobe (JP); Hajime Sugawara, Kobe (JP)

(73) Assignee: Daiichi Sankyo Company, Ltd., Tokyo (JP)

( * ) Notice: Subject to any disclaimer, the term of this patent is extended or adjusted under 35 U.S.C. 154(b) by 0 days.

(21) Appl. No.: 13/518,628

(22) PCT Filed: Dec. 24, 2010

(86) PCT No.: PCT/JP2010/073879
§ 371 (c)(1),
(2), (4) Date: Jun. 22, 2012

(87) PCT Pub. No.: WO2011/078413
PCT Pub. Date: Jun. 30, 2011

(65) Prior Publication Data
US 2012/0259111 A1      Oct. 11, 2012

(30) Foreign Application Priority Data
Dec. 25, 2009  (JP) ................................ 2009-296113

(51) Int. Cl.
| | | |
|---|---|---|
| C07D 243/08 | (2006.01) |
| C07D 401/12 | (2006.01) |
| C07D 403/12 | (2006.01) |
| C07D 487/04 | (2006.01) |
| C07D 498/04 | (2006.01) |
| A61K 31/551 | (2006.01) |
| C07D 405/12 | (2006.01) |
| C07D 409/12 | (2006.01) |
| C07D 413/12 | (2006.01) |

(52) U.S. Cl.
CPC ............ *C07D 243/08* (2013.01); *A61K 31/551* (2013.01); *C07D 401/12* (2013.01); *C07D 403/12* (2013.01); *C07D 405/12* (2013.01); *C07D 409/12* (2013.01); *C07D 413/12* (2013.01); *C07D 487/04* (2013.01); *C07D 498/04* (2013.01)
USPC ........... 514/218; 514/221; 540/492; 540/502; 540/503

(58) Field of Classification Search
USPC .................... 514/218, 221; 540/492, 502, 503
See application file for complete search history.

(56) References Cited

U.S. PATENT DOCUMENTS

| | | |
|---|---|---|
| 2002/0187989 A1 | 12/2002 | Fukami et al. |
| 2004/0082544 A1 | 4/2004 | Greco et al. |
| 2004/0110811 A1 | 6/2004 | Sakai et al. |
| 2005/0176769 A1 | 8/2005 | Hawkins et al. |
| 2007/0105908 A1 | 5/2007 | Yamaguchi |
| 2007/0129421 A1 | 6/2007 | Banner et al. |
| 2007/0142452 A1 | 6/2007 | Banner et al. |
| 2008/0096844 A1 | 4/2008 | Greco et al. |
| 2008/0096953 A1 | 4/2008 | Banner et al. |
| 2009/0111796 A1 | 4/2009 | Muto et al. |

FOREIGN PATENT DOCUMENTS

| | | |
|---|---|---|
| EP | 1486494 | 12/2004 |
| EP | 2 025 672 | 2/2009 |
| JP | 2003342265 | 12/2003 |
| JP | 2004067584 | 3/2004 |
| JP | 2004131442 | 4/2004 |
| WO | WO-2004007464 | 1/2004 |
| WO | WO-2008045688 | 4/2008 |
| WO | WO-2008084004 | 7/2008 |
| WO | WO-2008147697 | 12/2008 |
| WO | WO-2009023655 | 2/2009 |
| WO | WO-2010019417 | 2/2010 |
| WO | WO-2010030500 | 3/2010 |
| WO | WO-2010088195 | 8/2010 |

OTHER PUBLICATIONS

Schechter, Norman, "Chymotrypsin-like Proteinases of Human Skin Mast Cells" in Mast Cell Proteases in Immunology and Biology, 1995, pp. 47-69, Marcel Dekker, Inc., New York, Basel, Hong Kong.
Urata et al., "Identification of a Highly Specific Chymase as the Major Angiotensin II-forming Enzyme in the Human Heart", Journal of Biological Chemistry, 1990, pp. 22348-22357, vol. 265, No. 36, The American Society for Biochemistry and Molecular Biology, Inc., USA.
Vartio et al., "Susceptibility of Soluble and Matrix Fibronectins to Degradation by Tissue Proteinases, Mast Cell Chymase and Cathepsin G", Journal of Biological Chemistry, 1981, pp. 471-477, vol. 256, No. 1. USA.
Kofford et al., "Cleavage of Type I Procollagen by Human Mast Cell Chymase Initiates Collagen Fibril Formation and Generates a Unique Carboxyl-terminal Propetide", Journal of Biological Chemistry, 1997, pp. 7127-7131, vol. 272, No. 11; The American Society for Biochemistry and Molecular Biology, Inc., USA.

(Continued)

*Primary Examiner* — Bruck Kifle
(74) *Attorney, Agent, or Firm* — Drinker Biddle & Reath LLP

(57) ABSTRACT

A compound having a 7-membered nitrogen-containing ring skeleton represented by the formula (I), which is useful for the prevention or treatment of diseases, in which chymase is involved (I)

and a pharmaceutical containing the same for the prevention or treatment of a disease, in which chymase is involved.

18 Claims, No Drawings

(56) References Cited

OTHER PUBLICATIONS

Saarinen et al., "Activation of Human Interstitial Procollagenase through Direct Cleavage of the Leu[83]-Thr[84] Bond by Mast Cell Chymase", Journal of Biological Chemistry, 1994, pp. 18134-18140, vol. 269, No. 27, The American Society for Biochemistry and Molecular Biology, Inc., USA.

Taipale et al., "Human Mast Cell Chymase and Leukocyte Elastase Release Latent Transforming Growth Factor β-1 from the Extracellular Matrix of Cultured Human Epithelial and Endothelial Cells", Journal of Biological Chemistry, 1995, pp. 4689-4696, vol. 270, No. 9; The American Society for Biochemistry and Molecular Biology, Inc., USA.

Lindstedt et al., "Activation of Paracrine TGF-β1 Signaling Upon Stimulation and Degranulation of Rat Serosal Mast Cells: A Novel Function for Chymase", The FASEB Journal, 2001, vol. 15, pp. 1377-1388.

Mizutani et al., "Rapid and Specific Conversion of Precursor Interleukin 1β (IL-1β) to an Active IL-1 Species by Human Mast Cell Chymase", J. Exp. Med, 1991, pp. 821-825, vol. 174; The Rockefeller University Press.

Longley et al., "Chymase Cleavage of Stem Cell Factor Yields a Bioactive, Soluble Product", Proc. National Academy of Science, USA; 1997, vol. 94, pp. 9017-9021.

Kokkonen et al., "Low Density Lipoprotein Degradation by Secretory Granules of Rat Mast Cells", Journal of Biological Chemistry; vol. 261, No. 34, 1986; pp. 16067-16072; The American Society of Biological Chemists, Inc.

Lindstedt et al., "Chymase in Exocytosed Rat Mast Cell Granules Effectively Proteolyzes Apolipoprotein AI-containing Lipoproteins, So Reducing the Cholesterol Efflux-inducing Ability of Serum and Aortic Intimal Fluid", J. Clin. Invest., vol. 97, No. 10, May 1996, pp. 2174-2182; The American Society for Clinical Investigation, Inc.

Nakano et al., "Selective Conversion of Big Endothelins to Tracheal Smooth Muchle-Constricting 31-Amino Acid-Length Endothelins by Chymase from Human Mast Cells"; J. Immunology; vol. 159; 1997; pp. 1987-1992.

Tchougounova et al.; "A Key Role for Mast Cell Chymase in the Activation of Pro-matrix Metalloprotease-9 and Pro-matrix Metalloprotease-2", Journal of Biological Chemistry, 2005, pp. 9291-9296, vol. 280, No. 10, USA.

Simard et al.; "Chymase-Dependent Conversion of Big Endothelin-1 in the Mouse in Vivo"; The Journal of Pharmacology and Experimental Therapeutics, 2009, vol. 328, No. 2, pp. 540-548, USA.

Schick et al., "Rat Serosal Mast Cell Degranulation Mediated by Chymase, An Endogenous Secretory Granule Protease: Active Site-Dependent Initiation at 1° C."; The Journal of Immunology; vol. 136, No. 10, 1986, pp. 3812-3818.

He et al., Human Mast Cell Chymase Induces the Accumulation of Neutrophils, Eosinophils and Other Inflammatory Cells in vivo; British Journal of Pharmacology, (1998) 125, pp. 1491-1500.

He et al., "The Induction of a Prolonged Increase in Microvascular Permeability by Human Mast Cell Chymase"; European Journal of Pharmacology, vol. 352 (1998) pp. 91-98.

Powers et al., "Inhibitors of Serine Proteinases" in Proteinase Inhibitors, pp. 55-152; (1986), Research monographs in cell and tissue physiology, vol. 12.

Fukami et al., "Chymase: Its Pathophysiological Roles and Inhibitors"; Curr. Pharmaceutical Design, vol. 4; 1998; pp. 439-453.

Aoyama, "Non-Peptidic Chymase Inhibitors"; Expert Opin. Ther. Patents; 2001; vol. 11, pp. 1423-1429.

Muto et al., "Recent Chymase Inhibitors and Their Effects in in vivo Models"; IDrugs 2002 5(12); pp. 1141-1150.

Matsumoto et al., "Chymase Inhibition Prevents Cardiac Fibrosis and Improves Diastolic Dysfunction in the Progression of Heart Failure"; Circulation, vol. 107; 2003; pp. 2555-2558.

Jin et al., "Beneficial Effects of Cardiac Chymase Inhibition During the Acute Phase of Myocardial Infarction"; Life Sciences 71 (2002) pp. 437-446.

Takai et al., "A Single Treatment With a Specific Chymase Inhibitor, TY-51184, Prevents Vascular Proliferation in Canine Grafted Veins"; J. Pharmacological Sciences (2004); vol. 94, pp. 443-448.

Tsunemi et al.; "A Specific Chymase Inhibitor, 2-(5-Formylamino-6-oxo-2-phenyl-1, 6-dihydropyrimidine-1-yl)-*N*-[{3,4-dioxo-1-phenyl-7-(2-pyridyloxy)}-2-heptyl]acetamide (NK3201), Suppresses Development of Abdominal Aortic Aneurysm in Hamsters", The Journal of Pharmacology and Experimental Therapeutics, 2004, vol. 309, No. 3, pp. 879-883.

Furubayashi et al.; "Significance of Chymase in the Progression of Abdominal Aortic Aneurysms in Dogs", Hypertens. Res., vol. 30, No. 4 (2007), pp. 349-357.

Inoue et al., "Effects of chymase inhibitor on angiotensin II-induced abdominal aortic aneurysm development in apolipoproetein E-deficient mice", Atherosclerosis, 204 (2009), pp. 359-364.

Takai et al.; "A Novel Chymase Inhibitor, 2-(5-Formylamino-6-oxo-2-phenyl-1,6-dihydropyrimidine-1-yl)-*N*-[{3,4-dioxo-1-phenyl-7-(2-pyridyloxy)}-2-heptyl]acetamide (NK3201), Suppressed Intimal Hyperplasia after Balloon Injury", The Journal of Pharmacology and Experimental Therapeutics, 2003, vol. 304, No. 2, pp. 841-844.

Uehara et al.; "Chymase inhibition suppresses high-cholesterol diet-induced lipid accumulation in the hamster aorta", Cardiovascular Research 55 (2002), pp. 870-876.

Takai et al.; "Chymase Inhibition Provides Pancreatic Islet Protection in Hamsters With Streptozotocin-Induced Diabetes", Journal of Pharmacological Sciences, 2009, vol. 110, pp. 459-465.

Fan et al.; "Contribution of Chymase-Dependent Angiotensin II Formation to the Progression of Tubulointerstitial Fibrosis in Obstructed Kidneys in Hamsters", Journal of Pharmacological Sciences, 2009, vol. 111, pp. 82-90.

Tomimori et al.; "Involvement of mast cell chymase in bleomycin-induced pulmonary firosis in mice", European Journal of Pharmacology 478, 2003, pp. 179-185.

Sakaguchi et al.; "A specific chymase inhibitor, NK3201, suppresses bleomycin-induced pulmonary fibrosis in hamsters", European Journal of Pharmacology 493, 2004, pp. 173-176.

Okamoto et al., "Significance of chymase inhibition for prevention of adhesion formation", European Journal of Pharmacology 484, 2004, pp. 357-359.

Terakawa et al.; "Oral chymase inhibitior SUN13834 ameliorates skin inflammation as well as pruritus in mouse model for atopic dermatitis", European Journal of Pharmacology 601, 2008, pp. 186-191.

Maryanoff et al.; "Dual Inhibition of Cathepsin G and Chymase Is Effective in Animal Models of Pulmonary Inflammation", American Journal of Respiratory and Critical Care Medicine, vol. 181, 2010, pp. 247-253.

Ishida et al.' "Role of Chymase-Dependent Matrix Metalloproteinase-9 Activation in Mice with Dextran Sodium Sulfate-Induced Colitis", The Journal of Pharmacology and Experimental Therapeutics, vol. 324, No. 2, pp. 422-426, 2008.

Watanabe et al.; "Oral Administration of Chymase Inhibitor Improves Dermatitis in NC/Nga Mice", Journal of Investigative Dermatology, 2007, 127, pp. 971-973.

English Language Abstract of JP2004-131442.

Taisaku Tanaka et al., "Identification of 6-substituted 4-arylsulfonyl-1,4-diazepane-2,5-diones as a novel scaffold for human chymase inhibitors," Biorganic & Medicinal Chemistry Letters, 2007, pp. 3431-3434, vol. 17, No. 12.

Hiroshi Maruoka et al., "Development of 6-benzyl substituted 4-aminocarbonyl-1,4-diazepane-2,5-diones as orally active human chymase inhibitors," Biorganic & Medicinal Chemistry Letters, 2007, pp. 3435-3439, vol. 17, No. 12.

Tsuyoshi Muto et al., "4-aminocarbonyl-1,4-diazepane-2,5-diones Kokkaku o Yusuru Keiko Chymase Sogaizai no Sosei," Abstracts of Symposium on Medicinal Chemistry, 2007, pp. 210-211, vol. 26.

Tsuyoshi Muto et al., "4-sulfonyl-1,4-diazepane-2,5-diones Kokkaku o Yusuru Shinki Chymase Sogaizai no Gosei to Kozo Kassei Sokan," Abstracts of Symposium on Medicinal Chemistry, 2007, pp. 208-209, vol. 26.

International Search Report dated Feb. 1, 2011 mailed in PCT Application No. PCT/JP2010/073829 filed Dec. 24, 2010.

(56) References Cited

OTHER PUBLICATIONS

Colombian Application No. 12-113824-2—Office Action mailed May 13, 2014 (with English translation).

Silverman, R.B. (2004), Drug Discovery, Design, and Development, in *The Organic Chemistry of Drug Design and Drug Action* $2^{nd}$ ed. (p. 30) Elsevier.

Ali, et al., "Synthesis of some new imines via Mono and dithiopyridine dicarboximides", National Journal of Chemistry, 2008, vol. 30, pp. 343-349.

SEVEN-MEMBERED RING COMPOUND AND PHARMACEUTICAL USE THEREFOR

RELATED APPLICATION DATA

This application is a §371 National Stage Application of PCT International Application No. PCT/JP2010/073879 filed Dec. 24, 2010, and claims priority under 35 U.S.C. §119 and/or §365 to Japanese Application No. 2009-296113 filed Dec. 25, 2009.

TECHNICAL FIELD

The present invention relates to a 7-membered ring compound having a chymase inhibitory activity and useful as a pharmaceutical for the prevention and/or treatment of diseases, in which chymase is involved, such as bronchial asthma, chronic obstructive pulmonary disease, urticaria, atopic dermatitis, allergic conjunctivitis, rhinitis, rheumatoid arthritis, food allergies, colitis, allergic enteritis, mastocytosis, scleroderma, heart failure, cardiac hypertrophy, hypertension, arrhythmia, atherosclerosis, abdominal aortic aneurysm, myocardial infarction, restenosis after PTCA, restenosis after bypass graft surgery, ischemic peripheral circulatory disorders, hyperaldosteronism, diabetes, diabetic retinopathy, diabetic nephropathy, nephritis, glomerulosclerosis, renal insufficiency, solid tumor, fibrosis, postoperative adhesion, cicatrix, glaucoma, and ocular hypertension.

BACKGROUND ART

Chymase is stored as an ingredient in granules of mast cells (MC), which are one of the inflammatory cells closely related to inflammation, and is widely present mainly in the tissue such as skin, heart, vascular walls, intestines etc. (see Non-Patent Document 1). Human chymase is known as an enzyme for specifically producing angiotensin II (i.e., Ang II) from angiotensin I (i.e., Ang I) independently from angiotensin converting enzyme. There is a report that, in human cardiac tissue, 80% of the production of angiotensin II is derived from by chymase (see Non-Patent Document 2). Ang II is known to be closely related to regulation of the blood pressure, diuretic regulation, and hypertrophy and remodeling of the cardiovascular system, that is, the migration and proliferation of smooth muscle cells etc. and the growth of the extracellular matrix in the cardiovascular system tissue. From these findings, it is suggested that chymase is closely related to cardiovascular lesions through production of Ang II. In addition to production of Ang II, it is reported that chymase has the following actions based on its protease activity:

1) degradation of the extracellular matrix (see Non-Patent Document 3) and production of collagen (see Non-Patent Document 4);
2) activation of matrix metalloprotease (see Non-Patent Document 5 and Non-Patent Document 6).
3) processing and activation of cytokine, for example, release of latent TGFβ1 from extracellular matrix (see Non-Patent Document 7), activation of latent TGFβ1 to active TGFβ1 (see Non-Patent Document 8) and activation of IL-1β (see Non-Patent Document 9);
4) activation of stem cell factor (SCF) which induces differentiation and proliferation of MCs (see Non-Patent Document 10);
5) degradation of apolipoprotein B in LDL (see Non-Patent Document 11) and degradation of apolipoprotein A in HDL (see Non-Patent Document 12); and
6) conversion of big endothelin to a bioactive peptide comprised of 31 amino acid residues (ET(1-31)) (see Non-Patent Document 14).

Further, it is reported that chymase stimulates rat peritoneal mast cells to induce degranulation (see Non-Patent Document 15) and that administration of human chymase intraperitoneally to mice or subcutaneously to guinea pigs induces infiltration of eosinophil and other leukocytes (see Non-Patent Document 16), and causes continuous increase of vascular permeability not through the action of histamine (see Non-Patent Document 17). These various reports relating to the action of chymase suggest that chymase plays an important role in the processes of tissue inflammation, repair, and healing, and in allergic conditions. It is believed that in these processes, the excessive reaction of chymase is involved in various diseases.

From the above-mentioned findings, a chymase inhibitor can be expected to be useful as a pharmaceutical for the prevention or treatment of, for example, bronchial asthma, chronic obstructive pulmonary disease, urticaria, atopic dermatitis, allergic conjunctivitis, rhinitis, rheumatoid arthritis, food allergies, colitis, allergic enteritis, mastocytosis, scleroderma, heart failure, cardiac hypertrophy, hypertension, arrhythmia, atherosclerosis, abdominal aortic aneurysm, myocardial infarction, restenosis after PTCA, restenosis after bypass graft surgery, ischemic peripheral circulatory disorders, hyperaldosteronism, diabetes, diabetic retinopathy, diabetic nephropathy, nephritis, glomerulosclerosis, renal insufficiency, solid tumor, fibrosis, postoperative adhesion, cicatrix, glaucoma, and ocular hypertension.

On the other hand, small molecule chymase inhibitors are already shown in books (see Non-Patent Document 18) or review articles (see Non-Patent Documents 19, 20, and 21). The efficacy of several inhibitors among these in animal disease models has been reported.

Heart failure: see Non-Patent Document 22,
Myocardial infarction: see Non-Patent Document 23 and see Non-Patent Document 24,
Arrhythemia; see Non-Patent Document 25,
Abdominal aortic aneurysm: see Non-Patent Document 26 and Non-Patent Document 27,
Vascular restenosis: see Non-Patent Document 28,
Lipid accumulation in the aorta: see Non-Patent Document 29,
Diabetes: see Non-Patent Document 30,
Nephritis: see Non-Patent Document 31,
Fibrosis: see Non-Patent Document 32 and Non-Patent Document 33,
Post-operative adhesion: see Non-Patent Document 34,
Glaucoma: see Patent Document 1,
Hypereosinophilia: see Patent Document 2,
Atopic dermatitis: see Non-Patent Document 35,
Pruritus: see Non-Patent Document 36,
Asthma: see Non-Patent Document 37,
Enteritis: see Non-Patent Document 38.

Further, recently, in addition to the chymase inhibitors described in the above books and reviews, imidazoledinedione derivatives (see Patent Document 3), phosphonic acid and phosphinic acid derivatives (see Patent Document 4, Patent Document 5, and Patent Document 6), benzothiophene sulfonamide derivatives (see Patent Document 7 and Patent Document 8), imidazole, thiazolimine, and oxazolimine derivatives (see Patent Document 9 and Patent Document 10), triazolidine derivatives (see Patent Document 11), pyridone derivatives (see Patent Document 12), indole derivatives (see Patent Document 13 and Patent Document 14), ring-fused pyrrole derivatives (see Patent Document 15), imidazopyridine derivatives (see Patent Document 16), benzimidazolone derivatives (see Patent Document 17), quinazolinedinone derivatives (see Patent Document 18), phthalazinone derivatives (see Patent Document 20), azabenzoimidazolone derivatives (see Patent Document 21), and azaquinazolinedinone derivatives (see Patent Document 22) are disclosed as novel chymase inhibitors. However, there are no examples of practical application of the above chymase inhibitors as pharmaceuticals.

Further, 1,4-diazepan-2,5-dione derivatives are disclosed in documents as chymase inhibitors similar in structure to the present invention (see Patent Document 19), but these compounds and the compounds of the present invention are different in structure.

CITATIONS LIST

Patent Documents

Patent Document 1: Japanese Patent Publication (A) No. 2004-131442
Patent Document 2: U.S. 2002-187989
Patent Document 3: U.S. 2004-110811
Patent Document 4: U.S. 2004-82544
Patent Document 5: U.S. 2005-176769
Patent Document 6: U.S. 2008-96844
Patent Document 7: E.P. 1486464
Patent Document 8: WO08-084004
Patent Document 9: WO04-07464
Patent Document 10: U.S. 2007-105908
Patent Document 11: Japanese Patent Publication (A) No. 2003-342265
Patent Document 12: Japanese Patent Publication (A) No. 2004-67584
Patent Document 13: U.S. 2007-129421
Patent Document 14: U.S. 2008-96953
Patent Document 15: U.S. 2007-142452
Patent Document 16: WO08-045688
Patent Document 17: WO08-147697
Patent Document 18: WO09-023655
Patent Document 19: U.S. 2009-111796
Patent Document 20: WO2010-019417
Patent Document 21: WO2010-030500
Patent Document 22: WO2010-088195

Non-Patent Document

Non-Patent Document 1: Mast Cell Proteases in Immunology and Biology; Caughey, G. H., Ed; Marcel Dekker, Inc.: New York, 1995
Non-Patent Document 2: J Biol. Chem., 1990, 265 (36), 22348
Non-Patent Document 3: J. Biol. Chem., 1981, 256 (1), 471
Non-Patent Document 4: J. Biol. Chem., 1997, 272 (11), 7127
Non-Patent Document 5: J. Biol. Chem., 1994, 269 (27), 18134
Non-Patent Document 6: J Biol. Chem., 2005, 280 (10), 9291.
Non-Patent Document 7: J. Biol. Chem., 1995, 270 (9), 4689
Non-Patent Document 8: FASEB J., 2001, 15 (8), 1377
Non-Patent Document 9: J. Exp. Med., 1991, 174 (4), 821
Non-Patent Document 10: Proc. Natl. Acad. Sci. USA., 1997, 94 (17), 9017
Non-Patent Document 11: J. Biol. Chem., 1986, 261 (34), 16067
Non-Patent Document 12: J. Clin. Invest., 1996, 97 (10), 2174
Non-Patent Document 13: J. Immunol., 1997, 159 (4), 1987
Non-Patent Document 14: J. Pharmacol. Exp. Ther., 2009, 328 (2), 540
Non-Patent Document 15: J. Immunol., 1986, 136 (10), 3812
Non-Patent Document 16: Br. J. Pharmacol., 1998, 125 (7), 1491
Non-Patent Document 17: Eur. J. Pharmacol., 1998, 352 (1), 91
Non-Patent Document 18: Protease Inhibitors; Barrett et al., Eds; Elsevier Science B.V.: Amsterdam, 1986
Non-Patent Document 19: Curr. Pharm. Des., 1998, 4 (6), 439
Non-Patent Document 20: Exp. Opin. Ther. Patents, 2001, 11, 1423
Non-Patent Document 21: Idrugs, 2002, 5 (12), 1141
Non-Patent Document 22: Circulation, 2003, 107 (20), 2555
Non-Patent Document 23: Life Sci., 2002, 71 (4), 437-46
Non-Patent Document 24: J. Pharmacol. Sci., 2004, 94 (4), 443
Non-Patent Document 25: J. Pharmacol. Exp. Ther., 2004, 309 (2), 490
Non-Patent Document 26: Hypertens Res., 2007, 30 (4), 349
Non-Patent Document 27: Atherosclerosis, 2009, 204 (2), 359
Non-Patent Document 28: J. Pharmacol. Exp., Ther. 2003, 304 (2), 841
Non-Patent Document 29: Cardiovasc Res., 2002, 55 (4), 870
Non-Patent Document 30: J. Pharmacol Sci., 2009, 110 (4), 459
Non-Patent Document 31: J. Pharmacol. Sci., 2009, 111 (1), 82
Non-Patent Document 32: Eur. J. Pharmacol., 2003, 478 (2-3), 179
Non-Patent Document 33: Eur. J. Pharmacol., 2004, 493 (1-3), 173
Non-Patent Document 34: Eur. J. Pharmacol., 2004, 484 (2-3), 357
Non-Patent Document 35: J. Invest. Dermatol., 2007, 127 (4), 971
Non-Patent Document 36: Eur. J. Pharmacol., 2008, 601 (1-3), 186
Non-Patent Document 37: Am. J. Respir. Crit. Care Med, 2009 Oct. 29
Non-Patent Document 38: J. Pharmacol. Exp. Ther., 2008, 324 (2), 422

SUMMARY OF INVENTION

Problems to be Solved by Present Invention

As explained above, at present, several types of small molecule chymase inhibitors have been disclosed. However, up until now, no chymase inhibitors have been provided for clinical applications. The object of the present invention is to provide a novel chymase inhibitor leading to the prevention or treatment of diseases, in which chymase is involved, such as bronchial asthma, chronic obstructive pulmonary disease, urticaria, atopic dermatitis, allergic conjunctivitis, rhinitis, rheumatoid arthritis, food allergies, colitis, allergic enteritis, mastocytosis, scleroderma, heart failure, cardiac hypertrophy, hypertension, arrhythmia, atherosclerosis, abdominal aortic aneurysm, myocardial infarction, restenosis after PTCA, restenosis after bypass graft surgery, ischemic peripheral circulatory disorders, hyperaldosteronism, diabetes, diabetic retinopathy, diabetic nephropathy, nephritis, glomerulosclerosis, renal insufficiency, solid tumor, fibrosis, postoperative adhesion, cicatrix, glaucoma, and ocular hypertension.

Means for Solving Problem

To solve the above problem, the present invention provides a compound, or a salt or solvate thereof, having the following formula (I) characterized in chemical structure by having a 7-membered ring skeleton:

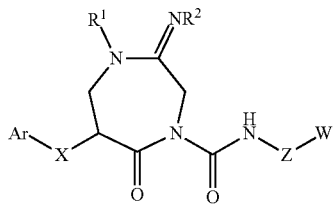

wherein Ar indicates (1) a $C_6$ to $C_{14}$ aromatic hydrocarbon group, (2) a 5- to 8-membered aromatic heterocyclic group including 1 to 4 hetero atoms selected from a nitrogen atom, sulfur atom, and oxygen atom, other than a carbon atom or (3) a bicyclic or tricyclic aromatic group formed by condensation of the above aromatic heterocyclic group and a $C_6$ to $C_{14}$ aromatic hydrocarbon ring, wherein the above groups (1) to (3) of Ar are unsubstituted, or substituted with 1 to 5 groups selected from the group consisting of
(i) a halogen atom,
(ii) nitro,
(iii) cyano,
(iv) $C_1$ to $C_6$ alkyl unsubstituted, or substituted with 1 to 3 halogen atoms,
(v) $C_2$ to $C_6$ alkenyl unsubstituted, or substituted with 1 to 3 halogen atoms,
(vi) $C_2$ to $C_6$ alkynyl unsubstituted, or substituted with 1 to 3 halogen atoms,
(vii) $C_3$ to $C_6$ cycloalkyl,
(viii) hydroxyl,
(ix) $C_1$ to $C_6$ alkoxy unsubstituted, or substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atoms,
(x) $C_1$ to $C_5$ alkylenedioxy,
(xi) $C_1$ to $C_6$ alkylthio unsubstituted, or substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atoms,
(xii) amino,
(xiii) mono-$C_1$ to $C_6$ alkylamino,
(xiv) di-$C_1$ to $C_6$ alkylamino,
(xv) 5- to 6-membered cyclic amino,
(xvi) $C_1$ to $C_6$ alkylcarbonyl,
(xvii) carboxyl,
(xviii) $C_1$ to $C_6$ alkoxycarbonyl,
(xix) carbamoyl,
(xx) thiocarbamoyl,
(xxi) mono-$C_1$ to $C_6$ alkylcarbamoyl,
(xxii) di-$C_1$ to $C_6$ alkylcarbamoyl,
(xxiii) 5- to 6-membered cyclic aminocarbonyl,
(xxiv) sulfo,
(xxv) $C_1$ to $C_6$ alkylsulfonyl,
(xxvi) $C_1$ to $C_6$ alkoxycarbonylamino,
(xxvii) $C_1$ to $C_6$ alkylcarbonylamino,
(xxviii) mono- or di-$C_1$ to $C_6$ alkylaminocarbonylamino,
(xxix) aminosulfonyl, and
(xxx) mono- or di-$C_1$ to $C_6$ alkylaminosulfonyl, or substituted with
(xxxi) 1 to 9 deuterium atoms, X indicates (1) a connecting bond, (2) linear or branched $C_1$ to $C_6$ alkylene unsubstituted, or substituted with 1 to 12 deuterium atoms, (3) an oxygen atom, (4) $NR^3$, where $R^3$ indicates a hydrogen atom or a $C_1$ to $C_6$ alkyl group, or (5) —$S(O)_m$—, where m indicates an integer of 0 to 2, Z indicates (1) a connecting bond or (2) $CR^4R^5$, where $R^4$ and $R^5$ are, independently,
(A) a hydrogen atom,
(B) a deuterium atom,
(C) $C_1$ to $C_6$ alkyl unsubstituted, or substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl, or substituted with (viii) 1 to 13 deuterium atoms,
(D) $C_3$ to $C_6$ cycloalkyl unsubstituted, or substituted with 1 to 5 groups selected from the group consisting of (i) a halogen atom and (ii) an alkyl group unsubstituted, or substituted with 1 to 3 halogen atoms or substituted with (iii) 1 to 11 deuterium atoms,
(E) $COOR^6$ wherein $R^6$ indicates a hydrogen atom or $C_1$ to $C_6$ alkyl, or
(F) $CONR^7R^8$ wherein $R^7$ and $R^8$ are, independently,
(a) hydrogen atom,
(b) $C_1$ to $C_6$ alkyl unsubstituted, or substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl and (x) $C_1$ to $C_{10}$ heteroaryl,
(c) $C_6$ to $C_{14}$ aromatic hydrocarbon group,
(d) a 5- to 8-membered aromatic heterocyclic group including 1 to 4 hetero atoms selected from a nitrogen atom, sulfur atom, and oxygen atom, other than a carbon atom, or
(e) a bicyclic or tricyclic aromatic group formed by condensation of the above aromatic heterocyclic group and a $C_6$ to $C_{14}$ aromatic hydrocarbon ring, wherein each of the groups (c) to (e) is unsubstituted, or substituted with 1 to 5 groups selected from the group consisting of (i) a halogen atom, (ii) nitro, (iii) cyano, (iv) $C_1$ to $C_6$ alkyl unsubstituted, or substituted with 1 to 3 halogen atoms, (v) $C_2$ to $C_6$ alkenyl unsubstituted, or substituted with 1 to 3 halogen atoms, (vi) $C_2$ to $C_6$ alkynyl unsubstituted, or substituted with 1 to 3 halogen atoms, (vii) $C_3$ to $C_6$ cycloalkyl, (viii) hydroxyl, (ix) $C_1$ to $C_6$ alkoxy unsubstituted, or substituted with 1 to 3 halogen atoms, (x) $C_1$ to $C_5$ alkylenedioxy, (xi) $C_1$ to $C_6$ alkylthio unsubstituted, or substituted with 1 to 3 halogen atoms, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xxiii) $C_1$ to $C_6$ alkoxycarbonyl, (xix) carbamoyl, (xx) thiocarbamoyl, (xxi) mono-$C_1$ to $C_6$ alkylcarbamoyl, (xxii) di-$C_1$ to $C_6$ alkylcarbamoyl, (xxiii) $C_6$ to $C_{10}$ arylcarbamoyl, (xxiv) $C_1$ to $C_{10}$ heteroarylcarbamoyl, (xxv) sulfo, (xxvi) $C_1$ to $C_6$ alkylsulfonyl, (xxvii) aminosulfonyl, and (xxviii) mono- or di-$C_1$ to $C_6$ alkylaminosulfonyl, or substituted with (xxix) 1 to 9 deuterium atoms, W indicates (1) a hydrogen atom, (2) a $C_6$ to $C_{14}$ aromatic hydrocarbon group, (3) a 5- to 8-membered aromatic heterocyclic group including 1 to 4 hetero atoms selected from a nitrogen atom, a sulfur atom, and an oxygen atom, other than a carbon atom, (4) a bicyclic or tricyclic aromatic group formed by condensation of the above aromatic heterocyclic group and a $C_6$ to $C_{14}$ aromatic hydrocarbon ring, or (5) deuterium atom, where each of the groups (2) to (4) of the above W is unsubstituted, or substituted with 1 to 5 groups selected from the group consisting of (i) a halogen atom, (ii) nitro, (iii) cyano, (iv) $C_1$ to $C_6$ alkyl unsubstituted, or substituted with 1 to 3 groups selected from a halogen atom, amino, $C_1$ to $C_6$ alkoxycarbonyl, $C_1$ to $C_6$ alkoxycarbonylamino and carboxyl, (v) $C_2$ to $C_6$ alkenyl unsubstituted, or substituted with 1 to 3 halogen atoms, (vi) $C_2$ to $C_6$ alkynyl unsubstituted, or substituted with 1 to 3 halogen atoms, (vii) $C_3$ to $C_6$ cycloalkyl, (viii) hydroxyl, (ix) $C_1$ to $C_6$ alkoxy unsubstituted, or substituted with 1 to 3 groups selected from a halogen atom, hydroxyl, $C_1$ to $C_6$ alkoxy, amino and mono- or di-$C_1$ to $C_6$ alkylamino, (x) $C_1$ to $C_5$ alkylenedioxy, (xi) $C_1$ to $C_6$ alkylthio unsubstituted, or substituted with 1 to 3 groups selected from a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkyl-carbonyl, (xvii) carboxyl, (xviii) $C_1$ to $C_6$ alkoxycarbonyl unsubstituted, or substituted with a halogen atom, (xix) $C_7$ to $C_{16}$ arakyloxycarbonyl unsubstituted, or substituted with a halogen atom, (xx) carbamoyl, (xxi) mono-$C_1$ to $C_6$ alkylcarbamoyl unsubstituted, or substituted with 1 to 3 groups which are selected from a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl unsubstituted, or substituted with hydroxyl, (xxvii) 5- to 6-membered cyclic aminocarbonyl unsubstituted, or substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino unsubstituted, or substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (ilii) $C_7$ to $C_{16}$ arakyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl; and (xlvii) $C_1$ to $C_{10}$ heteroaryl-$C_1$ to $C_6$ alkyloxycarbamoyl, or substituted with (xlviii) 1 to 9 deuterium atoms, $R^1$ indicates (1) a hydrogen atom, (2) $C_1$ to $C_6$ alkyl unsubstituted, or substituted with 1 to 3 of (i) a halogen atom or (ii) $C_3$ to $C_6$ cycloalkyl, or substituted with (iii) 1 to 13 deuterium atoms, (3) $C_2$ to $C_6$ alkenyl, or substituted with 1 to 3 of (i) a halogen atom or (ii) $C_3$ to $C_6$ cycloalkyl, or substituted with (iii) 1 to 11 deuterium atoms, (4) $C_2$ to $C_6$ alkynyl, or substituted with 1 to 3 of (i) a halogen atom or (ii) $C_3$ to $C_6$ cycloalkyl or, substituted with (iii) 1 to 9 deuterium atoms, or (5) $C_3$ to $C_6$ cycloalkyl unsubstituted, or substituted with 1 to 3 of (i) a halogen atom or (ii) $C_3$ to $C_6$ cycloalkyl, or substituted with (iii) 1 to 11 deuterium atoms, $R^2$ indicates (1) $OR^9$ or (2) $NR^{10}R^{11}$ where $R^9$, $R^{10}$, and $R^{11}$ respectively independently indicate (A) a hydrogen atom, (B) $C_1$ to $C_6$ alkyl, (C) $C_2$ to $C_6$ alkenyl, (D) $C_2$ to $C_6$ alkynyl, (E) $C_3$ to $C_6$ cycloalkyl (F) $C_6$ to $C_{14}$ aromatic hydrocarbon group, (G) a 5- to 8-membered aromatic heterocyclic group including 1 to 4 hetero atoms selected from a nitrogen atom, sulfur atom and oxygen atom, other than a carbon atom, or (H) a bicyclic or tricyclic aromatic group formed by condensation of the above aromatic heterocyclic group and a $C_6$ to $C_{14}$ aromatic hydrocarbon ring, where each of the groups of the above (B) to (E) is unsubstituted, or substituted with 1 to 3 groups selected from the group consisting of (i) a halogen atom, (ii) $C_3$ to $C_6$ cycloalkyl, (iii) hydroxyl, (iv) $C_1$ to $C_6$ alkoxy unsubstituted, or substituted with 1 to 3 halogen atoms, (v) amino, (vi) mono-$C_1$ to $C_6$ alkylamino, (vii) di-$C_1$ to $C_6$ alkylamino, (viii) 5- to 6-membered cyclic amino, (ix) carboxyl, (x) $C_1$ to $C_6$ alkoxycarbonyl, (xi) $C_1$ to $C_6$ alkylcarbonyl, (xii) carbamoyl, (xiii) mono-$C_1$ to $C_6$ alkylcarbamoyl, (xiv) di-$C_1$ to $C_6$ alkylcarbamoyl, (xv) $C_6$ to $C_{12}$ aryl, and (xvi) $C_1$ to $C_{10}$ heteroaryl, or substituted with (xvii) 1 to 13 deuterium atoms, further, each of the groups of the above (F) to (H) is unsubstituted, or substituted with 1 to 5 groups which are selected from the group consisting of (i) a halogen atom, (ii) nitro, (iii) cyano, (iv) $C_1$ to $C_6$ alkyl unsubstituted, or substituted with 1 to 3 halogen atoms, (v) $C_3$ to $C_6$ cycloalkyl unsubstituted, or substituted with 1 to 3 halogen atoms, (vi) hydroxyl, (vii) $C_1$ to $C_6$ alkoxy unsubstituted, or substituted with 1 to 3 halogen atoms, (viii) amino, (ix) mono-$C_1$ to $C_6$ alkylamino, (x) di-$C_1$ to $C_6$ alkylamino, (xi) 5- to 6-membered cyclic amino, (xii) $C_1$ to $C_6$ alkylcarbonyl, (xiii) carboxyl, (xiv) $C_1$ to $C_6$ alkoxycarbonyl, (xv) carbamoyl, (xvi) mono-$C_1$ to $C_6$ alkylcarbamoyl, (xvii) di-$C_1$ to $C_6$ alkylcarbamoyl, (xviii) $C_1$ to $C_6$ alkylsulfonyl, (xix) aminosulfonyl, and (xx) mono- or di-$C_1$ to $C_6$ alkylaminosulfonyl, or substituted with (xxi) 1 to 9 deuterium atoms, or $R^1$ and $R^2$ may form 5- or 6-member heterocyclic ring together with the atoms they are bonded with, where the above 5- or 6-member heterocyclic ring is unsubstituted or substituted with 1 to 3 groups selected from (A) a halogen atom (B) oxo (C) hydroxyl (D) $C_1$ to $C_6$ alkyl, (E) $C_2$ to $C_6$ alkenyl, (F) $C_2$ to $C_6$ alkynyl, (G) $C_3$ to $C_6$ cycloalkyl (H) $C_6$ to $C_{14}$ aromatic hydrocarbon group, (I) a 5- to 8-membered aromatic heterocyclic group including 1 to 4 hetero atoms selected from a nitrogen atom, sulfur atom, and oxygen atom, other than a carbon atom, and (J) a bicyclic or tricyclic aromatic group formed by condensation of the above aromatic heterocyclic group and a $C_6$ to $C_{14}$ aromatic hydrocarbon ring, or substituted with (K) 1 to 6 deuterium atoms, where each of the groups of the above (D) to (G) is unsubstituted, or substituted with 1 to 3 groups selected from the group consisting of (i) a halogen atom, (ii) $C_3$ to $C_6$ cycloalkyl, (iii) hydroxyl, (iv) $C_1$ to $C_6$ alkoxy unsubstituted, or substituted with 1 to 3 halogen atoms, (v) amino, (vi) mono-$C_1$ to $C_6$ alkylamino, (vii) di-$C_1$ to $C_6$ alkylamino, (viii) 5- to 6-membered cyclic amino, (ix) carboxyl, (x) $C_1$ to $C_6$ alkoxycarbonyl, (xi) $C_1$ to $C_6$ alkyl-carbonyl, (xii) carbamoyl, (xiii) mono-$C_1$ to $C_6$ alkylcarbamoyl, (xiv) di-$C_1$ to $C_6$ alkylcarbamoyl, (xv) $C_6$ to $C_{12}$ aryl, and (xvi) $C_1$ to $C_{10}$ heteroaryl, or substituted with (xvii) 1 to 13 deuterium atoms, each of the groups of the above (H) to (J) is unsubstituted, or substituted with 1 to 5 groups which are selected from the group consisting of (i) a halogen atom, (ii) nitro, (iii) cyano, (iv) $C_1$ to $C_6$ alkyl unsubstituted, or substituted with 1 to 3 halogen atoms, (v) $C_3$ to $C_6$ cycloalkyl unsubstituted, or substituted with 1 to 3 halogen atoms, (vi) hydroxyl, (vii) $C_1$ to $C_6$ alkoxy unsubstituted, or substituted with 1 to 3 halogen atoms, (viii) amino, (ix) mono-$C_1$ to $C_6$ alkylamino, (x) di-$C_1$ to $C_6$ alkylamino, (xi) 5- to 6-membered cyclic amino, (xii) $C_1$ to $C_6$ alkylcarbonyl, (xiii) carboxyl, (xiv) $C_1$ to $C_6$ alkoxycarbonyl, (xv) carbamoyl, (xvi) mono-$C_1$ to $C_6$ alkylcarbamoyl, (xvii) di-$C_1$ to $C_6$ alkylcarbamoyl, (xviii) $C_1$ to $C_6$ alkylsulfonyl, (xix) aminosulfonyl, and (xx) mono- or di-$C_1$ to $C_6$ alkylaminosulfonyl, or substituted with (xxi) 1 to 9 deuterium atoms.

Further, the present invention provides a compound having the formula (I) or a salt or solvates thereof, a pharmaceutical composition comprising the compound having the formula (I) or a pharmaceutically acceptable salt or solvates thereof as an active ingredient, and a chymase inhibitor containing a compound having the formula (I).

Furthermore, the present invention provides a method for producing a compound having the above formula (I) or a salt or solvate thereof and an intermediate compound, which is useful for the producing of a compound (I), or a salt thereof having the formula (V):

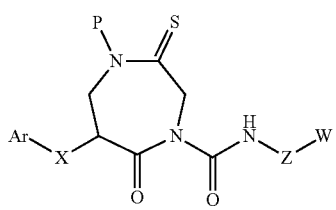

(V)

where Ar, W, X and Z are as defined above, P is a protective group of allyl, allyloxycarbonyl, 9-fluorenylmethylcarbonyl, $C_1$ to $C_6$ alkyloxycarbonyl unsubstituted, or substituted with 1 to 3 halogen atoms, $C_1$ to $C_6$ alkylcarbonyl unsubstituted, or substituted with 1 to 3 halogen atoms, $C_7$ to $C_{16}$ aralkyl unsubstituted, or substituted with 1 to 3 of (i) a halogen atom, (ii) $C_1$ to $C_6$ alkyl, (iii) $C_1$ to $C_6$ alkoxy, or (iv) nitro, $C_5$ to $C_{16}$ arylcarbonyl unsubstituted, or substituted with 1 to 3 of (i) a halogen atom, (ii) $C_1$ to $C_6$ alkyl, (iii) $C_1$ to $C_6$ alkoxy, or (iv) nitro, $C_7$ to $C_{16}$ arakyloxycarbonyl unsubstituted, or substituted with 1 to 3 of (i) a halogen atom, (ii) $C_1$ to $C_6$ alkyl, (iii) $C_1$ to $C_6$ alkoxy, or (iv) nitro, $C_5$ to $C_{16}$ arylsulfonyl unsubstituted, or substituted with 1 to 3 of (i) a halogen atom, (ii) $C_1$ to $C_6$ alkyl, (iii) $C_1$ to $C_6$ alkoxy, or (iv) nitro or $R^1$ ($R^1$ is as defined above),
or the formula (XIII):

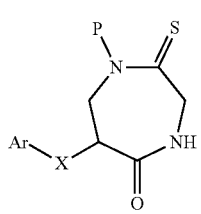

(XIII)

where Ar, X, and P are as defined above.

When the compounds, or a salt thereof or solvate thereof, having the formulae (I), (V), or (XIII) have asymmetric carbon atoms in their structures, their optically active substances and their mixtures are also included in the scope of the present invention. When they have two or more asymmetric carbon, the diastereomer mixtures are also included in the scope of the present invention. Further, when the compounds, or a salt or solvate thereof, having the formulae (I), (V), or (XIII) have double bonds in their structures, all of the cis-forms, trans-forms, and their mixtures are also included in the scope of the present invention. Further, possible resonance types and tautomers of the compounds having the formulae (I), (V), or (XIII) are also included in the scope of the present invention.

Further, the compounds having the formulae (I), (V), or (XIII) or a salt thereof may be brought into contact with a solvent such as water, methanol, ethanol, 1-propanol, 2-propanol, formic acid, ethyl formate, acetic acid, methyl acetate, ethyl acetate, propyl acetate and isobutyl acetate or mixed solvent including these solvents, or recrystallized from these solvents etc. so as to form their solvates. These solvates are also included in the scope of the present invention.

Further, the compounds having the above formulae (I), (V), or (VIII) or salt or solvate thereof may contain unnatural ratios of isotopes of above 1 of the atoms forming the compounds. As the atomic isotope, for example, deuterium ($^2H$), tritium ($^3H$), iodine-125 ($^{125}I$), carbon-14 ($^{14}C$), etc. may be mentioned. Further, the compounds may be radioactively labeled by, for example, tritium (3H), iodine-125 ($^{125}I$) or carbon-14 ($^{14}C$), or other radioactive isotopes. Radioactively labeled compounds are useful as pharmaceutical for treatment or prevention of disease, research reagents, for example, assay reagents, and diagnostic agents, for example, in vivo image diagnostic agents. All isotope variants of the compounds of the present invention are included in the scope of the present invention, without regard as to radioactivity.

Advantageous Effects of Invention

The compound having formula (I) of the present invention has a chymase inhibitory activity, is superior in stability in blood plasma and in vivo pharmacokinetics and is useful as a pharmaceutical for the prevention or treatment of diseases such as bronchial asthma, chronic obstructive pulmonary disease, urticaria, atopic dermatitis, allergic conjunctivitis, rhinitis, rheumatoid arthritis, food allergies, colitis, allergic enteritis, mastocytosis, scleroderma, heart failure, cardiac hypertrophy, hypertension, arrhythmia, atherosclerosis, abdominal aortic aneurysm, myocardial infarction, restenosis after PTCA, restenosis after bypass graft surgery, ischemic peripheral circulatory disorders, hyperaldosteronism, diabetes, diabetic retinopathy, diabetic nephropathy, nephritis, glomerulosclerosis, renal insufficiency, solid tumor, fibrosis, postoperative adhesion, cicatrix, glaucoma, and ocular hypertension.

DESCRIPTION OF EMBODIMENTS

In the description, the terms "alkyl", "alkenyl", "alkynyl" and "alkoxy" include both linear and branched forms.
1. Explanation of Compounds Having Formula (I)
In the above-mentioned formula (I), as examples of the "$C_6$ to $C_{14}$ aromatic hydrocarbon group" expressed by Ar, a monocyclic or polycyclic aromatic hydrocarbon group, more specifically, phenyl, biphenyl, naphthyl, indenyl, anthryl, phenanthryl (preferably, phenyl, biphenyl, naphthyl, etc., particularly preferably phenyl etc.), or other 6- to 14-membered monocyclic or polycyclic aromatic hydrocarbon group etc. may be mentioned.

Further, as examples of the "5- to 8-membered aromatic heterocyclic group including 1 to 4 hetero atoms selected from a nitrogen atom, sulfur atom, and oxygen atom, other than a carbon atom" expressed by Ar, for example, a monocyclic group including 1 or more (e.g., 1 to 4, preferably 1 to 3) hetero atoms which preferably consist of 1 or 2 species of hetero atoms selected from, other than a carbon atom, a nitrogen atom, oxygen atom, and sulfur atom, or its condensed aromatic heterocyclic group, more specifically, thienyl, furyl, pyrrolyl, imidazolyl, pyrazolyl, triazolyl, tetrazolyl, thiazolyl, isothiazolyl, oxazolyl, isoxazolyl, pyridyl, pyradinyl, pyrimidinyl, pyridazinyl, naphthylidinyl, purinyl, and other aromatic heterocyclic groups (preferably pyridyl, thienyl, and furyl) etc. may be mentioned.

Further, as the "bicyclic or tricyclic aromatic group formed by condensation of the above aromatic heterocyclic group and a $C_6$ to $C_{14}$ aromatic hydrocarbon group" represented by Ar, benzothienyl, benzofuryl, indolyl, isoindolyl, benzimidazolyl, benzopyrazolyl, benzotriazolyl, benzothiazolyl, benzisothiazolyl, benzoxazolyl, benzisoxazolyl, benzodioxolyl, quinolyl, isoquinolyl, quinoxalinyl, phthalazinyl (preferably, benzothienyl, benzofuryl, benzodioxolyl, and quinolyl), etc. may be mentioned.

Among these, as examples of the above-mentioned (1) aromatic hydrocarbon group, (2) aromatic heterocyclic group, or (3) bicyclic or tricyclic aromatic group formed by condensation of the above aromatic heterocyclic group and a C6 to C14 aromatic hydrocarbon ring represented by Ar, phenyl and naphthyl are particularly preferred.

Next, the substituent groups (i) to (xxxi) of the groups represented by Ar in the above-mentioned formula (I) are shown together with specific examples:

(i) a halogen atom (for example, fluorine, chlorine, bromine, and iodine may be mentioned.)
(ii) nitro
(iii) cyano
(iv) $C_1$ to $C_6$ alkyl unsubstituted, or substituted with 1 to 3 halogen atoms (as the halogen atom, fluorine, chlorine, bromine, and iodine may be mentioned, and as the $C_1$ to $C_6$ alkyl, methyl, ethyl, n-propyl, i-propyl, n-butyl, i-butyl, s-butyl, t-butyl, n-pentyl and n-hexyl, etc. may be mentioned. As specific examples, methyl, fluoromethyl, difluoromethyl, trifluoromethyl, chloromethyl, dichloromethyl, trichloromethyl, ethyl, 2,2,2-trifluoroethyl, n-propyl, i-propyl, n-butyl, i-butyl, s-butyl, t-butyl, n-pentyl and n-hexyl, etc. (preferably methyl, ethyl, and trifluoromethyl, etc.) may be mentioned.),
(v) $C_2$ to $C_6$ alkenyl unsubstituted, or substituted with 1 to 3 halogen atoms (as the halogen atom, fluorine, chlorine, bromine, and iodine may be mentioned, and as the $C_2$ to $C_6$ alkenyl, for example, vinyl, propenyl, isopropenyl, 2-buten-1-yl, 4-penten-1-yl and 5-hexen-1-yl, etc. may be mentioned.)
(vi) $C_2$ to $C_6$ alkynyl unsubstituted, or substituted with 1 to 3 halogen atoms (as the halogen atom, fluorine, chlorine, bromine, and iodine may be mentioned, and as the $C_2$ to $C_6$ alkynyl, for example, 2-butyn-1-yl, 4-pentyn-1-yl, 5-hexyn-1-yl, etc. may be mentioned.),
(vii) $C_3$ to $C_6$ cycloalkyl (for example, cyclopropyl, cyclobutyl, cyclopentyl and cyclohexyl, etc. may be mentioned.)
(viii) hydroxyl
(ix) $C_1$ to $C_6$ alkoxy unsubstituted, or substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atoms (as the $C_1$ to $C_6$ alkoxy, for example, methoxy, ethoxy, n-propoxy, i-propoxy, n-butoxy, i-butoxy, s-butoxy, t-butoxy, n-pentyloxy, n-hexyloxy, etc. may be mentioned. As the substituent of alkoxy group, fluorine, chlorine, bromine, iodine, N-methylamino, N,N-dimethylamino, methoxy, ethoxy, N-methylcarbamoyl, N,N-dimethylcarbamoyl, N-benzylcarbamoyl, N-(2-picolyl)carbamoyl, methoxycarbonyl, t-butoxycarbonyl, carboxyl and deuterium atoms, etc. may be mentioned. As specific examples, methoxy, ethoxy, n-propoxy, i-propoxy, n-butoxy, i-butoxy, t-butoxy, trifluoromethyloxy, trichloromethyloxy, methoxymethyloxy, ethoxymethyloxy, N-methyl-carbamoylmethyloxy, N,N-dimethylcarbamoylmethyloxy, N-benzylcarbamoylmethyloxy, N-(2-picolyl)-carbamoylmethyloxy, methoxycarbonylmethyloxy, t-butoxycarbonylmethyloxy and carboxylmethyloxy, etc. (preferably methoxy, ethoxy, N-methylcarbamoylmethyloxy, N-benzylcarbamoylmethyloxy, N-(2-picolyl)-carbamoylmethyloxy, methoxycarbonylmethyloxy, t-butoxycarbonylmethyloxy, carboxylmethyloxy, $[^2H_3]$methoxy, $[^2H_5]$ethoxy, $[^2H_7]_n$-propoxy and $[^2H_7]$i-propoxy may be mentioned.)
(x) $C_1$ to $C_5$ alkylenedioxy (for example, methylenedioxy and ethylenedioxy, etc. may be mentioned.),
(xi) $C_1$ to $C_6$ alkylthio unsubstituted, or substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atoms (as the $C_1$ to $C_6$ alkylthio, for example, methylthio, ethylthio, n-propylthio, propylthio, n-butylthio, i-butylthio, s-butylthio, t-butylthio, n-pentylthio, n-hexylthio, etc. may be mentioned, as examples of substituent groups of $C_1$ to $C_6$ alkylthio, fluorine, chlorine, bromine, iodine, N-methylamino, N,N-dimethylamino, methoxy, ethoxy, N-methylcarbamoyl, N,N-dimethylcarbamoyl, N-benzylcarbamoyl, N-(2-picolyl)-carbamoyl, methoxycarbonyl, t-butoxycarbonyl, carboxyl and deuterium atoms, etc. may be mentioned. As specific examples, methylthio, ethylthio, n-propylthio, i-propylthio, n-butylthio, i-butylthio, t-butylthio, trifluoromethylthio, trichloromethylthio, methoxymethylthio, ethoxymethylthio, N-methylcarbamoylmethylthio, N-benzylcarbamoylmethylthio, N-(2-picolyl)-carbamoylmethylthio, methoxycarbonylmethylthio, t-butoxycarbonylmethylthio, carboxylmethylthio, $[^2H_3]$methylthio, $[^2H_5]$ethylthio, $[^2H_7]_n$-propylthio and $[^2H_7]$i-propylthio, etc. may be mentioned.)
(xii) amino
(xiii) mono-$C_1$ to $C_6$ alkylamino (for example, N-methylamino etc. may be mentioned.)
(xiv) di-$C_1$ to $C_6$ alkylamino (for example, N,N-dimethylamino, etc. may be mentioned.)
(xv) 5- to 6-membered cyclic amino (for example, morpholino, piperidino, piperazino, etc. may be mentioned.)
(xvi) $C_1$ to $C_6$ alkylcarbonyl (for example, acetyl, propionyl, butyryl, isobutyryl, pivaroyl, etc. may be mentioned.)
(xvii) carboxyl
(xviii) $C_1$ to $C_6$ alkoxycarbonyl (for example, methoxycarbonyl, ethoxycarbonyl, etc. may be mentioned.)
(xix) carbamoyl
(xx) thiocarbamoyl
(xxi) mono-$C_1$ to $C_6$ alkylcarbamoyl (for example, N-methylcarbamoyl, N-ethylcarbamoyl, etc. may be mentioned.)

(xxii) di-$C_1$ to $C_6$ alkylcarbamoyl (for example, N,N-dimethylcarbamoyl, N,N-diethylcarbamoyl, etc. may be mentioned.)
(xxiii) 5- to 6-membered cyclic aminocarbonyl (for example, morpholinocarbonyl, piperidinocarbonyl, piperadinocarbonyl, etc. may be mentioned.)
(xxiv) sulfo
(xxv) $C_1$ to $C_6$ alkylsulfonyl (for example, methanesulfonyl etc. may be mentioned.)
(xxvi) $C_1$ to $C_6$ alkoxycarbonylamino (for example, methoxycarbonylamino, ethoxycarbonylamino, etc. may be mentioned.)
(xxvii) $C_1$ to $C_6$ alkylcarbonylamino (for example, acetoamide group etc. may be mentioned.)
(xxviii) mono- or di-$C_1$ to $C_6$ alkylaminocarbonylamino (for example, N-methylaminocarbonylamino etc. may be mentioned.)
(xxix) aminosulfonyl
(xxx) mono- or di-$C_1$ to $C_6$ alkylaminosulfonyl (for example, N-methylaminosulfonyl etc. may be mentioned.) and
(xxxi) deuterium atoms.

Among the substituent groups for the groups expressed by the above Ar, (i) a halogen atom, (ii) nitro, (iii) cyano, (iv) $C_1$ to $C_6$ alkyl unsubstituted, or substituted with 1 to 3 halogen atoms, (viii) hydroxyl, (ix) $C_1$ to $C_6$ alkoxy unsubstituted, or substituted with 1 to 3 groups selected from a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atoms, and (xxxi) deuterium atoms etc. are particularly preferable.

In the above formula (I), X indicates (1) a connecting bond, (2) linear or branched $C_1$ to $C_6$ alkylene unsubstituted, or substituted with 1 to 12 deuterium atoms, (3) an oxygen atom, (4) $NR^3$, where, $R^3$ indicates a hydrogen atom or $C_1$ to $C_6$ alkyl group, or (5) —$S(O)_m$—, where, m indicates an integer of 0 to 2.

As specific examples of the "linear or branched $C_1$ to $C_6$ alkylene" expressed by X, methylene, 1,1-ethylene, 1,2-ethylene, 1,1-propylene, etc. may be mentioned. Further, as specific examples of the "$NR^3$, where $R^3$ indicates a hydrogen atom or $C_1$ to $C_6$ alkyl group" expressed by X, —NH—, —NMe-, —NEt-, —N″ Pr—, —$N^iPr$—, etc. may be mentioned. As X, a methylene group is particularly preferable.

Next, in the above-mentioned formula (I), the (A) to (F), which the $R^4$ and $R^5$ of "$CR^4R^5$" expressed by Z independently indicate, are shown below along with specific examples:
  (A) a hydrogen atom
  (B) deuterium atoms
  (C) $C_1$ to $C_6$ alkyl unsubstituted, or substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl, or substituted with (viii) 1 to 13 deuterium atoms (as examples of $C_1$ to $C_6$ alkyl, methyl, ethyl, n-propyl, i-propyl, n-butyl, i-butyl, s-butyl, t-butyl, n-pentyl, n-hexyl, etc. may be mentioned. As examples of the substituent groups of $C_1$ to $C_6$ alkyl, carboxyl, methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, phenyl, hydroxyl, methoxy, ethoxy, n-propoxy, i-propoxy, n-butoxy, i-butoxy, t-butoxy, fluorine, chlorine, bromine, iodine, cyclopropyl, cyclobutyl, cyclopentyl, cyclohexyl, deuterium atoms, etc. may be mentioned.)
  (D) $C_3$ to $C_6$ cycloalkyl unsubstituted, or substituted with 1 to 5 groups selected from the group consisting of (i) a halogen atom and (ii) an alkyl group unsubstituted, or substituted with 1 to 3 halogen atoms or substituted with (iii) 1 to 11 deuterium atoms (as examples of $C_3$ to $C_6$ cycloalkyl, cyclopropyl, cyclobutyl, cyclopentyl, cyclohexyl, etc. may be mentioned. As examples of the substituent group, fluorine, chlorine, bromine, iodine, methyl, ethyl, trifluoromethyl, [$^2H_3$]methyl etc. may be mentioned.)
  (E) $COOR^6$ ($R^6$ indicates a hydrogen atom or $C_1$ to $C_6$ alkyl) (as specific examples, carboxyl, methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, etc. may be mentioned.)
  (F) $CONR^7R^8$ (where specific examples of (a) to (e) which $R^7$ and $R^8$ show independently are as follows)
    (a) a hydrogen atom
    (b) $C_1$ to $C_6$ alkyl unsubstituted, or substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl (as specific examples of $C_1$ to $C_6$ alkyl groups, methyl, ethyl, n-propyl, i-propyl, n-butyl, i-butyl, s-butyl, t-butyl, n-pentyl, n-hexyl, etc. may be mentioned. Here, as examples of the substituent groups (i) to (x) of the $C_1$ to $C_6$ alkyl groups,
    (i) a halogen atom (for example, fluorine, chlorine, bromine, and iodine may be mentioned.)
    (ii) $C_3$ to $C_6$ cycloalkyl (for example, cyclopropyl, cyclobutyl, cyclopentyl and cyclohexyl, etc. may be mentioned.)
    (iii) carboxyl
    (iv) $C_1$ to $C_6$ alkoxycarbonyl (for example, methoxycarbonyl and ethoxycarbonyl, etc. may be mentioned.)
    (v) $C_1$ to $C_6$ alkylcarbonyl (for example, acetyl, propionyl, butyryl, isobutyryl, pivaroyl, etc. may be mentioned.)
    (vi) carbamoyl
    (vii) mono-$C_1$ to $C_6$ alkylcarbamoyl (for example, N-methylcarbamoyl, N-ethylcarbamoyl, etc. may be mentioned.)
    (viii) di-$C_1$ to $C_6$ alkylcarbamoyl (for example, N,N-dimethylcarbamoyl, N,N-diethylcarbamoyl, etc. may be mentioned.)
    (ix) $C_6$ to $C_{12}$ aryl (for example, phenyl, tolyl, xylyl, biphenyl, naphthyl and indenyl, etc. may be mentioned.)
    (x) $C_1$ to $C_{10}$ heteroaryl (for example, thienyl, furyl, pyrrolyl, imidazolyl, pyrazolyl, triazolyl, tetrazolyl, thiazolyl, isothiazolyl, oxazolyl, isoxazolyl, pyridyl, pyrazinyl, pyrimidinyl, pyridazinyl, benzothienyl, benzofuryl, indolyl, isoindolyl, benzimidazolyl, benzopyrazolyl, benzotriazolyl, benzothiazolyl, benzisothiazolyl, benzoxazolyl, benzisoxazolyl, quinolyl, isoquinolyl, quinoxalinyl, phthalazinyl, naphthylidinyl and purinyl, etc.) may be mentioned.)
    (c) $C_6$ to $C_{14}$ aromatic hydrocarbon group (specific examples same as "$C_6$ to $C_{14}$ aromatic hydrocarbon group" in Ar explained above. As preferable example, phenyl may be mentioned.)
    (d) a 5- to 8-membered aromatic heterocyclic group including 1 to 4 hetero atoms selected from a nitrogen atom, sulfur atom, and oxygen atom, other than a carbon atom, (specific examples are same as "a 5- to 8-membered aromatic heterocyclic group including 1 to 4 hetero atoms selected from a nitrogen atom, sulfur atom, and oxygen atom, other than a carbon atom" in Ar explained above. As preferable example, pyridyl, thienyl, furyl, pyrrolyl, imidazolyl, pyrazolyl, triazolyl and tetrazolyl, etc. may be mentioned.)
(e) bicyclic or tricyclic aromatic group formed by condensation of the above aromatic heterocyclic group of the above (d) and a $C_6$ to $C_{14}$ aromatic hydrocarbon ring (specific examples are same as "bicyclic or tricyclic aromatic group formed by condensation of the above aromatic heterocyclic group and a $C_6$ to $C_{14}$ aromatic hydrocarbon group" in Ar explained above. As preferable examples, benzothienyl, benzofuryl, indolyl, benzimidazolyl, benzopyrazolyl, and benzotriazolyl may be mentioned.)

Specific examples of the substituent groups (i) to (xxviii) which said groups (c) to (e) may have are shown next.
(i) a halogen atom (for example, fluorine, chlorine, bromine, and iodine may be mentioned.)
(ii) nitro
(iii) cyano
(iv) $C_1$ to $C_6$ alkyl unsubstituted, or substituted with 1 to 3 halogen atoms (for example, $C_1$ to $C_6$ alkyl unsubstituted, or substituted with 1 to 3 halogen atoms selected from fluorine, chlorine, bromine, and iodine (for example, methyl, ethyl, n-propyl, i-propyl, n-butyl, i-butyl, s-butyl, t-butyl, n-pentyl, n-hexyl, etc.) may be mentioned, as specific examples, methyl, fluoromethyl, difluoromethyl, trifluoromethyl, chloromethyl, dichloromethyl, trichloromethyl, ethyl, 2,2,2-trifluoroethyl, n-propyl, i-propyl, n-butyl, butyl, s-butyl, t-butyl, n-pentyl and n-hexyl, etc. (preferably methyl, ethyl and trifluoromethyl, etc.) may be mentioned.)
(v) $C_2$ to $C_6$ alkenyl unsubstituted, or substituted with 1 to 3 halogen atoms (for example, $C_2$ to $C_6$ alkenyl unsubstituted, or substituted with 1 to 3 halogen atoms selected from fluorine, chlorine, bromine, and iodine (for example, vinyl, propenyl, isopropenyl, 2-buten-1-yl, 4-penten-1-yl and 5-hexen-1-yl, etc.) may be mentioned.)
(vi) $C_2$ to $C_6$ alkynyl unsubstituted, or substituted with 1 to 3 halogen atoms (for example, $C_2$ to $C_6$ alkynyl unsubstituted, or substituted with 1 to 3 halogen atoms selected from fluorine, chlorine, bromine, and iodine (for example, 2-butyn-1-yl, 4-pentyn-1-yl and 5-hexyn-1-yl, etc.) may be mentioned.)
(vii) $C_3$ to $C_6$ cycloalkyl (for example, cyclopropyl, cyclobutyl, cyclopentyl and cyclohexyl, etc. may be mentioned.)
(viii) hydroxyl
(ix) $C_1$ to $C_6$ alkoxy unsubstituted, or substituted with 1 to 3 halogen atoms (for example, methoxy, ethoxy, n-propoxy, i-propoxy, n-butoxy, i-butoxy, t-butoxy, trifluoromethyloxy and trichloromethyloxy, etc. may be mentioned.)
(x) $C_1$ to $C_5$ alkylenedioxy (for example, methylenedioxy and ethylenedioxy, etc. may be mentioned.)
(xi) $C_1$ to $C_6$ alkylthio unsubstituted, or substituted with 1 to 3 halogen atoms (for example, methylthio, ethylthio, n-propylthio, i-propylthio, n-butylthio, i-butylthio, s-butylthio, t-butylthio, n-pentylthio, n-hexylthio, trifluoromethylthio and trichloromethylthio, etc. may be mentioned.)
(xii) amino
(xiii) mono-$C_1$ to $C_6$ alkylamino (for example, N-methylamino, etc. may be mentioned.)
(xiv) di-$C_1$ to $C_6$ alkylamino (for example, N,N-dimethylamino, etc. may be mentioned.)
(xv) 5- to 6-membered cyclic amino (for example, morpholino, piperidino and piperazino, etc. may be mentioned.)
(xvi) $C_1$ to $C_6$ alkylcarbonyl (for example, acetyl, propionyl, butyryl, isobutyryl and pivaroyl, etc. may, be mentioned.)
(xvii) carboxyl
(xviii) $C_1$ to $C_6$ alkoxycarbonyl (for example, methoxycarbonyl and ethoxycarbonyl, etc. may be mentioned.)
(xix) carbamoyl
(xx) thiocarbamoyl
(xxi) mono-$C_1$ to $C_6$ alkylcarbamoyl (for example, N-methylcarbamoyl and N-ethylcarbamoyl, etc. may be mentioned.)
(xxii) di-$C_1$ to $C_6$ alkylcarbamoyl (for example, N,N-dimethylcarbamoyl and N,N-diethylcarbamoyl, etc. may be mentioned.)
(xxiii) $C_6$ to $C_{10}$ arylcarbamoyl (for example, N-phenylcarbamoyl etc. may be mentioned.)
(xxiv) $C_1$ to $C_{10}$ heteroarylcarbamoyl (for example, N-pyridylcarbamoyl etc. may be mentioned.)
(xxv) sulfo
(xxvi) $C_1$ to $C_6$ alkylsulfonyl (for example, methanesulfonyl etc. may be mentioned.)
(xxvii) aminosulfonyl
(xxviii) mono- or di-$C_1$ to $C_6$ alkylaminosulfonyl (for example, N-methylaminosulfonyl etc. may be mentioned.), and
(xxix) deuterium atoms.

As examples of the "$C_6$ to $C_{14}$ aromatic hydrocarbon group", "a 5- to 8-membered aromatic heterocyclic group including 1 to 4 hetero atoms selected from a nitrogen atom, sulfur atom, and oxygen atom, other than a carbon atom", and "a bicyclic or tricyclic aromatic group formed by condensation of the above aromatic heterocyclic group and a $C_6$ to $C_{14}$ aromatic hydrocarbon group" expressed by W, ones the same as the examples of the "$C_6$ to $C_{14}$ aromatic hydrocarbon group", "a 5- to 8-membered aromatic heterocyclic group including 1 to 4 hetero atoms selected from a nitrogen atom, sulfur atom, and oxygen atom, other than a carbon atom", and "a bicyclic or tricyclic aromatic group formed by condensation of the above aromatic heterocyclic group and a $C_6$ to $C_{14}$ aromatic hydrocarbon group" represented by Ar explained above may be mentioned.

As examples of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom, other than a carbon atom", and "a bicyclic or tricyclic aromatic group formed by condensation of the above aromatic heterocyclic group and a $C_6$ to $C_{14}$ aromatic hydrocarbon group" expressed by W, in particular, phenyl, pyridyl, thienyl, furyl, thiazolyl, oxazolyl, and isooxazolyl are preferable.

Next, the substituent groups (i) to (xlviii) of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom, other than a carbon atom", and "bicyclic or tricyclic aromatic group formed by condensation of the above aromatic heterocyclic group and a $C_6$ to $C_{14}$ aromatic hydrocarbon group" expressed by W in the above formula (I) will be shown together with specific examples.
(i) a halogen atom (for example, fluorine, chlorine, bromine, and iodine may be mentioned.)
(ii) nitro
(iii) cyano (iv) $C_1$ to $C_6$ alkyl unsubstituted, or substituted with 1 to 3 groups which are selected from the group consisting of a halogen atom, amino, $C_1$ to $C_6$ alkoxycarbonyl, $C_1$ to $C_6$ alkoxycarbonylamino and carboxyl (as $C_1$ to $C_6$ alkyl, methyl, ethyl, n-propyl, i-propyl, n-butyl, i-butyl, s-butyl, t-butyl, n-pentyl, n-hexyl, etc. may be mentioned, as substituent groups of $C_1$ to $C_6$ alkyl, fluorine, chlorine, bromine, iodine, amino, methoxycarbonyl, ethoxycarbonyl, methoxycarbonylamino, ethoxycarbonylamino, t-butoxycarbonylamino, and carboxyl may be mentioned, as specific examples, methyl, fluoromethyl, difluoromethyl, trifluoromethyl, chloromethyl, dichloromethyl, trichloromethyl, carboxylmethyl, ethyl, 2,2,2-trifluoroethyl, aminoethyl, methoxycarbonylethyl, t-butoxycarbonylaminoethyl, carboxylethyl, n-propyl, i-propyl, n-butyl, i-butyl, s-butyl, t-butyl, n-pentyl and n-hexyl, etc. (preferably methyl, ethyl, trifluoromethyl, methoxycarbonylethyl, aminoethyl and carboxylmethyl, etc.) may be mentioned.)

(v) $C_2$ to $C_6$ alkenyl which unsubstituted, or substituted with 1 to 3 halogen atoms (as halogen atom, fluorine, chlorine, bromine, and iodine may be mentioned, as $C_2$ to $C_6$ alkenyl, for example, vinyl, propenyl, isopropenyl, 2-buten-1-yl, 4-penten-1-yl and 5-hexen-1-yl, etc. may be mentioned.)

(vi) $C_2$ to $C_6$ alkynyl unsubstituted, or substituted with 1 to 3 halogen atoms, (as halogen atom, fluorine, chlorine, bromine, and iodine may be mentioned, as $C_2$ to $C_6$ alkynyl, for example, 2-butyn-1-yl, 4-pentynl-yl and 5-hexyn-1-yl, etc. may be mentioned.)

(vii) $C_3$ to $C_6$ cycloalkyl (for example, cyclopropyl, cyclobutyl, cyclopentyl and cyclohexyl, etc. may be mentioned.)

(viii) hydroxyl (ix) $C_1$ to $C_6$ alkoxy unsubstituted, or substituted with 1 to 3 groups which are selected from a halogen atom, hydroxyl, $C_1$ to $C_6$ alkoxy, and amino, and mono- or di-$C_1$ to $C_6$ alkylamino (as $C_1$ to $C_6$ alkoxy, for example, methoxy, ethoxy, n-propoxy, i-propoxy, n-butoxy, butoxy, s-butoxy, t-butoxy, n-pentyloxy and n-hexyloxy, etc. may be mentioned. As substituent groups of $C_1$ to $C_6$ alkoxy, fluorine, chlorine, bromine, iodine, hydroxyl, amino, N-methylamino, N,N-dimethylamino, methoxy and ethoxy, etc. may be mentioned. As specific examples, methoxy, ethoxy, n-propoxy, i-propoxy, n-butoxy, i-butoxy, t-butoxy, trifluoromethyloxy, trichloromethyloxy, methoxymethyloxy and ethoxymethyloxy, etc. (preferably methoxy and ethoxy) may be mentioned.)

(x) $C_1$ to $C_5$ alkylenedioxy (for example, methylenedioxy and ethylenedioxy, etc. may be mentioned.)

(xi) $C_1$ to $C_6$ alkylthio unsubstituted, or substituted with 1 to 3 groups which are selected from a halogen atom, hydroxyl, $C_1$ to $C_6$ alkoxy and amino, and mono- or di-$C_1$ to $C_6$ alkylamino (as $C_1$ to $C_6$ alkylthio, for example, methylthio, ethylthio, n-propylthio, i-propylthio, n-butylthio, i-butylthio, s-butylthio, t-butylthio, n-pentylthio and n-hexylthio, etc. may be mentioned. As substituent groups of $C_1$ to $C_6$ alkylthio, fluorine, chlorine, bromine, iodine, hydroxyl, amino, N-methylamino, N,N-dimethylamino, methoxy and ethoxy, etc. may be mentioned. As specific examples, methylthio, ethylthio, n-propylthio, i-propylthio, n-butylthio, butylthio, t-butylthio, trifluoromethylthio, trichloromethylthio, methoxymethylthio and ethoxymethylthio, etc. may be mentioned.)

(xii) amino (xiii) mono-$C_1$ to $C_6$ alkylamino (for example, N-methylamino etc. may be mentioned.)

(xiv) di-$C_1$ to $C_6$ alkylamino (for example, N,N-dimethylamino etc. may be mentioned.)

(xv) 5- to 6-membered cyclic amino (for example, morpholino, piperidino and piperadino, etc. may be mentioned.)

(xvi) $C_1$ to $C_6$ alkylcarbonyl (for example, acetyl, propionyl, butyryl, isobutyryl and pivaroyl, etc. may be mentioned.)

(xvii) carboxyl (xviii) $C_1$ to $C_6$ alkoxycarbonyl unsubstituted, or substituted with a halogen atom (for example, methoxycarbonyl and ethoxycarbonyl etc. may be mentioned.)

(xix) $C_7$ to $C_{16}$ aralkyloxycarbonyl unsubstituted, or substituted with a halogen atom (for example, benzyloxycarbonyl etc. may be mentioned.)

(xx) carbamoyl (xxi) mono-$C_1$ to $C_6$ alkylcarbamoyl unsubstituted, or substituted with 1 to 3 groups which are selected from a halogen atom, hydroxyl, carboxyl, $C_1$ to $C_6$ alkoxy, amino, and mono- or di-$C_1$ to $C_6$ alkylamino (as mono-$C_1$ to $C_6$ alkylcarbamoyl, for example, N-methylcarbamoyl and N-ethylcarbamoyl, etc. may be mentioned. As substituent groups of mono-$C_1$ to $C_6$ alkyl-carbamoyl, fluorine, chlorine, bromine, iodine, hydroxyl, carboxyl, methoxy, ethoxy, amino, N-methylamino and N,N-dimethylamino, etc. may be mentioned.)

(xxii) di-$C_1$ to $C_6$ alkylcarbamoyl unsubstituted, or substituted with hydroxyl (for example, N,N-dimethylcarbamoyl, N,N-diethylcarbamoyl and N-hydroxyethyl-N-methylcarbamoyl, etc. may be mentioned.)

(xxiii) 5- to 6-membered cyclic aminocarbonyl unsubstituted, or substituted with $C_1$ to $C_6$ alkoxycarbonyl (for example, morpholinocarbonyl, piperidinocarbonyl, piperadinocarbonyl and t-butoxycarbonylpiperadinocarbonyl, etc. may be mentioned.)

(xxiv) $C_6$ to $C_{10}$ arylcarbamoyl (for example, N-phenylcarbamoyl etc. may be mentioned.)

(xxv) $C_1$ to $C_{10}$ heteroarylcarbamoyl (for example, N-pyridylcarbamoyl etc. may be mentioned.)

(xxvi) $C_7$ to $C_{16}$ aralkylcarbamoyl (for example, N-benzylaminocarbonyl etc. may be mentioned.)

(xxvii) $C_1$ to $C_{10}$ heteroaryl-$C_1$ to $C_6$ alkylcarbamoyl (for example, N-pyridylmethylcarbamoyl and N-pyridylethylcarbamoyl, etc. may be mentioned.)

(xxviii) N—$C_1$ to $C_6$ alkyl-N—$C_6$ to $C_{12}$ arylcarbamoyl (for example, N-methyl-N-phenylcarbamoyl etc. may be mentioned.)

(xxix) $C_3$ to $C_6$ cycloalkylcarbamoyl (for example, N-cyclopropylcarbamoyl and N-cyclohexylcarbamoyl, etc. may be mentioned.)

(xxx) sulfo (xxxi) $C_1$ to $C_6$ alkylsulfonyl (for example, methanesulfonyl etc. may be mentioned.)

(xxxii) $C_1$ to $C_6$ alkylsulfonylamino (for example, methanesulfonylamino etc. may be mentioned.)

(xxxiii) $C_6$ to $C_{12}$ arylsulfonylamino unsubstituted, or substituted with $C_1$ to $C_6$ alkyl (for example, benzenesulfonylamino and methylbenzenesulfonylamino, etc. may be mentioned.)

(xxxiv) $C_1$ to $C_{10}$ heteroarylsulfonylamino (for example, pyridylsulfonylamino etc. may be mentioned.)

(xxxv) $C_1$ to $C_6$ alkoxycarbonylamino (for example, methoxycarbonylamino, ethoxycarbonylamino and t-butoxycarbonylamino, etc. may be mentioned.)

(xxxvi) $C_1$ to $C_6$ alkylcarbonylamino (for example, acetoamide etc. may be mentioned.)

(xxxvii) mono- or di-$C_1$ to $C_6$ alkylaminocarbonylamino (for example, N-methylaminocarbonylamino and N-ethylaminocarbonylamino, etc. may be mentioned.)

(xxxviii) $C_6$ to $C_{12}$ aryl (for example, phenyl etc. may be mentioned.)

(xxxix) $C_1$ to $C_{10}$ heteroaryl ($C_1$ to $C_{10}$ heteroaryl including 1 to 4 hetero atoms selected from a nitrogen atom, sulfur atom, and oxygen atom (for example, pyridyl, pyrazolyl and imidazolyl, etc.) may be mentioned.)

(xl) $C_6$ to $C_{10}$ aryloxy (for example, phenoxy etc. may be mentioned.)

(xli) $C_1$ to $C_{10}$ heteroaryloxy ($C_1$ to $C_{10}$ heteroaryloxy including 1 to 4 hetero atoms selected from a nitrogen atom, sulfur atom, and oxygen atom (for example, pyridyloxy, pyrazolyloxy and imidazolyloxy, etc.) may be mentioned.)

(xlii) $C_7$ to $C_{16}$ aralkyloxy (for example, benzyloxy etc. may be mentioned.)

(xliii) $C_1$ to $C_{10}$ heteroaryl-$C_1$ to $C_6$ alkyloxy ($C_1$ to $C_{10}$ heteroaryl-$C_1$ to $C_6$ alkyloxy including 1 to 4 hetero atoms selected from a nitrogen atom, sulfur atom, and oxygen atom (for example, pyridylmethyloxy, pyrazolylmethyloxy and imidazolylmethyloxy, etc.) may be mentioned.)

(xliv) aminosulfonyl (xlv) mono- or di-$C_1$ to $C_6$ alkylaminosulfonyl (for example, N-methylaminosulfonyl etc. may be mentioned.)

(xlvi) $C_7$ to $C_{16}$ aralkyloxycarbamoyl (for example, N-benzyloxycarbamoyl etc. may be mentioned.)

(xlvii) $C_1$ to $C_{10}$ heteroaryl-$C_1$ to $C_6$ alkyloxycarbamoyl ($C_1$ to $C_{10}$ heteroaryl-$C_1$ to $C_6$ alkyloxycarbamoyl including 1 to 4 hetero atoms selected from a nitrogen atom, sulfur atom, and oxygen atom (for example, N-pyridylmethyloxycarbamoyl, N-pyrazolylmethyloxycarbamoyl and N-imidazolylmethyloxycarbamoyl, etc.) may be mentioned.)

(xlviii) deuterium atoms.

As examples of the substituent groups of the "$C_6$ to $C_{14}$ aromatic hydrocarbon group", "5- to 8-membered aromatic heterocyclic group including 1 to 4 hetero atoms selected from a nitrogen atom, sulfur atom, and oxygen atom, other than a carbon atom", and "bicyclic or tricyclic aromatic group formed by condensation of the above aromatic heterocyclic group and a $C_6$ to $C_{14}$ aromatic hydrocarbon group" expressed by W, in particular (i) a halogen atom, (ii) nitro, (iv) $C_1$ to $C_6$ alkyl unsubstituted, or substituted with 1 to 3 groups which are selected from the group consisting of a halogen atom, amino, $C_1$ to $C_6$ alkoxycarbonyl, $C_1$ to $C_6$ alkoxycarbonylamino, and carboxyl, (viii) hydroxyl, (xii) amino, (xvii) carboxyl, and (xlviii) deuterium atoms are preferable.

The groups of (1) to (5) which are expressed by $R^1$ in the above formula (I) are shown below together with specific examples:

(1) a hydrogen atom;

(2) $C_1$ to $C_6$ alkyl unsubstituted, or substituted with 1 to 3 of (i) a halogen atom or (ii) $C_3$ to $C_6$ cycloalkyl, or substituted with (iii) 1 to 13 deuterium atoms (as a halogen atom, fluorine, chlorine, bromine, and iodine may be mentioned, as $C_3$ to $C_6$ cycloalkyl, for example, cyclopropyl, cyclobutyl, cyclopentyl and cyclohexyl, etc. may be mentioned, as $C_1$ to $C_6$ alkyl, methyl, ethyl, n-propyl, i-propyl, n-butyl, i-butyl, s-butyl, t-butyl, n-pentyl and n-hexyl, etc. may be mentioned. As specific examples, methyl, fluoromethyl, difluoromethyl, trifluoromethyl, chloromethyl, dichloromethyl, trichloromethyl, cyclopropylmethyl, cyclopentylmethyl, [$^2$H$_3$]methyl and [$^2$H$_5$]ethyl, etc. may be mentioned.)

(3) $C_2$ to $C_6$ alkenyl unsubstituted, or substituted with 1 to 3 of (i) a halogen atom or (ii) $C_3$ to $C_6$ cycloalkyl, or substituted with (iii) 1 to 11 deuterium atoms, (as a halogen atom, fluorine, chlorine, bromine, and iodine may be mentioned, as $C_3$ to $C_6$ cycloalkyl, for example, cyclopropyl, cyclobutyl, cyclopentyl and cyclohexyl, etc. may be mentioned, as $C_2$ to $C_6$ alkenyl, for example, vinyl, propenyl, isopropenyl, 2-buten-1-yl, 4-penten-1-yl and 5-hexen-1-yl, etc. may be mentioned.)

(4) $C_2$ to $C_6$ alkynyl unsubstituted, or substituted with 1 to 3 of (i) a halogen atom or (ii) $C_3$ to $C_6$ cycloalkyl, or substituted with (iii) 1 to 9 deuterium atoms (as a halogen atom, fluorine, chlorine, bromine, and iodine may be mentioned, as $C_3$ to $C_6$ cycloalkyl, for example, cyclopropyl, cyclobutyl, cyclopentyl and cyclohexyl, etc. may be mentioned, as $C_2$ to $C_6$ alkynyl, for example, 2-butyn-1-yl, 4-pentyn-1-yl and 5-hexyn-1-yl, etc. may be mentioned.)

(5) $C_3$ to $C_6$ cycloalkyl unsubstituted, or substituted with 1 to 3 of (i) a halogen atom or (ii) $C_3$ to $C_6$ cycloalkyl, or substituted with (iii) 1 to 11 deuterium atoms, (as a halogen atom, fluorine, chlorine, bromine, and iodine may be mentioned, as $C_3$ to $C_6$ cycloalkyl, for example, cyclopropyl, cyclobutyl, cyclopentyl and cyclohexyl, etc. may be mentioned.)

As examples of the group expressed by $R^1$, a hydrogen atom and methyl are preferable.

In the above formula (I), the groups of (A) to (H) which the $R^9$, $R^{10}$, and $R^{11}$ of the "$OR^9$" and "$NR^{10}R^{11}$" expressed by $R^2$ independently indicate will be shown below together with specific examples.

(A) a hydrogen atom (B) $C_1$ to $C_6$ alkyl (for example, methyl, ethyl, n-propyl, i-propyl, n-butyl, i-butyl, s-butyl, t-butyl, n-pentyl and n-hexyl, etc. may be mentioned.)

(C) $C_2$ to $C_6$ alkenyl (for example, vinyl, propenyl, isopropenyl, 2-buten-1-yl, 4-penten-1-yl and 5-hexen-1-yl, etc. may be mentioned.)

(D) $C_2$ to $C_6$ alkynyl (for example, 2-butyn-1-yl, 4-pentyn-1-yl and 5-hexyn-1-yl, etc. may be mentioned.)

(E) $C_3$ to $C_6$ cycloalkyl (for example, cyclopropyl, cyclobutyl, cyclopentyl and cyclohexyl, etc. may be mentioned.)

(F) $C_6$ to $C_{14}$ aromatic hydrocarbon group (specific examples are the same as "$C_6$ to $C_{14}$ aromatic hydrocarbon group" in Ar explained above. As preferable examples, phenyl may be mentioned.)

(G) 5- to 8-membered aromatic heterocyclic group including 1 to 4 hetero atoms selected from a nitrogen atom, sulfur atom, and oxygen atom, other than a carbon atom (specific examples are the same as "5- to 8-membered aromatic heterocyclic group including 1 to 4 hetero atoms selected from a nitrogen atom, sulfur atom, and oxygen atom, other than a carbon atom" in Ar explained above. As preferable examples, pyridyl may be mentioned.)

(H) bicyclic or tricyclic aromatic group formed by condensation of the above aromatic heterocyclic group and a $C_6$ to $C_{14}$ aromatic hydrocarbon ring (specific examples are the same as "bicyclic or tricyclic aromatic group formed by condensation of the above aromatic heterocyclic group and a $C_6$ to $C_{14}$ aromatic hydrocarbon group" in Ar explained above. As preferable examples, benzothienyl, benzofuryl, and indolyl may be mentioned.)

As examples of the groups which the $R^9$, $R^{10}$ and $R^{11}$ of the "$OR^9$" and "$NR^{10}R^{11}$" expressed by $R^2$ indicate, a hydrogen atom, methyl, ethyl, n-propyl, i-propyl, n-butyl, i-butyl, t-butyl, propenyl, cyclopropyl, cyclopentyl, phenyl and pyridyl are preferable.

Next, specific examples of the substituent groups (i) to (xvii) which may optionally be possessed by the groups of (B) to (E) respectively independently shown by $R^9$, $R^{10}$, and of the "$OR^9$" and "$NR^{10}R^{11}$" expressed by $R^2$ in the above formula (I), will now be shown.

(i) a halogen atom (for example, fluorine, chlorine, bromine, and iodine may be mentioned.)

(ii) $C_3$ to $C_6$ cycloalkyl (for example, cyclopropyl, cyclobutyl, cyclopentyl and cyclohexyl, etc. may be mentioned.)

(iii) hydroxyl (iv) $C_1$ to $C_6$ alkoxy unsubstituted, or substituted with 1 to 3 halogen atoms (for example, methoxy, ethoxy, n-propoxy, i-propoxy and trifluoromethyloxy, etc. may be mentioned.)
(v) amino
(vi) mono-$C_1$ to $C_6$ alkylamino (for example, N-methylamino etc. may be mentioned.)
(vii) di-$C_1$ to $C_6$ alkylamino (for example, N,N-dimethylamino etc. may be mentioned.)
(viii) 5- to 6-membered cyclic amino (for example, morpholino, piperidino and piperadino, etc. may be mentioned.)
(ix) carboxyl
(x) $C_1$ to $C_6$ alkoxycarbonyl (for example, methoxycarbonyl and ethoxycarbonyl, etc. may be mentioned.)
(xi) $C_1$ to $C_6$ alkylcarbonyl (for example, acetyl, propionyl, butyryl, isobutyryl and pivaroyl, etc. may be mentioned.)
(xii) carbamoyl
(xiii) mono-$C_1$ to $C_6$ alkylcarbamoyl (for example, N-methylcarbamoyl and N-ethylcarbamoyl, etc. may be mentioned.)
(xiv) di-$C_1$ to $C_6$ alkylcarbamoyl (for example, N,N-dimethylcarbamoyl and N,N-diethylcarbamoyl, etc. may be mentioned.)
(xv) $C_6$ to $C_{12}$ aryl (for example, phenyl, naphthyl and biphenyl, etc. may be mentioned.)
(xvi) $C_1$ to $C_{10}$ heteroaryl (for example, pyridyl, thienyl and furyl, etc. may be mentioned.)
(xvii) deuterium atoms.

Among these, (i) a halogen atom, (ii) $C_3$ to $C_6$ cycloalkyl, (iii) hydroxyl, (iv) $C_1$ to $C_6$ alkoxy unsubstituted, or substituted with 1 to 3 halogen atoms, and (xvii) deuterium atoms are preferable.

Specific examples of the substituent groups (i) to (xxi) which may optionally be possessed by the groups of (F) to (H) respectively independently shown by $R^9$, and $R^{11}$ of the "$OR^9$" and "$NR^{10}R^{11}$" expressed by $R^2$ in the above formula (I), will now be shown.
(i) a halogen atom (for example, fluorine, chlorine, bromine, and iodine may be mentioned.)
(ii) nitro
(iii) cyano
(iv) $C_1$ to $C_6$ alkyl unsubstituted, or substituted with 1 to 3 halogen atoms (for example, methyl, trifluoromethyl, ethyl, n-propyl and i-propyl, etc. may be mentioned.)
(v) $C_3$ to $C_6$ cycloalkyl unsubstituted, or substituted with 1 to 3 halogen atoms (for example, cyclopropyl, cyclobutyl, cyclopentyl and cyclohexyl, etc. may be mentioned.)
(vi) hydroxyl
(vii) $C_1$ to $C_6$ alkoxy unsubstituted, or substituted with 1 to 3 halogen atoms (for example, methoxy, ethoxy, n-propoxy, i-propoxy and trifluoromethyloxy, etc. may be mentioned.)
(viii) amino
(ix) mono-$C_1$ to $C_6$ alkylamino (for example, N-methylamino etc. may be mentioned.)
(x) di-$C_1$ to $C_6$ alkylamino (for example, N,N-dimethylamino etc. may be mentioned.)
(xi) 5- to 6-membered cyclic amino (for example, morpholino, piperidino and piperadino, etc. may be mentioned.)
(xii) $C_1$ to $C_6$ alkylcarbonyl (for example, acetyl, propionyl, butyryl, isobutyryl and pivaroyl, etc. may be mentioned.)
(xiii) carboxyl
(xiv) $C_1$ to $C_6$ alkoxycarbonyl (for example, methoxycarbonyl and ethoxycarbonyl, etc. may be mentioned.)
(xv) carbamoyl
(xvi) mono-$C_1$ to $C_6$ alkylcarbamoyl (for example, N-methylcarbamoyl and N-ethylcarbamoyl, etc. may be mentioned.)
(xvii) di-$C_1$ to $C_6$ alkylcarbamoyl (for example, N,N-dimethylcarbamoyl and N,N-diethylcarbamoyl, etc. may be mentioned.)
(xviii) $C_1$ to $C_6$ alkylsulfonyl (for example, methanesulfonyl etc. may be mentioned.)
(xix) aminosulfonyl
(xx) mono- or di-$C_1$ to $C_6$ alkylaminosulfonyl (for example, N-methylaminosulfonyl etc. may be mentioned.)
(xxi) deuterium atoms Among these, (i) a halogen atom, (iii) cyano, (vi) hydroxyl, (xxi) deuterium atoms are preferred.

In the above formula (I), as the 5- or 6-member heterocyclic groups which are formed by $R^1$ and $R^2$ together with the atoms they are bonded with, for example, imidazole, triazole, tetrazole, oxadiazole, thiadiazole, pyrimidine, triazine, oxadiazine, thiadiazine, and other aromatic heterocyclic groups or their saturated or partially saturated heterocyclic groups may be mentioned, more specifically, imidazole, imidazoline, 1,2,4-triazole, 1,2,4-triazoline, tetrazole, 1,2,4-oxadiazoline, 1,2,4-thiadiazoline, dihydropyrimidine, tetrahydropyrimidine, dihydro-1,2,4-triazine, tetrahydro-1,2,4-triazine, dihydro-1,2,4-oxadiazine, tetrahydro-1,2,4-oxadiazine, dihydro-1,2,4-thiadiazine, tetrahydro-1,2,4-thiadiazine (preferably imidazole, 1,2,4-triazole, 1,2,4-triazoline, 1,2,4-oxadiazoline, and tetrahydro-1,2,4-oxadiazine) may be mentioned.

In the above formula (I), the substituent groups (A) to (K), which may be optionally possessed by the 5- or 6-member heterocyclic groups formed by $R^1$ and $R^2$ together with the atoms they are bonded with, will be shown below, together with specific examples thereof:
(A) a halogen atom (for example, fluorine, chlorine, bromine and iodine may be mentioned.)
(B) oxo
(C) hydroxyl
(D) $C_1$ to $C_6$ alkyl (for example, methyl, ethyl, n-propyl, i-propyl, n-butyl, i-butyl, s-butyl, t-butyl, n-pentyl and n-hexyl, etc. may be mentioned.)
(E) $C_2$ to $C_6$ alkenyl (for example, vinyl, propenyl, isopropenyl, 2-buten-1-yl, 4-penten-1-yl and 5-hexen-1-yl, etc. may be mentioned.)
(F) $C_2$ to $C_6$ alkynyl (for example, 2-butyn-1-yl, 4-pentyn-1-yl and 5-hexyn-1-yl, etc. may be mentioned.)
(G) $C_3$ to $C_6$ cycloalkyl (for example, cyclopropyl, cyclobutyl, cyclopentyl and cyclohexyl, etc. may be mentioned.)
(H) $C_6$ to $C_{14}$ aromatic hydrocarbon group (specific examples are the same as "$C_6$ to $C_{14}$ aromatic hydrocarbon group" in Ar explained above. As preferable examples, phenyl may be mentioned.)
(I) a 5- to 8-membered aromatic heterocyclic group including 1 to 4 hetero atoms selected from a nitrogen atom, sulfur atom, and oxygen atom, other than a carbon atom (specific examples are the same as "a 5- to 8-membered aromatic heterocyclic group including 1 to 4 hetero atoms selected from a nitrogen atom, sulfur atom, and oxygen atom, other than a carbon atom" in Ar explained above. As preferable example, pyridyl may be mentioned.)
(J) a bicyclic or tricyclic aromatic group formed by condensation of the above aromatic heterocyclic group and a $C_6$ to $C_{14}$ aromatic hydrocarbon ring (specific examples are the same as "a bicyclic or tricyclic aromatic group formed by condensation of the above aromatic heterocyclic group and a $C_6$ to $C_{14}$ aromatic hydrocarbon group" in Ar explained above. As preferable examples, benzothienyl, benzofuryl and indolyl may be mentioned.)
(K) deuterium atoms.

Among these, (A) a halogen atom, (B) oxo, (C) hydroxyl, (D) $C_1$ to $C_6$ alkyl, and (K) deuterium atoms are preferred.

In the above formula (I), specific examples of the substituent groups (i) to (xvii) which the groups of the 1 to 3 substituent groups (D) to (G), which may be optionally possessed by the 5- or 6-member heterocyclic groups formed by $R^1$ and $R^2$ together with the atoms they are bonded with, may be optionally substituted with, will now be shown.

(i) a halogen atom (for example, fluorine, chlorine, bromine and iodine may be mentioned.)
(ii) $C_3$ to $C_6$ cycloalkyl (for example, cyclopropyl, cyclobutyl, cyclopentyl and cyclohexyl, etc. may be mentioned.)
(iii) hydroxyl
(iv) $C_1$ to $C_6$ alkoxy unsubstituted, or substituted with 1 to 3 halogen atoms (for example, methoxy, ethoxy, n-propoxy, i-propoxy and trifluoromethyloxy, etc. may be mentioned.)
(v) amino
(vi) mono-$C_1$ to $C_6$ alkylamino (for example, N-methylamino etc. may be mentioned.)
(vii) di-$C_1$ to $C_6$ alkylamino (for example, N,N-dimethylamino etc. may be mentioned.)
(viii) 5- to 6-membered cyclic amino (for example, morpholino, piperidino and piperadino, etc. may be mentioned.)
(ix) carboxyl
(x) $C_1$ to $C_6$ alkoxycarbonyl (for example, methoxycarbonyl and ethoxycarbonyl, etc. may be mentioned.)
(xi) $C_1$ to $C_6$ alkylcarbonyl (for example, acetyl, propionyl, butyryl, isobutyryl and pivaroyl, etc. may be mentioned.)
(xii) carbamoyl
(xiii) mono-$C_1$ to $C_6$ alkylcarbamoyl (for example, N-methylcarbamoyl and N-ethylcarbamoyl, etc. may be mentioned.)
(xiv) di-$C_1$ to $C_6$ alkylcarbamoyl (for example, N,N-dimethylcarbamoyl and N,N-diethylcarbamoyl, etc. may be mentioned.)
(xv) $C_6$ to $C_{12}$ aryl and (for example, phenyl, naphthyl and biphenyl, etc. may be mentioned.)
(xvi) $C_1$ to $C_{10}$ heteroaryl (for example, pyridyl, thienyl and furyl, etc. may be mentioned.)
(xvii) deuterium atoms.

In the above formula (I), specific examples of the substituent groups (i) to (xxi) which the groups of the 1 to 3 substituent groups (H) to (J), which may be optionally possessed by the 5- or 6-member heterocyclic groups formed by $R^1$ and $R^2$ together with the atoms they are bonded with, will now be shown.

(i) a halogen atom (for example, fluorine, chlorine, bromine, and iodine may be mentioned.)
(ii) nitro
(iii) cyano
(iv) $C_1$ to $C_6$ alkyl unsubstituted, or substituted with 1 to 3 halogen atoms (for example, methyl, trifluoromethyl, ethyl, n-propyl and i-propyl, etc. may be mentioned.)
(v) $C_3$ to $C_6$ cycloalkyl unsubstituted, or substituted with 1 to 3 halogen atoms (for example, cyclopropyl, cyclobutyl, cyclopentyl and cyclohexyl, etc. may be mentioned.)
(vi) hydroxyl
(vii) $C_1$ to $C_6$ alkoxy unsubstituted, or substituted with 1 to 3 halogen atoms (for example, methoxy, ethoxy, n-propoxy, i-propoxy and trifluoromethyloxy, etc. may be mentioned.)
(viii) amino
(ix) mono-$C_1$ to $C_6$ alkylamino (for example, N-methylamino etc. may be mentioned.)
(x) di-$C_1$ to $C_6$ alkylamino (for example, N,N-dimethylamino etc. may be mentioned.)
(xi) 5- to 6-membered cyclic amino (for example, morpholino, piperidino and piperadino, etc. may be mentioned.)
(xii) $C_1$ to $C_6$ alkylcarbonyl (for example, acetyl, propionyl, butyryl, isobutyryl and pivaroyl, etc. may be mentioned.)
(xiii) carboxyl
(xiv) $C_1$ to $C_6$ alkoxycarbonyl (for example, methoxycarbonyl and ethoxycarbonyl, etc. may be mentioned.)
(xv) carbamoyl
(xvi) mono-$C_1$ to $C_6$ alkylcarbamoyl (for example, N-methylcarbamoyl and N-ethylcarbamoyl, etc. may be mentioned.)
(xvii) di-$C_1$ to $C_6$ alkylcarbamoyl (for example, N,N-dimethylcarbamoyl and N,N-diethylcarbamoyl, etc. may be mentioned.)
(xviii) $C_1$ to $C_6$ alkylsulfonyl (for example, methanesulfonyl etc. may be mentioned.)
(xix) aminosulfonyl
(xx) mono- or di-$C_1$ to $C_6$ alkylaminosulfonyl (for example, N-methylaminosulfonyl etc. may be mentioned.)
(xxi) deuterium atoms.

As preferable examples of the compounds having the above formula (I), the following may be mentioned.

1. The compound, or a salt or solvate thereof, wherein, in the formula (I), X is linear or branched $C_1$ to $C_6$ alkylene, and Ar is a $C_6$ to $C_{14}$ aromatic hydrocarbon group.

2. A compound, or a salt or solvate thereof, where, in the formula (I), Ar is a phenyl group, of which Ar group may be optionally unsubstituted, or substituted with 1 to 5 groups which are selected from the group consisting of (i) a halogen atom, (ii) nitro, (iii) cyano, (iv) $C_1$ to $C_6$ alkyl unsubstituted, or substituted with 1 to 3 halogen atoms, (viii) hydroxyl, (ix) $C_1$ to $C_6$ alkoxy unsubstituted, or substituted with 1 to 3 halogen atoms or with 1 to 13 deuterium atoms, and (xxxi) deuterium atoms.

3. A compound, or a salt or a solvate thereof, where, in the formula (I), W is (1) a $C_6$ to $C_{14}$ aromatic hydrocarbon group or (2) a 5- to 8-membered aromatic heterocyclic group including 1 to 4 hetero atoms selected from a nitrogen atom, sulfur atom, and oxygen atom, other than a carbon atom.

4. The compound, or a salt, or a solvate thereof, as indicated in the above 3, where, in the formula (I), Z is (1) a connecting bond or (2) $CR^4R^5$ where, $R^4$ and $R^5$ are, respectively independently,
(A) a hydrogen atom,
(B) deuterium atoms
(C) $C_1$ to $C_6$ alkyl unsubstituted, or substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl or substituted with (viii) 1 to 13 deuterium atoms, or
(D) $C_3$ to $C_6$ cycloalkyl unsubstituted, or substituted with 1 to 5 groups selected from the group consisting of (i) a halogen atom and (ii) an alkyl group unsubstituted, or substituted with 1 to 3 halogen atoms, or substituted with (iii) 1 to 11 deuterium atoms.

5. A compound, or a salt or a solvate thereof, where, in the formula (I), W is a hydrogen atom or a deuterium atom.

6. A compound, or a salt or solvate thereof, as indicated in the above 5, where, in the formula (I), Z is (1) a connecting bond or (2) $CR^4R^5$ where, $R^4$ and $R^5$ are, respectively independently,
(A) a hydrogen atom,
(B) deuterium atoms
(C) $C_1$ to $C_6$ alkyl unsubstituted, or substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl, or substituted with (viii) 1 to 13 deuterium atoms,
(D) $C_3$ to $C_6$ cycloalkyl unsubstituted, or substituted with 1 to 5 groups selected from the group consisting of (i) a halogen atom and (ii) an alkyl group unsubstituted, or substituted with 1 to 3 halogen atoms, or substituted with (iii) 1 to 11 deuterium atoms,
(E) $COOR^6$ where $R^6$ indicates a hydrogen atom or $C_1$ to $C_6$ alkyl, or (F) CONR⁷R⁸ where R⁷ and R⁶ independently are,
(a) a hydrogen atom,
(b) $C_1$ to $C_6$ alkyl unsubstituted, or substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl,
(c) $C_6$ to $C_{14}$ aromatic hydrocarbon cyclic group, or
(d) a 5- to 8-membered aromatic heterocyclic group including 1 to 4 hetero atoms selected from a nitrogen atom, sulfur atom, and oxygen atom, other than a carbon atom,
where the above groups (c) to (d) may be optionally substituted with 1 to 5 groups selected from the group consisting of (i) a halogen atom, (iv) $C_1$ to $C_6$ alkyl unsubstituted, or substituted with 1 to 3 halogen atoms, (viii) hydroxyl, (ix) $C_1$ to $C_6$ alkoxy unsubstituted, or substituted with 1 to 3 halogen atoms, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xxvii) aminosulfonyl and (xxviii) mono- or di-$C_1$ to $C_6$ alkylaminosulfonyl, or substituted with (xxix) 1 to 9 deuterium atoms.

7. A compound, or a salt or a solvate thereof, as indicated in the above 1 to 6, where, in the formula (I), $R^1$ is (1) a hydrogen atom or (2) $C_1$ to $C_6$ alkyl unsubstituted, or substituted with 1 to 3 of (i) a halogen atom or (ii) $C_3$ to $C_6$ cycloalkyl, or substituted with (iii) 1 to 13 deuterium atoms, and $R^2$ indicates (1) $OR^9$ or (2) $NR^{10}R^{11}$
where $R^9$, $R^{10}$, and $R^{11}$ independently are
(A) a hydrogen atom,
(B) $C_1$ to $C_6$ alkyl,
(C) $C_2$ to $C_6$ alkenyl,
(E) $C_3$ to $C_6$ cycloalkyl,
(F) $C_6$ to $C_{14}$ aromatic hydrocarbon group, or
(G) a 5- to 8-membered aromatic heterocyclic group including 1 to 4 hetero atoms selected from a nitrogen atom, sulfur atom and oxygen atom, other than a carbon atom,
where each group of the above (B) to (E) may be optionally substituted with 1 to 3 groups selected from the group consisting of (i) a halogen atom, (ii) $C_3$ to $C_6$ cycloalkyl, (iii) hydroxyl, (iv) $C_1$ to $C_6$ alkoxy unsubstituted, or substituted with 1 to 3 halogen atoms, (v) amino, (vi) mono-$C_1$ to $C_6$ alkylamino, (vii) di-$C_1$ to $C_6$ alkylamino, (viii) 5- to 6-membered cyclic amino, (ix) carboxyl, and (xv) $C_6$ to $C_{12}$ aryl or substituted with (xviii) 1 to 13 deuterium atoms,
further, each group of the above (F) to (G) may be optionally substituted with 1 to 5 groups selected from the group consisting of (i) a halogen atom, (iv) $C_1$ to $C_6$ alkyl unsubstituted, or substituted with 1 to 3 halogen atoms, (vi) hydroxyl, (vii) $C_1$ to $C_6$ alkoxy unsubstituted, or substituted with 1 to 3 halogen atoms, (viii) amino, (ix) mono-$C_1$ to $C_6$ alkylamino, (x) di-$C_1$ to $C_6$ alkylamino, (xi) 5- to 6-membered cyclic amino, and (xiii) carboxyl, or substituted with (xxi) 1 to 9 deuterium atoms.

8. A compound, or a salt, or a solvate thereof, as indicated in the above 1 to 6, wherein, in the formula (I), the heterocyclic group which is formed by $R^1$ and $R^2$ together with the atoms they are bonded with is (1)imidazole, (2) triazole, (3) oxadiazole, or (4) oxadiazine, or partially saturated heterocyclic rings of the same, where (1) to (4) may be optionally substituted with 1 to 3 groups selected from the group consisting of
(A) a halogen atom,
(B) oxo,
(C) hydroxyl,
(D) $C_1$ to $C_6$ alkyl and
(K) deuterium atoms.

9. A compound, or a salt, or a solvate thereof, as set forth in the above 1, wherein the compound is
(1) 4-{(1R)-1-[({(6R)-6-(5-chloro-2-methoxybenzyl)-7-oxo-3-[(pyridin-2-yloxy)imino]-1,4-diazepan-1-yl}carbonyl)amino]propyl}benzoic acid,
(2) 2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid,
(3) 2-amino-4-{(1R)-1-[({(6S)-6-(5-chloro-2-methoxybenzyl)-7-oxo-3-[(2,2,2-trifluoroethoxy)imino]-1,4-diazepan-1-yl}carbonyl)amino]butyl}benzoic acid,
(4) 2-amino-4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}benzoic acid,
(5) 2-amino-4-[(1R)-1-({[(6S)-6-(5-chloro-2-methoxybenzyl)-3-(methoxyimino)-4-methyl-7-oxo-1,4-diazepan-1-yl]carbonyl}amino)butyl]benzoic acid,
(6) (4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}phenyl)acetic acid,
(7) 2-amino-4-{[({(6R)-6-(5-chloro-2-methoxybenzyl)-3-[(3,5-difluorophenoxy)imino]-7-oxo-1,4-diazepan-1-yl}carbonyl)amino]methyl}benzoic acid,
(8) {4-[(1R)-1-({[(6R)-6-(5-chloro-2-methoxybenzyl)-7-oxo-3-(phenoxyimino)-1,4-diazepan-1-yl]carbonyl}amino)propyl]phenyl}acetic acid,
(9) 2-amino-4-[(1R)-1-({[(6R)-6-(5-chloro-2-methoxybenzyl)-7-oxo-3-(phenoxyimino)-1,4-diazepan-1-yl]carbonyl}amino)propyl]benzoic acid, or
(10) 2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid.

The compound having the formula (I) may be formed a pharmaceutically acceptable salt, if necessary. When it has an amine or other basic group as a substituent group, for example, salts with hydrochloric acid, hydrobromic acid, sulfuric acid, phosphoric acid, and other mineral acids, salts with formic acid, acetic acid, fumaric acid, maleic acid, oxalic acid, citric acid, malic acid, tartaric acid, asparatic acid, glutamic acid, and other organic carboxylic acids or salts with methanesulfonic acid, benzenesulfonic acid, p-toluenesulfonic acid, hydroxybenzenesulfonic acid, and other sulfonic acids, etc. may be mentioned. When the compound having the formula (I) has a carboxylic acid or other acid group as a substituent group, for example, sodium, potassium, or other alkali metal salt, calcium, magnesium or other alkali earth metal salt, a salt with or ammonia, triethylamine, or ethylenediamine, propanediamine, pyrrolidine, piperidine, piperadine, pyridine, lysine, choline, ethanolamine, N,N-dimethylethanolamine, 4-hydroxypiperidine, glucosamine, N-methylglucamine, or other organic bases may be mentioned.

The compound having the formula (I) or a salt thereof may be a nonsolvate or a solvate with water, methanol, ethanol, 1-propanol, 2-propanol, formic acid, ethyl formate, acetic acid, methyl acetate, ethyl acetate, propyl acetate and isobutyl acetate, etc.

2. Explanation of Methods of Production of Compound having Formula (I) or Salt or Solvate Thereof Below, methods of production the compound having the formula (I) or a salt or solvates thereof will be explained. The compound having the formula (I) or salt thereof can be produced by either or both of the two methods of production (A) and (B) explained below.

Method of Production (A)

The compound having the formula (I) or a salt or solvate thereof may be synthesized by the method shown by the following scheme, for example:

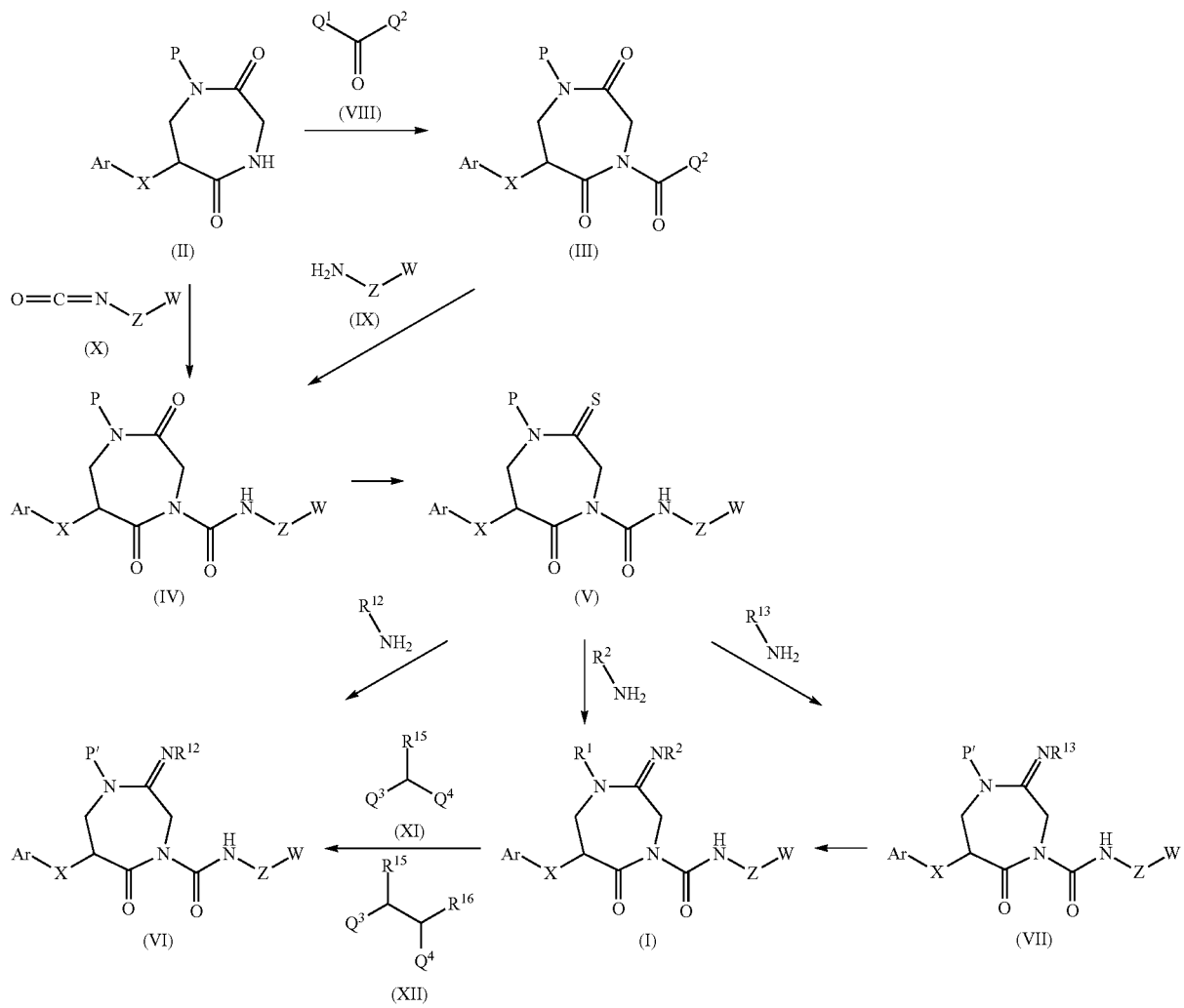

where Ar, W, X, Z, $R^1$ and $R^2$ are the same as defined above, $R^{12}$ indicates (1) OH or (2) $NHR^{11}$ where $R^{11}$ is the same as defined above, $R^{13}$ indicates (1) $OR^{14}$, (2) $NR^{11}R^{14}$ where $R^{11}$ is the same as defined above, $R^{14}$ indicates formyl, a $C_1$ to $C_6$ alkylcarbonyl, $C_2$ to $C_6$ alkenylcarbonyl, $C_2$ to $C_6$ alkynylcarbonyl, $C_3$ to $C_6$ cycloalkylcarbonyl, $C_6$ to $C_{14}$ arylcarbonyl, $C_1$ to $C_{10}$ heteroarylcarbonyl, or $C_1$ to $C_6$ alkoxycarbonyl, or (3) $C_2$ to $C_6$ alkyl group substituted with two $C_1$ to $C_6$ alkoxy's, $R^{15}$ and $R^{16}$ independently indicate a hydrogen atom or oxo, P indicates a protective group such as allyl, allyloxycarbonyl, 9-fluorenylmethylcarbonyl, $C_1$ to $C_6$ alkyloxycarbonyl unsubstituted, or substituted with 1 to 3 halogen atoms, $C_1$ to $C_6$ alkylcarbonyl unsubstituted, or substituted with 1 to 3 halogen atoms, $C_7$ to $C_{16}$ aralkyl unsubstituted, or substituted with 1 to 3 of (i) a halogen atom, (ii) $C_1$ to $C_6$ alkyl, (iii) $C_1$ to $C_6$ alkoxy, or (iv) nitro, $C_5$ to $C_{16}$ arylcarbonyl unsubstituted, or substituted with 1 to 3 of (i) a halogen atom, (ii) $C_1$ to $C_6$ alkyl, (iii) $C_1$ to $C_6$ alkoxy, or (iv) nitro, $C_7$ to $C_{16}$ aralkyloxycarbonyl unsubstituted, or substituted with 1 to 3 of (i) a halogen atom, (ii) $C_1$ to $C_6$ alkyl, (iii) $C_1$ to $C_6$ alkoxy, or (iv) nitro, or $C_5$ to $C_{16}$ arylsulfonyl unsubstituted, or substituted with 1 to 3 of (i) a halogen atom, (ii) $C_1$ to $C_6$ alkyl, (iii) $C_1$ to $C_6$ alkoxy, or (iv) nitro or indicates $R^1$ ($R^1$ is the same as defined above), P' indicates a hydrogen atom or P (P is the same as defined above), $Q^1$ and $Q^2$ independently indicate a halogen atom or $C_6$ to $C_{10}$ aryloxy unsubstituted, or substituted with 1 to 3 halogen atoms or nitro, $Q^3$ and $Q^4$ independently indicate a halogen atom, $C_6$ to $C_{10}$ arylsulfonyloxy group unsubstituted, or substituted with 1 to 3 halogen atoms, $C_1$ to $C_4$ alkylsulfonyloxy group unsubstituted, or substituted with 1 to 3 halogen atoms, or $C_6$ to $C_{10}$ aryloxy 1 to 3 halogen atoms or nitro.

As the $C_2$ to $C_6$ alkyl group substituted with two $C_1$ to $C_6$ alkoxy's expressed by $R^{13}$, for example, an aminoacetoaldehydedimethylacetal etc. may be used.

As the group expressed by $R^{14}$, for example, formyl, $C_1$ to $C_6$ alkylcarbonyl (for example, acetyl, propionyl and trifluoroacetyl, etc.), $C_2$ to $C_6$ alkenylcarbonyl (for example, acryloyl etc.), $C_2$ to $C_6$ alkynylcarbonyl (for example, propioloyl etc.), $C_3$ to $C_6$ cycloalkylcarbonyl (for example, cyclopropylcarbonyl, cyclopentylcarbonyl and cyclohexylcarbonyl, etc.), $C_6$ to $C_{14}$ arylcarbonyl (for example, benzoyl and naphtholyl, etc.), $C_1$ to $C_{10}$ heteroarylcarbonyl (for example, pyridylcarbonyl and imidazoylcarbonyl, etc.), $C_1$ to $C_6$ alkoxycarbonyl (for example, methoxycarbonyl), etc. may be used.

As the "protective group" represented by P, for example, allyl, allyloxycarbonyl, 9-fluorenylmethylcarbonyl, linear or branched $C_1$ to $C_6$ alkyloxycarbonyl unsubstituted, or substituted with 1 to 3 halogen atoms (for example, t-butoxycarbonyl etc.), linear or branched $C_1$ to $C_6$ alkylcarbonyl unsubstituted, or substituted with 1 to 3 halogen atoms (for example, trifluoroacetyl etc.), $C_7$ to $C_{16}$ aralkyl unsubstituted, or substituted with 1 to 3 of (i) a halogen atom, (ii) $C_1$ to $C_6$ alkyl, (iii) $C_1$ to $C_6$ alkoxy or (iv) nitro (for example, benzyl, p-methoxybenzyl, 2,4-dimethoxybenzyl and 2,4,6-trimethoxybenzyl, etc.), $C_5$ to $C_{16}$ arylcarbonyl unsubstituted, or substituted with 1 to 3 of (i) a halogen atom, (ii) $C_1$ to $C_6$ alkyl, (iii) $C_1$ to $C_6$ alkoxy, or (iv) nitro (for example, benzoyl and p-nitrobenzoyl), $C_7$ to $C_{16}$ aralkyloxycarbonyl unsubstituted, or substituted with 1 to 3 of (i) a halogen atom, (ii) $C_1$ to $C_6$ alkyl, (iii) $C_1$ to $C_6$ alkoxy, or (iv) nitro (for example, benzyloxycarbonyl etc.), $C_5$ to $C_{16}$ arylsulfonyl unsubstituted, or substituted with 1 to 3 of (i) a halogen atom, (ii) $C_1$ to $C_6$ alkyl, (iii) $C_1$ to $C_6$ alkoxy, or (iv) nitro (for example, p-toluenesulfonyl etc.), etc. may be used.

As the substituent groups expressed by $Q^1$ and $Q^2$, a halogen atom (for example, chlorine or bromine), $C_6$ to $C_{10}$ aryloxy unsubstituted, or substituted with 1 to 3 of a halogen atom or nitro (for example, phenyloxy, p-nitrophenyloxy, p-chlorophenyloxy and 2-chlorophenyloxy, etc.), etc. may be used. As the substituent groups expressed by $Q^3$ and $Q^4$, a halogen atom (for example, chlorine or bromine), $C_6$ to $C_{10}$ arylsulfonyloxy unsubstituted, or substituted with 1 to 3 halogen atoms (for example, benzenesulfonyloxy and p-toluenesulfonyloxy, etc.), $C_1$ to $C_4$ alkylsulfonyloxy unsubstituted, or substituted with 1 to 3 halogen atoms (for example, methanesulfonyloxy and trifluoromethanesulfonyloxy, etc.), or $C_6$ to $C_{10}$ aryloxy unsubstituted, or substituted with 1 to 3 of a halogen atom or nitro (for example, phenyloxy, p-nitrophenyloxy, p-chlorophenyloxy and 2-chlorophenyloxy, etc.), etc. may be used.

The compound (II), compound (III), compound (IV), compound (V), compound (VI), compound (VII), compound (VIII), compound (IX), compound (X), compound (XI) and compound (XII) may also be salts. Specific examples of preferred salts are the same as the illustrations of salts of the compound having the formula (I).

Next, the above reaction scheme which shows the production method (A) will be explained.

First, for example, according to the method described in WO06-059801, the compound (II) and the compound (VIII) may be reacted to convert them to the compound (III), then the compound (IX) reacted with to obtain the compound (IV). Further, the compound (IV) may, for example, be also obtained by the reaction of the compound (II) with the compound (X) according to the method described in WO07-139230. In the compound (IV), a compound where P is a hydrogen atom may be obtained by removing the protective group P from the compound (IV) or may be obtained by the deprotection of protective group P of the compound (III), followed by the reaction with the compound (IX).

Next, the compound (IV) can be processed by a known method using, for example, a general thiocarbonylation reagent (Lawesson's reagent and Belleau's reagent, etc.) to obtain the compound (V). Further, in the compound (V), a compound where P is a hydrogen atom can be obtained by a thionation reaction of the compound (IV) where P is a hydrogen atom.

In the compound (I), a compound where $R^2$ is (1) $OR^9$ and (2) $NR^{10}R^{11}$ can be obtained by, for example, the reaction of compound (V) in the presence of a metal catalyst (for example, mercury acetate and silver acetate, etc.), with $R^2$—$NH_2$ (where $R^2$ is (1) $OR^9$ or (2) $NR^{10}R^{11}$) or a salt thereof, and optionally performing a deprotection reaction. The deprotection reaction when P is a protective group may be performed before the reaction of the compound (V) and $R^2$—$NH_2$ or may be performed after it. When using a salt of $R^2$—$NH_2$, for example, the reaction may be performed in the presence of a base such as triethylamine etc.

In the compound (I), a compound where $R^1$ and $R^2$ form a 5- or 6-membered heterocyclic ring together with the atoms they are bonded with may be obtained by, for example, the reaction of the compound (V) in the presence of a metal catalyst (for example, mercury acetate and silver acetate, etc.), with $R^{12}$—$NH_2$ (where $R^{12}$ is (1) OH or (2) $NHR^{11}$) or a salt thereof to obtain the compound (VI), and subsequent cyclization by the reaction with the compound (XI) or the compound (XII), and optionally performing a deprotection reaction. The deprotection reaction when P' is a protective group may be performed before the reaction of the compound (V) and $R^{12}$—$NH_2$ or may be performed after it. When using a salt of $R^{12}$—$NH_2$, for example, the reaction for conversion to the compound (VI) may be performed in the presence of a base such as triethylamine etc. Further, the cyclization reaction of the compound (VI) with the compound (XI) or the compound (XII) may be performed all together in the same system, or performed step by step, that is, the intermediate which is obtained by the reaction of the compound (VI) and the compound (XI) or the compound (XII) is isolated and subsequently a cyclization reaction is performed.

Further, in the compound (I), a compound where $R^1$ and $R^2$ form a 5- or 6-membered heterocyclic ring together with the atoms they are bonded with may be obtained, for example, by the reaction of the compound (V) in the presence of a metal catalyst (for example, mercury acetate and silver acetate, etc.), with $R^{13}$—$NH_2$ (where $R^{13}$ is (1) $OR^{14}$, (2) $NR^{11}R^{14}$ ($R^{11}$ and $R^{14}$ are the same as defined above) or (3) a $C_2$ to $C_6$ alkyl group substituted with two $C_1$ to $C_6$ alkoxy's) or a salt thereof to obtain the compound (VII), and subsequent cyclization reaction in the presence or absence of an acid catalyst (for example, pyridinium p-toluenesulfonic acid etc.) from the compound (VII), and optionally performing a deprotection reaction. The deprotection reaction when P' is a protective group may be performed before the reaction of the compound (V) and $R^{13}$—$NH_2$ or may be performed after it. When using a salt of $R^{13}$—$NH_2$, for example, the reaction for conversion to the compound (VII) may be performed in the presence such as a base of triethylamine etc. Further, the cyclization reaction of the compound (VII) may be performed all together in the same system of the reaction of the compound (V) with the compound (VII), or the compound (VII) may be isolated and a cyclization reaction performed step by step.

Method of Production (B)

The compound having the formula (I) or a salt or solvate thereof may be synthesized by the method shown by the following scheme, for example:

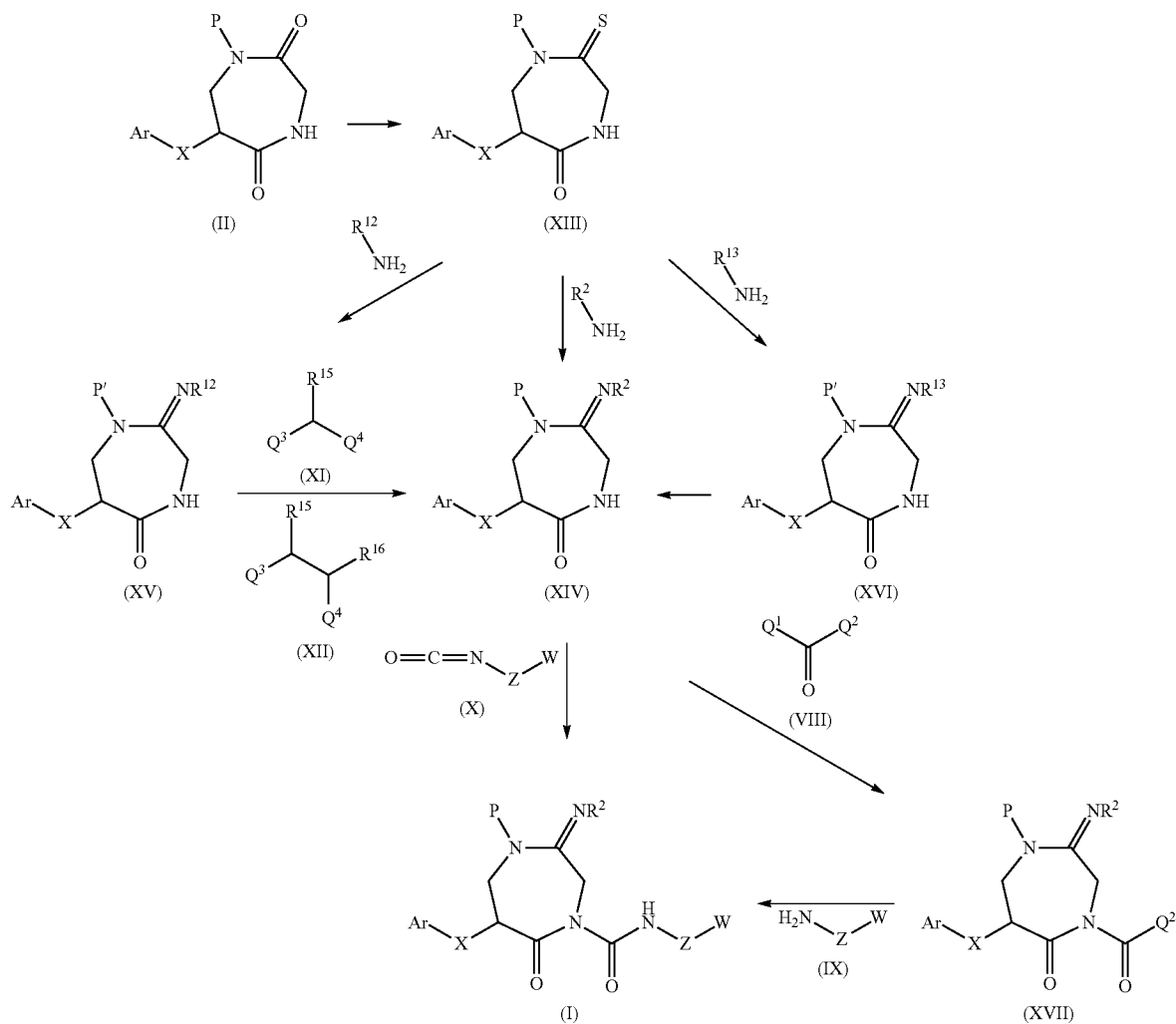

where Ar, W, X, Z, $R^1$, $R^2$, $R^{12}$, $R^{13}$, $R^{15}$, $R^{16}$, P, P', $Q^1$, $Q^2$, $Q^3$, and $Q^4$ are the same as defined above.

The compound (II), compound (XIII), compound (XIV), compound (XV), compound (XVI), compound (XVII), compound (VIII), compound (IX), compound (X), compound (XI), and compound (XII) may also be in the form of salts. Specific examples of preferred salts are the same as the illustrations of salts of the compound having the formula (I).

First, from the compound (II), the compound (XIII) may be obtained by a known method using, for example, a general thiocarbonylation reagent (Lawesson's reagent and Belleau's reagent, etc.)

In the compound (XIV), a compound where $R^2$ is (1) $OR^9$ and (2) $NR^{10}R^{11}$ where $R^9$, $R^{10}$ and $R^{11}$ are the same as defined above, may be obtained by, for example, the reaction of the compound (XIII) obtained above in the presence of a metal catalyst (for example, mercury acetate and silver acetate etc.), with $R^2$—$NH_2$ or a salt thereof.

Further, in the compound (XIV), a compound where $R^2$ and P (where P indicates $R^1$: $R^1$ and $R^2$ are the same as defined above) form a 5- or 6-membered heterocyclic ring together with the atoms they are bonded with may be obtained by, for example, the reaction of the compound (XIII) obtained above in the presence of a metal catalyst (for example, mercury acetate and silver acetate, etc.), with $R^{12}$—$NH_2$ where $R^{12}$ is (1) OH and (2) $NHR^{11}$) or a salt thereof to obtain the compound (XV), and subsequent cyclization by the reaction with the compound (XI) or the compound (XII).

Furthermore, in the compound (XIV), a compound where $R^2$ and P (where P indicates $R^1$: $R^1$ and $R^2$ are the same as defined above) form a 5- or 6-membered heterocyclic ring together with the atoms they are bonded with may be obtained by for example, the reaction of the compound (XIII) obtained above, in the presence of a metal catalyst (for example, mercury acetate and silver acetate, etc.), with $R^{13}$—$NH_2$ {where $R^{13}$ is (1) $OR^{14}$, (2) $NR^{11}R^{14}$ ($R^{11}$ and $R^{14}$ are the same as defined above), or (3) a $C_2$ to $C_6$ alkyl group substituted with two $C_1$ to $C_6$ alkoxy's} or salt thereof to obtain the compound (XVI), and subsequent cyclization reaction from the compound (XVI) in the presence or absence of an acid catalyst (for example, pyridinum p-toluenesulfonic acid etc.).

From the compound (XIV) obtained above, the compound (I) may be obtained by reaction with the compound (X) according to the method described in, for example, WO07-139230, and optionally performing a deprotection reaction. Further, from the compound (XIV), the compound (I) may be obtained by reaction with the compound (VIII) according to the method described in, for example, WO06-059801 to convert it to the compound (XVII), then performing a reaction with the compound (IX), and optionally performing a deprotection reaction.

It is possible, when needed, to convert the functional groups after the reaction of the above (A) or (B) to produce the compound (I) converted in functional groups by 1 to 5 steps of an ordinary method, such as a deprotection reaction when the compound (I) of the present invention produced by the method of (A) or (B) has a protective group, the hydrogenation reaction when it has a carbon-carbon double bond or triple bond, the reduction reaction when it has a nitro group, the esterification reaction and amidation reaction when it has a carboxylic acid, the hydrolysis reaction when it has an ester group, the (i) alkylation reaction, (ii) acylation reaction, and (iii) sulfonylation reaction when it has an amino group or hydroxyl group, and the (i) alkylation reaction, (ii) acylation reaction, and (iii) sulfonylation reaction when it has a primary or secondary amide group.

In the above production method (A) or (B), the compound (II) used as a starting material, or the compounds (IX) and (X) used as reactants can be obtained, for example, by the method described in WO06-059801 or WO07-139230. Further, the compounds (IX) and (X) used may be commercially available products or known compounds.

Further, in the compound (II), the compound where X indicates methylene may be synthesized by the method shown by, for example, the scheme:

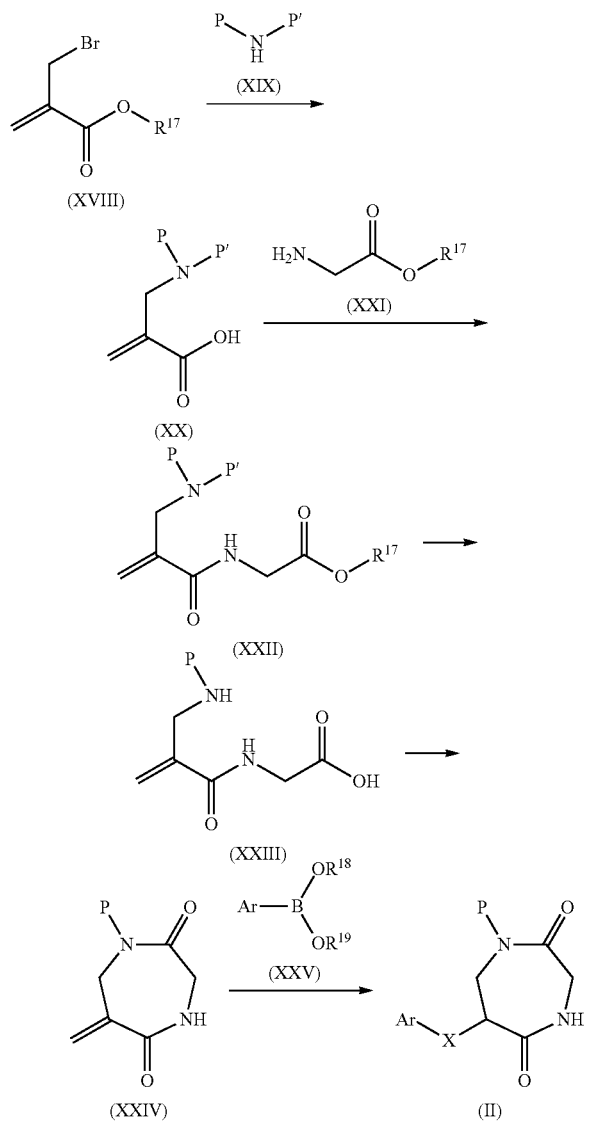

where Ar, P, and P' are the same as defined above, $R^{17}$ indicates (1) $C_1$ to $C_6$ alkyl unsubstituted, or substituted with 1 to 3 halogen atoms (for example, methyl, ethyl and trichloroethyl, etc.) or (2) $C_7$ to $C_{16}$ aralkyl unsubstituted, or substituted with 1 to 3 of (i) $C_1$ to $C_6$ alkoxy or (ii) nitro (for example, benzyl and 4-methoxybenzyl, etc.), $R^{18}$ and $R^{19}$ independently indicate (i) a hydrogen atom or (ii) $C_1$ to $C_6$ alkyl, where $R^{18}$ and $R^{19}$ may form a 5- or 6-member ring together with the atoms with which they are bonded. Here, X indicates methylene.

That is, the commercially available or known compound (XVIII) and compound (XIX) may be reacted and in accordance with need a deprotection reaction performed so as to obtain the compound (XX). Next, compound (XXII) may be obtained by the condensation reaction of the compound (XX) with a glycine derivative (XXI) or a salt thereof by, for example, using a general condensation agent (for example, DCC etc.) or other known method. From the obtained compound (XXII), for example, a hydrolysis reaction using sodium hydroxide etc. or another known method may be used to remove the protective groups to obtain the compound (XXIII). When necessary at this time, before or after the hydrolysis reaction, or before and after the hydrolysis reaction, for example, the P' protective groups may be removed in accordance with a known method using an acid and base, etc., but when P' is a hydrogen atom, this deprotection is not necessarily required. Next, from the obtained compound (XXIII), for example, a condensation reaction using a general condensation agent (for example, DCC etc.) or other known method may be followed to cyclization to obtain the compound (XXIV). Further, the obtained compound (XXIV) and a boronic acid derivative (XXV) may be reacted by a coupling reaction using, for example, a transition metal catalyst which has rhodium and palladium, etc. at as the center metal, to obtain the compound (II).

The $R^2$—$NH_2$, $R^{12}$—$NH_2$, and $R^{13}$—$NH_2$ (or their salts) which are used as reaction agents in the above method of production (A) or (B) may be obtained, for example, according to the method described in the J. Med. Chem., 2005, 48, 1576, etc. Further, the $R^2$—$NH_2$, $R^{12}$—$NH_2$, and $R^{13}$—$NH_2$ (or their salts) used may be commercially available products or known compounds.

Further, the compounds (XI) and (XII) used may be commercially available products or known compounds, or compounds obtained by known methods.

In a compound (I) or a salt or solvate thereof of the present invention and the synthetic intermediates for production of the compound (I), a compound including deuterium in the substituent group can be synthesized by the method of the above (A) or (B) by using suitably deuterated starting materials and reaction agents. The deuterated starting materials and reaction agents used may be commercially available products or known ones. Furthermore, in the compound (I) or its salt or solvates thereof of the present invention, the synthetic intermediates and the starting materials for production of the compound (I), and reaction agents used in the synthesis methods of the above (A) and (B), compounds including deuterium in the substituent groups may be obtained by substituting the desired positions with deuterium according to the known method described in, for example, Synthesis, 2009, 2674 or Angewandte Chemie International Edition, 47, 29, 5394, etc.

The compound (I) of the present invention or a salt or solvate thereof, produced by the method of (A) or (B) and the synthetic intermediates for production of the compound (I) may be purified by known methods, for example, solvent extraction, pH change, solvent exchange, salting out, crystallization, recrystallization and chromatography, etc. When the compound (I) of the present invention and the synthetic intermediate for production of the compound (I) are optically active compounds and include another optical isomer, a general optical resolution method may be used for separation into the enantiomers.

When the compound (I) of the present invention produced by the method of the above (A) or (B) has an amine or other basic group as a substituent group, salts with hydrochloric acid, hydrobromic acid, sulfuric acid, phosphoric acid, and other mineral acids, salts with formic acid, acetic acid, fumaric acid, maleic acid, oxalic acid, citric acid, malic acid, tartaric acid, asparatic acid, glutamic acid, and other organic carboxylic acids, salts with methanesulfonic acid, benzenesulfonic acid, p-toluenesulfonic acid, hydroxybenzenesulfonic acid, and other sulfonic acids, etc. may be formed according to an ordinary method. When the compound (I) has a carboxylic acid or other acid group as a substituent group, sodium, potassium, or other alkali metal salt, calcium, magnesium, or other alkali earth metal salt, or a salts with ammonia, triethylamine, ethylenediamine, propanediamine, pyrrolidine, piperidine, piperadine, pyridine and lysine, choline, ethanolamine, N,N-dimethylethanolamine, 4-hydroxypiperidine, glucosamine, N-methylglucamine, or other organic base may be formed according to an ordinary method.

The compound (I) or a salt thereof of the present invention produced by the method of (A) or (B) may be brought into contact with a solvent such as water, methanol, ethanol, 1-propanol, 2-propanol, formic acid, ethyl formate, acetic acid, methyl acetate, ethyl acetate, propyl acetate, and isobutyl acetate, or mixed solvent including these solvent, or recrystallized from these solvents etc. so as to form their solvates.

The compound (I) or a salt or solvate thereof of the present invention, have superior chymase inhibitory activity and have low toxicity ($LD_{50}$>1 g/kg), so can be safely used for mammals (for example, humans, rats, mice, dogs and cattle, etc.) for the prevention and/or treatment of bronchial asthma, chronic obstructive pulmonary disease, urticaria, atopic dermatitis, allergic conjunctivitis, rhinitis, rheumatoid arthritis, food allergies, colitis, allergic enteritis, mastocytosis, scleroderma, heart failure, cardiac hypertrophy, hypertension, arrhythmia, atherosclerosis, abdominal aortic aneurysm, myocardial infarction, restenosis after PTCA, restenosis after bypass graft surgery, ischemic peripheral circulatory disorders, hyperaldosteronism, diabetes, diabetic retinopathy, diabetic nephropathy, nephritis, glomerulosclerosis, renal insufficiency, solid tumor, fibrosis, postoperative adhesion, cicatrix, glaucoma, and ocular hypertension.

The administration route of the pharmaceutical for prevention or treatment of above-mentioned diseases may be oral or parenteral.

The preparation used in the present invention may also contain, as active ingredients, other pharmaceutical ingredients, other than the compound (I) or pharmaceutically acceptable salt thereof.

As such a pharmaceutical active ingredient, for example, steroids (for example, betamethasone etc.), immunosuppressants (for example, tacrolimus and pimecrolimus etc.), antiallergic agent (clemastine fumarate, d-chlorpheniramine maleate, cyproheptadine hydrochloride, promethazine hydrochloride, homochlorcyclizine hydrochloride, mequitazine, diphenhydramine hydrochloride, ebastine, cetirizine hydrochloride, olopatadine hydrochloride, fexofenadine hydrochloride, sodium cromoglicate, emedastine fumarate, suplatast tosilate and epinastine hydrochloride, etc.) etc. may be mentioned. These ingredients are not particularly limited so long as the object of the present invention is achieved, and may be used in approximate ratios. As specific examples of the dosage forms, for example, tablets (including sugar-coated tablets and film-coated tablets), pills, capsules (including microcapsules), granules, fine subtilaes, powders, syrups, emulsions, suspensions, injections, inhalants, ointments and eye drops etc. may be used. These drug products may be prepared according to ordinary methods (for example, methods described in the Japan Pharmacopeia etc.)

In the preparations of the present invention, the content of the compound according to the present invention differs according to the type of the preparation, but usually is about 0.01 to about 100% by weight, based upon the total weight of the preparation, preferably about 0.1 to about 50% by weight, more preferably about 0.5 to about 20% by weight or so.

Specifically, tablets can be produced by granulating a homogenous mixture of pharmaceutical as it is or with an excipient, binder, disintegrating agent, or other suitable additives by a suitable method, then adding a lubricant agent, and subjecting the mixture to compressive shaping; subjecting a homogenous mixture of pharmaceutical as it is or with an excipient, binder, disintegrating agent, or other suitable additives, to directly compressive shaping; or subjecting a homogenous mixture of granules of pharmaceutical as it is prepared in advance or with suitable additives, to directly compressive shaping. Further, these tablets may, if necessary, be given a coloring agent, flavoring agent, and may be coated with a suitable coating agent.

As the production method of an injections, it is possible to dissolve, suspend, or emulsify a certain amount of the pharmaceutical in injection water, physiological saline and Ringer's solution, etc. in the case of a water-based solvent, or in an ordinary vegetable oil etc. in the case of a non-water-based solvent, to obtain a certain volume, or to take a certain amount of the pharmaceutical and seal it in an injection use container.

As the carriers for oral preparations, for example, starch, mannitol, crystalline cellulose, sodium carboxylmethylcellulose, and other substances commonly used in the field of preparations may be used. As the carriers for injections, for example, distilled water, physiological saline, glucose solution and transfusions, etc. may be used. In addition, it is possible to suitably add additives generally used in preparations.

The dosage of these preparations differs according to age, body weight, symptoms, route of administration, number of dosages, etc., but for example, for an adult patient, daily dose of these preparation is usually about 0.1 to about 100 mg/kg, preferably about 1 to 50 mg/kg, more preferably about 1 to about 10 mg/kg, based on daily dose of active ingredient (the compound of the present invention), administered orally once or in three portions daily.

EXAMPLES

Reference Examples, Examples, and Test Examples will now be used to explain the present invention in more detail, but the present invention is by no means limited thereto. The fractions including the desired substances in the Examples and Reference Examples were detected by TLC (thin-layer chromatography) or LC/MS (liquid chromatography/mass spectrometry). In TLC observation, as a TLC plate, a Merck $60F_{254}$ was used, while as the detection method, a UV detector was used. For the MS, the ESI method (i.e., electron spray ionization method) was used to detect the positive ions.

Reference Example 1 tert-butyl 4-[(1S)-1-hydroxyethyl]benzoate (compound S1)

To tert-butyl 4-acetylbenzoate (3.33 g) in a tetrahydrofuran (23 ml) solution, (−)-B-chlorodiisopinocampheylborane in a 65% hexane solution (11.2 ml) was added dropwise under ice cooling, then the mixture was stirred at that temperature for 1.5 hours. The reaction solution was concentrated, and the residue was diluted by diethyl ether. To the thus solution obtained, diethanolamine (4.3 ml) was added under ice cooling, and the mixture was stirred at room temperature for 2 hours. The precipitates were removed by filtration, and the filtrate was concentrated. The residue was purified by flash column chromatography (silica gel, hexane/ethyl acetate=9/1 to 4/1) to obtain the title compound (3.47 g).

$^1$H-NMR (CDCl$_3$) δ 1.50 (3H, d, J=6.5 Hz), 1.59 (9H, s), 1.90 (1H, br.s), 4.87-4.99 (1H, m), 7.41 (2H, d, J=8.3 Hz), 7.96 (2H, d, J=8.3 Hz)

Reference Example 2 tert-butyl 4-[(1R)-1-aminoethyl]benzoate hydrochloride (compound S2)

Step (1): To the compound S1 (2.45 g) in a tetrahydrofuran (24 ml) solution, phthalimide (2.43 g), triphenylphosphine (5.78 g) and diethyl azodicarboxylate in a 10% toluene solution (10 ml) were successively added under ice cooling, and the mixture was stirred at room temperature for 1 hour. The reaction solution was concentrated, then the residue was purified by flash column chromatography (silica gel, hexane/ethyl acetate=5/1 to 1/1) to obtain tert-butyl 4-[(1R)-1-(1,3-dioxoisoindolyn-2-yl)ethyl]benzoate (compound S2a) (2.21 g).

Step (2): To the compound S2a (2.21 g) in a methanol (22 ml) solution, hydrazine hydrate (0.92 ml) was added at 60° C., and the mixture was stirred at that temperature for 1.5 hours. The reaction solution was concentrated, water was added to the residue, then the mixture was extracted with ethyl acetate. The organic layer was back extracted by 1M hydrochloric acid, then the aqueous layer was basified using a 4M aqueous sodium hydroxide solution, and the mixture extracted with ethyl acetate. The organic layer was dried over anhydrous sodium sulfate, then 4M hydrochloric acid in an ethyl acetate solution (1.6 ml) was added to the solution, and the resulting mixture was concentrated. The residue was triturated using diethyl ether and hexane, then the appeared solid was filtered to obtain the title compound (1.02 g).

$^1$H-NMR (DMSO-d$_6$) δ 1.51 (3H, d, J=6.5 Hz), 1.55 (9H, s), 4.48 (1H, m), 7.64 (2H, d, J=8.1 Hz), 7.93 (2H, d, J=8.1 Hz), 8.66 (3H, br.s)

Reference Example 3 tert-butyl 4-[(1R)-1-azidopropyl]benzoate (compound S3)

Step (1): Instead of the starting material of Reference Example 1, that is, tert-butyl 4-acetylbenzoate, tert-butyl 4-propionylbenzoate was used for a similar procedure as in Reference Example 1 to obtain tert-butyl 4-[(1S)-1-hydroxypropyl]benzoate (compound S3a).

Step (2): To the compound S3a (3.62 g) in a tetrahydrofuran solution, triethylamine (4.38 ml) and methanesulfonyl chloride (1.46 ml) were added under ice cooling, and the mixture was stirred at that temperature for 30 minutes. Further, triethylamine (1.1 ml) and methanesulfonyl chloride (0.48 ml) were added, and the mixture was further stirred for 30 minutes. To the reaction solution, water was added, and the mixture was extracted with ethyl acetate. The organic layer was washed with brine, then dried over anhydrous sodium sulfate, then concentrated. The residue was dissolved in N,N-dimethylformamide (15 ml), sodium azide was added under ice cooling (1.32 g), and the mixture was stirred at room temperature for 1.5 hours. To the reaction solution, water was added, and the mixture was extracted with ethyl acetate. The organic layer was washed with brine, then dried over anhydrous sodium sulfate, then was concentrated. The residue was purified by flash column chromatography (silica gel, hexane/ethyl acetate=19/1 to 9/1) to obtain the title compound (1.63 g).

$^1$H-NMR (CDCl$_3$) δ 0.92 (3H, t, J=7.3 Hz), 1.60 (9H, s), 1.70-1.95 (2H, m), 4.41 (1H, t, J=7.1 Hz), 7.34 (2H, d, J=8.1 Hz), 8.00 (2H, d, J=8.1 Hz)

Reference Example 4 tert-butyl 4-[(1R)-1-aminopropyl]benzoate (compound S4)

To the compound S3 (1.63 g) in a tetrahydrofuran (15.2 ml) solution, water (0.8 ml) and triphenylphosphine (1.64 g) were added under ice cooling, and the mixture was stirred at 50° C. for 16 hours. The reaction solution was concentrated, toluene (20 ml) was added to the residue, and the mixture was extracted with 0.5M hydrochloric acid (20 ml×3). The aqueous layer was basified using a 1M aqueous sodium hydroxide solution, then the mixture was extracted with ethyl acetate. The organic layer was dried over anhydrous sodium sulfate, then concentrated. The residue was purified by flash column chromatography (NH$_2$ silica gel, hexane/ethyl acetate=8/1 to 3/1) to obtain the title compound (1.37 g).

$^1$H-NMR (CDCl$_3$) δ 0.86 (3H, t, J=7.3 Hz), 1.58 (9H, s), 1.63-1.80 (2H, m), 3.87 (1H, t, J=6.7 Hz), 7.35 (2H, d, J=8.3 Hz), 7.95 (2H, d, J=8.3 Hz)

MS: 236 (M+H)$^+$

Reference Example 5 tert-butyl 4-[(1R)-1-aminopentyl]benzoate (compound S5)

Instead of the starting material of Reference Example 1, that is, tert-butyl 4-acetylbenzoate, tert-butyl 4-pentanoylbenzoate was used for a similar procedure as successively in Reference Example 1, Reference Example 3, and Reference Example 4 to obtain the title compound.

$^1$H-NMR (CDCl$_3$) δ 0.86 (3H, t, J=7.1 Hz), 1.09-1.22 (1H, m), 1.23-1.35 (3H, m), 1.59 (9H, s), 1.60-1.717 (2H, m), 3.90-3.96 (1H, m), 7.35 (2H, d, J=8.5 Hz), 7.95 (2H, d, J=8.5 Hz)

MS: 219 (M-NH$_2$)$^+$

Reference Example 6 tert-butyl 4-chloro-2-nitrobenzoate (compound S6)

To 4-chloro-2-nitrobenzoic acid (262 g) in a pyridine (1.3 liter) solution, p-toluenesulfonyl chloride (272.6 g) was slowly added at room temperature, and the mixture was stirred at that temperature for 15 minutes. To the reaction solution, tert-butyl alcohol (249 ml) was added dropwise, then the mixture was stirred for 5 hours. To the reaction mixture toluene (1 liter) was added, and the mixture was stirred for 1.5 hours, then the precipitate were removed by filtration. The filtrate was concentrated, ethyl acetate (1.3 liter) was added to the residue, the mixture was successively washed with water, saturated aqueous potassium hydrogensulfate solution, aqueous saturated sodium hydrogencarbonate solution, and brine, then the organic layer was dried over anhydrous sodium sulfate, then concentrated. Methanol (470 ml) was added to the residue, and after the precipitation of the crystals was confirmed, water (142 ml) was added. The mixture was stirred under ice cooling for 1.5 hours, then the crystals were collected by filtration. The same recrystallization procedure as the above was performed again to obtain the title compound (297 g).

$^1$H-NMR (CDCl$_3$) δ 1.55 (9H, s), 7.61 (1H, dd, J=2.0, 8.5 Hz), 7.71 (1H, d, J=8.5 Hz), 7.79 (1H, d, J=2.0 Hz)

Reference Example 7 tert-butyl 2-nitro-4-butyrylbenzoate (compound S7)

The compound S6 (15.45 g), tris(dibenzylidene acetone) dipalladium (1.1 g), 2-(di-tert-butyl phosphino)-2'-methylbiphenyl (1.5 g), and tripotassium phosphate (18.6 g) were added to a reaction flask, the inside of the reaction system was made an argon atmosphere, then dimethoxyethane (300 ml) and n-nitrobutane (12 ml) were successively added, and the mixture was vigorously stirred at room temperature for 3 minutes. Furthermore, the reaction mixture was stirred at 60° C. for 24 hours. To the reaction mixture, water (75 ml) was added, the reaction system was made an oxygen atmosphere, and the mixture was stirred for 2 days. The dimethoxyethane was distilled off, and the aqueous mixture thus obtained was extracted with ethyl acetate. The organic layer was successively washed with water and brine, was dried over anhydrous sodium sulfate, then was concentrated. The residue was purified by flash column chromatography (silica gel, hexane/ethyl acetate=9/1 to 6/1) to obtain the title compound (17.5 g).

$^1$H-NMR (CDCl$_3$) δ 1.02 (3H, t, J=7.5 Hz), 1.57-1.59 (9H, m), 1.74-1.86 (2H, m), 2.98 (2H, t, J=7.3 Hz), 7.80 (1H, d, J=7.7 Hz), 8.20 (1H, dd, J=1.6, 7.7 Hz), 8.40 (1H, d, J=1.6 Hz)

Reference Example 8 tert-butyl 4-[(1R)-1-aminobutyl]-2-nitrobenzoate D-tartrate (compound S8)

Instead of the starting material of Reference Example 1, that is, tert-butyl 4-acetylbenzoate, the compound S7 was used for successively similar procedures as in Reference Example 1, Reference Example 3, and Reference Example 4 to obtain tert-butyl 4-[(1R)-1-aminobutyl]-2-nitrobenzoate (1.48 g). This was dissolved in ethanol (10 ml), then D-tartaric acid (565 mg) was added to this solution, and the mixture was stirred at 80° C. for 1 hour. The solution was gradually cooled down to room temperature, then ethyl acetate (10 ml) was added, and the mixture was stirred at 0° C. for further 2 hours. The precipitated crystals were collected by filtration to obtain the title compound (1.21 g).

$^1$H-NMR (DMSO-d$_6$) δ 0.85 (3H, t, J=7.3 Hz), 1.08-1.30 (2H, m), 1.50 (9H, s), 1.64-1.84 (2H, m), 3.95 (2H, s), 4.23-4.32 (1H, m), 7.83-7.87 (2H, m), 8.11 (1H, s)

Reference Example 9 tert-butyl 4-[(1R)-1-aminopentyl]-2-nitrobenzoate D-tartrate (compound S9)

Step (1): Instead of the reaction agent, that is, n-nitrobutane, of Reference Example 7, n-nitropentane was used for a similar procedure as in Reference Example 7 to obtain tert-butyl 2-nitro-4-pentanoyl benzoate (compound S9a).

Step (2): Instead of the starting material, that is, tert-butyl 4-acetylbenzoate, of Reference Example 1, the compound S9a was used for a similar procedure as in Reference Example 8 to obtain the title compound.

MS: 309 (M+H)$^+$

Reference Example 10 tert-butyl 4-[(1R)-1-aminoethyl]-2-nitrobenzoate D-tartrate (compound S10)

Step (1): Instead of the reaction agent, that is, n-nitrobutane, of Reference Example 7, nitroethane was used for a similar procedure as in Reference Example 7 to obtain tert-butyl 2-nitro-4-acetylbenzoate (compound S10a).

Step (2): Instead of the starting material, that is, tert-butyl 4-acetylbenzoate, of Reference Example 1, the compound S10a was used for a similar procedure as in Reference Example 8 to obtain the title compound.

$^1$H-NMR (DMSO-d$_6$) δ 1.44 (3H, d, J=6.9 Hz), 1.50 (9H, s), 3.17 (3H, s), 3.94 (2H, s), 4.47 (1H, q, J=6.9 Hz), 7.83-7.91 (2H, m), 8.13 (1H, d, J=0.8 Hz)

MS: 267 (M+H)$^+$

Reference Example 11 tert-butyl 2-amino-4-aminomethyl benzoate (compound S11)

Step (1): Instead of the reaction agent, that is, n-nitrobutane, of Reference Example 7, nitromethane was used for a similar procedure as in Reference Example 7 to obtain tert-butyl 2-nitro-4-nitromethylbenzoate (compound S11a).

Step (2): To the compound S11a (1.69 g) in an ethanol solution, Raney nickel was added, and the mixture was stirred under a hydrogen atmosphere for 2.5 hours. The reaction mixture was diluted by chloroform, then was filtered by a glass filter spread with Celite®. The filtrate was concentrated, then the residue was purified by flash column chromatography (NH$_2$ silica gel, chloroform/ethyl acetate/methanol=10/4/1) to obtain the title compound (308 mg).

$^1$H-NMR (CDCl$_3$) δ 1.58 (9H, s), 3.78 (2H, s), 5.70 (2H, br.s), 6.56 (1H, dd, J=1.2, 8.3 Hz), 6.60 (1H, s), 7.77 (1H, d, J=8.3 Hz)

Reference Example 12 tert-butyl 2-(benzyloxy)-4-(1-aminoethyl)benzoate (compound S12)

Step (1): Instead of the starting material, that is, 4-chloro-2-nitrobenzoic acid, of Reference Example 6, 2-(benzyloxy)-4-chlorobenzoic acid was used for a similar procedure as in Reference Example 6 to obtain tert-butyl 2-(benzyloxy)-4-chlorobenzoate (compound S12a).

Step (2): Instead of the starting material, that is, the compound S6, of Reference Example 7, the compound S12a was used and instead of the reaction agent, that is, n-nitrobutane, nitroethane was used for a similar procedure as in Reference Example 7 to obtain tert-butyl 2-(benzyloxy)-4-acetylbenzoate (compound S12b) as a crude product.

Step (3): To the compound S12b as a crude product (6.89 g) in an ethanol (10 ml) solution, hydroxylamine hydrochloride (1.3 g) and sodium acetate (2.09 g) were added, then the mixture was heated and refluxed for 4 hours. The mixture was allowed to cool to room temperature, then concentrated. To the residue, water was added, and the mixture was extracted with ethyl acetate. The organic layer was dried over magnesium sulfate, then concentrated. The residue was dissolved in acetic acid (170 ml), zinc powder (17 g) was added, and the mixture was stirred at 50° C. for 1 hour. The reaction mixture was filtered, and the filtrate was concentrated. The residue was diluted with ethyl acetate, then was washed with an saturated aqueous sodium hydrogencarbonate solution and brine. The organic layer was dried over anhydrous magnesium sulfate, then concentrated. The residue was purified by flash column chromatography ($NH_2$ silica gel, chloroform/ethyl acetate/methanol=4/6 to 0/1) to obtain the title compound (3.21 g).

$^1$H-NMR (CDCl$_3$) δ 1.34 (3H, d, J=6.9 Hz), 1.51-1.54 (9H, m), 4.07-4.14 (1H, m), 5.16 (2H, s), 6.94 (1H, dd, J=1.2, 8.1 Hz), 7.02 (1H, d, J=1.2 Hz), 7.28-7.34 (1H, m), 7.34-7.41 (2H, m), 7.49 (2H, d, J=7.3 Hz), 7.68 (1H, d, J=8.1 Hz)

Reference Example 13 tert-butyl 2-(benzyloxy)-4-(1-aminopropyl)benzoate (compound S13)

Step (1): Instead of the starting material, that is, the compound S6, of Reference Example 7, the compound S12a was used and instead of the reaction agent, that is, n-nitrobutane, n-nitropropane was used for a similar procedure as in Reference Example 7 to obtain tert-butyl 2-(benzyloxy)-4-propionylbenzoate (compound S13a) as a crude product.

Step (2): Instead of the starting material, that is, the compound S12b crude product, of Reference Example 12, Step (3), the compound S13a crude product obtained at Step (1) was used for a similar procedure as in Reference Example 12, Step (3), to obtain the title compound.

$^1$H-NMR (CDCl$_3$) δ 0.81 (3H, t, J=7.5 Hz), 1.52 (9H, s), 1.58-1.80 (2H, m), 2.03 (3H, s), 3.83 (1H, t, J=7.1 Hz), 4.60 (3H, br.s), 5.16 (2H, s), 6.90 (1H, dd, J=1.2, 8.1 Hz), 6.98 (1H, d, J=1.2 Hz), 7.28-7.34 (1H, m), 7.34-7.41 (2H, m), 7.48 (2H, d, J=7.3 Hz), 7.68 (1H, d, J=8.1 Hz)

MS: 342 (M+H)$^+$

Reference Example 14 tert-butyl 2-amino-4-[(1R)-1-aminopentyl]benzoate tosylate (compound S14)

Instead of the starting material, that is the compound S12b, of Reference Example 12 Step (3), the compound S9a crude product was used for a similar procedure as in Reference Example 12 Step (3) to obtain the title compound.

$^1$H-NMR (DMSO-d$_6$) δ 0.82 (3H, t, J=7.1 Hz), 0.96-1.32 (4H, m), 1.53 (9H, s), 1.64-1.88 (2H, m), 2.29 (3H, s), 3.98-4.08 (1H, m), 6.59 (1H, dd, J=1.6, 8.1 Hz), 6.73 (1H, d, J=1.6 Hz), 7.06-7.16 (2H, m), 7.44-7.51 (2H, m), 7.69 (1H, d, J=8.1 Hz), 8.19 (2H, br.s)

Reference Example 15

2,2,2-trichloroethyl 2-[(1R)-1-aminopropyl]oxazole-4-carboxylate hydrochloride (compound S15)

Step (1): To (2R)-2-(tert-butoxycarbonylamino)butanoic acid (5 g) in a dichloromethane (100 ml) solution, 1-(3-dimethylaminopropyl)-3-ethylcarbodiimide hydrochloride (7.1 g), 1-hydroxybenzotriazole (5 g), L-serine methylester hydrochloride (5.7 g), and N,N-diethylisopropylamine (6.4 ml) were successively added, and the mixture was stirred at room temperature for 3 hours. The reaction solution was diluted with ethyl acetate, successively washed with water, saturated aqueous potassium hydrogensulfate solution, saturated aqueous sodium hydrogencarbonate solution, and brine, dried over anhydrous sodium sulfate, then concentrated. The residue was purified by flash column chromatography (silica gel, hexane/ethyl acetate=4/6 to 3/7) to obtain methylester methyl (2S)-2-{[(2R)-2-tert-butoxycarbonylamino]butyrylamino}-3-hydroxypropanoate (compound S15a) (5.27 g).

Step (2): To the compound S15a (2.64 g) in a dichloromethane (50 ml) solution, N,N-diethylsulfur trifluoride (DAST) (1.26 ml) was added dropwise at −20° C., and the mixture was stirred at that temperature for 1 hour. To the reaction solution, bromotrichloromethane (3.0 ml) and 1,8-diazabicyclo[5.4.0]undeca-7-ne (4.5 ml) were successively added, the mixture was stirred at 0° C. for 4 hours. Then saturated aqueous sodium hydrogencarbonate solution was added and the mixture was extracted with ethyl acetate. The organic layer was combined, washed with brine, dried over anhydrous sodium sulfate, then concentrated. The residue was purified by flash column chromatography (silica gel, hexane/ethyl acetate=8/2 to 7/3) to obtain methyl 2-[(1R)-1-(tert-butoxycarbonylamino)propyl]oxazole 4-carboxylate (compound S15b) (1.0 g).

$^1$H-NMR (CDCl$_3$) δ 0.93 (3H, t, J=7.5 Hz), 1.44 (9H, s), 1.78-1.91 (1H, m), 1.91-2.04 (1H, m), 3.92 (3H, s), 4.83-4.94 (1H, m), 5.17-5.26 (1H, m), 8.19 (1H, s)

MS: 229 (M−tBu)$^+$

Step (3): To the compound S15b (1.0 g) in a methanol (20 ml) solution, 4M aqueous sodium hydroxide solution (1.18 ml) was added, and the mixture was stirred at room temperature for 3 hours. The methanol was distilled off, then the residue was diluted with water and ethyl acetate, and the layers were separated. The aqueous layer was adjusted to pH 4 by 6M hydrochloric acid, then the mixture was extracted with ethyl acetate. The extract was combined, washed with brine, dried over anhydrous sodium sulfate, and concentrated to obtain 2-[(1R)-1-(tert-butoxycarbonylamino)propyl]oxazole 4-carboxylic acid (compound S15c) (0.76 g).

Step (4): To the compound S15c (0.76 g) in a dichloromethane (15 ml) solution, 1-(3-dimethylaminopropyl)-3-ethylcarbodiimide hydrochloride (0.65 g), 4-dimethylaminopyridine (34 mg), and 2,2,2-trichloroethanol (0.4 ml) were successively added, and the mixture was stirred at room temperature for 3 hours. The reaction solution was concentrated, then the residue was diluted by ethyl acetate, and successively washed with water, saturated aqueous potassium hydrogensulfate solution, saturated aqueous sodium hydrogencarbonate solution, and brine. The organic layer was dried over anhydrous sodium sulfate, then was concentrated. The residue was purified by flash column chromatography (silica gel, hexane/ethyl acetate=6/1 to 3/1) to obtain 2,2,2-trichloroethyl 2-[(1R)-1-(tert-butoxycarbonylamino)propyl]oxazole-4-carboxylate (compound S15d) (0.75 g).

Step (5): To the compound S15d (0.75 g), 4M hydrochloric acid in ethyl acetate solution (5 ml) was added, and the mixture was stirred at room temperature for 2 hours. The reaction solution was concentrated to obtain the title compound (0.51 g).

$^1$H-NMR (CDCl$_3$) δ 1.11 (3H, t, J=7.5 Hz), 2.27-2.38 (2H, m), 4.75-4.83 (1H, m), 4.92 (1H, d, J=14.2 Hz), 4.93 (1H, d, J=14.2 Hz), 8.39 (1H, s), 9.43 (3H, br.s)

MS: 301 (M+H)$^+$

Reference Example 16

2-[(1R)-1-aminopropyl]thiazole 4-carboxylic acid 2,2,2-trichloroethyl hydrochloride (compound S16)

Step (1): To tert-butyl {[(1R)-1-amino-1-thioxo]butan-2-yl}carbamate (2.8 g) in a dimethoxyethane (60 ml) solution, potassium hydrogencarbonate (10.3 g) and ethyl bromopyruvate (4.9 ml) were successively added at 0° C., and the mixture was stirred at that temperature for 30 minutes and at room temperature for 18 hours. The reaction solution was concentrated, the residue was diluted with chloroform, and the mixture was successively washed with water and brine. The organic layer was washed with brine, then concentrated. The residue was dissolved in dimethoxyethane (60 ml), trifluoroacetic acid anhydride (3.6 ml) and pyridine (4.7 ml) were successively added at 0° C., and the mixture was stirred at that temperature for 1 hour. The reaction solution was concentrated, then the residue was diluted by ethyl acetate, and successively washed with saturated aqueous potassium hydrogensulfate solution, saturated aqueous sodium hydrogencarbonate solution, and brine. The organic layer was dried over anhydrous sodium sulfate, then concentrated. The residue was purified by flash column chromatography (silica gel, hexane/ethyl acetate=9/1 to 6/1) to obtain ethyl 2-[(1R)-1-(tert-butoxycarbonylamino)propyl]thiazole 4-carboxylate (compound S16a) (4.25 g).

$^1$H-NMR (CDCl$_3$) δ 0.98 (3H, t, J=7.3 Hz), 1.40 (3H, t, J=7.7 Hz), 1.45 (9H, s), 1.79-1.94 (1H, m), 2.09-2.22 (1H, m), 4.38-4.46 (2H, m), 4.88-5.00 (1H, m), 5.17-5.27 (2H, m), 8.08 (1H, s)

MS: 315 (M+H)$^+$

Step (2): Instead of the starting material of Reference Example 15, Step (3), that is, the compound S15b, the compound S16a was used for a similar procedure as in Reference Example 15, Steps (3) to (5), to obtain the title compound.

$^1$H-NMR (CDCl$_3$) δ 1.02 (3H, t, J=7.3 Hz), 1.70-1.88 (1H, m), 1.97-2.11 (1H, m), 4.28-4.34 (1H, m), 4.95-5.03 (2H, m), 8.26 (1H, s)

MS: 316 (M+H)$^+$

Reference Example 17

(6S)-6-(5-chloro-2-methoxybenzyl)-1-methyl-1,4-diazepane-2,5-dione (compound S17)

Step (1): To a 60% mineral oil dispersion of sodium hydride (1.9 g) in a tetrahydrofuran (50 ml) solution, methyl iodide (2.7 ml) was added under ice cooling, then the (2S)-3-[(tert-butoxycarbonyl)amino]-2-(5-chloro-2-methoxybenzyl)propanoic acid (5 g), described in WO 06-059801A, in a tetrahydrofuran (20 ml) solution was slowly added, then the mixture was stirred at room temperature for 72 hours. To the reaction solution, water (50 ml) and ethyl acetate (20 ml) were added and the layers were separated. The organic layer was extracted with water (20 ml) and was combined with the aqueous layer previously obtained, and acidified (pH2) with 6M hydrochloric acid. This aqueous mixture was extracted with ethyl acetate, then the combined extract was washed with water, saturated aqueous sodium thiosulfate solution, and brine. The organic layer was dried over sodium sulfate, then concentrated to obtain (2S)-3-[tert-butoxycarbonyl(methyl)amino]-2-(5-chloro-2-methoxybenzyl)propanoic acid (5.28 g) (compound S17a).

Step (2): To the compound S17a obtained at Step (1) (7.12 g) in an acetonitrile solution (75 ml), glycine ethylester hydrochloride (3.05 g), 1-hydroxybenzotriazole (1.83 g), and triethylamine (2.62 ml) were added at room temperature, and the mixture was stirred at room temperature for 20 minutes. To the reaction solution, N-(3-dimethylaminopropyl)-N'-ethylcarbodiimide hydrochloride (4.77 g) was added, and the mixture was stirred at room temperature for 1 hour. To the reaction solution, a 3% aqueous sodium hydrogencarbonate solution was added, and the mixture was extracted with ethyl acetate. The extract was combined, washed with saturated potassium hydrogensulfate and brine, dried over sodium sulfate, then concentrated to obtain N-[(2S)-3-[tert-butoxycarbonyl(methyl)amino]-2-(5-chloro-2-methoxybenzyl)propanoyl]glycine ethylester (9.04 g) (compound S17b).

Step (3): To the compound S17b obtained at Step (2) (9.04 g) in an ethanol (35 ml) solution, methanesulfonic acid (2.7 ml) was added, and the mixture was stirred at 40° C. for 14 hours, then 4M aqueous sodium hydroxide solution was added, and the mixture was stirred at room temperature for 2 hours. To the reaction solution, 6M hydrochloric acid was added, the mixture was completely concentrated, then water (10 ml) was added to the residue. The suspension thus obtained was stirred at 80° C. for 30 minutes. The suspension was allowed to cool down to room temperature, then was further cooled down to −20° C., and the mixture was stirred at that temperature for 1.5 hours. The solid was collected by filtration and dried to obtain N-[(2S)-3-(methylamino)-2-(5-chloro-2-methoxybenzyl)propanoyl]glycine as a crude product (2.7 g) (compound S17c).

Step (4): 1-hydroxybenzotriazole (339 mg) and N-(3-dimethylaminopropyl)-N'-ethylcarbodiimide hydrochloride (319 mg) in an acetonitrile (15 ml) solution were heated to 60° C. To this solution, the compound S17c obtained at Step (3) (473 mg) was added in batches. After the end of addition, the mixture was stirred at 60° C. for 15 minutes. The reaction solution was allowed to cool down to room temperature, then water and ethyl acetate were added and the solution separated. The organic layer was washed with saturated aqueous sodium hydrogencarbonate solution and brine, dried over sodium sulfate, then concentrated to obtain the title compound as a crude product. The crude product of the title compound obtained by the same procedure as above in another experimental was combined and purified by flash column chromatography (silica gel, hexane/ethyl acetate/methanol=45/45/10 to 40/40/20) to obtain the title compound (3.30 g).

$^1$H-NMR (CDCl$_3$) δ 2.69 (1H, dd, J=7.9, 13.6 Hz), 2.91 (3H, s), 3.15-3.36 (3H, m), 3.41-3.52 (1H, m), 3.83 (3H, s), 3.91 (1H, dd, J=6.1, 16.6 Hz), 4.04 (1H, dd, J=5.7, 16.6 Hz), 6.00-6.13 (1H, m), 6.80 (1H, d, J=8.5 Hz), 7.16-7.18 (1H, m), 7.18-7.22 (1H, m)

MS: 297 (M+H)$^+$

Reference Example 18

O-(3,4-difluorophenyl) hydroxylamine hydrochloride (compound S18)

Step (1): To molecular sieves 4A (1.5 g) in a dichloroethane (120 ml) suspension, 3,4-difluorobenzene boronic acid (5.2 g), N-hydroxyphthalimide (3.9 g), and pyridine (1.5 ml) were successively added, then the mixture was stirred under an oxygen atmosphere at 60° C. for 18 hours. The reaction mixture was filtered using a silica gel column, then the eluate was concentrated to obtain 2-(3,4-difluorophenoxy)isoindolyn-1,3-dione (compound S18a) (2.55 g).

Step (2): To the compound S18a (1.64 g) in a chloroform (25 ml) and methanol (2 ml) solution, hydrazine monohydrate was added, and the mixture was stirred at room temperature for 3 hours. The reaction mixture was filtered, the filtrate was concentrated, then the residue was purified by flash column chromatography (silica gel, hexane/ethyl acetate=4/1 to 3/2) to obtain 3,4-difluorophenyl hydroxylamine (1.18 g). This was dissolved in diethyl ether (10 ml), 4M hydrochloric acid in dioxane solution was added at 0° C., and the mixture was stirred at that temperature for 1 hour. The precipitates were collected by filtration to obtain the title compound (0.92 g).

$^1$H-NMR (CDCl$_3$) δ 6.94-7.01 (1H, m), 7.05-7.19 (2H, m), 7.80-7.87 (2H, m), 7.89-7.96 (2H, m)

MS: 276 (M+H)$^+$

Reference Example 19 tert-butyl 4-[(1R)-1-isocyanatopropyl]benzoate (compound S19)

To the compound S4 (891 mg) in a methylene chloride (15 ml) solution, 2M aqueous sodium hydroxide solution (15 ml) and trichloromethyl chloroformate (0.46 ml) were added under ice cooling, and the mixture was stirred at that temperature for 20 minutes. The reaction solution was extracted with methylene chloride. The extract was washed with brine, dried over anhydrous sodium sulfate, then concentrated to obtain the title compound (988 mg).

$^1$H-NMR (CDCl$_3$) δ 0.97 (3H, t, J=7.3 Hz), 1.59 (9H, s), 1.77-1.92 (2H, m), 4.61 (1H, t, J=6.7 Hz), 7.34 (2H, d, J=8.5 Hz), 7.98 (2H, d, J=8.5 Hz)

Reference Example 20 tert-butyl 4-[(1R)-1-({[(6R)-6-(5-chloro-2-methoxybenzyl)-3,7-dioxo-4-(2,4,6-trimethoxybenzyl)-1,4-diazepan-1-yl]carbonyl}amino)propyl]benzoic acid (compound S20)

To the compound S140c described in WO 06-059801A, that is, (6R)-6-(5-chloro-2-methoxybenzyl)-1-(2,4,6-trimethoxybenzyl)-1,4-diazepane-2,5-dione (1.35 g) in an acetonitrile (20 ml) solution, the compound S19 obtained at Reference Example 19 (988 mg) was added under ice cooling, and the mixture was stirred for several minutes. Then potassium tert-butoxide in a 1M tetrahydrofuran solution (0.29 ml) was added, and the mixture was stirred at that temperature for 10 minutes. Saturated aqueous ammonium chloride solution was added, and the mixture was extracted with ethyl acetate. The extract was combined, washed with brine, dried over anhydrous sodium sulfate, then concentrated. The residue was purified by flash column chromatography (silica gel, hexane/ethyl acetate=1/1 to 1/2) to obtain the title compound (2.07 g).

$^1$H-NMR (CDCl$_3$) δ 0.90 (3H, t, J=7.3 Hz), 1.57 (9H, s), 1.71-1.97 (2H, m), 2.40 (1H, dd, J=9.3, 14.0 Hz), 2.96-3.07 (2H, m), 3.12 (1H, dd, J=4.5, 14.0 Hz), 3.45-3.63 (1H, m), 3.71 (6H, s), 3.78 (3H, s), 3.85 (3H, s), 4.20 (1H, d, J=17.3 Hz), 4.33 (1H, d, J=13.8 Hz), 4.78 (1H, d, J=13.8 Hz), 4.85 (1H, dt, J=7.7, 7.7 Hz), 5.31 (1H, d, J=17.3 Hz), 6.08 (2H, s), 6.75 (1H, d, J=8.8 Hz), 6.93 (1H, d, J=2.5 Hz), 7.19 (1H, dd, J=2.5, 8.8 Hz), 7.33 (2H, d, J=8.3 Hz), 7.95 (2H, d, J=8.3 Hz), 9.52 (1H, d, J=7.7 Hz)

MS: 724 (M+H)$^+$

Reference Example 21 tert-butyl 4-[(1R)-1-({[(6R)-6-(5-chloro-2-methoxybenzyl)-3,7-dioxo-1,4-diazepan-1-yl]carbonyl}amino)propyl]benzoate (compound S21)

To the compound S20 (1.67 g) in a methylene chloride (20 ml) solution, water (1 ml) and 2,3-dichloro-5,6-dicyano-p-benzoquinone (1.57 g) were added, and the mixture was stirred at room temperature for 3 days. To the reaction mixture, sodium sulfate and chloroform were added. The mixture was stirred at room temperature for 1 hour, then filtered. The filtrate was concentrated, then the residue was purified by flash column chromatography (NH$_2$ silica gel, hexane/ethyl acetate=3/2 to 1/2) to obtain the title compound (1.0 g).

$^1$H-NMR (CDCl$_3$) δ 0.92 (3H, t, J=7.5 Hz), 1.58 (9H, s), 1.75-1.97 (2H, m), 2.61 (1H, dd, J=8.5, 13.8 Hz), 3.19 (1H, dd, J=5.3, 13.8 Hz), 3.25-3.38 (2H, m), 3.58-3.74 (1H, m), 3.82 (3H, s), 4.07 (1H, d, J=17.5 Hz), 4.82 (1H, dt, J=7.3, 7.3 Hz), 5.34 (1H, d, J=17.5 Hz), 5.97 (1H, br.s), 6.79 (1H, d, J=8.7 Hz), 7.13 (1H, d, J=2.8 Hz), 7.22 (1H, dd, J=2.8, 8.7 Hz), 7.33 (2H, d, J=8.3 Hz), 7.96 (2H, d, J=8.3 Hz), 9.54 (1H, d, J=7.3 Hz)

Reference Example 22 tert-butyl 4-[(1R)-1-({[(6R)-6-(5-chloro-2-methoxybenzyl)-7-oxo-3-thioxo-1,4-diazepan-1-yl]carbonyl}amino)propyl]benzoate (compound S22)

To the compound S21 (995 mg) in a tetrahydrofuran (25 ml) solution, Belleau's reagent (582 mg) was added under ice cooling, and the mixture was stirred at that temperature for 4 hours. The reaction mixture was diluted with ethyl acetate, then was successively washed with an saturated aqueous sodium hydrogencarbonate solution, water, and brine. The organic layer was dried over anhydrous sodium sulfate, then concentrated. The residue was purified by flash column chromatography (silica gel, hexane/ethyl acetate=3/1 to 2/1) to obtain the title compound (717 mg).

$^1$H-NMR (CDCl$_3$) δ 0.92 (3H, t, J=7.3 Hz), 1.55 (9H, s), 1.76-1.96 (2H, m), 2.60 (1H, dd, J=8.7, 13.8 Hz), 3.20 (1H, dd, J=4.7, 13.8 Hz), 3.33-3.52 (2H, m), 3.73-3.88 (4H, m), 4.36 (1H, d, J=17.9 Hz), 4.71-4.89 (1H, m), 5.91 (1H, d, J=17.9 Hz), 6.81 (1H, d, J=8.5 Hz), 7.13 (1H, d, J=2.2 Hz), 7.23 (1H, dd, J=2.2, 8.5 Hz), 7.29-7.41 (2H, d, J=8.1 Hz), 7.89 (1H, br.s), 7.92-8.04 (2H, d, J=8.1 Hz), 9.43 (1H, d, J=7.3 Hz)

MS: 504 (M−tBu)$^+$

Example 1

4-[(1R)-1-({[(6R)-6-(5-chloro-2-methoxybenzyl)-3-(isopropoxyimino)-7-oxo-1,4-diazepan-1-yl]carbonyl}amino)propyl]benzoic acid (compound 1)

Step (1): To the compound S22 (110 mg) in a tetrahydrofuran (2 ml) and methanol (4 ml) solution, O-isopropyl hydroxylamine hydrochloride (44 mg), triethylamine (55 μl), and mercury acetate (75 mg) were successively added under ice cooling, and the mixture was stirred at that temperature for 20 minutes. The reaction mixture was filtered, then the filtrate was concentrated. The residue was purified by flash column chromatography (silica gel, hexane/ethyl acetate=2/1) to obtain tert-butyl 4-[(1R)-1-({[(6R)-6-(5-chloro-2-methoxybenzyl)-3-(isopropoxyimino)-7-oxo-1,4-diazepan-1-yl]carbonyl}amino)propyl]benzoate (106 mg) (compound 1a).

Step (2): To the compound 1a obtained at Step (1) (102 mg), 4M hydrochloric acid in ethyl acetate (4 ml) was added and the mixture was stirred at room temperature for 3.5 hours. The reaction mixture was concentrated, then the residue was triturated with chloroform/hexane. The solid thus obtained was collected by filtration to obtain the title compound (61 mg).

$^1$H-NMR (CDCl$_3$) δ 0.93 (3H, t, J=7.3 Hz), 1.16 (3H, d, J=6.3 Hz), 1.18 (3H, d, J=6.3 Hz), 1.72-1.97 (2H, m), 2.62

(1H, dd, J=8.3, 13.6 Hz), 3.07-3.30 (2H, m), 3.30-3.44 (1H, m), 3.65-3.73 (1H, m), 3.81 (3H, s), 4.11 (1H, d, J=16.2 Hz), 4.15-4.25 (1H, m), 4.84 (1H, dt, J=7.3, 7.3 Hz), 5.12-5.31 (2H, m), 6.78 (1H, d, J=8.6 Hz), 7.14 (1H, d, J=2.7 Hz), 7.20 (1H, dd, J=2.7, 8.6 Hz), 7.37 (2H, d, J=8.3 Hz), 8.04 (2H, d, J=8.3 Hz), 9.62 (1H, d, J=7.3 Hz)
MS: 545 (M+H)$^+$

Example 2

4-[(1R)-1-({[(6R)-6-(5-chloro-2-methoxybenzyl)-3-(isobutoxyimino)-7-oxo-1,4-diazepan-1-yl]carbonyl}amino)propyl]benzoic acid (compound 2)

Instead of the reaction agent in Example 1, that is, O-isopropyl hydroxylamine hydrochloride, O-isobutyl hydroxylamine hydrochloride was used for a similar procedure as in Example 1 to obtain the title compound.
$^1$H-NMR (CDCl$_3$) δ 0.85-0.95 (9H, m), 1.76-2.02 (3H, m), 2.62 (1H, dd, J=8.3, 14.0 Hz), 3.11-3.30 (2H, m), 3.32-3.43 (1H, m), 3.61-3.75 (3H, m), 3.82 (3H, s), 4.11 (1H, d, J=16.2 Hz), 4.85 (1H, dt, J=7.3, 7.3 Hz), 5.14-5.29 (2H, m), 6.79 (1H, d, J=8.8 Hz), 7.15 (1H, d, J=2.7 Hz), 7.21 (1H, dd, J=2.7, 8.8 Hz), 7.37 (2H, d, J=8.3 Hz), 8.04 (2H, d, J=8.3 Hz), 9.61 (1H, d, J=7.3 Hz)
MS: 559 (M+H)$^+$

Example 3

4-{(1R)-1-[({(6R)-6-(5-chloro-2-methoxybenzyl)-7-oxo-3-[(pyridin-2-yloxy)imino]-1,4-diazepan-1-yl}carbonyl)amino]propyl}benzoic acid (compound 3)

Instead of the reaction agent in Example 1, that is, O-isopropyl hydroxylamine hydrochloride, O-(pyridin-2-yl)hydroxylamine was used for a similar procedure as in Example 1 to obtain the title compound.
$^1$H-NMR (CDCl$_3$) δ 0.95 (3H, t, J=7.3 Hz), 1.81-1.95 (2H, m), 2.71 (1H, dd, J=7.3, 13.8 Hz), 3.16 (1H, dd, J=5.7, 13.8 Hz), 3.34-3.51 (1H, m), 3.60 (1H, m), 3.77 (1H, m), 3.84 (3H, s), 4.25 (1H, d, J=16.8 Hz), 4.80 (1H, dt, J=6.9, 6.9 Hz), 5.29 (1H, d, J=16.8 Hz), 6.80 (1H, d, J=8.4 Hz), 6.88 (1H, br.s), 7.16-7.25 (3H, m), 7.38 (2H, d, J=8.1 Hz), 7.77 (1H, d, J=8.3 Hz), 8.05 (2H, d, J=8.1 Hz), 8.09-8.21 (2H, m), 9.60 (1H, d, J=6.9 Hz)
MS: 580 (M+H)$^+$

Example 4

4-{(1R)-1-[({(6R)-6-(5-chloro-2-methoxybenzyl)-3-[(cyclopropylmethoxy)imino]-7-oxo-1,4-diazepan-1-yl}carbonyl)amino]propyl}benzoic acid (compound 4)

Instead of the reaction agent, that is, O-isopropyl hydroxylamine hydrochloride, in Example 1, O-(cyclopropylmethyl)hydroxylamine was used for a similar procedure as in Example 1 to obtain the title compound.
$^1$H-NMR (DMSO-d$_6$) δ 0.18-0.26 (2H, m), 0.44-0.48 (2H, m), 0.85 (3H, t, J=7.3 Hz), 1.01-1.11 (1H, m), 1.76-1.86 (2H, m), 2.70 (1H, dd, J=8.9, 14.3 Hz), 2.98 (1H, dd, J=5.1, 14.3 Hz), 3.22 (2H, d, J=8.5 Hz), 3.56-3.74 (2H, m), 3.80 (3H, s), 3.83-3.95 (1H, m), 4.64 (1H, d, J=16.6 Hz), 4.69-4.93 (2H, m), 7.02 (1H, d, J=8.8 Hz), 7.28 (1H, dd, J=2.7, 8.8 Hz), 7.33 (1H, d, J=2.7 Hz), 7.42 (2H, d, J=8.5 Hz), 7.91 (2H, d, J=8.5 Hz), 9.46 (1H, d, J=7.3 Hz)
MS: 557 (M+H)$^+$

Example 5

4-{(1R)-1-[({(6R)-6-(5-chloro-2-methoxybenzyl)-3-[(3,4-difluorophenoxy)imino]-7-oxo-1,4-diazepan-1-yl}carbonyl)amino]propyl}benzoic acid (compound 5)

Instead of the reaction agent, that is, O-isopropyl hydroxylamine hydrochloride, in Example 1, the compound S18 was used for a similar procedure as in Example 1 to obtain the title compound.
$^1$H-NMR (DMSO-d$_6$) δ 0.84 (3H, t, J=7.7 Hz), 1.74-1.85 (2H, m), 2.72 (1H, dd, J=8.9, 14.0 Hz), 3.00 (1H, dd, J=4.9, 14.0 Hz), 3.18-3.22 (2H, m), 3.80 (3H, s), 3.85-4.01 (1H, m), 4.66 (1H, d, J=16.2 Hz), 4.76 (1H, dt, J=7.7, 7.7 Hz), 4.88 (1H, d, J=16.2 Hz), 6.80-6.85 (1H, m), 7.00-7.07 (3H, m), 7.23-7.37 (3H, m), 7.42 (2H, d, J=8.3 Hz), 7.91 (2H, d, J=8.3 Hz), 9.50 (1H, d, J=7.7 Hz), 12.85 (1H, br.s)
MS: 615 (M+H)$^+$

Example 6

4-{(1R)-1-[({(6R)-6-(5-chloro-2-methoxybenzyl)-3-[(4-fluorophenoxy)imino]-7-oxo-1,4-diazepan-1-yl}carbonyl)amino]propyl}benzoic acid (compound 6)

Instead of the reaction agent, that is, O-isopropyl hydroxylamine hydrochloride, in Example 1, O-(4-fluorophenyl)hydroxylamine hydrochloride was used for a similar procedure as in Example 1 to obtain the title compound.
$^1$H-NMR (DMSO-d$_6$) δ 0.84 (3H, t, J=7.3 Hz), 1.70-1.93 (2H, m), 2.72 (1H, dd, J=8.7, 14.3 Hz), 3.00 (1H, dd, J=4.9, 14.3 Hz), 3.10-3.29 (2H, m), 3.81 (3H, s), 3.84-4.01 (1H, m), 4.65 (1H, d, J=16.2 Hz), 4.76 (1H, dt, J=7.7, 7.7 Hz), 4.88 (1H, d, J=16.2 Hz), 6.94 (1H, s), 6.98-7.16 (5H, m), 7.28 (1H, dd, J=2.5, 8.7 Hz), 7.35 (1H, d, J=2.5 Hz), 7.42 (2H, d, J=8.3 Hz), 7.91 (2H, d, J=8.3 Hz), 9.51 (1H, d, J=7.7 Hz)
MS: 597 (M+H)$^+$

Example 7

4-{(1R)-1-[({(6R)-6-(5-chloro-2-methoxybenzyl)-3-[(3-fluorophenoxy)imino]-7-oxo-1,4-diazepan-1-yl}carbonyl)amino]propyl}benzoic acid (compound 7)

Instead of the reaction agent, that is, O-isopropyl hydroxylamine hydrochloride, in Example 1, O-(3-fluorophenyl)hydroxylamine hydrochloride was used for a similar procedure as in Example 1 to obtain the title compound.
$^1$H-NMR (DMSO-d$_6$) δ 0.78-0.93 (3H, m), 1.70-1.88 (2H, m), 2.72 (1H, dd, J=8.9, 14.5 Hz), 3.00 (1H, dd, J=4.7, 14.5 Hz), 3.14-3.28 (2H, m), 3.79 (3H, s), 3.86-4.05 (1H, m), 4.66 (1H, d, J=16.4 Hz), 4.77 (1H, dt, J=7.3, 7.3 Hz), 4.89 (1H, d, J=16.4 Hz), 6.65-6.78 (1H, m), 6.81-6.93 (2H, m), 6.96-7.07 (2H, m), 7.22-7.32 (2H, m), 7.35 (1H, d, J=2.8 Hz), 7.42 (2H, d, J=8.3 Hz), 7.91 (2H, d, J=8.3 Hz), 9.50 (1H, d, J=7.3 Hz)
MS: 597 (M+H)$^+$

Example 8

4-[(1R)-1-({[(6R)-3-[(benzyloxy)imino]-6-(5-chloro-2-methoxybenzyl)-7-oxo-1,4-diazepan-1-yl]carbonyl}amino)propyl]benzoic acid (compound 8)

Instead of the reaction agent, that is, O-isopropyl hydroxylamine hydrochloride, in Example 1, O-benzyl hydroxylamine hydrochloride was used for a similar procedure as in Example 1 to obtain the title compound.

$^1$H-NMR (CDCl$_3$) δ 0.94 (3H, t, J=7.5 Hz), 1.78-2.00 (2H, m), 2.61 (1H, dd, J=8.5, 13.8 Hz), 3.06-3.27 (2H, m), 3.27-3.43 (1H, m), 3.57-3.73 (1H, m), 3.80 (3H, s), 4.11 (1H, d, J=16.2 Hz), 4.85 (1H, dt, J=7.3, 7.3 Hz), 4.90-5.04 (2H, m), 5.14-5.37 (2H, m), 6.78 (1H, d, J=8.8 Hz), 7.13 (1H, d, J=2.7 Hz), 7.20 (1H, dd, J=2.7, 8.8 Hz), 7.28-7.35 (5H, m), 7.38 (2H, d, J=8.3 Hz), 8.05 (2H, d, J=8.3 Hz), 9.61 (1H, d, J=7.3 Hz)

MS: 593 (M+H)$^+$

Example 9

4-{(1R)-1-[({(6R)-6-(5-chloro-2-methoxybenzyl)-3-[(cyclopentyloxy)imino]-7-oxo-1,4-diazepan-1-yl}carbonyl)amino]propyl}benzoic acid (compound 9)

Instead of the reaction agent, that is, O-isopropyl hydroxylamine hydrochloride, in Example 1, O-cyclopentyl hydroxylamine hydrochloride was used for a similar procedure as in Example 1 to obtain the title compound.

$^1$H-NMR (CDCl$_3$) δ 0.93 (3H, t, J=7.5 Hz), 1.46-1.91 (10H, m), 2.61 (1H, dd, J=8.5, 13.8 Hz), 3.09-3.29 (2H, m), 3.29-3.44 (1H, m), 3.58-3.76 (1H, m), 3.81 (3H, s), 4.11 (1H, d, J=16.6 Hz), 4.45-4.62 (1H, m), 4.85 (1H, dt, J=7.3, 7.3 Hz), 5.15-5.34 (2H, m), 6.78 (1H, d, J=8.8 Hz), 7.14 (1H, d, J=2.5 Hz), 7.20 (1H, dd, J=2.5, 8.8 Hz), 7.37 (2H, d, J=8.3 Hz), 8.04 (2H, d, J=8.3 Hz), 9.61 (1H, d, J=7.3 Hz)

MS: 571 (M+H)$^+$

Reference Example 23 tert-butyl 4-[(1R)-1-({[(6S)-6-(5-chloro-2-methoxybenzyl)-7-oxo-3-thioxo-1,4-diazepan-1-yl]carbonyl}amino)propyl]benzoate (compound S23)

Instead of the starting material, that is, (6R)-6-(5-chloro-2-methoxybenzyl)-1-(2,4,6-trimethoxybenzyl)-1,4-diazepane-2,5-dione (1.35 g), of Reference Example 20, the compound S140B described in WO 06-059801A, that is, (6S)-6-(5-chloro-2-methoxybenzyl)-1-(2,4,6-trimethoxybenzyl)-1,4-diazepane-2,5-dione, was used for a similar procedure as in Reference Examples 20, 21, and 22 to obtain the title compound.

Example 10

4-[(1R)-1-({[(6S)-6-(5-chloro-2-methoxybenzyl)-3-(ethoxyimino)-7-oxo-1,4-diazepan-1-yl]carbonyl}amino)propyl]benzoic acid (compound 10)

Step (1): To the compound S23 (55 mg) in a tetrahydrofuran (1 ml) and methanol (0.54 ml) solution, O-ethyl hydroxylamine hydrochloride (14 mg), triethylamine (21 μl), and mercury acetate (38 mg) were successively added under ice cooling, and the mixture was stirred at that temperature for 1 hour. The reaction mixture was filtered, then the filtrate was concentrated to obtain tert-butyl 4-[(1R)-1-({[(6S)-6-(5-chloro-2-methoxybenzyl)-3-(ethoxyimino)-7-oxo-1,4-diazepan-1-yl]carbonyl}amino)propyl]benzoate (compound 10a) as a crude product.

Step (2): To the compound 10a crude product obtained at Step (1), trifluoroacetic acid (2 ml) was added, and the mixture was stirred at room temperature for 3 hours. The reaction mixture was concentrated, then the residue was purified by preparative thin layer chromatography (silica gel, chloroform/ethyl acetate/methanol/acetic acid) to obtain the title compound (15 mg).

$^1$H-NMR (DMSO-d$_6$) δ 0.83 (3H, t, J=7.4 Hz), 1.07 (3H, t, J=6.9 Hz), 1.70-1.85 (2H, m), 2.67 (1H, dd, J=9.0, 14.2 Hz), 2.96 (1H, dd, J=5.3, 14.2 Hz), 3.00-3.19 (2H, m), 3.79 (3H, s), 3.71-3.87 (3H, m), 4.48 (1H, d, J=16.2 Hz), 4.70-4.81 (2H, m), 6.12 (1H, br.s), 7.00 (1H, d, J=8.5 Hz), 7.27 (1H, dd, J=2.4, 8.5 Hz), 7.32 (1H, d, J=2.4 Hz), 7.40 (2H, d, J=8.2 Hz), 7.90 (2H, d, J=8.2 Hz), 9.51 (1H, d, J=7.7 Hz)

MS: 531 (M+H)$^+$

Reference Example 24 tert-butyl 4-[(1R)-1-({[(6S)-6-(5-chloro-2-methoxybenzyl)-7-oxo-3-thioxo-1,4-diazepan-1-yl]carbonyl}amino)pentyl]benzoate (compound S24)

Step (1): Instead of the starting material of Reference Example 19, that is, the compound S4, the compound S5 was used for a similar reaction as in Reference Example 19 to obtain tert-butyl 4-[(1R)-1-isocyanatopentyl]benzoate (compound S24a).

Step (2): Instead of the starting material of Reference Example 20, that is, (6R)-6-(5-chloro-2-methoxybenzyl)-1-(2,4,6-trimethoxybenzyl)-1,4-diazepane-2,5-dione (1.35 g), the compound S140B described in WO 06-059801A, that is, (6S)-6-(5-chloro-2-methoxybenzyl)-1-(2,4,6-trimethoxybenzyl)-1,4-diazepane-2,5-dione was used, and instead of the reaction agent, that is, the compound S19, the compound S24a was used for a similar procedure as in Reference Examples 20, 21, and 22 to obtain the title compound.

Example 11

4-[(1R)-1-({[(6S)-6-(5-chloro-2-methoxybenzyl)-3-(ethoxyimino)-7-oxo-1,4-diazepan-1-yl]carbonyl}amino)pentyl]benzoic acid (compound 11)

Instead of the starting material, that is, the compound S23, of Example 10, the compound S24 was used for a similar reaction as in Example 10 to obtain the title compound.

$^1$H-NMR (DMSO-d$_6$) δ 0.83 (3H, t, J=7.1 Hz), 1.07 (3H, t, J=6.9 Hz), 1.22-1.33 (4H, m), 1.66-1.85 (2H, m), 2.66 (1H, dd, J=9.0, 13.9 Hz), 2.96 (1H, dd, J=5.5, 13.9 Hz), 3.00-3.20 (2H, m), 3.79 (3H, s), 3.71-3.87 (3H, m), 4.48 (1H, d, J=16.2 Hz), 4.71-4.85 (2H, m), 6.12 (1H, br.s), 7.00 (1H, d, J=8.9 Hz), 7.26 (1H, dd, J=2.4, 8.9 Hz), 7.31 (1H, d, J=2.4 Hz), 7.42 (2H, d, J=8.2 Hz), 7.90 (2H, d, J=8.2 Hz), 9.51 (1H, d, J=7.7 Hz)

MS: 599 (M+H)$^+$

Reference Example 25 tert-butyl 4-[(1R)-1-({[(6S)-6-(5-chloro-2-methoxybenzyl)-7-oxo-3-thioxo-1,4-diazepan-1-yl]carbonyl}amino)butyl]-2-nitrobenzoate (compound S25)

Step (1): Instead of the starting material, that is, the compound S4, of Reference Example 19, the compound S8 was used for a similar reaction as in Reference Example 19 to obtain tert-butyl 4-[(1R)-1-isocyanatobutyl]-2-nitrobenzoate (compound S25a).

Step (2): To the compound S25a obtained at Step (1) (2.69 g) and the compound S140B described in WO 06-059801A, that is, (6S)-6-(5-chloro-2-methoxybenzyl)-1-(2,4,6-trimethoxybenzyl)-1,4-diazepane-2,5-dione (3.74 g), in an acetonitrile (55 ml) solution, a 1M solution of potassium tert-butoxide in tetrahydrofuran (0.7 ml) was added under ice cooling, and the mixture was stirred at that temperature for 30 minutes. Further, a 1M solution of potassium tert-butoxide in tetrahydrofuran (0.19 ml) was added, and the mixture was stirred at that temperature for 30 minutes. To the reaction solution, aqueous saturated potassium hydrogensulfate solution was added, and the mixture was extracted with ethyl acetate. The extract was combined, washed with brine, dried over anhydrous sodium sulfate, then concentrated. The residue was purified by flash column chromatography (silica gel, hexane/ethyl acetate=1/1 to 0/1) to obtain tert-butyl 4-[(1R)-1-({[(6S)-6-(5-chloro-2-methoxybenzyl)-3,7-dioxo-1-(2,4,6-trimethoxybenzyl)-1,4-diazepan-1-yl]carbonyl}amino)butyl]-2-nitrobenzoate (compound S25b) (5.0 g).

Step (3): To the compound S25b obtained at Step (2) (0.76 g) in a methylene chloride (8 ml) solution, water (0.4 ml) and 2,3-dichloro-5,6-dicyano-p-benzoquinone (0.66 g) were added, and the mixture was stirred at room temperature for 15 hours. To the reaction mixture, sodium sulfate and chloroform were added, and the mixture was stirred at room temperature for 20 minutes and filtered. The filtrate was concentrated, then the residue was purified by flash column chromatography ($NH_2$ silica gel, hexane/ethyl acetate=1/1 to 3/7) to obtain tert-butyl 4-[(1R)-1-({[(6S)-6-(5-chloro-2-methoxybenzyl)-3,7-dioxo-1,4-diazepan-1-yl]carbonyl}amino)butyl]-2-nitrobenzoate (compound S25c) (0.41 g).

Step (4): To the compound S25c obtained at Step (3) (0.36 g) in a tetrahydrofuran (7 ml) solution, Belleau's reagent (0.19 g) was added under ice cooling, and the mixture was stirred at that temperature for 4 hours. The reaction mixture was diluted with ethyl acetate and successively washed with saturated aqueous sodium hydrogencarbonate solution, water, and brine. The organic layer was dried over anhydrous sodium sulfate, then concentrated to obtain the title compound (396 mg).

Example 12

2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid (compound 12)

Step (1): To the compound S25 (62 mg) in a tetrahydrofuran (1 ml) and methanol (0.5 ml) solution, O-ethyl hydroxylamine hydrochloride (15 mg), triethylamine (21 μl), and mercury acetate (38 mg) were successively added under ice cooling, and the mixture was stirred at that temperature for 1 hour. The reaction mixture was filtered, then the filtrate was concentrated to obtain tert-butyl 4-[(1R)-1-({[(6S)-6-(5-chloro-2-methoxybenzyl)-3-(ethoxyimino)-7-oxo-1,4-diazepan-1-yl]carbonyl}amino)butyl]-2-nitrobenzoate (compound 12a) as a crude product (36 mg).

Step (2): To the compound 12a crude product obtained at Step (1) (35 mg), trifluoroacetic acid (1 ml) was added, and the mixture was stirred at room temperature for 1.5 hours. To the reaction mixture, zinc powder (100 mg) was added, and the mixture was stirred at room temperature for 3 hours. The insolubles were filtered out, the filtrate was concentrated, then the residue was purified by flash column chromatography (silica gel, chloroform/ethyl acetate/methanol/acetic acid=15/15/1/0.1) to obtain the title compound (28 mg).

$^1$H-NMR (DMSO-$d_6$) δ 0.87 (3H, t, J=7.3 Hz), 1.08 (3H, t, J=7.1 Hz), 1.14-1.34 (2H, m), 1.57-1.78 (2H, m), 2.62-2.71 (1H, m), 2.95 (1H, dd, J=4.9, 14.2 Hz), 2.99-3.08 (1H, m), 3.10-3.18 (1H, m), 3.73-3.87 (3H, m), 3.79 (3H, s), 4.49 (1H, d, J=16.2 Hz), 4.62 (1H, dt, J=7.3, 7.3 Hz), 4.80 (1H, d, J=16.2 Hz), 6.19 (1H, br.s), 6.44 (1H, dd, J=1.8, 8.3 Hz), 6.64 (1H, d, J=1.8 Hz), 7.00 (1H, d, J=8.5 Hz), 7.27 (1H, dd, J=2.8, 8.5 Hz), 7.31 (1H, d, J=2.8 Hz), 7.65 (1H, d, J=8.3 Hz), 9.44 (1H, d, J=7.3 Hz)

MS: 560 (M+H)$^+$

Reference Example 26 tert-butyl 4-[(1R)-1-({[(6S)-6-(5-chloro-2-methoxybenzyl)-7-oxo-3-thioxo-1,4-diazepan-1-yl]carbonyl}amino)pentyl]-2-nitrobenzoate (compound S26)

Step (1): Instead of the starting material, that is, the compound S4, of Reference Example 19, the compound S9 was used for a similar reaction as in Reference Example 19 to obtain tert-butyl 4-[(1R)-1-isocyanatopentyl]-2-nitrobenzoate (compound S26a).

Step (2): Instead of the starting material, that is, (6R)-6-(5-chloro-2-methoxybenzyl)-1-(2,4,6-trimethoxybenzyl)-1,4-diazepane-2,5-dione (1.35 g), of Reference Example 20, the compound S140B described in WO 06-059801A, that is, (6S)-6-(5-chloro-2-methoxybenzyl)-1-(2,4,6-trimethoxybenzyl)-1,4-diazepane-2,5-dione was used, and instead of the reaction agent, that is, the compound S19, the compound S26a was used for a similar procedure as in Reference Examples 20, 21, and 22 to obtain the title compound.

Example 13

2-amino-4-[(1R)-1-({[(6S)-6-(5-chloro-2-methoxybenzyl)-3-(ethoxyimino)-7-oxo-1,4-diazepan-1-yl]carbonyl}amino)pentyl]benzoic acid (compound 13)

Instead of the starting material, that is, the compound S25, of Example 12, the compound S26 was used for a similar procedure as in Example 12 to obtain the title compound.

$^1$H-NMR (DMSO-$d_6$) δ 0.83 (3H, t, J=6.1 Hz), 1.09 (3H, t, J=7.1 Hz), 1.19-1.32 (4H, m), 1.61-1.78 (2H, m), 2.62-2.70 (1H, m), 2.96 (1H, dd, J=5.3, 14.2 Hz), 3.00-3.10 (1H, m), 3.10-3.18 (1H, m), 3.74-3.89 (3H, m), 3.79 (3H, s), 4.51 (1H, d, J=16.2 Hz), 4.60 (1H, dt, J=7.7, 7.7 Hz), 4.80 (1H, d, J=16.2 Hz), 6.28 (1H, br.s), 6.44 (1H, dd, J=1.6, 8.5 Hz), 6.64 (1H, d, J=1.6 Hz), 7.00 (1H, d, J=8.5 Hz), 7.26 (1H, dd, J=2.8, 8.5 Hz), 7.31 (1H, d, J=2.8 Hz), 7.65 (1H, d, J=8.5 Hz), 9.44 (1H, d, J=7.7 Hz)

MS: 574 (M+H)$^+$

Example 14

2-amino-4-[(1R)-1-({[(6S)-6-(5-chloro-2-methoxybenzyl)-3-(hydroxyimino)-7-oxo-1,4-diazepan-1-yl]carbonyl}amino)butyl]benzoic acid (compound 14)

Instead of the reaction agent, that is, O-ethyl hydroxylamine hydrochloride, of Example 12, hydroxylamine hydrochloride was used for a similar procedure as in Example 12 to obtain the title compound.

$^1$H-NMR (DMSO-$d_6$) δ 0.86 (3H, t, J=7.7 Hz), 1.14-1.35 (2H, m), 1.57-1.76 (2H, m), 2.62-2.70 (1H, m), 2.91-3.07 (2H, m), 3.09-3.18 (1H, m), 3.76-3.88 (3H, m), 3.79 (3H, s), 4.45 (1H, d, J=16.2 Hz), 4.62 (1H, dt, J=7.7, 7.7 Hz), 4.83 (1H, d, J=16.2 Hz), 5.98 (1H, br.s), 6.41 (1H, d, J=8.1 Hz), 6.60 (1H, s), 7.00 (1H, d, J=8.9 Hz), 7.26 (1H, dd, J=2.8, 8.9 Hz), 7.31 (1H, d, J=2.8 Hz), 7.64 (1H, d, J=8.1 Hz), 9.27 (1H, s), 9.45 (1H, d, J=7.7 Hz)

MS: 532 (M+H)$^+$

Example 15

2-amino-4-[(1R)-1-({[(6S)-6-(5-chloro-2-methoxybenzyl)-3-(isopropoxyimino)-7-oxo-1,4-diazepan-1-yl]carbonyl}amino)butyl]benzoic acid (compound 15)

Instead of the reaction agent, that is, O-ethyl hydroxylamine hydrochloride, of Example 12, O-isopropyl hydroxylamine hydrochloride was used for a similar procedure as in Example 12 to obtain the title compound.

$^1$H-NMR (DMSO-d$_6$) δ 0.87 (3H, t, J=7.0 Hz), 1.07 (6H, d, J=6.1 Hz), 1.17-1.35 (2H, m), 1.59-1.76 (2H, m), 2.64-2.69 (1H, m), 2.90-3.08 (1H, m), 3.10-3.18 (2H, m), 3.75-3.87 (2H, m), 3.79 (3H, s), 4.48 (1H, d, J=16.2 Hz), 4.63 (1H, dt, J=7.7, 7.7 Hz), 4.80 (1H, d, J=16.2 Hz), 6.02 (1H, br.s), 6.44 (1H, d, J=8.5 Hz), 6.64 (1H, s), 7.00 (1H, d, J=8.9 Hz), 7.27 (1H, dd, J=2.4, 8.9 Hz), 7.31 (1H, d, J=2.4 Hz), 7.65 (1H, d, J=8.5 Hz), 9.45 (1H, d, J=7.7 Hz)

MS: 574 (M+H)$^+$

Example 16

2-amino-4-[(1R)-1-({[(6S)-3-(tert-butoxyimino)-6-(5-chloro-2-methoxybenzyl)-7-oxo-1,4-diazepan-1-yl]carbonyl}amino)butyl]benzoic acid (compound 16)

Instead of the reaction agent, that is, O-ethyl hydroxylamine hydrochloride, of Example 12, O-tert-butyl hydroxylamine hydrochloride was used for a similar procedure as in Example 12 to obtain the title compound.

$^1$H-NMR (CDCl$_3$) δ 0.87 (3H, t, J=7.3 Hz), 1.12 (9H, s), 1.17-1.36 (2H, m), 1.59-1.77 (2H, m), 2.62-2.71 (1H, m), 2.95 (1H, dd, J=4.7, 14.0 Hz), 3.00-3.09 (1H, m), 3.10-3.18 (1H, m), 3.73-3.85 (1H, m), 3.79 (3H, s), 4.49 (1H, d, J=16.2 Hz), 4.64 (1H, dt, J=7.3, 7.3 Hz), 4.84 (1H, d, J=16.2 Hz), 5.97 (1H, br.s), 6.44 (1H, dd, J=1.6, 8.5 Hz), 6.64 (1H, d, J=1.6 Hz), 7.00 (1H, d, J=8.5 Hz), 7.27 (1H, dd, J=2.8, 8.5 Hz), 7.31 (1H, d, J=2.8 Hz), 7.64 (1H, d, J=8.5 Hz), 9.46 (1H, d, J=7.3 Hz)

MS: 588 (M+H)$^+$

Example 17

2-amino-4-{(1R)-1-[({(6S)-6-(5-chloro-2-methoxybenzyl)-3-[(2-methoxyethoxy)imino]-7-oxo-1,4-diazepan-1-yl}carbonyl)amino]butyl}benzoic acid (compound 17)

Instead of the reaction agent, that is, O-ethyl hydroxylamine hydrochloride, of Example 12, O-(2-methoxyethyl) hydroxylamine hydrochloride was used for a similar procedure as in Example 12 to obtain the title compound.

$^1$H-NMR (DMSO-d$_6$) δ 0.87 (3H, t, J=7.3 Hz), 1.14-1.35 (2H, m), 1.57-1.77 (2H, m), 2.62-2.69 (1H, m), 2.95 (1H, dd, J=5.5, 14.4 Hz), 2.99-3.08 (1H, m), 3.11-3.19 (2H, m), 3.18 (3H, s), 3.40-3.46 (2H, m), 3.76-3.88 (1H, m), 3.79 (3H, s), 4.49 (1H, d, J=16.2 Hz), 4.62 (1H, dt, J=7.7, 7.7 Hz), 4.79 (1H, d, J=16.2 Hz), 6.17 (1H, br.s), 6.43 (1H, dd, J=1.4, 8.5 Hz), 6.63 (1H, d, J=1.4 Hz), 7.00 (1H, d, J=8.9 Hz), 7.27 (1H, dd, J=2.4, 8.9 Hz), 7.31 (1H, d, J=2.4 Hz), 7.65 (1H, d, J=8.5 Hz), 9.44 (1H, d, J=7.7 Hz)

MS: 590 (M+H)$^+$

Example 18

2-amino-4-{(1R)-1-[({(6S)-6-(5-chloro-2-methoxybenzyl)-3-[(2-hydroxyethoxy)imino]-7-oxo-1,4-diazepan-1-yl}carbonyl)amino]butyl}benzoic acid (compound 18)

Instead of the reaction agent, that is, O-ethyl hydroxylamine hydrochloride, of Example 12, O-(2-hydroxyethyl) hydroxylamine hydrochloride was used for a similar procedure as in Example 12 to obtain the title compound.

$^1$H-NMR (DMSO-d$_6$) δ 0.87 (3H, t, J=7.3 Hz), 1.12-1.35 (2H, m), 1.57-1.77 (2H, m), 2.62-2.71 (1H, m), 2.96 (1H, dd, J=4.9, 14.2 Hz), 3.01-3.18 (2H, m), 3.44-3.52 (2H, m), 3.71-3.88 (3H, m), 3.79 (3H, s), 4.41-4.53 (2H, m), 4.62 (1H, dt, J=7.7, 7.7 Hz), 4.79 (1H, d, J=16.2 Hz), 6.26 (1H, br.s), 6.43 (1H, dd, J=1.8, 8.1 Hz), 6.63 (1H, d, J=1.8 Hz), 7.00 (1H, d, J=8.9 Hz), 7.27 (1H, dd, J=2.8, 8.9 Hz), 7.32 (1H, d, J=2.8 Hz), 7.65 (1H, d, J=8.1 Hz), 9.45 (1H, s, J=7.7 Hz)

MS: 576 (M+H)$^+$

Example 19

2-amino-4-[(1R)-1-({[(6S)-6-(5-chloro-2-methoxybenzyl)-3-(methoxyimino)-7-oxo-1,4-diazepan-1-yl]carbonyl}amino)butyl]benzoic acid (compound 19)

Instead of the reaction agent, that is, O-ethyl hydroxylamine hydrochloride, of Example 12, O-methyl hydroxylamine hydrochloride was used for a similar procedure as in Example 12 to obtain the title compound.

$^1$H-NMR (DMSO-d$_6$) δ 0.87 (2H, t, J=7.7 Hz), 1.13-1.35 (2H, m), 1.57-1.76 (2H, m), 2.61-2.69 (1H, m), 2.91-3.07 (2H, m), 3.09-3.16 (1H, m), 3.54 (3H, s), 3.79 (3H, s), 3.78-3.88 (1H, m), 4.48 (1H, d, J=16.6 Hz), 4.62 (1H, dt, J=8.1, 8.1 Hz), 4.78 (1H, d, J=16.6 Hz), 6.22 (1H, br.s), 6.43 (1H, dd, J=1.2, 8.5 Hz), 6.63 (1H, d, J=1.2 Hz), 7.00 (1H, d, J=8.9 Hz), 7.27 (1H, dd, J=2.8, 8.9 Hz), 7.31 (1H, d, J=2.8 Hz), 7.65 (1H, d, J=8.5 Hz), 9.45 (1H, d, J=8.1 Hz)

MS: 546 (M+H)$^+$

Example 20

2-amino-4-{(1R)-1-[({(6S)-6-(5-chloro-2-methoxybenzyl)-7-oxo-3-[(2,2,2-trifluoroethoxy)imino]-1,4-diazepan-1-yl}carbonyl)amino]butyl}benzoic acid (compound 20)

Instead of the reaction agent, that is, O-ethyl hydroxylamine hydrochloride, of Example 12, O-(2,2,2-trifluoroethyl)hydroxylamine hydrochloride was used for a similar procedure as in Example 12 to obtain the title compound.

$^1$H-NMR (DMSO-d$_6$) δ 0.87 (3H, t, J=7.3 Hz), 1.11-1.36 (2H, m), 1.55-1.79 (2H, m), 2.66 (1H, dd, J=8.7, 14.2 Hz), 2.96 (1H, dd, J=5.1, 14.2 Hz), 3.01-3.11 (1H, m), 3.11-3.20 (1H, m), 3.79 (3H, s), 3.81-3.91 (1H, m), 4.34 (2H, q, J=9.1 Hz), 4.55 (1H, d, J=16.4 Hz), 4.62 (1H, dt, J=7.7, 7.7 Hz), 4.78 (1H, d, J=16.4 Hz), 6.39-6.49 (2H, m), 6.64 (1H, d, J=1.2 Hz), 7.00 (1H, d, J=8.8 Hz), 7.27 (1H, dd, J=2.8, 8.8 Hz), 7.32 (1H, d, J=2.8 Hz), 7.65 (1H, d, J=8.1 Hz), 9.43 (1H, d, J=7.7 Hz)

MS: 614 (M+H)$^+$

Example 21 tert-butyl 2-amino-4-[(1R)-1-({[(6S)-6-(5-chloro-2-methoxybenzyl)-3-(dimethylhydrazono)-7-oxo-1,4-diazepan-1-yl]carbonyl}amino)butyl]benzoate (compound 21)

Step (1): To the compound S25 (80 mg) in a tetrahydrofuran (1 ml) and 2-propanol (2 ml) solution, N,N-dimethyl hydrazine (15 µl) and mercury acetate (60 mg) were successively added under ice cooling, and the mixture was stirred at room temperature for 2 hours. Further, mercury acetate (12 mg) was added, and the mixture was stirred at room temperature for 1 hour. The reaction mixture was filtered, saturated aqueous ammonium chloride solution was added to the filtrate, and the mixture was extracted with ethyl acetate. The organic layer was washed with brine, dried over anhydrous sodium sulfate, then concentrated to obtain tert-butyl 4-[(1R)-1-({[(6S)-6-(5-chloro-2-methoxybenzyl)-3-(dimethylhydrazon)-7-oxo-1,4-diazepan-1-yl]carbonyl}amino) butyl]-2-nitrobenzoate (compound 21a) as a crude product (36 mg).

Step (2): The compound 21a crude product obtained at Step (1) (35 mg) was dissolved in acetic acid (2 ml), zinc powder (160 mg) was added to the solution, then the mixture was stirred at 50° C. for 2 hours. The insolubles were filtered out, the filtrate was concentrated. Then ethyl acetate and saturated aqueous ammonium chloride solution were added to the residue, and the solution was separated. The organic layer was washed with brine, dried over anhydrous sodium sulfate, then concentrated. The residue was purified by flash column chromatography (NH$_2$ silica gel, hexane/ethyl acetate=1/1 to 1/4) and preparative thin layer chromatography (NH$_2$ silica gel, hexane/ethyl acetate=1/2) to obtain the title compound (28 mg).

Example 22

2-amino-4-[(1R)-1-({[(6S)-6-(5-chloro-2-methoxybenzyl)-3-(dimethylhydrazono)-7-oxo-1,4-diazepan-1-yl]carbonyl}amino)butyl]benzoic acid (compound 22)

To the compound 21 (16 mg), 1 M hydrochloric acid in acetic acid solution was added, and the mixture was stirred at room temperature for 4 hours. To the reaction solution, toluene (5 ml) was added and the precipitated solid was collected by filtration to obtain the title compound (12.7 mg).

$^1$H-NMR (DMSO-d$_6$) δ 0.88 (3H, t, J=7.3 Hz), 1.14-1.40 (2H, m), 1.58-1.82 (2H, m), 2.48 (6H, s), 2.69 (1H, dd, J=9.1, 14.4 Hz), 3.00 (1H, dd, J=4.5, 14.4 Hz), 3.24-3.43 (2H, m), 3.80 (3H, s), 3.89-4.03 (1H, m), 4.66 (1H, dt, J=7.7, 7.7 Hz), 4.94 (1H, d, J=17.5 Hz), 5.10 (1H, d, J=17.5 Hz), 6.49 (1H, d, J=8.3 Hz), 6.67 (1H, s), 7.04 (1H, d, J=8.7 Hz), 7.30 (1H, dd, J=2.6, 8.7 Hz), 7.35 (1H, d, J=2.6 Hz), 7.66 (1H, d, J=8.3 Hz), 9.24-9.34 (2H, m), 11.02 (1H, br.s)

MS: 559 (M+H)$^+$

Reference Example 27 tert-butyl 4-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]benzoate (compound S27)

Instead of the starting material, that is, the compound S21, of Reference Example 22, the compound S20 was used for a similar reaction as in Reference Example 22 to obtain the title compound (compound S27).

$^1$H-NMR (CDCl$_3$) δ 0.89 (3H, t, J=7.3 Hz), 1.58 (9H, s), 1.75-1.94 (2H, m), 2.38 (1H, dd, J=9.5, 13.7 Hz), 3.08 (1H, dd, J=4.1, 13.7 Hz), 3.11-3.29 (2H, m), 3.29-3.42 (1H, m), 3.66 (6H, s), 3.75 (3H, s), 3.86 (3H, s), 4.79-4.91 (2H, m), 4.94 (1H, d, J=14.2 Hz), 5.09 (1H, d, J=14.2 Hz), 5.57 (1H, d, J=17.0 Hz), 6.09 (1H, s), 6.74 (1H, d, J=8.7 Hz), 6.79 (1H, d, J=2.5 Hz), 7.18 (1H, dd, J=2.5, 8.7 Hz), 7.33 (2H, d, J=8.5 Hz), 7.95 (2H, d, J=8.5 Hz), 9.49 (1H, d, J=7.7 Hz)

MS: 740 (M+H)$^+$

Example 23

4-[(1R)-1-({[(6R)-6-(5-chloro-2-methoxybenzyl)-3-(ethoxyimino)-7-oxo-1,4-diazepan-1-yl] carbonyl}amino)propyl]benzoic acid (compound 23)

Step (1): To the compound S27 (102 mg) in a tetrahydrofuran (1 ml) and methanol (2 ml) solution, O-ethyl hydroxylamine hydrochloride (20 mg), triethylamine (29 µl), and mercury acetate (53 mg) were successively added under ice cooling, and the mixture was stirred at that temperature for 10 minutes. The reaction mixture was filtered, then the filtrate was concentrated to obtain tert-butyl 4-[(1R)-1-({[(6R)-6-(5-chloro-2-methoxybenzyl)-3-(ethoxyimino)-7-oxo-4-(2,4,6-trimethoxybenzyl)-1,4-diazepan-1-yl]carbonyl}amino)propyl]benzoate (compound 23a) as a crude product (88 mg).

Step (2): To the compound 23a crude product obtained at Step (1) (86 mg), anisole (0.15 ml) and trifluoroacetic acid (2 ml) were added, and the mixture was stirred at room temperature for 1.5 hours. The reaction mixture was concentrated, then the residue was purified by flash column chromatography (silica gel, chloroform/ethyl acetate/methanol/acetic acid-40/40/1/0.1) to obtain the title compound (31 mg).

$^1$H-NMR (CDCl$_3$) δ 0.93 (3H, t, J=7.3 Hz), 1.20 (3H, t, J=7.1 Hz), 1.79-1.93 (2H, m), 2.62 (1H, m), 3.07-3.31 (2H, m), 3.38 (1H, m), 3.70 (1H, m), 3.82 (3H, s), 3.89-4.07 (2H, m), 4.12 (1H, d, J=16.4 Hz), 4.84 (1H, dt, J=7.7, 7.7 Hz), 5.21 (1H, d, J=16.4 Hz), 5.30 (1H, br.s), 6.79 (1H, d, J=8.7 Hz), 7.14 (1H, d, J=2.4 Hz), 7.20 (1H, dd, J=2.4, 8.7 Hz), 7.37 (2H, d, J=8.3 Hz), 8.04 (2H, d, J=8.3 Hz), 9.60 (1H, d, J=7.7 Hz)

MS: 531 (M+H)$^+$

Example 24

4-{(1R)-1-[({(6R)-6-(5-chloro-2-methoxybenzyl)-3-[(3,5-difluorophenoxy)imino]-7-oxo-1,4-diazepan-1-yl}carbonyl)amino]propyl}benzoic acid (compound 24)

Instead of the reaction agent, that is, O-ethyl hydroxylamine hydrochloride, in Example 23, O-(3,5-difluorophenyl)hydroxylamine hydrochloride was used for a similar procedure as in Example 23 to obtain the title compound.

$^1$H-NMR (DMSO-d$_6$) δ 0.84 (3H, t, J=7.7 Hz), 1.70-1.89 (2H, m), 2.72 (1H, dd, J=9.1, 14.3 Hz), 3.00 (1H, dd, J=4.9, 14.3 Hz), 3.14-3.26 (2H, m), 3.80 (3H, s), 3.84-3.99 (1H, m), 4.68 (1H, d, J=16.6 Hz), 4.76 (1H, dt, J=7.3, 7.3 Hz), 4.88 (1H, d, J=16.6 Hz), 6.63-6.81 (3H, m), 7.02 (1H, d, J=8.8 Hz), 7.11 (1H, s), 7.28 (1H, dd, J=2.7, 8.8 Hz), 7.35 (1H, d, J=2.7 Hz), 7.43 (2H, d, J=8.3 Hz), 7.91 (1H, d, J=8.3 Hz), 9.50 (1H, d, J=7.3 Hz), 12.87 (1H, br.s)

MS: 615 (M+H)$^+$

Reference Example 28 tert-butyl 5-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]-2-furane carboxylate (compound S28)

Step (1): Instead of the starting material, that is, the compound S4, of Reference Example 19, the compound S85 described in WO 06-059801A, that is, tert-butyl 5-[(1R)-1-aminopropyl]-2-furane carboxylate D-tartrate, was used for a similar reaction as in Reference Example 19 to obtain tert-butyl 5-[(1R)-1-isocyanatopropyl]-2-furane carboxylate (compound S28a).

Step (2): Instead of the reaction agent, that is, the compound S19, of Reference Example 20, the compound S28a was used for a similar procedure as in Reference Examples 20 and 22 to obtain the title compound.

$^1$H-NMR (CDCl$_3$) δ 0.92 (3H, t, J=7.3 Hz), 1.49-1.60 (9H, s), 1.83-2.03 (2H, m), 2.36 (1H, dd, J=9.5, 14.0 Hz), 3.08 (1H, dd, J=3.9, 14.0 Hz), 3.11-3.37 (3H, m), 3.66 (6H, s), 3.75 (3H, s), 3.86 (3H, s), 4.89-5.12 (4H, m), 5.53 (1H, d, J=17.0 Hz), 6.08 (2H, s), 6.31 (1H, d, J=3.2 Hz), 6.74 (1H, d, J=8.8 Hz), 6.78 (1H, d, J=2.7 Hz), 6.97 (1H, d, J=3.2 Hz), 7.18 (1H, dd, J=2.7, 8.8 Hz), 9.40 (1H, d, J=8.1 Hz)

MS: 730 (M+H)$^+$

Example 25

5-[(1R)-1-({[(6R)-6-(5-chloro-2-methoxybenzyl)-7-oxo-3-(phenoxyimino)-1,4-diazepan-1-yl]carbonyl}amino)propyl]-2-furane carboxylic acid (compound 25)

Instead of the starting material, that is, the compound S27, of Example 23, the compound S28 was used, and instead of the reaction agent, that is, O-ethyl hydroxylamine hydrochloride, O-phenyl hydroxylamine hydrochloride was used for a similar procedure as in Example 23 to obtain the title compound.

$^1$H-NMR (DMSO-d$_6$) δ 0.86 (3H, t, J=7.3 Hz), 1.74-1.93 (2H, m), 2.70 (1H, dd, J=9.1, 14.5 Hz), 2.98 (1H, dd, J=4.9, 14.5 Hz), 3.09-3.25 (2H, m), 3.80 (3H, s), 3.84-4.00 (1H, m), 4.69 (1H, d, J=16.2 Hz), 4.81-5.06 (2H, m), 6.48 (1H, d, J=3.4 Hz), 6.81-6.96 (2H, m), 7.01 (1H, d, J=8.9 Hz), 7.03-7.09 (2H, m), 7.14 (1H, d, J=3.4 Hz), 7.19-7.31 (3H, m), 7.34 (1H, d, J=2.8 Hz), 9.41 (1H, d, J=8.1 Hz), 13.16 (1H, br.s)

MS: 569 (M+H)$^+$

Reference Example 29 tert-butyl 4-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]ethyl}benzoate (compound S29)

Step (1): Instead of the starting material, that is, the compound S4, of Reference Example 19, the compound S2 was used for a similar procedure as in Reference Example 19 to obtain tert-butyl 4-[(1R)-1-isocyanato ethyl]benzoate (compound S29a).

Step (2): Instead of the reaction agent, that is, the compound S19, of Reference Example 20, the compound S29a was used for a similar procedure as in Reference Examples 20 and 22 to obtain the title compound.

$^1$H-NMR (CDCl$_3$) δ 1.52 (3H, d, J=6.9 Hz), 1.58 (9H, s), 2.35 (1H, dd, J=9.7, 13.8 Hz), 3.08 (1H, dd, J=4.1, 13.8 Hz), 3.12-3.29 (2H, m), 3.29-3.40 (1H, m), 3.67 (6H, s), 3.75 (3H, s), 3.86 (3H, s), 4.89 (1H, d, J=17.0 Hz), 4.95 (1H, d, J=14.2 Hz), 5.04-5.16 (2H, m), 5.58 (1H, d, J=17.0 Hz), 6.09 (2H, s), 6.74 (1H, d, J=8.9 Hz), 6.78 (1H, d, J=2.8 Hz), 7.18 (1H, dd, J=2.8, 8.9 Hz), 7.38 (2H, d, J=8.5 Hz), 7.95 (2H, d, J=8.5 Hz), 9.46 (1H, d, J=7.3 Hz)

MS: 726 (M+H)$^+$

Example 26

4-{(1R)-1-[({(6R)-6-(5-chloro-2-methoxybenzyl)-3-[(4-fluorophenoxy)imino]-7-oxo-1,4-diazepan-1-yl}carbonyl)amino]ethyl}benzoic acid (compound 26)

Instead of the starting material, that is, the compound S27, of Example 23, the compound S29 was used, and instead of the reaction agent, that is, O-ethyl hydroxylamine hydrochloride, O-(4-fluorophenyl)hydroxylamine hydrochloride was used for a similar procedure as in Example 23 to obtain the title compound.

$^1$H-NMR (DMSO-d$_6$) δ 1.45 (3H, d, J=6.9 Hz), 2.70 (1H, dd, J=8.7, 14.2 Hz), 2.99 (1H, dd, J=4.9, 14.2 Hz), 3.11-3.26 (2a, m), 3.80 (3H, s), 3.85-3.97 (1H, m), 4.66 (1H, d, J=16.2 Hz), 4.84-5.01 (2H, m), 6.96 (1H, br.s), 6.99-7.13 (5H, m), 7.28 (1H, dd, J=2.8, 8.7 Hz), 7.35 (1H, d, J=2.8 Hz), 7.45 (1H, d, J=8.3 Hz), 7.91 (1H, d, J=8.3 Hz), 9.46 (1H, d, J=7.3 Hz), 12.94 (1H, br.s)

MS: 583 (M+H)$^+$

Example 27

4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}benzoic acid (compound 27)

Instead of the starting material, that is, the compound S27, of Example 23, the compound S29 was used, and instead of the reaction agent, that is, O-ethyl hydroxylamine hydrochloride, O-(3,5-difluorophenyl)hydroxylamine hydrochloride was used for a similar procedure as in Example 23 to obtain the title compound.

$^1$H-NMR (DMSO-d$_6$) δ 1.46 (3H, d, J=6.9 Hz), 2.70 (1H, dd, J=8.7, 14.2 Hz), 2.99 (1H, dd, J=4.9, 14.2 Hz), 3.15-3.25 (2H, m), 3.80 (3H, s), 3.87-4.00 (1H, m), 4.68 (1H, d, J=16.2 Hz), 4.84-5.02 (2H, m), 6.62-6.79 (3H, m), 7.02 (1H, d, J=8.7 Hz), 7.11 (1H, br.s), 7.28 (1H, dd, J=2.4, 8.7 Hz), 7.35 (1H, d, J=2.4 Hz), 7.45 (1H, d, J=8.1 Hz), 7.91 (1H, d, J=8.1 Hz), 9.44 (1H, d, J=7.3 Hz), 12.93 (1H, br.s)

MS: 601 (M+H)$^+$

Reference Example 30 tert-butyl 4-[(1R)-1-({[(6S)-6-(5-chloro-2-methoxybenzyl)-7-oxo-3-thioxo-4-(2,4,6-trimethoxybenzyl)-1,4-diazepan-1-yl]carbonyl}amino)butyl]-2-nitrobenzoate (compound S30)

To the compound S25b obtained at Reference Example 25 Steps (1) and (2) (4.5 g) in a tetrahydrofuran (90 ml) solution, Belleau's reagent (1.82 g) was added under ice cooling, and the mixture was stirred at that temperature for 1 hour. Further, Belleau's reagent (0.61 g) was added, and the mixture was stirred at that temperature for 1 hour. To the reaction mixture, aqueous saturated sodium hydrogencarbonate solution was added and the mixture was extracted with ethyl acetate. The organic layer was washed with brine, then dried over anhydrous sodium sulfate, and concentrated. The residue was purified by flash column chromatography (silica gel, hexane/ethyl acetate=3/7 to 2/3) to obtain the title compound (3.5 g).

$^1$H-NMR (CDCl$_3$) δ 0.94 (3H, t, J=7.3 Hz), 1.22-1.45 (2H, m), 1.68-1.88 (2H, m), 2.48 (1H, dd, J=9.3, 13.8 Hz), 3.04-3.16 (2H, m), 3.17-3.35 (2H, m), 3.59 (6H, s), 3.74 (3H, s), 3.86 (3H, s), 4.94 (1H, dt, J=6.9, 6.9 Hz), 4.98 (1H, d, J=14.6 Hz), 5.00 (1H, d, J=14.6 Hz), 5.08 (1H, d, J=16.6 Hz), 5.32 (1H, d, J=16.6 Hz), 6.05 (2H, s), 6.74 (1H, d, J=8.9 Hz), 6.83 (1H, d, J=2.4 Hz), 7.19 (1H, dd, J=2.4, 8.9 Hz), 7.57 (1H, dd, J=1.6, 8.1 Hz), 7.68 (1H, d, J=8.1 Hz), 7.72 (1H, d, J=1.6 Hz), 9.57 (1H, d, J=6.9 Hz)

MS: 799 (M+H)$^+$

Example 28

2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid sesquitosylate (compound 28)

Step (1): To the compound S30 (2.9 g) in a tetrahydrofuran (60 ml) and methanol (60 ml) solution, O-ethyl hydroxylamine hydrochloride (0.53 g), triethylamine (0.76 ml), and mercury acetate (1.39 g) were successively added under ice cooling, and the mixture was stirred at that temperature for 30 minutes and at room temperature for 2 hours. To the reaction solution, O-ethyl hydroxylamine hydrochloride (0.18 g), triethylamine (0.25 ml), and mercury acetate (0.46 g) were successively added, and the mixture was stirred at room temperature for 30 minutes. The reaction mixture was filtered, then the filtrate was concentrated to obtain tert-butyl 4-[(1R)-1-({[(6S)-6-(5-chloro-2-methoxybenzyl)-3-(ethoxyimino)-7-oxo-1-(2,4,6-trimethoxybenzyl)-1,4-diazepan-1-yl]carbonyl}amino)butyl]-2-nitrobenzoate (compound 28a) as a crude product (4.28 g).

Step (2): To the compound 28a crude product obtained at Step (1) (4.28 g), trifluoroacetic acid (50 ml) was added, and the mixture was stirred at room temperature for 3 hours. The reaction solution was cooled to 0° C., zinc powder (8.5 g) was added, and the mixture was stirred at room temperature for 2 hours. The insolubles were filtered out, and the filtrate was concentrated. The residue was diluted with ethyl acetate, successively washed with saturated aqueous ammonium chloride solution and brine, dried over sodium sulfate, then concentrated. The residue was purified by flash column chromatography (silica gel, chloroform/ethyl acetate/methanol/acetic acid=15/15/1/0.1) to obtain 2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid (compound 12).

Step (3): The compound 12 obtained at Step (2) (503 mg) was dissolved in acetonitrile (0.5 ml), p-toluenesulfonic acid monohydrate in an acetonitrile solution (0.69M, 2 ml) was added at 60° C., then the mixture was allowed to gradually cool to room temperature. After 3 hours, the mixture was cooled to 0° C. and further stirred for 1.5 hours, then the precipitates were collected by filtration to obtain the title compound (535 mg) as a colorless crystals.

$^1$H-NMR (DMSO-d$_6$) δ 0.88 (3H, t, J=7.3 Hz), 1.14 (3H, t, J=7.1 Hz), 1.17-1.39 (2H, m), 1.56-1.82 (2H, m), 2.29 (4.5H, s), 2.69 (1H, dd, J=9.3, 14.2 Hz), 2.99 (1H, dd, J=4.5, 14.2 Hz), 3.14-3.40 (2H, m), 3.80 (3H, s), 3.82-4.05 (3H, m), 4.58-4.71 (1H, m), 4.71-4.89 (1H, m), 4.89-5.03 (1H, m), 6.47-6.57 (1H, m), 6.69 (1H, br.s), 7.03 (1H, d, J=8.8 Hz), 7.11 (3H, d, J=7.7 Hz), 7.29 (1H, dd, J=2.5, 8.8 Hz), 7.35 (1H, d, J=2.5 Hz), 7.47 (3H, d, J=7.7 Hz), 7.67 (1H, d, J=8.3 Hz), 9.33 (1H, d, J=7.7 Hz)

MS: 560 (M+H)$^+$

Reference Example 31 tert-butyl 4-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]ethyl}-2-nitrobenzoate (compound S31)

Step (1): Instead of the starting material, that is, the compound S4, of Reference Example 19, the compound S10 was used for a similar procedure as in Reference Example 19 to obtain tert-butyl 4-[(1R)-1-isocyanatoethyl]-2-nitrobenzoate (compound S31a).

Step (2): Instead of the reaction agent, that is, the compound S19, of Reference Example 20, the compound S31a was used for a similar procedure as in Reference Examples 20 and 22 to obtain the title compound.

$^1$H-NMR (CDCl$_3$) δ 1.51-1.56 (12H, m), 2.34 (1H, dd, J=9.7, 13.8 Hz), 3.10 (1H, dd, J=4.5, 13.8 Hz), 3.13-3.29 (2H, m), 3.32-3.47 (1H, m), 3.68 (6H, s), 3.76 (3H, s), 3.86 (3H, s), 4.87 (1H, d, J=16.6 Hz), 4.93-5.19 (3H, m), 5.56 (1H, d, J=16.6 Hz), 6.09 (2H, s), 6.74 (1H, d, J=8.8 Hz), 6.78 (1H, d, J=2.7 Hz), 7.19 (1H, dd, J=2.7, 8.8 Hz), 7.61 (1H, dd, J=1.6, 8.1 Hz), 7.69 (1H, d, J=8.1 Hz), 7.77 (1H, d, J=1.6 Hz), 9.50 (1H, d, J=6.9 Hz)

MS: 771 (M+H)$^+$

Example 29

2-amino-4-{(1R)-1-[({(6R)-6-(5-chloro-2-methoxybenzyl)-3-[(4-fluorophenoxy)imino]-7-oxo-1,4-diazepan-1-yl}carbonyl)amino]ethyl}benzoic acid (compound 29)

Step (1): To the compound S31 (218 mg) in a tetrahydrofuran (2 ml) and methanol (4 ml) solution, O-(4-fluorophenyl)hydroxylamine hydrochloride (70 mg), triethylamine (59 μl), and mercury acetate (110 mg) were successively added under ice cooling, and the mixture was stirred at that temperature for 1 hour. The reaction mixture was filtered, then the filtrate was concentrated to obtain tert-butyl 4-{(1R)-1-[({(6R)-6-(5-chloro-2-methoxybenzyl)-3-[(4-fluorophenoxy)imino]-7-oxo-4-(2,4,6-trimethoxybenzyl)-1,4-diazepan-1-yl}carbonyl)amino]ethyl}-2-nitrobenzoate (compound 29a) as a crude product.

Step (2): To the compound 29a crude product obtained at Step (1), anisole (0.31 ml) and trifluoroacetic acid (2 ml) were added, and the mixture was stirred at room temperature for 15 minutes. The reaction mixture was cooled to 0° C., then zinc powder (440 mg) was added, and the mixture was stirred at that temperature for 20 minutes. Then the insolubles were filtered out, and the filtrate was concentrated. The residue was diluted with ethyl acetate, washed with saturated aqueous ammonium chloride solution and brine, dried over sodium sulfate, then concentrated. The residue was purified by flash column chromatography (silica gel, chloroform/ethyl acetate=4/1 to/2/1) to obtain the title compound (98 mg).

$^1$H-NMR (DMSO-d$_6$) δ 1.39 (3H, d, J=6.9 Hz), 2.70 (1H, dd, J=9.1, 14.3 Hz), 2.98 (1H, dd, J=4.5, 14.3 Hz), 3.11-3.26 (2H, m), 3.80 (3H, s), 3.84-4.01 (1H, m), 4.66 (1H, d, J=16.2 Hz), 4.75 (1H, m), 4.93 (1H, d, J=16.2 Hz), 6.47 (1H, dd, J=1.6, 8.3 Hz), 6.68 (1H, d, J=1.6 Hz), 6.95 (1H, s), 6.98-7.14

(5H, m), 7.28 (1H, dd, J=2.6, 8.9 Hz), 7.35 (1H, d, J=2.6 Hz), 7.66 (1H, d, J=8.3 Hz), 9.40 (1H, d, J=7.3 Hz)

MS: 598 (M+H)+

Example 30

2-amino-4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}benzoic acid (compound 30)

Instead of the reaction agent, that is, O-(4-fluorophenyl)hydroxylamine hydrochloride, in Example 29, O-(3,5-difluorophenyl)hydroxylamine hydrochloride was used for a similar procedure as in Example 29 to obtain the title compound.

1H-NMR (DMSO-d6) δ 1.39 (3H, d, J=6.9 Hz), 2.69 (1H, dd, J=9.3, 14.5 Hz), 2.98 (1H, dd, J=4.7, 14.5 Hz), 3.19 (2H, m), 3.80 (3H, s), 3.84-4.03 (1H, m), 4.59-4.83 (2H, m), 4.93 (1H, d, J=16.2 Hz), 6.48 (1H, dd, J=1.8, 8.2 Hz), 6.61-6.84 (4H, m), 7.02 (1H, d, J=8.8 Hz), 7.11 (1H, s), 7.28 (1H, dd, J=2.5, 8.8 Hz), 7.35 (1H, d, J=2.5 Hz), 7.66 (1H, d, J=8.2 Hz), 9.38 (1H, d, J=7.3 Hz)

MS: 616 (M+H)+

Example 31

2-amino-4-{(1R)-1-[({(6R)-6-(5-chloro-2-methoxybenzyl)-7-oxo-3-[(pyridin-2-yloxy)imino]-1,4-diazepan-1-yl}carbonyl)amino]ethyl}benzoic acid (compound 31)

Instead of the reaction agent, that is, O-(4-fluorophenyl)hydroxylamine hydrochloride, in Example 29, O-(pyridin-2-yl)hydroxylamine hydrochloride was used for a similar procedure as in Example 29 to obtain the title compound.

1H-NMR (DMSO-d6) δ 1.39 (3H, d, J=6.9 Hz), 2.68 (1H, dd, J=8.5, 14.3 Hz), 2.97 (1H, dd, J=5.1, 14.3 Hz), 3.06-3.26 (2H, m), 3.79 (3H, s), 3.86-4.02 (1H, m), 4.62-4.85 (2H, m), 4.95 (1H, d, J=16.2 Hz), 6.46 (1H, dd, J=1.4, 8.3 Hz), 6.66 (1H, s), 6.90-7.08 (3H, m), 7.17 (1H, d, J=8.3 Hz), 7.26 (1H, dd, J=2.6, 8.9 Hz), 7.33 (1H, d, J=2.6 Hz), 7.65 (1H, d, J=8.3 Hz), 7.69-7.80 (1H, m), 8.13 (1H, dd, J=2.0, 4.9 Hz), 9.38 (1H, d, J=7.3 Hz)

MS: 581 (M+H)+

Example 32

2-amino-4-[(1R)-1-({[(6R)-6-(5-chloro-2-methoxybenzyl)-7-oxo-3-(phenoxyimino)-1,4-diazepan-1-yl]carbonyl}amino)ethyl]benzoic acid (compound 32)

Instead of the reaction agent, that is, O-(4-fluorophenyl)hydroxylamine hydrochloride, in Example 29, O-phenyl hydroxylamine hydrochloride was used for a similar procedure as in Example 29 to obtain the title compound.

1H-NMR (DMSO-d6) δ 1.39 (3H, d, J=7.1 Hz), 2.70 (1H, dd, J=8.9, 14.1 Hz), 2.98 (1H, dd, J=4.7, 14.1 Hz), 3.09-3.25 (2H, m), 3.80 (3H, s), 3.85-4.01 (1H, m), 4.67 (1H, d, J=16.4 Hz), 4.74 (1H, m), 4.95 (1H, d, J=16.4 Hz), 6.47 (1H, dd, J=1.7, 8.4 Hz), 6.68 (1H, d, J=1.7 Hz), 6.84-6.97 (2H, m), 7.00-7.07 (3H, m), 7.20-7.32 (3H, m), 7.35 (1H, d, J=2.4 Hz), 7.66 (1H, d, J=8.4 Hz), 9.40 (1H, d, J=7.3 Hz)

MS: 580 (M+H)+

Reference Example 32 tert-butyl-4-[(1R)-1-({[(6S)-6-(5-chloro-2-methoxybenzyl)-4-methyl-7-oxo-3-thioxo-1,4-diazepan-1-yl]carbonyl}amino)butyl]-2-nitrobenzoate (compound S32)

Instead of the starting material, that is, (6R)-6-(5-chloro-2-methoxybenzyl)-1-(2,4,6-trimethoxybenzyl)-1,4-diazepan-2,5-dione, of Reference Example 20, the compound S17 was used, and instead of the reaction agent, that is, the compound S19, the compound S25a was used for a similar procedure as in Reference Examples 20 and 22 to obtain the title compound.

1H-NMR (CDCl3) δ 0.94 (3H, t, J=7.3 Hz), 1.23-1.46 (2H, m), 1.56 (9H, s), 1.68-1.91 (2H, m), 2.63 (1H, dd, J=7.7, 14.0 Hz), 3.21 (1H, dd, J=5.5, 14.0 Hz), 3.35 (3H, s), 3.42-3.49 (1H, m), 3.55-3.65 (1H, m), 3.78-3.90 (4H, m), 4.59 (1H, d, J=17.7 Hz), 4.94 (1H, dt, J=7.3, 7.3 Hz), 5.92 (1H, d, J=17.7 Hz), 6.82 (1H, d, J=8.7 Hz), 7.17 (1H, d, J=2.6 Hz), 7.24 (1H, dd, J=2.6, 8.7 Hz), 7.58 (1H, dd, J=1.6, 8.1 Hz), 7.68 (1H, d, J=8.1 Hz), 7.73 (1H, d, J=1.6 Hz), 9.45 (1H, d, J=7.3 Hz)

MS: 633 (M+H)+

Example 33

2-amino-4-[(1R)-1-({[(6S)-6-(5-chloro-2-methoxybenzyl)-3-(ethoxyimino)-4-methyl-7-oxo-1,4-diazepan-1-yl]carbonyl}amino)butyl]benzoic acid (compound 33)

Instead of the starting material, that is, the compound S25, of Example 12, the compound S32 was used for a similar procedure as in Example 12 to obtain the title compound.

1H-NMR (DMSO-d6) δ 0.86 (3H, t, J=7.3 Hz), 1.14 (3H, t, J=7.1 Hz), 1.17-1.33 (2H, m), 1.56-1.78 (2H, m), 2.47 (3H, s), 2.62-2.76 (2H, m), 2.88-3.05 (2H, m), 3.61-3.74 (1H, m), 3.79 (3H, s), 3.82-3.95 (2H, m), 4.20 (1H, d, J=19.1 Hz), 4.60 (1H, dt, J=7.7, 7.7 Hz), 5.90 (1H, d, J=19.1 Hz), 6.44 (1H, d, J=8.1 Hz), 6.64 (1H, s), 6.98 (1H, d, J=8.5 Hz), 7.25 (1H, dd, J=2.4, 8.5 Hz), 7.30 (1H, d, J=2.4 Hz), 7.65 (1H, d, J=8.1 Hz), 9.52 (1H, d, J=7.7 Hz)

MS: 574 (M+H)+

Example 34

2-amino-4-[(1R)-1-({[(6S)-6-(5-chloro-2-methoxybenzyl)-3-(methoxyimino)-4-methyl-7-oxo-1,4-diazepan-1-yl]carbonyl}amino)butyl]benzoic acid (compound 34)

Instead of the starting material, that is, the compound S25, of Example 12, the compound S32 was used, and instead of the reaction agent, that is, O-ethyl hydroxylamine hydrochloride, O-methyl hydroxylamine hydrochloride was used for a similar procedure as in Example 12 to obtain the title compound.

1H-NMR (DMSO-d6) δ 0.86 (3H, t, J=7.3 Hz), 1.23 (2H, dt, J=8.7, 15.9 Hz), 1.57-1.78 (2H, m), 2.48 (3H, s), 2.63-2.78 (2H, m), 2.90-3.06 (2H, m), 3.65 (3H, s), 3.66-3.75 (1H, m), 3.79 (3H, s), 4.20 (1H, d, J=18.9 Hz), 4.60 (1H, dt, J=7.7, 7.7 Hz), 5.89 (1H, d, J=18.9 Hz), 6.44 (1H, d, J=8.1 Hz), 6.63 (1H, s), 6.98 (1H, d, J=8.7 Hz), 7.25 (1H, dd, J=2.4, 8.7 Hz), 7.29 (1H, d, J=2.4 Hz), 7.65 (1H, d, J=8.1 Hz), 9.51 (1H, d, J=7.7 Hz)

MS: 560 (M+H)+

Example 35

4-[(1R)-1-({[(6S)-6-(5-chloro-2-methoxybenzyl)-3-(ethoxyimino)-7-oxo-1,4-diazepan-1-yl]carbonyl}amino)butyl]-2-nitrobenzoic acid hydrochloride (compound 35)

To the compound 28a obtained at Example 28, Step (1) (300 mg), anisole (0.395 ml) and 4M hydrochloric acid in ethyl acetate solution (3 ml) were added, and the mixture was stirred at room temperature for 17 hours. The precipitated crystals were collected by filtration to obtain the title compound (214 mg) as a colorless crystals.

$^1$H-NMR (DMSO-$d_6$) δ 0.89 (3H, t, J=7.5 Hz), 1.09 (3H, t, J=6.9 Hz), 1.20-1.43 (2H, m), 1.66-1.89 (2H, m), 2.63-2.73 (1H, m), 2.99 (1H, dd, J=4.9, 14.2 Hz), 3.12-3.21 (2H, m), 3.75-3.89 (3H, m), 3.80 (3H, s), 4.60 (1H, d, J=17.0 Hz), 4.79 (1H, d, J=17.0 Hz), 4.89 (1H, dt, J=7.3, 7.3 Hz), 7.01 (1H, d, J=8.9 Hz), 7.28 (1H, dd, J=2.4, 8.9 Hz), 7.33 (1H, d, J=2.4 Hz), 7.74 (1H, dd, J=1.6, 8.1 Hz), 7.83 (1H, d, J=8.1 Hz), 7.96 (1H, d, J=1.6 Hz), 9.42 (1H, d, J=7.3 Hz)

MS: 590 (M+H)$^+$

Example 36

2-amino-4-[(1R)-1-({[(3Z,6S)-6-(5-chloro-2-methoxybenzyl)-3-(ethoxyimino)-7-oxo-1,4-diazepan-1-yl]carbonyl}amino)butyl]benzoic acid acetic acid solvate (compound 36)

To the compound 35 (874 mg) in an ethyl acetate (2.7 ml) and acetic acid (1.4 ml) suspension, zinc powder was added under ice cooling, and the mixture was stirred at that temperature for 10 minutes and at room temperature for 4 hours.

The reaction mixture was diluted with ethyl acetate (10 ml) and filtered by a glass filter spread with Celite®, and further the residue was washed with ethyl acetate (20 ml). The filtrate and the washings were combined, then successively washed with saturated aqueous ammonium chloride solution and brine, dried over sodium sulfate, then concentrated. The concentrated residue was purified by flash column chromatography to obtain 2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid (compound 12) (698 mg). To the compound 12 (558 mg) thus obtained, acetic acid (1.1 ml) was added and the mixture was stirred at room temperature for 30 minutes. Then water (2.75 ml) was added, and the mixture was stirred for 10 minutes. Further, acetic acid/water (2/5, 2.5 ml) was added, and the mixture was stirred for 15 minutes, then the mixture was cooled to 0° C. and stirred for 30 minutes. The precipitated crystals were collected by filtration to obtain the title compound (543 mg) as a light yellow crystals.

$^1$H-NMR (DMSO-$d_6$) δ 0.87 (3H, t, J=7.3 Hz), 1.08 (3H, t, J=7.1 Hz), 1.14-1.35 (2H, m); 1.55-1.77 (2H, m); 2.66 (1H, dd, J=8.9, 14.6 Hz), 2.95 (1H, dd, J=4.9, 14.6 Hz), 2.98-3.07 (1H, m); 3.08-3.19 (1H, m); 3.70-3.92 (6H, m); 4.48 (1H, d, J=15.8 Hz), 4.62 (1H, dt, J=7.7, 7.7 Hz), 4.79 (1H, d, J=15.8 Hz), 6.14 (1H, s); 6.44 (1H, dd, J=1.6, 8.5 Hz), 6.63 (1H, d, J=1.6 Hz), 7.00 (1H, d, J=8.9 Hz), 7.27 (1H, dd, J=2.6, 8.9 Hz), 7.31 (1H, d, J=2.6 Hz), 7.65 (1H, d, J=8.5 Hz), 9.46 (1H, d, J=7.7 Hz)

MS: 560 (M+H)$^+$

Reference Example 33 tert-butyl 5-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]-2-thiophene carboxylate (compound S33)

Step (1): Instead of the starting material, that is, the compound S4, of Reference Example 19, the compound S90 described in WO 06-059801A, that is, tert-butyl 5-(1-aminopropyl)-2-thiophene carboxylate hydrochloride was used for a similar procedure as in Reference Example 19 to obtain tert-butyl 5-(1-isocyanatopropyl)-2-thiophene carboxylate hydrochloride (compound S33a).

Step (2): Instead of the reaction agent, that is, the compound S19, of Reference Example 20, the compound S33a was used for a similar procedure as in Reference Example 20 to obtain tert-butyl 5-[(1R)-1-({[(6R)-6-(5-chloro-2-methoxybenzyl)-3,7-dioxo-4-(2,4,6-trimethoxybenzyl)-1,4-diazepan-1-yl]carbonyl}amino)propyl]-2-thiophene carboxylate (compound S33b) and tert-butyl 5-[(1S)-1-({[(6R)-6-(5-chloro-2-methoxybenzyl)-3,7-dioxo-4-(2,4,6-trimethoxybenzyl)-1,4-diazepan-1-yl]carbonyl}amino)propyl]-2-thiophene carboxylate (compound S33c).

Step (3): Instead of the starting material, that is, the compound S21, of Reference Example 22, the compound S33b was used for a similar procedure as in Reference Example 22 to obtain the title compound.

$^1$H-NMR (CDCl$_3$) δ 0.97 (3H, t, J=7.5 Hz), 1.85-2.01 (2H, m), 2.36 (1H, dd, J=9.7, 13.8 Hz), 3.08 (1H, dd, J=4.1, 13.8 Hz), 3.12-3.42 (3H, m), 3.67 (6H, s), 3.76 (3H, s), 3.86 (3H, s), 4.86-5.18 (4H, m), 5.57 (1H, d, J=16.6 Hz), 6.09 (2H, s), 6.74 (1H, d, J=8.9 Hz), 6.77 (1H, d, J=2.6 Hz), 6.95 (1H, dd, J=0.8, 3.9 Hz), 7.18 (1H, dd, J=2.6, 8.9 Hz), 7.56 (1H, d, J=3.9 Hz), 9.44 (1H, d, J=7.7 Hz)

MS: 746 (M+H)$^+$

Example 37

5-[(1R)-1-({[(6R)-6-(5-chloro-2-methoxybenzyl)-7-oxo-3-(phenoxyimino)-1,4-diazepan-1-yl]carbonyl}amino)propyl]thiophene-2-carboxylic acid (compound 37)

Instead of the starting material, that is, the compound S27, of Example 23, the compound S33 was used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (DMSO-$d_6$) δ 0.90 (3H, t, J=7.3 Hz), 1.82-1.96 (2H, m), 2.69 (1H, dd, J=8.9, 14.2 Hz), 2.99 (1H, dd, J=4.5, 14.2 Hz), 3.11-3.26 (2H, m), 3.80 (3H, s), 3.85-3.99 (1H, m), 4.70 (1H, d, J=16.2 Hz), 4.94 (1H, d, J=16.2 Hz), 5.01 (1H, dt, J=7.7, 7.7 Hz), 6.84-6.97 (2H, m), 6.98-7.12 (4H, m), 7.19-7.31 (3H, m), 7.34 (1H, d, J=2.8 Hz), 7.59 (1H, d, J=3.7 Hz), 9.48 (1H, d, J=7.7 Hz), 12.82 (1H, br.s)

MS: 585 (M+H)$^+$

Reference Example 34 tert-butyl 4-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]propyl}-2-fluorobenzoate (compound S34)

Step (1): Instead of the starting material, that is, the compound S4, of Reference Example 19, the compound S81 described in WO 06-059801A, that is, tert-butyl 4-(1-aminopropyl)-2-fluorobenzoate hydrochloride, was used for a similar reaction as in Reference Example 19 to obtain tert-butyl 4-(1-isocyanatopropyl)-2-fluorobenzoate (compound S34a).

Step (2): Instead of the reaction agent, that is, the compound S19, of Reference Example 20, the compound S34a was used for a similar reaction as in Reference Example 20 to obtain tert-butyl 4-{(1R)-1-[({(6R)-6-(5-chloro-2-methoxybenzyl)-3,7-dioxo-4-(2,4,6-trimethoxybenzyl)-1,4-diazepan-1-yl}carbonyl)amino]propyl}-2-fluorobenzoate (compound S34b) and tert-butyl 4-{(1S)-1-[({(6R)-6-(5-chloro-2-methoxybenzyl)-3,7-dioxo-4-(2,4,6-trimethoxybenzyl)-1,4-diazepan-1-yl}carbonyl)amino]propyl}-2-fluorobenzoate (compound S34c).

Step (3): Instead of the starting material, that is, the compound S21, of Reference Example 22, the compound S34b was used for a similar reaction as in Reference Example 22 to obtain the title compound.

$^1$H-NMR (CDCl$_3$) δ 0.91 (3H, t, J=7.3 Hz), 1.57-1.62 (9H, m), 1.72-1.91 (2H, m), 2.37 (1H, dd, J=9.7, 13.8 Hz), 3.10 (1H, dd, J=4.1, 13.8 Hz), 3.13-3.30 (2H, m), 3.31-3.47 (1H, m), 3.67 (6H, s), 3.76 (3H, s), 3.86 (3H, s), 4.75-4.91 (2H, m), 4.95 (1H, d, J=14.2 Hz), 5.08 (1H, J=14.2 Hz), 5.58 (1H, d, J=16.6 Hz), 6.09 (2H, s), 6.75 (1H, d, J=8.7 Hz), 6.78 (1H, d, J=2.4 Hz), 7.02 (1H, dd, J=1.4, 11.6 Hz), 7.11 (1H, dd, J=1.6, 8.0 Hz), 7.19 (1H, dd, J=2.4, 8.7 Hz), 7.82 (1H, t, J=8.0 Hz), 9.50 (1H, d, J=7.3 Hz)

MS: 758 (M+H)$^+$

Example 38

4-{(1R)-1-[({(6R)-6-(5-chloro-2-methoxybenzyl)-3-[(4-fluorophenoxy)imino]-7-oxo-1,4-diazepan-1-yl}carbonyl)amino]propyl}-2-fluorobenzoic acid (compound 38)

Instead of the starting material, that is, the compound S27, of Example 23, the compound S34 was used, and instead of the reaction agent, that is, O-ethyl hydroxylamine hydrochloride, O-(4-fluorophenyl)hydroxylamine hydrochloride was used for a similar reaction as in Example 23 to obtain the title compound.

$^1$H-NMR (DMSO-d$_6$) δ 0.85 (3H, t, J=7.3 Hz), 1.72-1.89 (2H, m), 2.72 (1H, dd, J=9.1, 14.1 Hz), 3.01 (1H, dd, J=4.9, 14.1 Hz), 3.12-3.25 (2H, m), 3.81 (3H, s), 3.84-4.00 (1H, m), 4.65 (1H, d, J=16.2 Hz), 4.75 (1H, dt, J=7.1, 7.1 Hz), 4.87 (1H, d, J=16.2 Hz), 6.95 (1H, s), 6.98-7.14 (5H, m), 7.19-7.32 (3H, m), 7.35 (1H, d, J=2.8 Hz), 7.83 (1H, t, J=7.7 Hz), 9.47 (1H, d, J=7.1 Hz), 13.14 (1H, br.s)

MS: 615 (M+H)$^+$

Example 39

4-[(1R)-1-({[(6R)-6-(5-chloro-2-methoxybenzyl)-7-oxo-3-(phenoxyimino)-1,4-diazepan-1-yl]carbonyl}amino)propyl]-2-fluorobenzoic acid (compound 39)

Instead of the starting material, that is, the compound S27, of Example 23, the compound S34 was used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (DMSO-d$_6$) δ 0.85 (3H, t, J=7.3 Hz), 1.72-1.87 (2H, m), 2.72 (1H, dd, J=9.1, 14.3 Hz), 3.01 (1H, dd, J=4.9, 14.3 Hz), 3.11-3.24 (2H, m), 3.81 (3H, s), 3.85-3.98 (1H, m), 4.66 (1H, d, J=16.0 Hz), 4.75 (1H, dt, J=7.3, 7.3 Hz), 4.88 (1H, d, J=16.0 Hz), 6.81-6.96 (2H, m), 6.96-7.10 (3H, m), 7.18-7.33 (5H, m), 7.35 (1H, d, J=2.8 Hz), 7.82 (1H, t, J=7.9 Hz), 9.47 (1H, d, J=7.3 Hz), 13.20 (1H, br.s)

MS: 597 (M+H)$^+$

Reference Example 35 tert-butyl(4-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]ethyl}phenyl)acetate (compound S35)

Step (1): Instead of the starting material, that is, the compound S4, of Reference Example 19, tert-butyl[4-(1-aminoethyl)phenyl]acetate was used for a similar reaction as in Reference Example 19 to obtain tert-butyl[4-(1-isocyanatoethyl)phenyl]acetate (compound S35a).

Step (2): Instead of the reaction agent, that is, the compound S19, of Reference Example 20, the compound S35a was used for a similar procedure as in Reference Example 20 to obtain tert-butyl(4-{(1R)-1-[({(6R)-6-(5-chloro-2-methoxybenzyl)-3,7-dioxo-4-(2,4,6-trimethoxybenzyl)-1,4-diazepan-1-yl}carbonyl)amino]ethyl}phenyl)acetate (compound S35b) and tert-butyl(4-{(1S)-1-[({(6R)-6-(5-chloro-2-methoxybenzyl)-3,7-dioxo-4-(2,4,6-trimethoxybenzyl)-1,4-diazepan-1-yl}carbonyl)amino]ethyl}phenyl)acetate (compound S35c).

Step (3): Instead of the starting material, that is, the compound S21, of Reference Example 22, the compound S35b was used for a similar reaction as in Reference Example 22 to obtain the title compound.

$^1$H-NMR (CDCl$_3$) δ 1.44 (9H, s), 1.51 (3H, d, J=6.9 Hz), 2.34 (1H, dd, J=9.7, 13.8 Hz), 3.07 (1H, dd, J=4.1, 13.8 Hz), 3.11-3.27 (2H, m), 3.29-3.39 (1H, m), 3.50 (2H, s), 3.66 (6H, s), 3.75 (3H, s), 3.86 (3H, s), 4.87 (1H, d, J=17.0 Hz), 4.94 (1H, d, J=14.2 Hz), 5.02-5.14 (2H, m), 5.61 (1H, d, J=17.0 Hz), 6.08 (2H, s), 6.74 (1H, d, J=8.7 Hz), 6.78 (1H, d, J=2.8 Hz), 7.18 (1H, dd, J=2.8, 8.7 Hz), 7.21-7.25 (2H, m), 7.27-7.31 (2H, m), 9.38 (1H, d, J=7.3 Hz)

MS: 740 (M+H)$^+$

Example 40

(4-{(1R)-1-[({(6R)-6-(5-chloro-2-methoxybenzyl)-3-[(4-fluorophenoxy)imino]-7-oxo-1,4-diazepan-1-yl}carbonyl)amino]ethyl}phenyl)acetic acid (compound 40)

Instead of the starting material, that is, the compound S27, of Example 23, the compound S35 was used, and instead of the reaction agent, that is, O-ethyl hydroxylamine hydrochloride, O-(4-fluorophenyl)hydroxylamine hydrochloride was used for a similar reaction as in Example 23 to obtain the title compound.

$^1$H-NMR (DMSO-d$_6$) δ 1.43 (3H, d, J=6.9 Hz), 2.69 (1H, dd, J=9.1, 14.4 Hz), 2.97 (1H, dd, J=4.5, 14.4 Hz), 3.12-3.25 (2H, m), 3.53 (2H, s), 3.80 (3H, s), 3.85-3.96 (1H, m), 4.64 (1H, d, J=16.2 Hz), 4.82-4.98 (2H, m), 6.95 (1H, br.s), 6.98-7.13 (5H, m), 7.19-7.24 (2H, m), 7.24-7.30 (3H, m), 7.34 (1H, d, J=2.8 Hz), 9.42 (1H, d, J=7.3 Hz), 12.41 (1H, br.s)

MS: 597 (M+H)$^+$

Example 41

(4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}phenyl)acetic acid (compound 41)

Instead of the starting material, that is, the compound S27, of Example 23, the compound S35 was used, and instead of the reaction agent, that is, O-ethyl hydroxylamine hydrochloride, O-(3,5-difluorophenyl)hydroxylamine hydrochloride was used for a similar reaction as in Example 23 to obtain the title compound.

$^1$H-NMR (DMSO-$d_6$) δ 1.43 (2H, d, J=6.9 Hz), 2.69 (1H, dd, J=8.9, 14.2 Hz), 2.97 (1H, dd, J=4.9, 14.2 Hz), 3.13-3.24 (2H, m), 3.53 (2H, s), 3.80 (3H, s), 3.85-3.98 (1H, m), 4.66 (1H, d, J=16.6 Hz), 4.80-4.98 (2H, m), 6.64-6.80 (3H, m), 7.01 (1H, d, J=8.5 Hz), 7.10 (1H, s), 7.19-7.25 (2H, m), 7.25-7.31 (3H, m), 7.34 (1H, d, J=2.8 Hz), 9.40 (1H, d, J=7.7 Hz), 12.27 (1H, br.s)

MS: 615 (M+H)$^+$

Example 42

(4-{(1R)-1-[({(6R)-6-(5-chloro-2-methoxybenzyl)-7-oxo-3-[(pyridin-2-yloxy)imino]-1,4-diazepan-1-yl}carbonyl)amino]ethyl}phenyl)acetic acid (compound 42)

Instead of the starting material, that is, the compound S27, of Example 23, the compound S35 was used, and instead of the reaction agent, that is, O-ethyl hydroxylamine hydrochloride, O-(pyridin-2-yl)hydroxylamine hydrochloride was used for a similar reaction as in Example 23 to obtain the title compound.

$^1$H-NMR (DMSO-$d_6$) δ 1.44 (3H, d, J=7.1 Hz), 2.68 (1H, dd, J=8.5, 14.6 Hz), 2.97 (1H, dd, J=5.3, 14.6 Hz), 3.11-3.30 (2H, m), 3.54 (2H, s), 3.80 (3H, s), 3.86-3.99 (1H, m), 4.68 (1H, d, J=16.6 Hz), 4.88 (1H, dq, J=7.1, 7.1 Hz), 4.96 (1H, d, J=16.6 Hz), 6.96-7.03 (2H, m), 7.05 (1H, s), 7.15-7.20 (1H, m), 7.20-7.25 (2H, m), 7.25-7.31 (3H, m), 7.34 (1H, d, J=2.4 Hz), 7.77 (1H, ddd, J=2.0, 7.1, 8.3 Hz), 8.15 (1H, ddd, J=0.8, 2.0, 4.9 Hz), 9.42 (1H, d, J=7.1 Hz), 12.34 (1H, br.s)

MS: 580 (M+H)$^+$

Reference Example 36 tert-butyl(4-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]propyl}-2-(benzyloxy)benzoate (compound S36)

Step (1): Instead of the starting material, that is, the compound S4, of Reference Example 19, the compound S13 was used for a similar reaction as in Reference Example 19 to obtain tert-butyl 4-(1-isocyanatopropyl)-2-benzyloxybenzoate (compound S36a).

Step (2): Instead of the reaction agent, that is, the compound S19, of Reference Example 20, the compound S36a was used for a similar procedure as in Reference Example 20 to obtain tert-butyl 4-{(1R)-1-[({(6R)-6-(5-chloro-2-methoxybenzyl)-3,7-dioxo-4-(2,4,6-trimethoxybenzyl)-1,4-diazepan-1-yl}carbonyl)amino]propyl}-2-benzyloxybenzoate (compound S36b) and tert-butyl 4-{(1S)-1-[({(6R)-6-(5-chloro-2-methoxybenzyl)-3,7-dioxo-4-(2,4,6-trimethoxybenzyl)-1,4-diazepan-1-yl}carbonyl)amino]propyl}-2-benzyloxybenzoate (compound S36c).

Step (3): Instead of the starting material, that is, the compound S21, of Reference Example 22, the compound S36b was used for a similar reaction as in Reference Example 22 to obtain the title compound.

$^1$H-NMR (CDCl$_3$) δ 0.85 (3H, t, J=7.5 Hz), 1.51 (9H, s), 1.69-1.88 (2H, m), 2.35 (1H, dd, J=9.7, 13.8 Hz), 3.05-3.28 (3H, m), 3.32-3.45 (1H, m), 3.66 (6H, s), 3.76 (3H, s), 3.86 (3H, s), 4.74-4.87 (2H, m), 4.92 (1H, d, J=14.2 Hz), 5.05-5.21 (3H, m), 5.61 (1H, d, J=17.0 Hz), 6.09 (2H, s), 6.74 (1H, d, J=8.5 Hz), 6.79 (1H, d, J=2.4 Hz), 6.86-6.93 (2H, m), 7.18 (1H, dd, J=2.4, 8.5 Hz), 7.27-7.33 (1H, m), 7.33-7.40 (2H, m), 7.48 (2H, d, J=6.9 Hz), 7.68 (1H, d, J=7.7 Hz), 9.42 (1H, d, J=7.7 Hz)

MS: 846 (M+H)$^+$

Example 43

4-{(1R)-1-[({(6R)-6-(5-chloro-2-methoxybenzyl)-3-[(4-fluorophenoxy)imino]-7-oxo-1,4-diazepan-1-yl}carbonyl)amino]propyl}-2-hydroxybenzoic acid (compound 43)

Instead of the starting material, that is, the compound S27, of Example 23, the compound S36 was used and instead of the reaction agent, that is, O-ethyl hydroxylamine hydrochloride, O-(4-fluorophenyl)hydroxylamine hydrochloride was used for a similar reaction as in Example 23 to obtain the title compound.

$^1$H-NMR (DMSO-$d_6$) δ 0.83 (2H, t, J=7.1 Hz), 1.69-1.85 (1H, m), 2.72 (1H, dd, J=9.1, 14.2 Hz), 3.00 (1H, dd, J=4.1, 14.2 Hz), 3.15-3.23 (2H, m), 3.81 (3H, s), 3.85-3.98 (1H, m), 4.58-4.73 (2H, m), 4.91 (1H, d, J=16.6 Hz), 6.77 (2H, br.s), 6.95 (1H, br.s), 6.99-7.14 (5H, m), 7.28 (1H, dd, J=2.4, 8.5 Hz), 7.35 (1H, d, J=2.4 Hz), 9.47 (1H, d, J=7.7 Hz)

MS: 613 (M+H)$^+$

Example 44

4-{(1R)-1-[({(6R)-6-(5-chloro-2-methoxybenzyl)-3-[(3,5-difluorophenoxy)imino]-7-oxo-1,4-diazepan-1-yl}carbonyl)amino]propyl}-2-hydroxybenzoic acid (compound 44)

Instead of the starting material, that is, the compound S27, of Example 23, the compound S36 was used, and instead of the reaction agent, that is, O-ethyl hydroxylamine hydrochloride, O-(3,5-difluorophenyl)hydroxylamine hydrochloride was used for a similar reaction as in Example 23 to obtain the title compound.

$^1$H-NMR (DMSO-$d_6$) δ 0.83 (3H, t, J=6.9 Hz), 1.76 (2H, s), 2.71 (1H, dd, J=9.1, 14.4 Hz), 3.00 (1H, dd, J=4.7, 14.0 Hz), 3.16-3.23 (2H, m), 3.80 (3H, s), 3.85-3.98 (1H, m), 4.66 (1H, s), 4.91 (1H, d, J=16.6 Hz), 6.61-6.81 (5H, m), 7.02 (1H, d, J=8.7 Hz), 7.10 (1H, s), 7.28 (1H, dd, J=2.6, 8.7 Hz), 7.35 (1H, d, J=2.6 Hz), 7.69 (1H, br.s), 9.44 (1H, d, J=8.1 Hz)

MS: 631 (M+H)$^+$

Reference Example 37 tert-butyl(4-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]ethyl}-2-(benzyloxy)benzoate (compound S37)

Step (1): Instead of the starting material, that is, the compound S4, of Reference Example 19, the compound S12 was used for a similar reaction as in Reference Example 19 to obtain tert-butyl 4-(1-isocyanatoethyl)-2-benzyloxybenzoate (compound S37a).

Step (2): Instead of the reaction agent, that is, the compound S19, of Reference Example 20, the compound S37a was used for a similar procedure as in Reference Example 20 to obtain tert-butyl 4-{(1R)-1-[({(6R)-6-(5-chloro-2-methoxybenzyl)-3,7-dioxo-4-(2,4,6-trimethoxybenzyl)-1,4-diazepan-1-yl}carbonyl)amino]ethyl}-2-benzyloxybenzoate (compound S37b) and tert-butyl 4-{(1S)-1-[({(6R)-6-(5-chloro-2-methoxybenzyl)-3,7-dioxo-4-(2,4,6-trimethoxybenzyl)-1,4-diazepan-1-yl}carbonyl)amino]ethyl}-2-benzyloxybenzoate (compound S37c).

Step (3): Instead of the starting material, that is, the compound S21, of Reference Example 22, the compound S37b was used for a similar reaction as in Reference Example 22 to obtain the title compound.

$^1$H-NMR (CDCl$_3$) δ 1.47 (3H, d, J=6.9 Hz), 1.50 (9H, s), 2.35 (1H, dd, J=10.1, 14.0 Hz), 3.09 (1H, dd, J=4.3, 14.0 Hz), 3.12-3.28 (2H, m), 3.31-3.43 (1H, m), 3.66 (6H, s), 3.76 (3H, s), 3.86 (3H, s), 4.87 (1H, d, J=17.0 Hz), 4.96 (1H, d, J=14.2 Hz), 4.99-5.19 (4H, m), 5.58 (1H, d, J=17.0 Hz), 6.08 (2H, s), 6.74 (1H, d, J=8.5 Hz), 6.78 (1H, d, J=2.4 Hz), 6.91-6.98 (2H, m), 7.18 (1H, dd, J=2.4, 8.5 Hz), 7.27-7.33 (1H, m), 7.33-7.40 (2H, m), 7.48 (2H, d, J=7.3 Hz), 7.68 (1H, d, J=7.7 Hz), 9.38 (1H, d, J=7.3 Hz)

MS: 832 (M+H)$^+$

Example 45

4-{(1R)-1-[({(6R)-6-(5-chloro-2-methoxybenzyl)-3-[(4-fluorophenoxy)imino]-7-oxo-1,4-diazepan-1-yl}carbonyl)amino]ethyl}-2-hydroxybenzoate (compound 45)

Instead of the starting material, that is, the compound S27, of Example 23, the compound S37 was used, and instead of the reaction agent, that is, O-ethyl hydroxylamine hydrochloride, O-(4-fluorophenyl)hydroxylamine hydrochloride was used for a similar reaction as in Example 23 to obtain the title compound.

$^1$H-NMR (DMSO-d$_6$) δ 1.42 (3H, d, J=6.9 Hz), 2.70 (1H, dd, J=9.1, 14.4 Hz), 2.99 (1H, dd, J=4.9, 14.4 Hz), 3.11-3.24 (2H, m), 3.81 (3H, s), 3.85-3.98 (1H, m), 4.66 (1H, d, J=16.2 Hz), 4.77-4.98 (2H, m), 6.80 (2H, br.s), 6.95 (1H, br.s), 6.98-7.14 (5H, m), 7.28 (1H, dd, J=2.4, 8.7 Hz), 7.35 (1H, d, J=2.4 Hz), 7.71 (1H, br.s), 9.41 (1H, d, J=7.3 Hz)

MS: 599 (M+H)$^+$

Example 46

4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}-2-hydroxybenzoic acid (compound 46)

Instead of the starting material, that is, the compound S27, of Example 23, the compound S37 was used, and instead of the reaction agent, that is, O-ethyl hydroxylamine hydrochloride, O-(3,5-difluorophenyl)hydroxylamine hydrochloride was used for a similar reaction as in Example 23 to obtain the title compound.

$^1$H-NMR (DMSO-d$_6$) δ 1.42 (3H, d, J=6.9 Hz), 2.70 (1H, dd, J=9.1, 14.0 Hz), 2.99 (1H, dd, J=4.7, 14.0 Hz), 3.15-3.23 (2H, m), 3.80 (3H, s), 3.85-3.99 (1H, m), 4.68 (1H, d, J=16.6 Hz), 4.79-4.98 (2H, m), 6.64-6.89 (5H, m), 7.02 (1H, d, J=8.7 Hz), 7.10 (1H, br.s), 7.28 (1H, dd, J=2.4, 8.7 Hz), 7.35 (1H, d, J=2.4 Hz), 7.72 (1H, br.s), 9.39 (1H, d, J=6.9 Hz)

MS: 617 (M+H)$^+$

Reference Example 38 tert-butyl 5-{(1R)-1-[({(6R)-6-(5-chloro-2-methoxybenzyl)-7-oxo-3-thioxo-4-(2,4,6-trimethoxybenzyl)-1,4-diazepan-1-yl}carbonyl)amino]propyl}-2-(benzyloxy)benzoate (compound S38)

Step (1): Instead of the starting material, that is, the compound S4, of Reference Example 19, the compound S89 described in WO 06-059801A, that is, tert-butyl 5-(1-aminopropyl)-2-benzyloxybenzoate hydrochloride, was used for a similar reaction as in Reference Example 19 to obtain tert-butyl 5-(1-isocyanatopropyl)-2-benzyloxybenzoate (compound S38a).

Step (2): Instead of the reaction agent, that is, the compound S19, of Reference Example 20, the compound S38a was used for a similar procedure as in Reference Example 20 to obtain tert-butyl 5-{(1R)-1-[({(6R)-6-(5-chloro-2-methoxybenzyl)-3,7-dioxo-4-(2,4,6-trimethoxybenzyl)-1,4-diazepan-1-yl}carbonyl)amino]propyl}-2-benzyloxybenzoate (compound S38b) and tert-butyl 5-{(1S)-1-[({(6R)-6-(5-chloro-2-methoxybenzyl)-3,7-dioxo-4-(2,4,6-trimethoxybenzyl)-1,4-diazepan-1-yl}carbonyl)amino]propyl}-2-benzyloxybenzoate (compound S38c).

Step (3): Instead of the starting material, that is, the compound S21, of Reference Example 22, the compound S38b was used for a similar reaction as in Reference Example 22 to obtain the title compound.

$^1$H-NMR (CDCl$_3$) δ 0.89 (3H, t, J=7.3 Hz), 1.51 (9H, s), 1.72-1.94 (2H, m), 2.34 (1H, dd, J=9.7, 13.8 Hz), 3.08 (1H, dd, J=4.1, 13.8 Hz), 3.11-3.28 (2H, m), 3.28-3.43 (1H, m), 3.65 (6H, s), 3.75 (3H, s), 3.86 (3H, s), 4.71-4.98 (3H, m), 5.05-5.16 (3H, m), 5.60 (1H, d, J=17.0 Hz), 6.08 (2H, s), 6.74 (1H, d, J=8.8 Hz), 6.77 (1H, d, J=2.5 Hz), 6.93 (1H, d, J=8.5 Hz), 7.18 (1H, dd, J=2.5, 8.8 Hz), 7.27-7.42 (4H, m), 7.43-7.50 (2H, m), 7.61 (1H, d, J=2.4 Hz), 9.39 (1H, d, J=7.7 Hz)

MS: 846 (M+H)$^+$

Example 47

5-{(1R)-1-[({(6R)-6-(5-chloro-2-methoxybenzyl)-7-oxo-3-(phenoxyimino)-1,4-diazepan-1-yl}carbonyl)amino]propyl}-2-hydroxybenzoic acid (compound 47)

Instead of the starting material, that is, the compound S27, of Example 23, the compound S38 was used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (DMSO-d$_6$) δ 0.81 (3H, t, J=7.3 Hz), 1.63-1.89 (2H, m), 2.72 (1H, dd, J=9.3, 14.2 Hz), 2.98 (1H, dd, J=4.9, 14.2 Hz), 3.08-3.24 (2H, m), 3.80 (3H, s), 3.83-3.99 (1H, m), 4.55-4.71 (2H, m), 4.91 (1H, d, J=16.2 Hz), 6.84-6.96 (3H, m), 7.01 (1H, d, J=8.9 Hz), 7.05 (2H, d, J=7.7 Hz), 7.18-7.31 (3H, m), 7.34 (1H, d, J=2.2 Hz), 7.45 (1H, d, J=8.9 Hz), 7.71 (1H, d, J=2.2 Hz), 9.42 (1H, d, J=7.7 Hz)

MS: 595 (M+H)$^+$

Reference Example 39 tert-butyl 2-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]isonicotinate (compound S39)

Step (1): To the compound 5105 described in WO 06-059801A, that is, tert-butyl 2-[(1R)-1-aminopropyl]-isonicotinate D-tartrate (157 mg) in an N,N-dimethylformamide (1.5 ml) solution, triethylamine (0.113 ml) was added under ice cooling, and the mixture was stirred at that temperature for 5 minutes. To the reaction solution, the compound S141C described in WO 06-059801A, that is, (6R)-2-chlorophenyl 6-(5-chloro-2-methoxybenzyl)-3,7-dioxo-4-(2,4,6-trimethoxybenzyl)-1,4-diazepane-1-carboxylate (250 mg) and 4-dimethylaminopyridine (49 mg) were added, and the mixture was stirred at 0° C. for 18 hours. The reaction solution was diluted with ethyl acetate, then was successively washed with saturated aqueous ammonium chloride solution and brine. The organic layer was dried over anhydrous sodium sulfate, then was concentrated. The residue was purified by flash column chromatography (silica gel, hexane/ethyl acetate=1/1 to 1/2) to obtain tert-butyl 2-[(1R)-1-({[(6R)-6-(5-chloro-2-methoxybenzyl)-3,7-dioxo-4-(2,4,6-trimethoxybenzyl)-1,4-diazepan-1-yl]carbonyl}amino)propyl]isonicotinate (compound S39a) (210 mg).

Step (2): Instead of the starting material, that is, the compound S21, of Reference Example 22, the compound S39a was used for a similar reaction as in Reference Example 22 to obtain the title compound.

$^1$H-NMR (CDCl$_3$) δ 0.88 (3H, t, J=7.5 Hz), 1.61 (9H, s), 1.93 (2H, m), 2.39 (1H, dd, J=9.9, 14.0 Hz), 3.05-3.31 (3H, m), 3.31-3.45 (1H, m), 3.67 (6H, s), 3.76 (3H, s), 3.86 (3H, s), 4.80-4.98 (2H, m), 5.05 (1H, dt, J=7.7, 7.7 Hz), 5.13 (1H, d, J=14.2 Hz), 5.60 (1H, d, J=17.5 Hz), 6.09 (2H, s), 6.74 (1H, d, J=8.8 Hz), 6.79 (1H, d, J=2.7 Hz), 7.18 (1H, dd, J=2.7, 8.8 Hz), 7.67 (1H, dd, J=1.6, 4.9 Hz), 7.73 (1H, s), 8.71 (1H, dd, J=0.8, 4.9 Hz), 9.80 (1H, d, J=7.7 Hz)

MS: 741 (M+H)$^+$

Example 48

2-[(1R)-1-({[(6R)-6-(5-chloro-2-methoxybenzyl)-7-oxo-3-(phenoxyimino)-1,4-diazepan-1-yl]carbonyl}amino)propyl]isonicotinic acid (compound 48)

Instead of the starting material, that is, the compound S27, of Example 23, the compound S39 was used, and instead of the reaction agent, that is, O-ethyl hydroxylamine hydrochloride, O-phenyl hydroxylamine hydrochloride was used for a similar procedure as in Example 23 to obtain the title compound.

$^1$H-NMR (DMSO-d$_6$) δ 0.79 (3H, t, J=7.3 Hz), 1.77-1.89 (2H, m), 2.71 (1H, dd, J=8.9, 14.1 Hz), 3.00 (1H, dd, J=4.7, 14.1 Hz), 3.12-3.25 (2H, m), 3.81 (3H, s), 3.84-3.99 (1H, m), 4.66 (1H, d, J=16.2 Hz), 4.89-5.02 (2H, m), 6.85-6.96 (2H, m), 7.01 (1H, d, J=8.9 Hz), 7.03-7.09 (2H, m), 7.21-7.30 (3H, m), 7.35 (1H, d, J=2.4 Hz), 7.72 (1H, dd, J=1.6, 4.9 Hz), 7.81 (1H, br.s), 8.76 (1H, dd, J=0.8, 4.9 Hz), 9.78 (1H, d, J=7.7 Hz), 13.69 (1H, br.s)

MS: 580 (M+H)$^+$

Reference Example 40 tert-butyl 5-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]nicotinate (compound S40)

Instead of the starting material, that is, tert-butyl 2-[(1R)-1-aminopropyl]-isonicotinate D-tartrate, of Reference Example 39, the compound 5103 described in WO 06-059801A, that is, 5-[(1R)-1-aminopropyl]-nicotinate D-tartrate was used for a similar reaction as in Reference Example 39 to obtain the title compound.

MS: 741 (M+H)$^+$

Example 49

5-[(1R)-1-({[(6R)-6-(5-chloro-2-methoxybenzyl)-7-oxo-3-(phenoxyimino)-1,4-diazepan-1-yl]carbonyl}amino)propyl]nicotinic acid (compound 49)

Instead of the starting material, that is, the compound S27, of Example 23, the compound S40 was used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (DMSO-d$_6$) δ 0.86 (3H, t, J=7.3 Hz), 1.72-1.99 (2H, m), 2.72 (1H, dd, J=9.1, 14.3 Hz), 3.01 (1H, dd, J=4.9, 14.3 Hz), 3.12-3.23 (2H, m), 3.81 (3H, s), 3.84-4.04 (1H, m), 4.64 (1H, d, J=16.2 Hz), 4.71-4.95 (2H, m), 6.79-6.96 (2H, m), 6.96-7.08 (3H, m), 7.16-7.31 (3H, m), 7.35 (1H, d, J=2.8 Hz), 8.22 (1H, t, J=2.2 Hz), 8.78 (1H, d, J=2.2 Hz), 8.96 (1H, d, J=2.2 Hz), 9.50 (1H, d, J=6.9 Hz), 13.51 (1H, br.s)

MS: 580 (M+H)$^+$

Reference Example 41 tert-butyl 6-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]nicotinate (compound S41)

Instead of the starting material, that is, tert-butyl 2-[(1R)-1-aminopropyl]-isonicotinate D-tartrate, of Reference Example 39, the compound 5106 described in WO 06-059801A, that is, tert-butyl 6-[(1R)-1-aminopropyl]-nicotinate D-tartrate, was used for a similar reaction as in Reference Example 39 to obtain the title compound.

$^1$H-NMR (CDCl$_3$) δ 0.87 (3H, t, J=7.3 Hz), 1.59 (9H, s), 1.82-2.01 (2H, m), 2.40 (1H, dd, J=9.7, 14.2 Hz), 3.03-3.19 (1H, m), 3.19-3.43 (3H, m), 3.67 (6H, s), 3.75 (3H, s), 3.86 (3H, s), 4.83-4.96 (2H, m), 4.96-5.15 (2H, m), 5.58 (1H, d, J=17.0 Hz), 6.09 (2H, s), 6.74 (1H, d, J=8.8 Hz), 6.79 (1H, d, J=2.5 Hz), 7.18 (1H, dd, J=2.5, 8.8 Hz), 7.30 (1H, d, J=8.1 Hz), 8.19 (1H, dd, J=2.0, 8.1 Hz), 9.16 (1H, d, J=2.0 Hz), 9.84 (1H, d, J=6.9 Hz)

MS: 741 (M+H)$^+$

Example 50

6-[(1R)-1-({[(6R)-6-(5-chloro-2-methoxybenzyl)-7-oxo-3-(phenoxyimino)-1,4-diazepan-1-yl]carbonyl}amino)propyl]nicotinic acid (compound 51)

Instead of the starting material, that is, the compound S27, of Example 23, the compound S41 as used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (CDCl$_3$) δ 0.92 (3H, t, J=7.3 Hz), 1.88-2.06 (2H, m), 2.66 (1H, dd, J=8.3, 13.9 Hz), 3.24 (1H, dd, J=4.9, 13.9 Hz), 3.28-3.40 (1H, m), 3.40-3.53 (1H, m), 3.74 (1H, m), 3.83 (3H, s), 4.25 (1H, d, J=16.6 Hz), 5.01 (1H, dt, J=6.9, 6.9 Hz), 5.40 (1H, d, J=16.6 Hz), 5.55 (1H, br.s), 6.79 (1H, d, J=8.5 Hz), 6.94 (1H, t, J=7.1 Hz), 7.04-7.31 (6H, m), 7.37 (1H, d, J=8.3 Hz), 8.30 (1H, d, J=8.3 Hz), 9.28 (1H, s), 9.86 (1H, d, J=6.9 Hz)

MS: 580 (M+H)$^+$

Reference Example 42 tert-butyl 4-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)ethyl]benzoate (compound S42)

Instead of the starting material, that is, tert-butyl 2-[(1R)-1-aminopropyl]-isonicotinate D-tartrate, of Reference Example 39, the compound S2 was used for a similar reaction as in Reference Example 39 to obtain the title compound.

$^1$H-NMR (CDCl$_3$) δ 1.52 (3H, d, J=6.9 Hz), 1.56-1.61 (9H, m), 2.36 (1H, dd, J=9.5, 13.9 Hz), 3.07 (1H, dd, J=4.1, 13.9 Hz), 3.12-3.38 (3H, m), 3.67 (6H, s), 3.75 (3H, s), 3.86 (3H, s), 4.79-5.21 (4H, m), 5.57 (1H, d, J=16.6 Hz), 6.08 (2H, s), 6.74 (1H, d, J=8.6 Hz), 6.79 (1H, d, J=2.5 Hz), 7.18 (1H, dd, J=2.5, 8.6 Hz), 7.33-7.43 (2H, d, J=8.5 Hz), 7.92-8.00 (2H, d, J=8.5 Hz), 9.45 (1H, d, J=7.3 Hz)

MS: 726 (M+H)$^+$

Example 51

4-[(1R)-1-({[(6R)-6-(5-chloro-2-methoxybenzyl)-7-oxo-3-(phenoxyimino)-1,4-diazepan-1-yl]carbonyl}amino)ethyl]benzoic acid (compound 51)

Instead of the starting material, that is, the compound S27, of Example 23, the compound S42 was used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (DMSO-d$_6$) δ 1.46 (3H, d, J=6.9 Hz), 2.70 (1H, dd, J=9.1, 14.3 Hz), 3.00 (1H, dd, J=4.9, 14.3 Hz), 3.11-3.26 (2H, m), 3.81 (3H, s), 3.84-4.04 (1H, m), 4.66 (1H, d, J=16.2 Hz), 4.82-5.06 (2H, m), 6.79-6.96 (2H, m), 6.96-7.12 (3H, m), 7.19-7.31 (3H, m), 7.35 (1H, d, J=2.4 Hz), 7.46 (2H, d, J=8.1 Hz), 7.91 (2H, d, J=8.1 Hz), 9.45 (1H, d, J=6.9 Hz), 12.85 (1H, br.s)

MS: 565 (M+H)$^+$

Reference Example 43 tert-butyl 2-amino-4-{[({(6R)-6-(5-chloro-2-methoxybenzyl)-7-oxo-3-thioxo-4-(2,4,6-trimethoxybenzyl)-1,4-diazepan-1-yl}carbonyl)amino]methyl}benzoate (compound S43)

Step (1): To the compound S11 (306 mg) and the compound S141C described in WO 06-059801A, that is, (6R)-2-chlorophenyl 6-(5-chloro-2-methoxybenzyl)-3,7-dioxo-4-(2,4,6-trimethoxybenzyl)-1,4-diazepane-1-carboxylate (850 mg) in an N,N-dimethylformamide (4 ml) solution, 4-dimethylaminopyridine (169 mg) was added under ice cooling, and the mixture was stirred at 0° C. for 18 hours. The reaction solution was diluted with ethyl acetate and washed with brine. The organic layer was dried over anhydrous sodium sulfate, then was concentrated. The residue was purified by flash column chromatography (silica gel, chloroform/ethyl acetate=2/1) to obtain tert-butyl 2-amino-4-{[({(6R)-6-(5-chloro-2-methoxybenzyl)-3,7-dioxo-4-(2,4,6-trimethoxybenzyl)-1,4-diazepan-1-yl}carbonyl)amino]methyl}benzoate (compound S43a) (685 mg).

Step (2): Instead of the starting material, that is, the compound S21, of Reference Example 22, the compound S43a was used for a similar reaction as in Reference Example 22 to obtain the title compound.

$^1$H-NMR (CDCl$_3$) δ 1.57 (9H, s), 2.38 (1H, dd, J=8.7, 13.7 Hz), 3.04 (1H, dd, J=3.7, 13.7 Hz), 3.12-3.34 (3H, m), 3.65 (6H, s), 3.74 (3H, s), 3.85 (3H, s), 4.42 (2H, d, J=5.7 Hz), 4.92-5.13 (3H, m), 5.53 (1H, d, J=16.6 Hz), 5.72 (2H, br.s), 6.07 (2H, s), 6.55 (1H, d, J=8.1 Hz), 6.58 (1H, s), 6.73 (1H, d, J=8.8 Hz), 6.80 (1H, d, J=2.7 Hz), 7.17 (1H, dd, J=2.7, 8.8 Hz), 7.76 (1H, d, J=8.1 Hz), 9.34 (1H, t, J=5.7 Hz)

MS: 727 (M+H)$^+$

Example 52

2-amino-4-{[({(6R)-6-(5-chloro-2-methoxybenzyl)-3-[(4-fluorophenoxy)imino]-7-oxo-1,4-diazepan-1-yl}carbonyl)amino]methyl}benzoic acid (compound 52)

Instead of the starting material, that is, the compound S27, of Example 23, the compound S43 was used, and instead of the reaction agent, that is, O-ethyl hydroxylamine hydrochloride, O-(4-fluorophenyl)hydroxylamine hydrochloride was used for a similar reaction as in Example 23 to obtain the title compound.

$^1$H-NMR (DMSO-d$_6$) δ 2.68 (1H, dd, J=8.1, 14.0 Hz), 2.99 (1H, dd, J=4.9, 14.0 Hz), 3.07-3.24 (2H, m), 3.80 (3H, s), 3.86-4.04 (1H, m), 4.21-4.38 (2H, m), 4.70 (1H, d, J=16.4 Hz), 4.98 (1H, d, J=16.4 Hz), 6.43 (1H, dd, J=1.4, 8.3 Hz), 6.64 (1H, d, J=1.4 Hz), 6.96 (1H, s), 7.01 (1H, d, J=8.8 Hz), 7.03-7.12 (4H, m), 7.27 (1H, dd, J=2.7, 8.8 Hz), 7.35 (1H, d, J=2.7 Hz), 7.63 (1H, d, J=8.3 Hz), 9.37 (1H, t, J=5.9 Hz)

MS: 584 (M+H)$^+$

Example 53

2-amino-4-{[({(6R)-6-(5-chloro-2-methoxybenzyl)-3-[(3,5-difluorophenoxy)imino]-7-oxo-1,4-diazepan-1-yl}carbonyl)amino]methyl}benzoic acid (compound 53)

Instead of the starting material, that is, the compound S27, of Example 23, the compound S43 was used, and instead of the reaction agent, that is, O-ethyl hydroxylamine hydrochloride, O-(3,5-difluorophenyl) hydroxylamine hydrochloride was used for a similar reaction as in Example 23 to obtain the title compound.

$^1$H-NMR (DMSO-d$_6$) δ 2.68 (1H, dd, J=8.7, 14.3 Hz), 2.99 (1H, dd, J=5.3, 14.3 Hz), 3.10-3.27 (2H, m), 3.80 (3H, s), 3.85-4.05 (1H, m), 4.22-4.40 (2H, m), 4.73 (1H, d, J=16.8 Hz), 4.97 (1H, d, J=16.8 Hz), 6.43 (1H, dd, J=1.4, 8.5 Hz), 6.64 (1H, d, J=1.4 Hz), 6.66-6.83 (3H, m), 7.01 (1H, d, J=8.9 Hz), 7.11 (1H, s), 7.27 (1H, dd, J=2.6, 8.9 Hz), 7.35 (1H, d, J=2.6 Hz), 7.63 (1H, d, J=8.5 Hz), 9.36 (1H, t, J=5.9 Hz)

MS: 602 (M+H)$^+$

Reference Example 44 tert-butyl (2R)-2-({[(6R)-6-(5-chloro-2-methoxybenzyl)-7-oxo-3-thioxo-4-(2,4,6-trimethoxybenzyl)-1,4-diazepan-1-yl]carbonyl}amino)butanoate (compound S44)

Instead of the starting material, that is, tert-butyl 2-[(1R)-1-aminopropyl]-isonicotinate D-tartrate, of Reference Example 39, tert-butyl (2R)-2-aminobutanoate hydrochloride was used for a similar reaction as in Reference Example 39 to obtain the title compound.

$^1$H-NMR (CDCl$_3$) δ 0.94 (3H, t, J=7.3 Hz), 1.48 (9H, s), 1.73-1.96 (2H, m), 2.34 (1H, dd, J=9.7, 13.8 Hz), 3.04-3.30 (3H, m), 3.36 (1H, m), 3.68 (6H, s), 3.76 (3H, s), 3.86 (3H, s), 4.39-4.49 (1H, m), 4.85-4.97 (2H, m), 5.11 (1H, d, J=14.2 Hz), 5.61 (1H, d, J=17.0 Hz), 6.09 (2H, s), 6.74 (1H, d, J=8.8 Hz), 6.77 (1H, d, J=2.7 Hz), 7.17 (1H, dd, J=2.7, 8.8 Hz), 9.48 (1H, d, J=7.3 Hz)

MS: 664 (M+H)$^+$

Example 54

(2R)-2-({[(6R)-6-(5-chloro-2-methoxybenzyl)-7-oxo-3-(phenoxyimino)-1,4-diazepan-1-yl]carbonyl}amino)butanoic acid (compound 54)

Instead of the starting material, that is, the compound S27, of Example 23, the compound S44 was used, and instead of the reaction agent, that is, O-ethyl hydroxylamine hydrochloride, O-phenyl hydroxylamine hydrochloride was used for a similar reaction as in Example 23 to obtain the title compound.

$^1$H-NMR (CDCl$_3$) δ 1.04 (3H, t, J=7.5 Hz), 1.80-2.08 (2H, m), 2.62 (1H, dd, J=8.9, 14.0 Hz), 3.23 (1H, dd, J=4.9, 14.0 Hz), 3.27-3.35 (1H, m), 3.38-3.50 (1H, m), 3.69-3.81 (1H, m), 3.84 (3H, s), 4.30 (1H, d, J=16.2 Hz), 4.43-4.55 (1H, m), 5.43 (1H, d, J=16.2 Hz), 5.54 (1H, s), 6.80 (1H, d, J=8.9 Hz), 6.94 (1H, t, J=7.3 Hz), 7.09-7.17 (3H, m), 7.18-7.28 (3H, m), 9.52 (1H, d, J=6.9 Hz)

MS: 503 (M+H)$^+$

Example 55

(6R)-6-(5-chloro-2-methoxybenzyl)-N-[(1R)-1-(methylcarbamoyl)propyl]-7-oxo-3-(phenoxyimino)-1,4-diazepane-1-carboxamide (compound 55)

To the compound 54 (70 mg) in a methylene chloride (3 ml) solution, dimethylamine in a methanol solution (2M, 0.14 ml), triethylamine (0.291 ml), and propyl phosphonate anhydride (T3P) (50% ethyl acetate solution, 0.21 ml) were successively added, and the mixture was stirred at room temperature for 30 minutes. The solvent was distilled off, and the residue was diluted with ethyl acetate. Then the resultant mixture was successively washed with saturated aqueous ammonium chloride solution, saturated aqueous sodium hydrogencarbonate solution, and brine. The organic layer was dried over anhydrous sodium sulfate, then was concentrated. The residue was purified by flash column chromatography (silica gel, chloroform/ethyl acetate=9/1 to 1/1) to obtain the title compound (42.5 mg).

$^1$H-NMR (DMSO-d$_6$) δ 0.81 (3H, t, J=7.3 Hz), 1.52-1.79 (2H, m), 2.60 (3H, d, J=4.5 Hz), 2.68 (1H, dd, J=8.5, 14.4 Hz), 3.00 (1H, dd, J=4.9, 14.4 Hz), 3.08-3.26 (2H, m), 3.81 (3H, s), 3.87-4.04 (1H, m), 4.21 (1H, dt, J=7.7, 7.7 Hz), 4.68 (1H, d, J=16.4 Hz), 4.96 (1H, d, J=16.4 Hz), 6.80-6.96 (2H, m), 7.02 (1H, d, J=8.9 Hz), 7.04-7.13 (2H, m), 7.18-7.31 (3H, m), 7.35 (1H, d, J=2.8 Hz), 8.06 (1H, dt, J=4.5 Hz), 9.40 (1H, d, J=7.7 Hz)

MS: 516 (M+H)$^+$

Example 56

(6R)—N-[(1R)-1-carbamoylpropyl]-6-(5-chloro-2-methoxybenzyl)-7-oxo-3-(phenoxyimino)-1,4-diazepane-1-carboxamide (compound 56)

To the compound 54 (114 mg) in a methylene chloride (2 ml) solution, carbonyl diimidazole (45 mg) was added, and the mixture was stirred at room temperature for 45 minutes. The reaction solution was cooled to 0° C., then 28% ammonia aqueous solution (2 ml) was added, and the mixture was stirred at that temperature for 1 hour. The reaction solution was diluted with chloroform and the resultant mixture successively washed with water, 1M hydrochloric acid, and brine. The organic layer was dried over anhydrous sodium sulfate, then was concentrated. The residue was purified by flash column chromatography (silica gel, chloroform/ethyl acetate=7/3 to 1/2) to obtain the title compound (40 mg).

$^1$H-NMR (DMSO-d$_6$) δ 0.82 (3H, t, J=7.3 Hz), 1.58-1.79 (2H, m), 2.68 (1H, dd, J=8.9, 14.3 Hz), 3.00 (1H, dd, J=4.7, 14.3 Hz), 3.07-3.26 (2H, m), 3.81 (3H, s), 3.85-4.02 (1H, m), 4.24 (1H, dt, J=7.3, 7.3 Hz), 4.68 (1H, d, J=16.2 Hz), 4.97 (1H, d, J=16.2 Hz), 6.85-6.95 (2H, m), 7.02 (1H, d, J=8.9 Hz), 7.04-7.11 (2H, m), 7.16 (1H, s), 7.19-7.31 (3H, m), 7.35 (1H, d, J=2.8 Hz), 7.57 (1H, s), 9.40 (1H, d, J=7.3 Hz)

MS: 502 (M+H)$^+$

Example 57

(6R)-6-(5-chloro-2-methoxybenzyl)-N-[(1R)-1-(dimethylcarbamoyl)propyl]-7-oxo-3-(phenoxyimino)-1,4-diazepane-1-carboxamide (compound 57)

Instead of the reaction agent, that is, methylamine in a methanol solution, in Example 55, dimethylamine in a tetrahydrofuran solution was used for a similar reaction as in Example 55 to obtain the title compound.

$^1$H-NMR (DMSO-d$_5$) δ 0.83 (3H, t, J=7.3 Hz), 1.46-1.85 (2H, m), 2.68 (1H, dd, J=8.5, 14.4 Hz), 2.85 (3H, s), 3.00 (1H, dd, J=5.3, 14.4 Hz), 3.05 (3H, s), 3.10-3.27 (2H, m), 3.81 (3H, s), 3.86-4.03 (1H, m), 4.68 (1H, d, J=16.0 Hz), 4.74 (1H, dt, J=7.7, 7.7 Hz), 4.97 (1H, d, J=16.0 Hz), 6.84-6.96 (2H, m), 7.01 (1H, d, J=8.9 Hz), 7.04-7.11 (2H, m), 7.19-7.31 (3H, m), 7.34 (1H, d, J=2.8 Hz), 9.46 (1H, d, J=7.7 Hz)

MS: 530 (M+H)$^+$

Example 58

(6R)-6-(5-chloro-2-methoxybenzyl)-7-oxo-3-(phenoxyimino)-N-[(1R)-1-(1H-tetrazole-5-ylcarbamoyl)propyl]-1,4-diazepane-1-carboxamide (compound 58)

Instead of the reaction agent, that is, methylamine in a methanol solution, in Example 55, 1H-tetrazole-5-amine monohydrate was used for a similar reaction as in Example 55 to obtain the title compound.

$^1$H-NMR (DMSO-d$_6$) δ 0.90 (3H, t, J=7.3 Hz), 1.66-1.96 (2H, m), 2.70 (1H, dd, J=8.9, 14.5 Hz), 3.01 (1H, dd, J=5.1, 14.5 Hz), 3.09-3.26 (2H, m), 3.81 (3H, s), 3.87-4.09 (1H, m), 4.53 (1H, dt, J=6.5, 6.5 Hz), 4.72 (1H, d, J=16.2 Hz), 4.95 (1H, d, J=16.2 Hz), 6.86-6.97 (2H, m), 7.02 (1H, d, J=8.9 Hz), 7.04-7.09 (2H, m), 7.17-7.32 (3H, m), 7.36 (1H, d, J=2.8 Hz), 9.53 (1H, d, J=6.5 Hz), 12.24 (1H, br.s), 15.99 (1H, br.s)
MS: 570 (M+H)$^+$

Reference Example 45

(6R)-2-chlorophenyl 6-(5-chloro-2-methoxybenzyl)-3,7-dioxo-1,4-diazepane-1-carboxylate (compound S45)

To the compound S141C described in WO 06-059801A, that is, (6R)-2-chlorophenyl 6-(5-chloro-2-methoxybenzyl)-3,7-dioxo-4-(2,4,6-trimethoxybenzyl)-1,4-diazepan-1-carboxylate (996 mg), anisole (1.75 ml) and trifluoroacetic acid (10 ml) were added, and the mixture was stirred at room temperature for 4.5 hours. The reaction solution was diluted with toluene and concentrated in vacuo. This operation was repeated two times and excessive anisole was distilled off under reduced pressure of a vacuum pump. To the residue, ethyl acetate was added. The precipitated solid was collected by filtration to obtain the title compound (396 mg). Furthermore, the filtrate was concentrated, and the residue was purified by flash column chromatography (silica gel, hexane/ethyl acetate=2/1 to 1/3) to obtain the title compound (198 mg).

$^1$H-NMR (CDCl$_3$) δ 2.63 (1H, dd, J=8.9, 14.2 Hz), 3.26-3.41 (2H, m), 3.48 (1H, t, J=12.4 Hz), 3.58-3.72 (1H, m), 3.85 (3H, s), 4.40 (1H, d, J=17.9 Hz), 5.07 (1H, d, J=17.9 Hz), 5.91 (1H, d, J=4.5 Hz), 6.82 (1H, d, J=8.5 Hz), 7.15 (1H, d, J=2.8 Hz), 7.19-7.36 (4H, m), 7.46 (1H, dd, J=1.6, 8.1 Hz)
MS: 437 (M+H)$^+$

Reference Example 46 tert-butyl 4-{(1R)-1-[({(6R)-6-(5-chloro-2-methoxybenzyl)-7-oxo-3-thioxo-1,4-diazepan-1-yl}carbonyl)amino]ethyl}benzoate (compound S46)

Step (1): Instead of the starting material, that is, tert-butyl 2-[(1R)-1-aminopropyl]-isonicotinate D-tartrate, of Reference Example 39, the compound S2 was used, and instead of (6R)-2-chlorophenyl 6-(5-chloro-2-methoxybenzyl)-3,7-dioxo-4-(2,4,6-trimethoxybenzyl)-1,4-diazepan-1-carboxylate, the compound S45 was used for a similar reaction as in Reference Example 39 to obtain tert-butyl 4-{(1R)-1-[({(6R)-6-(5-chloro-2-methoxybenzyl)-3,7-dioxo-1,4-diazepan-1-yl}carbonyl)amino]ethyl}benzoic acid (compound S46a).

Step (2): Instead of the starting material, that is, the compound S21, of Reference Example 22, the compound S46a was used for a similar reaction as in Reference Example 22 to obtain the title compound.

$^1$H-NMR (CDCl$_3$) δ 1.53 (3H, d, J=6.9 Hz), 1.58 (9H, s), 2.59 (1H, dd, J=8.5, 13.9 Hz), 3.20 (1H, dd, J=5.1, 13.9 Hz), 3.33-3.49 (2H, m), 3.69-3.87 (4H, m), 4.38 (1H, d, J=17.9 Hz), 5.05 (1H, dq, J=6.9, 6.9 Hz), 5.92 (1H, d, J=17.9 Hz), 6.81 (1H, d, J=8.8 Hz), 7.12 (1H, d, J=2.5 Hz), 7.23 (1H, dd, J=2.5, 8.8 Hz), 7.37 (2H, d, J=8.3 Hz), 7.91 (1H, br.s), 7.96 (2H, d, J=8.3 Hz), 9.37 (1H, d, J=6.9 Hz)
MS: 490 (M−tBu)$^+$

Example 59

4-{(1R)-1-[({(6R)-6-(5-chloro-2-methoxybenzyl)-3-[(3-fluorophenoxy)imino]-7-oxo-1,4-diazepan-1-yl}carbonyl)amino]ethyl}benzoic acid (compound 59)

Instead of the starting material, that is, the compound S22, of Example 1, the compound S46 was used, and instead of the reaction agent, that is, O-isopropyl hydroxylamine hydrochloride, O-(3-fluorophenyl) hydroxylamine hydrochloride was used for a similar reaction as in Example 1 to obtain the title compound.

$^1$H-NMR (DMSO-d$_6$) δ 1.46 (3H, d, J=6.9 Hz), 2.71 (1H, dd, J=8.9, 14.4 Hz), 2.99 (1H, dd, J=4.5, 14.4 Hz), 3.10-3.27 (2H, m), 3.80 (3H, s), 3.83-4.02 (1H, m), 4.67 (1H, d, J=16.6 Hz), 4.82-5.06 (2H, m), 6.67-6.77 (1H, m), 6.81-6.92 (2H, m), 6.97-7.07 (2H, m), 7.21-7.33 (2H, m), 7.35 (1H, d, J=2.4 Hz), 7.46 (2H, d, J=8.5 Hz), 7.91 (2H, d, J=8.5 Hz), 9.44 (1H, d, J=7.3 Hz)
MS: 583 (M+H)$^+$

Reference Example 47 tert-butyl 4-{[({(6R)-6-(5-chloro-2-methoxybenzyl)-7-oxo-3-thioxo-1,4-diazepan-1-yl}carbonyl)amino]methyl}benzoate (compound S47)

Step (1): Instead of the starting material, that is, the compound S11, of Reference Example 43, tert-butyl 4-(aminomethyl)benzoate was used, and instead of (6R)-2-chlorophenyl 6-(5-chloro-2-methoxybenzyl)-3,7-dioxo-4-(2,4,6-trimethoxybenzyl)-1,4-diazepan-1-carboxylate, the compound S45 was used for a similar reaction as in Reference Example 43 to obtain tert-butyl 4-{[({(6R)-6-(5-chloro-2-methoxybenzyl)-3,7-dioxo-1,4-diazepan-1-yl}carbonyl)amino]methyl}benzoate (compound S47a).

Step (2): Instead of the starting material, that is, the compound S21, of Reference Example 22, the compound S47a was used for a similar reaction as in Reference Example 22 to obtain the title compound.

$^1$H-NMR (CDCl$_3$) δ 1.59 (9H, s), 2.58 (1H, dd, J=8.1, 14.0 Hz), 3.17 (1H, dd, J=5.7, 14.0 Hz), 3.28-3.54 (2H, m), 3.72-3.90 (4H, m), 4.45 (1H, d, J=17.9 Hz), 4.48-4.64 (2H, m), 5.98 (1H, d, J=17.9 Hz), 6.81 (1H, d, J=8.8 Hz), 7.12 (1H, d, J=2.5 Hz), 7.22 (1H, dd, J=2.5, 8.8 Hz), 7.36 (2H, d, J=8.5 Hz), 7.91 (1H, br.s), 7.96 (2H, d, J=8.5 Hz), 9.34 (1H, t, J=5.5 Hz)
MS: 476 (M−tBu)$^+$

Example 60

4-{[({(6R)-6-(5-chloro-2-methoxybenzyl)-3-[(3-fluorophenoxy)imino]-7-oxo-1,4-diazepan-1-yl}carbonyl)amino]methyl}benzoic acid (compound 60)

Instead of the starting material, that is, the compound S22, of Example 1, the compound S47 was used, and instead of the reaction agent, that is, O-isopropyl hydroxylamine hydrochloride, O-(3-fluorophenyl)hydroxylamine hydrochloride was used for a similar reaction as in Example 1 to obtain the title compound.

¹H-NMR (DMSO-d₆) δ 2.68 (1H, dd, J=8.1, 14.3 Hz), 2.99 (1H, dd, J=5.1, 14.3 Hz), 3.10-3.25 (2H, m), 3.80 (3H, s), 3.94 (1H, m), 4.43-4.54 (2H, m), 4.71 (1H, d, J=16.4 Hz), 4.97 (1H, d, J=16.4 Hz), 6.66-6.77 (1H, m), 6.81-6.92 (2H, m), 6.97-7.08 (2H, m), 7.21-7.32 (2H, m), 7.35 (1H, d, J=2.4 Hz), 7.41 (2H, d, J=8.1 Hz), 7.90 (2H, d, J=8.1 Hz), 9.46 (1H, t, J=6.0 Hz)

MS: 569 (M+H)⁺

Reference Example 48

2,2,2-trichloroethyl 2-[(1R)-1-({[(6R)-6-(5-chloro-2-methoxybenzyl)-7-oxo-3-(thioxo)-1,4-diazepan-1-yl]carbonyl}amino)propyl]-1,3-oxazole-4-carboxylate (compound S48)

Step (1): Instead of the starting material, that is, tert-butyl 2-[(1R)-1-aminopropyl]-isonicotinate D-tartrate, of Reference Example 39, the compound S15 was used, and instead of (6R)-2-chlorophenyl 6-(5-chloro-2-methoxybenzyl)-3,7-dioxo-4-(2,4,6-trimethoxybenzyl)-1,4-diazepan-1-carboxylate, the compound S45 was used for a similar reaction as in Reference Example 39 to obtain 2,2,2-trichloroethyl 2-[(1R)-1-({[(6R)-6-(5-chloro-2-methoxybenzyl)-3,7-dioxo-1,4-diazepan-1-yl]carbonyl}amino)propyl]-1,3-oxazole-4-carboxylate (compound S48a).

Step (2): Instead of the starting material, that is, the compound S21, of Reference Example 22, the compound S48a was used for a similar reaction as in Reference Example 22 to obtain the title compound.

¹H-NMR (CDCl₃) δ 1.00 (3H, t, J=7.5 Hz), 1.92-2.13 (2H, m), 2.57 (1H, dd, J=8.5, 13.8 Hz), 3.22 (1H, dd, J=4.9, 13.8 Hz), 3.35-3.47 (2H, m), 3.77-3.86 (1H, m), 3.84 (3H, s), 4.43 (1H, d, J=17.9 Hz), 4.94 (2H, s), 5.11 (1H, dt, J=7.3, 7.3 Hz), 5.87 (1H, d, J=17.9 Hz), 6.81 (1H, d, J=8.9 Hz), 7.11 (1H, d, J=2.4 Hz), 7.22 (2H, dd, J=2.4, 8.9 Hz), 7.95 (1H, br.s), 8.26 (1H, s), 9.51 (1H, d, J=7.3 Hz)

MS: 627 (M+H)⁺

Example 61

2-[(1R)-1-({[(6R)-6-(5-chloro-2-methoxybenzyl)-7-oxo-3-(phenoxyimino)-1,4-diazepan-1-yl]carbonyl}amino)propyl]-1,3-oxazole-4-carboxylic acid (compound 61)

Step (1): Instead of the starting material, that is, the compound S22, of Example 1, the compound S48 was used, and instead of the reaction agent, that is, O-isopropyl hydroxylamine hydrochloride, O-phenyl hydroxylamine hydrochloride was used for a similar reaction as in Example 1, Step (1) to obtain 2,2,2-trichloroethyl 2-[(1R)-1-({[(6R)-6-(5-chloro-2-methoxybenzyl)-5-oxo-2-(phenoxyimino)-1,4-diazepan-4-yl]carbonyl}amino)propyl]-1,3-oxazole-4-carboxylate (compound 61a).

Step (2): To the compound 61a obtained in Step (1) (90 mg) was dissolved in acetic acid (2 ml), zinc powder (180 mg) was added, and the mixture was stirred at room temperature for 3 hours. The insolubles were filtered out, then the filtrate was concentrated, and the residue was purified by preparative thin layer chromatography (silica gel, chloroform/methanol/acetic acid=8/1/0.25) to obtain the title compound (17.4 mg).

¹H-NMR (DMSO-d₆) δ 0.78-0.89 (3H, m), 1.90 (2H, m), 2.65-2.76 (1H, m), 2.92-3.05 (1H, m), 3.15-3.22 (2H, m), 3.80 (3H, s), 3.92 (1H, m), 4.70 (1H, d, J=16.2 Hz), 4.86-5.00 (2H, m), 6.82-6.96 (2H, m), 6.97-7.10 (3H, m), 7.19-7.32 (3H, m), 7.35 (1H, s), 8.00 (1H, br.s), 9.56 (1H, d, J=6.5 Hz)

MS: 570 (M+H)⁺

Reference Example 49

(6R)-6-(5-chloro-2-methoxybenzyl)-N-[(1R)-1-(3-tert-butoxyisooxazole-5-yl)propyl]-7-oxo-3-thioxo-4-(2,4,6-trimethoxybenzyl)-1,4-diazepane-1-carboxamide (compound S49)

Step (1): To the compound S141C described in WO 06-059801A, that is, (6R)-2-chlorophenyl 6-(5-chloro-2-methoxybenzyl)-3,7-dioxo-4-(2,4,6-trimethoxybenzyl)-1,4-diazepane-1-carboxylate (395 mg) in an N,N-dimethylformamide (0.64 ml) solution, the compound S94 described in WO 06-059801A, that is, 1-(3-tert-butoxyisoxazol-5-yl)propylamine hydrochloride (150 mg), 4-dimethylaminopyridin (78 mg) and N,N-diisopropylethylamine (0.111 ml) were added at 0° C., and the mixture was stirred at that temperature for 15 hours. To the reaction solution, water was added, and the mixture was extracted with ethyl acetate. The extract was combined, successively washed with saturated aqueous potassium hydrogensulfate solution, saturated aqueous sodium hydrogencarbonate solution, and brine, dried over sodium sulfate, then concentrated. The residue was purified by flash column chromatography (silica gel, hexane/ethyl acetate=50/50 to 35/65) to obtain (6R)-6-(5-chloro-2-methoxybenzyl)-N-[(1R)-1-(3-tert-butoxyisooxazole-5-yl)propyl]-3,7-dioxo-4-(2,4,6-trimethoxybenzyl)-1,4-diazepane-1-carboxamide (189 mg) (compound S49a) and (6R)-6-(5-chloro-2-methoxybenzyl)-N-[(1S)-1-(3-tert-butoxyisooxazol-5-yl)propyl]-3,7-dioxo-4-(2,4,6-trimethoxybenzyl)-1,4-diazepane-1-carboxamide (compound S49b).

Step (2): Instead of the starting material, that is, the compound S21, of Reference Example 22, the compound S49a was used for a similar reaction as in Reference Example 22 to obtain the title compound.

Example 62

(6R)-6-(5-chloro-2-methoxybenzyl)-3-(ethoxyimino)-N-[(1R)-1-(3-hydroxyisooxazole-5-yl)propyl]-7-oxo-1,4-diazepane-1-carboxamide (compound 62)

Instead of the starting material, that is, the compound S23, of Example 10, the compound S49 was used for a similar reaction as in Example 10 to obtain the title compound.

¹H-NMR (DMSO-d₆) δ 0.87 (3H, t, J=7.3 Hz), 1.12 (3H, t, J=6.9 Hz), 1.78-1.88 (2H, m), 2.61-2.71 (1H, m), 2.95 (1H, dd, J=4.9, 14.2 Hz), 3.00-3.19 (2H, m), 3.76-3.90 (6H, m), 4.52 (1H, d, J=16.2 Hz), 4.72-4.88 (2H, m), 5.91 (1H, s), 6.34 (1H, br.s), 7.00 (1H, d, J=8.7 Hz), 7.27 (1H, dd, J=2.8, 8.7 Hz), 7.34 (1H, d, J=2.8 Hz), 9.41 (1H, d, J=8.1 Hz), 11.24 (1H, br.s)

MS: 494 (M+H)⁺

Example 63

(6R)-6-(5-chloro-2-methoxybenzyl)-N-[(1R)-1-(3-hydroxyisooxazole-5-yl)propyl]-7-oxo-3-(phenoxyimino)-1,4-diazepane-1-carboxamide (compound 63)

Instead of the starting material, that is, the compound S23, of Example 10, the compound S49 was used, and instead of the reaction agent, that is, O-ethyl hydroxylamine hydrochloride, O-phenyl hydroxylamine hydrochloride was used for a similar reaction as in Example 10 to obtain the title compound.
¹H-NMR (DMSO-d₆) δ 0.87 (3H, t, J=7.3 Hz), 1.75-1.88 (2H, m), 2.69 (1H, dd, J=9.6, 14.0 Hz), 2.99 (1H, dd, J=4.7, 14.0 Hz), 3.12-3.22 (2H, m), 3.81 (3H, s), 3.88-4.00 (1H, m), 4.70 (1H, d, J=16.2 Hz), 4.85 (1H, dt, J=7.7, 7.7 Hz), 4.94 (1H, d, J=16.2 Hz), 5.93 (1H, s), 6.83-6.95 (2H, m), 6.99-7.09 (3H, m), 7.22-7.31 (3H, m), 7.35 (1H, d, J=2.4 Hz), 9.41 (1H, d, J=7.7 Hz), 11.24 (1H, s)
MS: 542 (M+H)⁺

Reference Example 50 tert-butyl {4-[(1R)-1-({[(6R)-6-(5-chloro-2-methoxybenzyl)-7-oxo-3-thioxo-1,4-diazepan-1-yl]carbonyl}amino)propyl]phenyl}acetate (compound S50)

Step (1): Instead of the starting material, that is, 1-(3-tert-butoxyisoxazol-5-yl)propylamine hydrochloride, of Reference Example 49, the compound 5186 described in WO 06-059801A, that is, tert-butyl[4-(1-aminopropyl)phenyl]acetate hydrochloride was used for a similar reaction as in Reference Example 49 to obtain tert-butyl {4-[(1R)-1-({[(6R)-6-(5-chloro-2-methoxybenzyl)-3,7-dioxo-1,4-diazepan-1-yl]carbonyl}amino)propyl]phenyl}acetate (compound S50a) and tert-butyl {4-[(1S)-1-({[(6R)-6-(5-chloro-2-methoxybenzyl)-3,7-dioxo-1,4-diazepan-1-yl]carbonyl}amino)propyl]phenyl}acetate (compound S50b).
Step (2): Instead of the starting material, that is, the compound S21, of Reference Example 22, the compound S50a was used for a similar reaction as in Reference Example 22 to obtain the title compound.
MS: 754 (M+H)⁺

Example 64

{4-[(1R)-1-({[(6R)-6-(5-chloro-2-methoxybenzyl)-7-oxo-3-(phenoxyimino)-1,4-diazepan-1-yl]carbonyl}amino)propyl]phenyl}acetic acid (compound 64)

Instead of the starting material, that is, the compound S27, of Example 23, the compound S50 was used, and instead of the reaction agent, that is, O-ethyl hydroxylamine hydrochloride, O-phenyl hydroxylamine hydrochloride was used for a similar reaction as in Example 23 to obtain the title compound.
¹H-NMR (CDCl₃) δ 0.92 (3H, t, J=7.5 Hz), 1.75-1.95 (2H, m), 2.64 (1H, dd, J=8.9, 13.8 Hz), 3.19 (1H, dd, J=4.9, 13.8 Hz), 3.26-3.38 (1H, m), 3.39-3.50 (1H, m), 3.64 (2H, s), 3.67-3.78 (1H, m), 3.83 (3H, s), 4.20 (1H, d, J=16.0 Hz), 4.78 (1H, dt, J=7.5, 7.5 Hz), 5.41 (1H, d, J=16.0 Hz), 5.53 (1H, br.s), 6.79 (1H, d, J=8.9 Hz), 6.93 (1H, t, J=7.3 Hz), 7.10-7.17 (3H, m), 7.17-7.34 (7H, m), 9.52 (1H, d, J=7.5 Hz)
MS: 593 (M+H)⁺

Example 65

(4-{(1R)-1-[({(6R)-6-(5-chloro-2-methoxybenzyl)-3-[(4-fluorophenoxy)imino]-7-oxo-1,4-diazepan-1-yl}carbonyl)amino]propyl}phenyl)acetic acid (compound 65)

Instead of the starting material, that is, the compound S27, of Example 23, the compound S50 was used, and instead of the reaction agent, that is, O-ethyl hydroxylamine hydrochloride, O-(4-fluorophenyl)hydroxylamine hydrochloride was used for a similar reaction as in Example 23 to obtain the title compound.
¹H-NMR (DMSO-d₆) δ 0.82 (3H, t, J=7.3 Hz), 1.67-1.88 (2H, m), 2.71 (1H, dd, J=9.7, 14.7 Hz), 2.98 (1H, dd, J=5.1, 14.7 Hz), 3.10-3.26 (2H, m), 3.54 (2H, s), 3.80 (3H, s), 3.83-3.97 (1H, m), 4.56-4.74 (2H, m), 4.91 (1H, d, J=16.6 Hz), 6.94 (1H, s), 6.97-7.13 (5H, m), 7.18-7.25 (4H, m), 7.28 (1H, dd, J=2.7, 8.7 Hz), 7.34 (1H, d, J=2.7 Hz), 9.47 (1H, d, J=7.7 Hz), 12.26 (1H, br.s)
MS: 611 (M+H)⁺

Reference Example 51 tert-butyl 2-amino-4-[(1R)-1-({[(6S)-6-(5-chloro-2-methoxybenzyl)-7-oxo-3-thioxo-4-(2,4,6-trimethoxybenzyl)-1,4-diazepan-1-yl]carbonyl}amino)pentyl]benzoare (compound S51)

Step (1): Instead of the starting material, that is, 1-(3-tert-butoxyisoxazol-5-yl)propylamine hydrochloride, of Reference Example 49, the compound S14 was used for a similar reaction as in Reference Example 49 to obtain tert-butyl 2-amino-4-[(1R)-1-({[(6S)-6-(5-chloro-2-methoxybenzyl)-3,7-dioxo-4-(2,4,6-trimethoxybenzyl)-1,4-diazepan-1-yl]carbonyl}amino)pentyl]benzoate (compound S51a) and tert-butyl 2-amino-4-[(1S)-1-({[(6S)-6-(5-chloro-2-methoxybenzyl)-3,7-dioxo-4-(2,4,6-trimethoxybenzyl)-1,4-diazepan-1-yl]carbonyl}amino)pentyl]benzoate (compound S51b).
Step (2): Instead of the starting material, that is, the compound S21, of Reference Example 22, the compound S51a was used for a similar reaction as in Reference Example 22 to obtain the title compound.

Example 66

2-amino-4-[(1R)-1-({[(6S)-6-(5-chloro-2-methoxybenzyl)-3-(methoxyimino)-7-oxo-1,4-diazepan-1-yl]carbonyl}amino)pentyl]benzoic acid (compound 66)

Instead of the starting material, that is, the compound S27, of Example 23, the compound S51 was used, and instead of the reaction agent, that is, O-ethyl hydroxylamine hydrochloride, O-methyl hydroxylamine hydrochloride was used for a similar reaction as in Example 23 to obtain the title compound.
¹H-NMR (DMSO-d₆) δ 0.83 (3H, t, J=6.9 Hz), 1.05-1.32 (4H, m), 1.55-1.83 (2H, m), 2.66 (1H, dd, J=8.5, 14.4 Hz), 2.95 (1H, dd, J=5.3, 14.4 Hz), 2.99-3.07 (1H, m), 3.08-3.18 (1H, m), 3.54 (3H, s), 3.79 (3H, s), 3.81-3.91 (1H, m), 4.49 (1H, d, J=16.2 Hz), 4.60 (1H, dt, J=7.5, 7.5 Hz), 4.78 (1H, d, J=16.2 Hz), 6.26 (1H, br.s), 6.44 (1H, dd, J=1.4, 8.3 Hz), 6.64 (1H, d, J=1.4 Hz), 7.00 (1H, d, J=8.8 Hz), 7.26 (1H, dd, J=2.7, 8.8 Hz), 7.31 (1H, d, J=2.7 Hz), 7.65 (1H, d, J=8.3 Hz), 9.45 (1H, d, J=7.5 Hz)
MS: 560 (M+H)⁺

Reference Example 52

2,2,2-trichloroethyl 2-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)propyl]-1,3-thiazole-4-carboxylate (compound S52)

Step (1): Instead of the starting material, that is, the compound S4, of Reference Example 19, the compound S16 was used for a similar reaction as in Reference Example 19 to obtain 2,2,2-trichloroethyl(R)-2-(1-isocyanatopropyl)thiazole 4-carboxylate (compound S52a).

Step (2): Instead of the reaction agent, that is, the compound S19, of Reference Example 20, the compound S52a was used for a similar procedure as in Reference Examples 20 and 22 to obtain the title compound.

Example 67

2-[(1R)-1-({[(6R)-6-(5-chloro-2-methoxybenzyl)-7-oxo-3-(phenoxyimino)-1,4-diazepan-1-yl]carbonyl}amino)propyl]-1,3-thiazole-4-carboxylic acid (compound 67)

Step (1): Instead of the starting material, that is, the compound S31, of Example 29, the compound S52 was used, and instead of the reaction agent, that is, O-(4-fluorophenyl)hydroxylamine hydrochloride, O-phenyl hydroxylamine hydrochloride was used for a similar procedure as in Example 29 to obtain 2,2,2-trichloroethyl 2-[(1R)-1-({[(6R)-6-(5-chloro-2-methoxybenzyl)-7-oxo-3-(phenoxyimino)-1,4-diazepan-1-yl]carbonyl}amino)propyl]-1,3-thiazole-4-carboxylate (compound 67a) as a crude product.

Step (2): Instead of the starting material, that is, the compound 61a, of Example 61, Step (2), the compound 67a crude product obtained at Step (1) was used for a similar procedure as in Example 61, Step (2) to obtain the title compound.

$^1$H-NMR (DMSO-d$_6$) δ 0.89 (3H, br.s), 1.85-2.10 (2H, m), 2.65-2.77 (1H, m), 2.90-3.08 (1H, m), 3.13-3.26 (2H, m), 3.81 (3H, s), 3.85-4.00 (1H, m), 4.71 (1H, d, J=17.9 Hz), 4.87-5.00 (1H, m), 5.06 (1H, br.s), 6.84-6.97 (2H, m), 6.98-7.10 (3H, m), 7.19-7.30 (3H, m), 7.36 (1H, br.s), 7.56 (1H, br.s), 9.60 (1H, d, J=8.1 Hz)
MS: 586 (M+H)$^+$

Reference Example 53

(6R)-6-(5-chloro-2-methoxybenzyl)-2-thioxo-1-(2,4,6-trimethoxybenzyl)-1,4-diazepan-5-one (compound S53)

To the compound S140c described in WO 06-059801A, that is, (6R)-6-(5-chloro-2-methoxybenzyl)-1-(2,4,6-trimethoxybenzyl)-1,4-diazepane-2,5-dione (2.2 g) in a tetrahydrofuran (80 ml) solution, Belleau's reagent (1.5 g) was added under ice cooling, and the mixture was stirred at that temperature for 3 hours. The reaction solution was diluted with ethyl acetate, successively washed with saturated aqueous sodium hydrogencarbonate solution, water, and brine, dried over anhydrous sodium sulfate, then concentrated. The residue was purified by flash column chromatography (silica gel, hexane/ethyl acetate=35/65 to 1/99) to obtain the title compound (1.69 g).

$^1$H-NMR (CDCl$_3$) δ 2.23-2.34 (1H, m), 2.54 (1H, dd, J=11.0, 13.4 Hz), 3.07-3.16 (2H, m), 3.59-3.69 (1H, m), 3.64 (6H, s), 3.71 (3H, s), 3.84 (3H, s), 4.24 (1H, dd, J=7.9, 15.6 Hz), 4.52 (1H, d, J=14.2 Hz), 4.61 (1H, dd, J=3.4, 15.6 Hz), 5.46 (1H, d, J=14.2 Hz), 5.95 (2H, s), 6.11-6.18 (1H, m), 6.67 (1H, d, J=8.5 Hz), 6.85 (1H, d, J=2.4 Hz), 7.13 (1H, dd, J=2.4, 8.5 Hz)
MS: 479 (M+H)$^+$

Reference Example 54

(6R)-6-(5-chloro-2-methoxybenzyl)-2-(phenoxyimino)-1-(2,4,6-trimethoxybenzyl)-1,4-diazepan-5-one (compound S54)

To the compound S53 (0.5 g) in a tetrahydrofuran (5 ml) and methanol (10 ml) solution, O-phenyl hydroxylamine hydrochloride (0.23 g), triethylamine (0.22 ml), and mercury acetate (0.4 g) were successively added at 0° C., and the mixture was stirred at room temperature for 15 hours. The insolubles were filtered out, and the filtrate was concentrated. Then the residue was purified by flash column chromatography (silica gel, hexane/ethyl acetate=1/1 to 1/3) to obtain the title compound (0.28 g).

$^1$H-NMR (CDCl$_3$) δ 2.49 (1H, dd, J=10.1, 13.4 Hz), 2.60-2.71 (1H, m), 2.89 (1H, dd, J=5.9, 14.4 Hz), 3.08 (1H, dd, J=3.9, 13.4 Hz), 3.18 (1H, dd, J=12.0, 14.4 Hz), 3.68 (6H, s), 3.73 (3H, s), 3.81-3.85 (3H, m), 4.26 (1H, dd, J=5.1, 16.8 Hz), 4.36 (1H, d, J=13.4 Hz), 4.51 (1H, d, J=13.4 Hz), 4.58 (1H, dd, J=7.1, 16.8 Hz), 5.79-5.87 (1H, m), 6.03 (2H, s), 6.69 (1H, d, J=8.5 Hz), 6.90 (1H, d, J=2.4 Hz), 6.91-6.97 (1H, m), 7.13 (1H, dd, J=2.4, 8.5 Hz), 7.16-7.21 (2H, m), 7.27-7.31 (2H, m)
MS: 554 (M+H)$^+$

Example 68

4-[(1R)-1-({[(6R)-6-(5-chloro-2-methoxybenzyl)-7-oxo-3-(phenoxyimino)-1,4-diazepan-1-yl]carbonyl}amino)propyl]benzoic acid (compound 68)

Step (1): Instead of the starting material, that is, (6R)-6-(5-chloro-2-methoxybenzyl)-1-(2,4,6-trimethoxybenzyl)-1,4-diazepane-2,5-dione, of Reference Example 20, the compound S54 was used for a similar procedure as in Reference Example 20 to obtain tert-butyl 4-[(1R)-1-({[(6R)-6-(5-chloro-2-methoxybenzyl)-7-oxo-3-(phenoxyimino)-4-(2,4,6-trimethoxybenzyl)-1,4-diazepan-1-yl]carbonyl}amino)propyl]benzoate (compound 68a).

Step (2): To the compound 68a obtained at Step (1) (100 mg), anisole (0.113 ml) and trifluoroacetic acid (2 ml) were added, and the mixture was stirred at room temperature for 3 hours. The reaction solution was concentrated, then the residue was purified by flash column chromatography (silica gel, chloroform/ethyl acetate/methanol/acetic acid-20/20/1/0.1) to obtain the title compound (57 mg).

$^1$H-NMR (DMSO-d$_6$) δ 0.84 (3H, t, J=7.5 Hz), 1.74-1.86 (2H, m), 2.71 (1H, dd, J=8.8, 14.4 Hz), 3.00 (1H, dd, J=4.7, 14.4 Hz), 3.14-3.25 (2H, m), 3.81 (3H, s), 3.92 (1H, m), 4.65 (1H, d, J=16.2 Hz), 4.77 (1H, dt, J=7.3, 7.3 Hz), 4.90 (1H, d, J=16.2 Hz), 6.86-6.94 (2H, m), 6.99-7.08 (3H, m), 7.21-7.30 (3H, m), 7.35 (1H, d, J=2.8 Hz), 7.41 (2H, d, J=8.2 Hz), 7.91 (2H, d, J=8.2 Hz), 9.52 (1H, d, J=7.3 Hz), 12.81 (1H, s)
MS: 579 (M+H)$^+$

Reference Example 55 tert-butyl 3-[(1R)-1-({[(6R)-6-(5-chloro-2-methoxybenzyl)-7-oxo-3-thioxo-1,4-diazepan-1-yl]carbonyl}amino)propyl]benzoate (compound S55)

Instead of the starting material, that is, (6R)-6-(5-chloro-2-methoxybenzyl)-1-(2,4,6-trimethoxybenzyl)-1,4-diazepan-2,5-dione, of Reference Example 53, the compound S163 described in WO 06-059801A, that is, tert-butyl (3-[(1R)-1-({[(6R)-6-(5-chloro-2-methoxybenzyl)-3,7-dioxo- 1,4-diazepan-1-yl]carbonyl}amino)propyl]benzoate was used for a similar procedure as in Reference Example 53 to obtain the title compound.

Example 69

3-[(1R)-1-({[(6R)-6-(5-chloro-2-methoxybenzyl)-3-(hydroxyimino)-7-oxo-1,4-diazepan-1-yl]carbonyl}amino)propyl]benzoic acid (compound 69)

Step (1): To the compound S55 (100 mg) in a tetrahydrofuran (1 ml) and methanol (2 ml) solution, hydroxylamine hydrochloride (18.6 mg), triethylamine (37 µl), and mercury acetate (66 mg) were successively added under ice cooling, and the mixture was stirred at that temperature for 30 minutes. The reaction mixture was filtered, and the filtrate was concentrated to obtain tert-butyl 3-[(1R)-1-({[(6R)-6-(5-chloro-2-methoxybenzyl)-3-(hydroxyimino)-7-oxo-1,4-diazepan-1-yl]carbonyl}amino)propyl]benzoate (compound 69a) (18.4 mg).

Step (2): To the compound 69a obtained at Step (1) (35 mg), 1M hydrochloric acid in acetic acid solution (1 ml) was added, and the mixture was stirred at room temperature for 1 hour. The reaction solution was diluted with toluene and concentrated, then the residue was triturated with ethyl acetate-toluene to obtain the title compound (14.1 mg).

$^1$H-NMR (DMSO-$d_6$) δ 0.85 (3H, t, J=7.3 Hz), 1.71-1.91 (2H, m), 2.70 (1H, dd, J=9.5, 14.4 Hz), 3.00 (1H, dd, J=4.7, 14.4 Hz), 3.19-3.34 (2H, m), 3.80 (3H, s), 3.89-4.04 (1H, m), 4.68-4.87 (2H, m), 4.93 (1H, d, J=16.2 Hz), 7.02 (1H, d, J=8.9 Hz), 7.29 (1H, dd, J=2.8, 8.9 Hz), 7.35 (1H, d, J=2.8 Hz), 7.47 (1H, t, J=7.5 Hz), 7.58 (1H, d, J=7.5 Hz), 7.83 (1H, d, J=7.5 Hz), 7.89 (1H, s), 9.38 (1H, d, J=7.3 Hz), 13.01 (1H, br.s)

MS: 503 (M+H)$^+$

Example 70

3-[(1R)-1-({[(6R)-6-(5-chloro-2-methoxybenzyl)-3-(ethoxyimino)-7-oxo-1,4-diazepan-1-yl]carbonyl}amino)propyl]benzoic acid (compound 70)

Instead of the reaction agent, that is, hydroxylamine hydrochloride, in Example 69, O-ethyl hydroxylamine hydrochloride was used for a similar procedure as in Example 69 to obtain the title compound.

$^1$H-NMR (DMSO-$d_6$) δ 0.84 (3H, t, J=7.3 Hz), 1.15 (3H, t, J=6.9 Hz), 1.73-1.90 (2H, m), 2.70 (1H, dd, J=9.1, 14.2 Hz), 2.98 (1H, dd, J=4.5, 14.2 Hz), 3.13-3.29 (2H, m), 3.80 (3H, s), 3.82-3.94 (3H, m), 4.66 (1H, d, J=16.6 Hz), 4.73 (1H, dt, J=7.3, 7.3 Hz), 4.83 (1H, d, J=16.6 Hz), 7.02 (1H, d, J=8.9 Hz), 7.28 (1H, dd, J=2.6, 8.9 Hz), 7.34 (1H, d, J=2.6 Hz), 7.47 (1H, t, J=7.7 Hz), 7.57 (1H, d, J=7.7 Hz), 7.83 (1H, d, J=7.7 Hz), 7.88 (1H, s), 9.45 (1H, d, J=7.3 Hz)

MS: 531 (M+H)$^+$

Example 71

3-[(1R)-1-({[(6R)-3-[(allyloxy)imino]-6-(5-chloro-2-methoxybenzyl)-7-oxo-1,4-diazepan-1-yl]carbonyl}amino)propyl]benzoic acid (compound 71)

Step (1): Instead of the reaction agent, that is, hydroxylamine hydrochloride, in Example 69, O-allyl hydroxylamine hydrochloride was used for a similar procedure as in Example 69, Step (1) to obtain tert-butyl 3-[(1R)-1-({[(6R)-3-[(allyloxy)imino]-6-(5-chloro-2-methoxybenzyl)-7-oxo-1,4-diazepan-1-yl]carbonyl}amino)propyl]benzoate (compound 71a).

Step (2): The compound 71a obtained at Step (1) was used for a similar procedure as in Example 69, Step (2) to obtain the title compound.

$^1$H-NMR (DMSO-$d_6$) δ 0.84 (3H, t, J=7.3 Hz), 1.73-1.89 (2H, m), 2.69 (1H, dd, J=9.5, 14.2 Hz), 2.97 (1H, dd, J=4.9, 14.2 Hz), 3.12-3.22 (2H, m), 3.79 (3H, s), 3.82-3.91 (1H, m), 4.31 (2H, d, J=5.7 Hz), 4.56 (1H, d, J=15.8 Hz), 4.68-4.84 (2H, m), 5.16 (1H, d, J=10.6 Hz), 5.23-5.34 (1H, m), 5.83-5.97 (1H, m), 7.01 (1H, d, J=8.7 Hz), 7.27 (1H, dd, J=2.8, 8.7 Hz), 7.33 (1H, d, J=2.8 Hz), 7.47 (1H, t, J=7.5 Hz), 7.56 (1H, d, J=7.5 Hz), 7.83 (1H, d, J=7.5 Hz), 7.87 (1H, s), 9.48 (1H, d, J=7.3 Hz)

MS: 543 (M+H)$^+$

Example 72

3-[(1R)-1-({[(6R)-6-(5-chloro-2-methoxybenzyl)-7-oxo-3-(propoxyimino)-1,4-diazepan-1-yl]carbonyl}amino)propyl]benzoic acid (compound 72)

Step (1): To the compound 71a obtained at Example 71, Step (1) (46.4 mg) in a tetrahydrofuran solution (1 ml), platinum oxide (7.5 mg) was added, and the mixture was stirred under a hydrogen atmosphere for 30 minutes. The insolubles were filtered out, the filtrate was concentrated, and the residue was purified by flash column chromatography (silica gel, hexane/ethyl acetate=3/2/to 1/2) to obtain tert-butyl 3-[(1R)-1-({[(6R)-6-(5-chloro-2-methoxybenzyl)-7-oxo-3-(propoxyimino)-1,4-diazepan-1-yl]carbonyl}amino)propyl]benzoate (compound 72a) (57 mg).

Step (2): To the compound 72a obtained at Step (1) (36.5 mg), 1M hydrochloric acid in acetic acid solution (1 ml) was added and the mixture was stirred at room temperature for 1 hour. The reaction solution was diluted with toluene and concentrated, then the residue was triturated with ethyl acetate to obtain the title compound (22.8 mg).

$^1$H-NMR (DMSO-$d_6$) δ 0.80-0.90 (6H, m), 1.55 (1H, dq, J=7.1, 7.1 Hz), 1.74-1.90 (2H, m), 2.69 (1H, dd, J=9.1, 14.4 Hz), 2.97 (1H, dd, J=4.7, 14.4 Hz), 3.11-3.24 (1H, m), 3.75 (2H, t, J=7.1 Hz), 3.79 (3H, s), 3.81-3.92 (1H, m), 4.59 (1H, d, J=16.2 Hz), 4.70-4.83 (2H, m), 7.01 (1H, d, J=8.7 Hz), 7.27 (1H, dd, J=2.8, 8.7 Hz), 7.33 (1H, d, J=2.8 Hz), 7.47 (1H, t, J=7.7 Hz), 7.56 (1H, d, J=7.7 Hz), 7.83 (1H, d, J=7.7 Hz), 7.87 (1H, s), 9.47 (1H, d, J=7.3 Hz)

MS: 545 (M+H)$^+$

Example 73

3-[(1R)-1-({[(6R)-6-(5-chloro-2-methoxybenzyl)-7-oxo-3-(phenoxyimino)-1,4-diazepan-1-yl]carbonyl}amino)propyl]benzoic acid (compound 73)

Instead of the reaction agent, that is, hydroxylamine hydrochloride, in Example 69, O-phenyl hydroxylamine hydrochloride was used for a similar procedure as in Example 69 to obtain the title compound.

$^1$H-NMR (DMSO-$d_6$) δ 0.84 (3H, t, J=7.3 Hz), 1.72-1.88 (2H, m), 2.72 (1H, dd, J=8.9, 14.2 Hz), 3.00 (1H, dd, J=4.5, 14.2 Hz), 3.14-3.25 (2H, m), 3.81 (3H, s), 3.85-3.96 (1H, m), 4.65 (1H, d, J=16.6 Hz), 4.75 (1H, dt, J=7.3, 7.3 Hz), 4.90 (1H, d, J=16.6 Hz), 6.86-6.95 (2H, m), 6.99-7.08 (3H, m), 7.21-7.30 (3H, m), 7.35 (1H, d, J=2.8 Hz), 7.47 (1H, t, J=7.7 Hz), 7.57 (1H, d, J=7.7 Hz), 7.84 (1H, d, J=7.7 Hz), 7.88 (1H, s), 9.52 (1H, d, J=7.3 Hz), 13.00 (1H, br.s)

MS: 579 (M+H)$^+$

Example 74

3-[(1R)-1-({[(6R)-6-(5-chloro-2-methoxybenzyl)-3-(dimethylhydrazono)-7-oxo-1,4-diazepan-1-yl]carbonyl}amino)propyl]benzoic acid hydrochloride (compound 74)

Instead of the reaction agent, that is, hydroxylamine hydrochloride, in Example 69, N,N-dimethylhydrazine was used for a similar procedure as in Example 69 to obtain the title compound.

$^1$H-NMR (DMSO-$d_6$) δ 0.85 (3H, t, J=7.3 Hz), 1.75-1.91 (2H, m), 2.70 (1H, dd, J=9.5, 14.2 Hz), 3.00 (1H, dd, J=4.1, 14.2 Hz), 3.24-3.47 (2H, m), 3.33 (6H, s), 3.80 (3H, s), 3.90-4.01 (1H, m), 4.73 (1H, dt, J=7.3, 7.3 Hz), 4.84-5.01 (2H, m), 7.04 (1H, d, J=8.7 Hz), 7.29 (1H, dd, J=2.8, 8.7 Hz), 7.35 (1H, d, J=2.8 Hz), 7.47 (1H, t, J=7.7 Hz), 7.59 (1H, d, J=7.7 Hz), 7.83 (1H, dd, J=1.2, 7.7 Hz), 7.90 (1H, s), 9.24-9.39 (2H, m), 10.98 (1H, br.s), 13.01 (1H, br.s)

MS: 530 (M+H)$^+$

Reference Example 56 tert-butyl 2-amino-4-[(1R)-1-({[(6R)-6-(5-chloro-2-methoxybenzyl)-7-oxo-3-thioxo-1,4-diazepan-1-yl]carbonyl}amino)propyl]benzoic acid (compound S56)

Instead of the starting material, that is, (6R)-6-(5-chloro-2-methoxybenzyl)-1-(2,4,6-trimethoxybenzyl)-1,4-diazepane-2,5-dione, of Reference Example 53, the compound S164 described in WO 06-059801A, that is, tert-butyl 2-amino-4-[(1R)-1-({[(6R)-6-(5-chloro-2-methoxybenzyl)-3,7-dioxo-1,4-diazepan-1-yl]carbonyl}amino)propyl]benzoate, was used for a similar procedure as in Reference Example 53 to obtain the title compound.

Example 75

2-amino-4-[(1R)-1-({[(6R)-6-(5-chloro-2-methoxybenzyl)-3-(ethoxyimino)-7-oxo-1,4-diazepan-1-yl]carbonyl}amino)propyl]benzoic acid (compound 75)

Instead of the starting material, that is, the compound S22, of Example 1, the compound S56 was used, and instead of the reaction agent, that is, O-isopropyl hydroxylamine hydrochloride, O-ethyl hydroxylamine hydrochloride was used for a similar procedure as in Example 1 to obtain the title compound.

$^1$H-NMR (DMSO-$d_6$) δ 0.83 (3H, t, J=7.3 Hz), 1.15 (3H, t, J=7.0 Hz), 1.66-1.81 (2H, m), 2.63-2.73 (1H, m), 2.96 (1H, dd, J=4.7, 14.4 Hz), 3.14-3.20 (2H, m), 3.79 (3H, s), 3.80-4.00 (2H, m), 4.68 (1H, dt, J=7.7, 7.7 Hz), 4.62 (1H, d, J=17.1 Hz), 4.83 (1H, d, J=17.1 Hz), 6.45 (1H, dd, J=1.6, 8.5 Hz), 6.65 (1H, d, J=1.6 Hz), 7.01 (1H, d, J=8.9 Hz), 7.28 (1H, dd, J=2.6, 8.9 Hz), 7.33 (1H, d, J=2.6 Hz), 7.65 (1H, d, J=8.5 Hz), 9.42 (1H, d, J=7.7 Hz)

MS: 546 (M+H)$^+$

Example 76

2-amino-4-[(1R)-1-({[(6R)-6-(5-chloro-2-methoxybenzyl)-7-oxo-3-(phenoxyimino)-1,4-diazepan-1-yl]carbonyl}amino)propyl]benzoic acid (compound 76)

Instead of the starting material, that is, the compound S22, of Example 1, the compound S56 was used, and instead of the reaction agent, that is, O-isopropyl hydroxylamine hydrochloride, O-phenyl hydroxylamine hydrochloride was used for a similar procedure as in Example 1 to obtain the title compound.

$^1$H-NMR (DMSO-$d_6$) δ 0.83 (3H, t, J=7.3 Hz), 1.65-2.85 (2H, m), 2.72 (1H, dd, J=9.1, 14.4 Hz); 2.99 (1H, dd, J=4.7, 14.4 Hz), 3.15-3.26 (2H, m), 3.81 (3H, s), 3.88-3.98 (1H, m), 4.56 (1H, dt, J=7.7, 7.7 Hz), 4.67 (1H, d, J=16.2 Hz), 4.93 (2H, d, J=16.2 Hz), 6.48 (1H, dd, J=1.4, 8.3 Hz), 6.68 (1H, d, J=1.4 Hz), 6.85-7.40 (8H, m), 7.67 (1H, d, J=8.3 Hz), 9.47 (1H, d, J=7.7 Hz)

MS: 594 (M+H)$^+$

Example 77

2-amino-4-[(1R)-1-({[(6R)-6-(5-chloro-2-methoxybenzyl)-7-oxo-3-(phenoxyimino)-1,4-diazepan-1-yl]carbonyl}amino)propyl]benzoic acid hydrochloride (compound 77)

Step (1): To the compound S56 (958 mg) in a tetrahydrofuran (10 ml) and methanol (20 ml) solution, O-phenyl hydroxylamine hydrochloride (365 mg), triethylamine (0.348 ml), and mercury acetate (638 mg) were successively added under ice cooling, and the mixture was stirred at that temperature for 2 hours. The reaction mixture was filtered, the filtrate was concentrated, and the residue was purified by flash column chromatography (silica gel, hexane/ethyl acetate=9/1/to 3/1) to obtain tert-butyl 2-amino-4-[(1R)-1-({[(6R)-6-(5-chloro-2-methoxybenzyl)-7-oxo-3-(phenoxyimino)-1,4-diazepan-1-yl]carbonyl}amino)propyl]benzoate (compound 77a) (523 mg).

Step (2): To the compound 77a (523 mg) obtained at Step (1), 1M hydrochloric acid in acetic acid solution (18 ml) was added, and the mixture was stirred at room temperature for 2.5 hours. The reaction solution was concentrated, then the residue was diluted with ethyl acetate. To this solution, a 1M hydrochloric acid in acetic acid solution was added and the mixture was stirred. Further, diethyl ether was added, and the precipitated solid was collected by filtration to obtain the title compound (410 mg).

$^1$H-NMR (DMSO-$d_6$) δ 0.83 (3H, t, J=7.5 Hz), 1.63-1.84 (2H, m), 2.72 (1H, dd, J=8.9, 14.2 Hz), 2.99 (1H, dd, J=4.9, 14.2 Hz), 3.09-3.28 (2H, m), 3.81 (3H, s), 3.85-3.98 (1H, m), 4.56 (1H, dt, J=7.4, 7.4 Hz), 4.67 (1H, d, J=16.4 Hz), 4.93 (1H, d, J=16.4 Hz), 6.48 (1H, dd, J=1.5, 8.4 Hz), 6.69 (1H, d, J=1.5 Hz), 6.86-6.92 (1H, m), 6.95 (1H, br.s), 7.02 (1H, d, J=8.5 Hz), 7.03-7.11 (2H, m), 7.19-7.31 (3H, m), 7.35 (1H, d, J=2.8 Hz), 7.67 (1H, d, J=8.4 Hz), 9.46 (1H, d, J=7.4 Hz)

MS: 594 (M+H)$^+$

Example 78

2-amino-4-{(1R)-1-[({(6R)-6-(5-chloro-2-methoxybenzyl)-7-oxo-3-[(2,2,2-trifluoroethoxy)imino]-1,4-diazepan-1-yl}carbonyl)amino]propyl}benzoic acid (compound 78)

Instead of the starting material, that is, the compound S22, of Example 1, the compound S56 was used, and instead of the reaction agent, that is, O-isopropyl hydroxylamine hydrochloride, O-(2,2,2-trifluoroethyl) hydroxylamine hydrochloride was used for a similar procedure as in Example 1 to obtain the title compound.

$^1$H-NMR (DMSO-$d_6$) δ 0.83 (3H, t, J=7.3 Hz), 1.61-1.88 (2H, m), 2.67 (1H, dd, J=9.3, 14.3 Hz), 2.96 (1H, dd, J=5.1, 14.3 Hz), 3.02-3.22 (2H, m), 3.79 (3H, s), 3.81-3.91 (1H, m), 4.29-4.45 (2H, m), 4.47-4.60 (2H, m), 4.76 (1H, d, J=17.0 Hz), 6.42 (1H, dd, J=1.3, 8.2 Hz), 6.47 (1H, br.s), 6.63 (1H, d, J=1.3 Hz), 7.00 (1H, d, J=8.7 Hz), 7.27 (1H, dd, J=2.8, 8.7 Hz), 7.32 (1H, d, J=2.8 Hz), 7.64 (1H, d, J=8.2 Hz), 9.45 (1H, d, J=7.3 Hz)

MS: 600 (M+H)$^+$

Reference Example 57 tert-butyl 2-amino-4-[(1R)-1-({[(6S)-6-(5-chloro-2-methoxybenzyl)-7-oxo-3-thioxo-1,4-diazepan-1-yl]carbonyl}amino)propyl]benzoate (compound S57)

Instead of the starting material, that is, (6R)-6-(5-chloro-2-methoxybenzyl)-1-(2,4,6-trimethoxybenzyl)-1,4-diazepane-2,5-dione, of Reference Example 53, the compound 5165 described in WO 06-059801A, that is, tert-butyl 2-amino-4-[(1R)-1-({[(6S)-6-(5-chloro-2-methoxybenzyl)-3,7-dioxo-1,4-diazepan-1-yl]carbonyl}amino)propyl]benzoate, was used for a similar procedure as in Reference Example 53 to obtain the title compound.

Example 79

2-amino-4-[(1R)-1-({[(6S)-6-(5-chloro-2-methoxybenzyl)-3-(ethoxyimino)-7-oxo-1,4-diazepan-1-yl]carbonyl}amino)propyl]benzoic acid (compound 79)

Instead of the starting material, that is, the compound S22, of Example 1, the compound S57 was used, and instead of the reaction agent, that is, O-isopropyl hydroxylamine hydrochloride, O-ethyl hydroxylamine hydrochloride was used for a similar procedure as in Example 1 to obtain the title compound.

$^1$H-NMR (DMSO-d$_6$) δ 0.82 (3H, t, J=7.5 Hz), 1.08 (3H, t, J=6.9 Hz), 1.65-1.81 (2H, m), 2.61-2.71 (1H, m), 2.90-3.08 (3H, m), 3.79 (3H, s), 3.73-3.88 (3H, m), 4.44-4.59 (2H, m), 4.80 (1H, d, J=16.6 Hz), 6.14 (1H, br.s), 6.43 (1H, d, J=8.3 Hz), 6.62 (1H, s), 7.00 (1H, d, J=8.5 Hz), 7.27 (1H, dd, J=2.8, 8.5 Hz), 7.32 (1H, d, J=2.8 Hz), 7.65 (1H, d, J=8.3 Hz), 9.47 (1H, d, J=7.7 Hz)

MS: 546 (M+H)$^+$

Example 80

2-amino-4-[(1R)-1-({[(6S)-6-(5-chloro-2-methoxybenzyl)-7-oxo-3-(phenoxyimino)-1,4-diazepan-1-yl]carbonyl}amino)propyl]benzoic acid (compound 80)

Instead of the starting material, that is, the compound S22, of Example 1, the compound S57 was used, and instead of the reaction agent, that is, O-isopropyl hydroxylamine hydrochloride, O-phenyl hydroxylamine hydrochloride was used for a similar procedure as in Example 1 to obtain the title compound.

$^1$H-NMR (DMSO-d$_6$) δ 0.83 (3H, t, J=7.4 Hz), 1.67-1.79 (2H, m), 2.70 (1H, dd, J=9.5, 14.8 Hz), 2.99 (1H, dd, J=4.7, 14.8 Hz), 3.11-3.22 (2H, m), 3.81 (3H, s), 3.87-3.99 (1H, m), 4.57 (1H, dt, J=7.7, 7.7 Hz), 4.69 (1H, d, J=16.6 Hz), 4.96 (1H, d, J=16.6 Hz), 6.45 (1H, d, J=8.1 Hz), 6.64 (1H, s), 6.83-6.94 (2H, m), 6.99-7.05 (3H, m), 7.19-7.25 (2H, m), 7.28 (1H, dd, J=2.8, 8.5 Hz), 7.35 (1H, d, J=2.8 Hz), 7.65 (1H, d, J=8.1 Hz), 9.45 (1H, d, J=7.7 Hz)

MS: 594 (M+H)$^+$

Example 81

2-amino-4-[(1R)-1-({[(6S)-6-(5-chloro-2-methoxybenzyl)-3-(isopropoxyimino)-7-oxo-1,4-diazepan-1-yl]carbonyl}amino)propyl]benzoic acid (compound 81)

Instead of the starting material, that is, the compound S22, of Example 1, the compound S57 was used for a similar procedure as in Example 1 to obtain the title compound.

$^1$H-NMR (DMSO-d$_6$) δ 0.84 (3H, t, J=7.3 Hz), 1.11 (3H, d, J=6.0 Hz), 1.12 (3H, d, J=6.0 Hz), 1.67-1.81 (2H, m), 2.68 (1H, dd, J=9.2, 14.4 Hz), 2.99 (1H, dd, J=4.7, 14.4 Hz), 3.14-3.30 (2H, m), 3.80 (3H, s), 3.85-4.09 (2H, m), 4.58 (1H, dt, J=7.7, 7.7 Hz), 4.76 (1H, d, J=17.5 Hz), 4.96 (1H, d, J=17.5 Hz), 6.47 (1H, dd, J=1.6, 8.1 Hz), 6.67 (1H, dt, J=1.6 Hz), 7.02 (1H, d, J=8.9 Hz), 7.29 (1H, dd, J=2.4, 8.9 Hz), 7.34 (1H, d, J=2.4 Hz), 7.66 (1H, d, J=8.1 Hz), 9.36 (1H, d, J=7.7 Hz)

MS: 560 (M+H)$^+$

Example 82

2-amino-4-{(1R)-1-[({(6S)-6-(5-chloro-2-methoxybenzyl)-3-[(cyclopentyloxy)imino]-7-oxo-1,4-diazepan-1-yl}carbonyl)amino]propyl}benzoic acid (compound 82)

Instead of the starting material, that is, the compound S22, of Example 1, the compound S57 was used, and instead of the reaction agent, that is, O-isopropyl hydroxylamine hydrochloride, O-cyclopentyl hydroxylamine hydrochloride was used for a similar procedure as in Example 1 to obtain the title compound.

$^1$H-NMR (DMSO-d$_6$) δ 0.84 (3H, t, J=7.5 Hz), 1.38-1.83 (8H, m), 2.68 (1H, dd, J=9.2, 14.4 Hz), 2.98 (1H, dd, J=4.7, 14.4 Hz), 3.15-3.30 (2H, m), 3.80 (3H, s), 3.85-3.99 (1H, m), 4.35-4.43 (1H, m), 4.58 (1H, dt, J=7.7, 7.7 Hz), 4.75 (1H, d, J=17.0 Hz), 4.96 (1H, d, J=17.0 Hz), 6.48 (1H, dd, J=1.4, 8.1 Hz), 6.69 (1H, d, J=1.4 Hz), 7.03 (1H, d, J=8.9 Hz), 7.29 (1H, dd, J=2.4, 8.9 Hz), 7.34 (1H, d, J=2.4 Hz), 7.66 (1H, d, J=8.1 Hz), 9.36 (1H, d, J=7.7 Hz)

MS: 586 (M+H)$^+$

Example 83

2-amino-4-[(1R)-1-({[(6S)-6-(5-chloro-2-methoxybenzyl)-3-(hydroxyimino)-7-oxo-1,4-diazepan-1-yl]carbonyl}amino)propyl]benzoic acid (compound 83)

Instead of the starting material, that is, the compound S22, of Example 1, the compound S57 was used, and instead of the reaction agent, that is, O-isopropyl hydroxylamine hydrochloride, hydroxylamine hydrochloride was used for a similar procedure as in Example 1 to obtain the title compound.

$^1$H-NMR (DMSO-d$_6$) δ 0.79 (3H, t, J=7.3 Hz), 1.61-1.78 (2H, m), 2.60-2.71 (1H, m), 2.90-3.04 (2H, m), 3.09-3.20 (1H, m), 3.79 (3H, s), 3.80-3.92 (1H, m), 4.39-4.55 (2H, m), 4.85 (1H, d, J=16.2 Hz), 5.96 (1H, br.s), 6.36-6.42 (1H, m), 6.58 (1H, br.s), 6.98-7.02 (1H, m), 7.23-7.29 (1H, m), 7.30-7.35 (1H, m), 7.62-7.70 (1H, m), 9.26 (1H, s), 9.42 (1H, d, J=8.1 Hz)

MS: 518 (M+H)$^+$

Example 84

2-amino-4-[(1R)-1-({[(6S)-6-(5-chloro-2-methoxybenzyl)-3-(methoxyimino)-7-oxo-1,4-diazepan-1-yl]carbonyl}amino)propyl]benzoic acid (compound 84)

Instead of the starting material, that is, the compound S22, of Example 1, the compound S57 was used, and instead of the reaction agent, that is, O-isopropyl hydroxylamine hydrochloride, O-methyl hydroxylamine hydrochloride was used for a similar procedure as in Example 1 to obtain the title compound.

$^1$H-NMR (CDCl$_3$) δ 0.82 (3H, t, J=7.3 Hz), 1.65-1.79 (2H, m), 2.62-2.71 (1H, m), 2.91-3.08 (2H, m), 3.08-3.16 (1H, m), 3.54 (3H, s), 3.79 (3H, s), 3.75-3.87 (1H, m), 4.44-4.58 (2H, m), 4.79 (1H, d, J=16.6 Hz), 6.20 (1H, br.s), 6.42 (1H, d, J=8.1 Hz), 6.61 (1H, s), 7.00 (1H, d, J=8.9 Hz), 7.27 (1H, dd, J=2.4, 8.9 Hz), 7.31 (1H, d, J=2.4 Hz), 7.65 (1H, d, J=8.1 Hz), 9.45 (1H, d, J=7.7 Hz)

MS: 532 (M+H)$^+$

Reference Example 58 tert-butyl 3-[(1R)-1-({[(6S)-6-(5-chloro-2-methoxybenzyl)-7-oxo-3-thioxo-1,4-diazepan-1-yl]carbonyl}amino)propyl]benzoate (compound S58)

Instead of the starting material, that is, the compound S20, of Reference Example 21, the compound S142B described in WO 06-059801A, that is, tert-butyl 3-[(1R)-1-({[(6S)-6-(5-chloro-2-methoxybenzyl)-3,7-dioxo-4-(2,4,6-trimethoxybenzyl)-1,4-diazepan-1-yl]carbonyl}amino)propyl]benzoate was used in a similar procedure as Reference Examples 21 and 22 to obtain the title compound.

Example 85

3-[(1R)-1-({[(6S)-6-(5-chloro-2-methoxybenzyl)-7-oxo-3-(phenoxyimino)-1,4-diazepan-1-yl]carbonyl}amino)propyl]benzoic acid (compound 85)

Instead of the starting material, that is, the compound S56, of Example 77, Step (1), the compound S58 was used for a similar procedure as in Example 77, Step (1) and Example 22 to obtain the title compound.

$^1$H-NMR (DMSO-d$_6$) δ 0.84 (3H, t, J=7.3 Hz), 1.70-1.89 (2H, m), 2.71 (1H, dd, J=8.9, 14.4 Hz), 3.01 (1H, dd, J=4.9, 14.4 Hz), 3.09-3.25 (2H, m), 3.81 (3H, s), 3.86-3.96 (1H, m), 4.69 (1H, d, J=16.2 Hz), 4.78 (1H, dt, J=7.7, 7.7 Hz), 4.92 (1H, d, J=16.2 Hz), 6.84-6.92 (2H, m), 6.98-7.05 (3H, m), 7.18-7.25 (2H, m), 7.28 (1H, dd, J=2.4, 8.7 Hz), 7.35 (1H, d, J=2.4 Hz), 7.46 (1H, t, J=7.7 Hz), 7.57 (1H, d, J=7.7 Hz), 7.82 (1H, d, J=7.7 Hz), 7.88 (1H, s), 9.51 (1H, d, J=7.7 Hz), 12.94 (1H, br.s)

MS: 579 (M+H)$^+$

Reference Example 59

5-{(1R)-1-[({(6R)-6-(5-chloro-2-methoxybenzyl)-7-oxo-3-thioxo-1,4-diazepan-1-yl}carbonyl)amino]propyl}thiophene-3-carboxylic acid (compound S59)

Instead of the starting material, that is, the compound S21, of Reference Example 22, the compound 155 described in WO 06-059801A, that is, 5-[(1R)-1-({[(6R)-6-(5-chloro-2-methoxybenzyl)-3,7-dioxo-1,4-diazepan-1-yl]carbonyl}amino)propyl]-3-thiophenecarboxylic acid was used for a similar procedure as in Reference Example 22 to obtain the title compound (compound S59).

$^1$H-NMR (CDCl$_3$) δ 1.00 (3H, t, J=7.3 Hz), 1.90-2.03 (2H, m), 2.58 (1H, dd, J=8.5, 14.1 Hz), 3.20 (1H, dd, J=5.1, 14.1 Hz), 3.30-3.54 (2H, m), 3.69-3.92 (4H, m), 4.43 (1H, d, J=17.9 Hz), 5.08 (1H, dt, J=7.7, 7.7 Hz), 5.94 (1H, d, J=17.9 Hz), 6.81 (1H, d, J=8.8 Hz), 7.11 (1H, d, J=2.5 Hz), 7.22 (1H, dd, J=2.5, 8.8 Hz), 7.40 (1H, d, J=1.0 Hz), 8.03 (1H, br.s), 8.07 (1H, d, J=1.0 Hz), 9.37 (1H, d, J=7.7 Hz)

MS: 510 (M+H)$^+$

Example 86

5-{(1R)-1-[({(6R)-6-(5-chloro-2-methoxybenzyl)-3-[(3-fluorophenoxy)imino]-7-oxo-1,4-diazepan-1-yl}carbonyl)amino]propyl}thiophene-3-carboxylic acid (compound 86)

Instead of the starting material, that is, the compound S56, of Example 77, Step (1), the compound S59 was used for a similar procedure as in Example 77, Step (1) to obtain the title compound.

$^1$H-NMR (DMSO-d$_6$) δ 0.89 (3H, t, J=7.3 Hz), 1.81-1.98 (2H, m), 2.70 (1H, dd, J=9.3, 14.4 Hz), 2.98 (1H, dd, J=4.9, 14.4 Hz), 3.10-3.24 (2H, m), 3.80 (3H, s), 3.84-4.03 (1H, m), 4.70 (1H, d, J=16.2 Hz), 4.86-5.09 (2H, m), 6.65-6.78 (1H, m), 6.82-6.92 (2H, m), 6.96-7.07 (1H, m), 7.20-7.32 (3H, m), 7.34 (1H, d, J=2.4 Hz), 8.09 (1H, s), 9.43 (1H, d, J=7.7 Hz)

MS: 603 (M+H)$^+$

Example 87

2-amino-4-[(1R)-1-({[(6S)-6-(5-chloro-2-methoxybenzyl)-3-methyl-7-oxo-6,7-dihydro-5H-[1,2,4]triazolo[4,3-a][1,4]diazepin-8(9H)-yl]carbonyl}amino)propyl]benzoic acid (compound 87)

Step (1): To the compound S57 obtained at Reference Example 57 (100 mg) in a tetrahydrofuran (0.5 ml) and methanol (2 ml) solution, acetohydrazide (19 mg) and mercury acetate (66 mg) were successively added under ice cooling, and the mixture was stirred at that temperature for 40 minutes. The reaction mixture was diluted with ethyl acetate, and the insolubles were filtered out. Then the filtrate was washed with saturated aqueous potassium hydrogencarbonate and a brine. The organic layer was dried over anhydrous sodium sulfate, then concentrated to obtain tert-butyl 2-amino-4-[(1R)-1-({[3-(2-acetylhydrazono)-(6S)-6-(5-chloro-2-methoxybenzyl)-7-oxo-1,4-diazepan-1-yl]carbonyl}amino)propyl]benzoic acid (compound 87a) (58.2 mg).

Step (2): The compound 87a obtained at Step (1) (58.2 mg) was dissolved in 1,4-dioxane (1.5 ml), and the mixture was stirred at 100° C. for 30 minutes. The reaction solution was concentrated, then the residue was purified by flash column chromatography (silica gel, chloroform/ethyl acetate/methanol=7/7/2) to obtain tert-butyl 2-amino-4-[(1R)-1-({[(6S)-6-(5-chloro-2-methoxybenzyl)-3-methyl-7-oxo-6,7-dihydro-5H-[1,2,4]triazolo[4,3-a][1,4]diazepin-8(9H)-yl]carbonyl}amino)propyl]benzoate (compound 87b) (33.4 mg).

Step (3): To the compound 87b obtained at Step (2) (33.4 mg), 1M hydrochloric acid in acetic acid solution was added, and the mixture was stirred at room temperature for 3 hours. The reaction solution was concentrated, then the residue was diluted with ethyl acetate and washed with saturated aqueous ammonium chloride solution and brine. The organic layer was dried over anhydrous sodium sulfate, then concentrated. The residue was triturated with ethyl acetate/hexane to obtain the title compound (17.3 mg).

$^1$H-NMR (DMSO-$d_6$) δ 0.81 (3H, t, J=7.3 Hz), 1.65-1.83 (2H, m), 2.21 (3H, s), 2.82 (1H, dd, J=7.7, 14.4 Hz), 3.07 (1H, dd, J=5.9, 14.4 Hz), 3.82 (3H, s), 3.85-4.00 (2H, m), 4.11-4.23 (1H, m), 4.56 (1H, dt, J=7.7, 7.7 Hz), 4.94 (1H, d, J=16.6 Hz), 5.76 (1H, d, J=16.6 Hz), 6.42 (1H, dd, J=1.6, 8.5 Hz), 6.62 (1H, d, J=1.6 Hz), 7.02 (1H, d, J=8.9 Hz), 7.28 (1H, dd, J=2.4, 8.9 Hz), 7.38 (1H, d, J=2.4 Hz), 7.62 (1H, d, J=8.5 Hz), 9.41 (1H, d, J=7.7 Hz)

MS: 541 (M+H)$^+$

Example 88

2-amino-4-[(1R)-1-({[(6S)-6-(5-chloro-2-methoxybenzyl)-3-hydroxy-7-oxo-6,7-dihydro-5H-[1,2,4]triazolo[4,3-a][1,4]diazepin-8(9H)-yl]carbonyl}amino)propyl]benzoic acid (compound 88)

Instead of the reaction agent, that is, acetohydrazide, of Example 87, Step (1), methyl carbazate was used for a similar procedure as in Example 87 to obtain the title compound.

$^1$H-NMR (DMSO-$d_6$) δ 0.83 (3H, t, J=7.3 Hz), 1.67-1.80 (2H, m), 2.84 (1H, dd, J=9.5, 14.4 Hz), 3.03 (1H, dd, J=4.7, 14.4 Hz), 3.38-3.46 (2H, m), 3.81 (3H, s), 3.96-4.08 (1H, m), 4.57 (1H, dt, J=7.7, 7.7 Hz), 4.80 (1H, d, J=16.8 Hz), 5.38 (1H, d, J=16.8 Hz), 6.45 (1H, dd, J=1.4, 8.3 Hz), 6.60-6.65 (1H, m), 7.03 (1H, d, J=8.7 Hz), 7.29 (1H, dd, J=2.6, 8.7 Hz), 7.39 (1H, d, J=2.6 Hz), 7.64 (1H, d, J=8.3 Hz), 9.43 (1H, d, J=7.7 Hz), 11.66 (1H, s)

MS: 543 (M+H)$^+$

Example 89

2-amino-4-[(1R)-1-({[(6S)-6-(5-chloro-2-methoxybenzyl)-7-oxo-6,7-dihydro-5H-imidazo[1,2-a][1,4]diazepin-8(9H)-yl]carbonyl}amino)propyl]benzoate hydrochloride (compound 89)

Step (1): Instead of the reaction agent, that is, acetohydrazide, of Example 87, Step (1), aminoacetaldehyde dimethylacetal was used for a similar procedure as in Example 87, Step (1) to obtain tert-butyl 2-amino-4-[(1R)-1-({[(6S)-6-(5-chloro-2-methoxybenzyl)-3-(2,2-dimethoxyethylimino)-7-oxo-1,4-diazepan-1-yl]carbonyl}amino)propyl]benzoic acid (compound 89a) as a crude product (94.2 mg).

Step (2): The compound 89a crude product obtained at Step (1) (94.2 mg) was dissolved in 1,4-dioxane (4 ml), pyridinium p-toluenesulfonate (5 mg) was added, and the mixture was stirred at 100° C. for 2 hours. The reaction solution was concentrated, then the residue was purified by flash column chromatography (NH$_2$ silica gel, ethyl acetate/hexane=7/3 to 1/0) to obtain tert-butyl 2-amino-4-[(1R)-1-({[(6S)-6-(5-chloro-2-methoxybenzyl)-7-oxo-6,7-dihydro-5H-imidazo[1,2-a][1,4]diazepin-8(9H)-yl]carbonyl}amino)propyl]benzoate (compound 89b) (33.4 mg).

Step (3): The compound 89b obtained at Step (2) (27.2 mg) was dissolved in a 1M hydrochloric acid in acetic acid solution, then the mixture was stirred at room temperature for 3 hours. The precipitated solid was collected by filtration to obtain the title compound (17.8 mg).

$^1$H-NMR (DMSO-$d_6$) δ 0.84 (3H, t, J=7.3 Hz), 1.68-1.85 (2H, m), 2.79-2.89 (1H, m), 3.02-3.11 (1H, m), 3.83 (3H, s), 4.03-4.14 (1H, m), 4.21-4.32 (2H, m), 4.58 (2H, dt, J=7.7, 7.7 Hz), 5.14 (1H, d, J=17.9 Hz), 5.94 (1H, d, J=17.9 Hz), 6.48 (1H, d, J=8.5 Hz), 6.66 (1H, s), 7.05 (1H, d, J=8.7 Hz), 7.30 (1H, dd, J=2.4, 8.7 Hz), 7.40 (1H, d, J=2.4 Hz), 7.56-7.67 (3H, m), 9.35 (1H, d, J=7.7 Hz)

MS: 526 (M+H)$^+$

Example 90

2-amino-4-[(1R)-1-({[(6S)-6-(5-chloro-2-methoxybenzyl)-7-oxo-6,7-dihydro-5H-[1,2,4]triazolo[4,3-a][1,4]diazepin-8(9H)-yl]carbonyl}amino)propyl]benzoic acid (compound 90)

Instead of the reaction agent, that is, acetohydrazide, of Example 87, Step (1), formhydrazide was used for a similar procedure as in Example 87 to obtain the title compound.

$^1$H-NMR (DMSO-$d_6$) δ 0.83 (3H, t, J=7.3 Hz), 1.66-1.82 (2H, m), 2.83 (1H, dd, J=8.7, 14.4 Hz), 3.04 (1H, dd, J=4.7, 14.4 Hz), 3.82 (3H, s), 4.02-4.23 (3H, m), 4.57 (1H, dt, J=7.7, 7.7 Hz), 4.96 (1H, d, J=16.8 Hz), 5.84 (1H, d, J=16.8 Hz), 6.43 (1H, dd, J=1.6, 8.5 Hz), 6.62 (1H, d, J=1.6 Hz), 7.03 (1H, d, J=8.9 Hz), 7.28 (1H, dd, J=2.4, 8.9 Hz), 7.39 (1H, d, J=2.4 Hz), 7.63 (1H, d, J=8.5 Hz), 8.40 (1H, s), 9.43 (1H, d, J=7.7 Hz)

MS: 527 (M+H)$^+$

Reference Example 60 tert-butyl 4-[(1R)-1-({[(6S)-6-(5-chloro-2-methoxybenzyl)-7-oxo-3-thioxo-1,4-diazepan-1-yl]carbonyl}amino)propyl]-2-nitrobenzoate (compound S60)

Instead of the starting material, that is, the compound S21, of Reference Example 22, the compound 5162 described in WO 06-059801A, that is, tert-butyl 4-[(1R)-1-({[(6S)-6-(5-chloro-2-methoxybenzyl)-3,7-dioxo-1,4-diazepan-1-yl]carbonyl}amino)propyl]-2-nitrobenzoate was used for a similar reaction as in Reference Example 22 to obtain the title compound (compound S60).

$^1$H-NMR (CDCl$_3$) δ 0.95 (3H, t, J=7.3 Hz), 1.56 (9H, s), 1.79-1.94 (2H, m), 2.62 (1H, dd, J=8.5, 13.8 Hz), 3.20 (1H, dd, J=5.3, 13.8 Hz), 3.37-3.44 (2H, m), 3.74-3.82 (1H, m), 3.84 (3H, s), 4.44 (1H, d, J=17.9 Hz), 4.86 (1H, dt, J=6.9, 6.9 Hz), 5.87 (1H, d, J=17.9 Hz), 6.82 (1H, d, J=8.9 Hz), 7.14 (1H, d, J=2.8 Hz), 7.23 (1H, dd, J=2.8, 8.9 Hz), 7.57 (1H, dd, J=1.6, 7.7 Hz), 7.69 (1H, d, J=7.7 Hz), 7.73 (1H, d, J=1.6 Hz), 7.82 (1H, br.s), 9.46 (1H, d, J=6.9 Hz)

MS: 549 (M−tBu)$^+$

Example 91

2-amino-4-[(1R)-1-({[(6S)-6-(5-chloro-2-methoxybenzyl)-2-ethyl-3,7-dioxo-2,6,7,9-tetrahydro-3H-[1,2,4]triazolo[4,3-a][1,4]diazepin-8(5H)-yl]carbonyl}amino)propyl]benzoic acid (compound 91)

Step (1): Instead of the starting material, that is, the compound S57, of Example 87, Step (1), the compound S60 was used, and instead of the reaction agent, that is, acetylhydrazine, methyl carbazate was used for a similar procedure as in Example 87, Step (1) and Step (2) to obtain tert-butyl 4-[(1R)-1-({[(6S)-6-(5-chloro-2-methoxybenzyl)-3-hydroxy-7-oxo-6,7-dihydro-5H-[1,2,4]triazolo[4,3-a][1,4]diazepin-8(9H)-yl]carbonyl}amino)propyl]-2-nitrobenzoate (compound 91a).

Step (2): To the compound 91a obtained at Step (1) (234 mg) in an N,N-dimethylformamide (2.5 ml) solution, potassium carbonate (62 mg) and ethyl iodide (0.15 ml) were added, and the mixture was stirred at room temperature for 3 hours. To the reaction solution, water was added and the mixture was extracted with ethyl acetate. The extract was combined, washed with brine, dried over anhydrous sodium sulfate, then concentrated. The residue was purified by flash column chromatography (silica gel, hexane/ethyl acetate=1/1 to 1/3) to obtain tert-butyl 4-[(1R)-1-({[(6S)-6-(5-chloro-2-methoxybenzyl)-2-ethyl-3,7-dioxo-2,6,7,9-tetrahydro-3H-[1,2,4]triazolo[4,3-a][1,4]diazepin-8(5H)-yl]carbonyl}amino)propyl]-2-nitrobenzoate (compound 91b) (91 mg).

Step (3): To the compound 91b obtained at Step (2) (91 mg), trifluoroacetic acid (2 ml) was added, and the mixture was stirred at room temperature for 1.5 hours. To the reaction solution, zinc powder (0.2 g) was added, and the mixture was stirred for 2 hours. Then the insolubles were filtered out. The filtrate was concentrated, then the residue was purified by flash column chromatography (silica gel, chloroform/ethyl acetate/methanol/acetic acid=15/15/1/0.1) to obtain the title compound (45 mg).

$^1$H-NMR (DMSO-d$_6$) δ 0.82 (3H, t, J=7.3 Hz), 1.12 (3H, t, J=7.1 Hz), 1.66-1.80 (2H, m), 2.82 (1H, dd, J=9.3, 14.6 Hz), 3.03 (1H, dd, J=4.7, 14.6 Hz), 3.40-3.48 (2H, m), 3.52-3.67 (2H, m), 3.80 (3H, s), 3.97-4.08 (1H, m), 4.56 (1H, dt, J=7.7, 7.7 Hz), 4.80 (1H, d, J=16.2 Hz), 5.40 (1H, d, J=16.2 Hz), 6.44 (1H, dd, J=1.6, 8.1 Hz), 6.62 (1H, d, J=1.6 Hz), 7.02 (1H, d, J=8.9 Hz), 7.28 (1H, dd, J=2.8, 8.9 Hz), 7.38 (1H, d, J=2.8 Hz), 7.63 (1H, d, J=8.1 Hz), 9.41 (1H, d, J=7.7 Hz

MS: 571 (M+H)$^+$

Example 92

3-[(1R)-1-({[(6S)-6-(5-chloro-2-methoxybenzyl)-3-hydroxy-7-oxo-6,7-dihydro-5H-[1,2,4]triazolo[4,3-a][1,4]diazepin-8(9H)-yl]carbonyl}amino)propyl]benzoic acid (compound 92)

Step (1): Instead of the starting material, that is, the compound S57, of Example 87, Step (1), the compound S58 was used, and instead of the reaction agent, that is, acetohydrazide, methyl carbazate was used for a similar procedure as in Example 87, Step (1) and Step (2) to obtain tert-butyl 3-[(1R)-1-({[(6S)-6-(5-chloro-2-methoxybenzyl)-3-hydroxy-7-oxo-6,7-dihydro-5H-[1,2,4]triazolo[4,3-a][1,4]diazepin-8(9H)-yl]carbonyl}amino)propyl]benzoate (compound 92a).

Step (2): Instead of the starting material of Example 87, Step (3), that is, the compound 87b, the compound 92a was used for a similar procedure as in Example 87, Step (3) to obtain the title compound.

$^1$H-NMR (DMSO-d$_6$) δ 0.84 (3H, t, J=7.3 Hz), 1.70-1.90 (2H, m), 2.84 (1H, dd, J=9.3, 14.4 Hz), 3.04 (1H, dd, J=4.7, 14.4 Hz), 3.36-3.45 (2H, m), 3.80 (3H, s), 3.95-4.08 (1H, m), 4.70-4.86 (2H, m), 5.35 (1H, d, J=17.0 Hz), 7.03 (1H, d, J=8.7 Hz), 7.29 (1H, dd, J=2.4, 8.7 Hz), 7.39 (1H, d, J=2.4 Hz), 7.47 (1H, t, J=7.7 Hz), 7.58 (1H, d, J=7.7 Hz), 7.83 (1H, d, J=7.7 Hz), 7.87 (1H, s), 9.48 (1H, d, J=7.7 Hz), 11.63 (1H, s), 12.93 (1H, br.s)

MS: 528 (M+H)$^+$

Example 93

3-[(1R)-1-({[(6S)-6-(5-chloro-2-methoxybenzyl)-2-ethyl-3,7-dioxo-2,6,7,9-tetrahydro-3H-[1,2,4]triazolo[4,3-a][1,4]diazepin-8(5H)-yl]carbonyl}amino)propyl]benzoic acid (compound 93)

Instead of the starting material, that is, the compound 91a, of Example 91, Step (2), the compound 92a was used for a similar procedure as in Example 91, Step (2) and Example 87, Step (3) to obtain the title compound.

$^1$H-NMR (DMSO-d$_6$) δ 0.83 (3H, t, J=7.3 Hz), 1.12 (3H, t, J=7.1 Hz), 1.70-1.90 (2H, m), 2.83 (1H, dd, J=9.3, 14.4 Hz), 3.04 (1H, dd, J=4.7, 14.4 Hz), 3.40-3.48 (2H, m), 3.51-3.66 (2H, m), 3.81 (3H, s), 3.96-4.10 (1H, m), 4.70-4.88 (2H, m), 5.37 (1H, d, J=17.0 Hz), 7.03 (1H, d, J=8.7 Hz), 7.29 (1H, dd, J=2.4, 8.7 Hz), 7.40 (1H, d, J=2.4 Hz), 7.46 (1H, t, J=7.7 Hz), 7.57 (1H, d, J=7.7 Hz), 7.83 (1H, dd, J=1.2, 7.7 Hz), 7.87 (1H, s), 9.47 (1H, d, J=7.7 Hz), 13.00 (1H, br.s)

MS: 556 (M+H)$^+$

Example 94

2-amino-4-[(1R)-1-({[(6S)-6-(5-chloro-2-methoxybenzyl)-3,7-dioxo-6,7-dihydro-5H-[1,2,4]oxadiazolo[4,3-a][1,4]diazepin-8(9H)-yl]carbonyl}amino)propyl]benzoic acid (compound 94)

Step (1): Instead of the starting material, that is, the compound S56, of Example 77, the compound S60 was used, and instead of the reaction agent, that is, O-isopropyl hydroxylamine hydrochloride, hydroxylamine hydrochloride was used for a similar procedure as in Example 77, Step (1) to obtain tert-butyl 4-[(1R)-1-({[(6S)-6-(5-chloro-2-methoxybenzyl)-3-(hydroxyimino)-7-oxo-1,4-diazepan-1-yl]carbonyl}amino)propyl]-2-nitrobenzoate (compound 94a).

Step (2): To the compound 94a obtained at Step (1) (167 mg) in a methylene chloride (5 ml) solution, triethylamine (0.154 ml) and phenyl chloroformate (42 μl) were added at 0° C., and the mixture was stirred at 0° C. for 2.5 hours. Furthermore, phenyl chloroformate (275 μl) was added, and the mixture was stirred at 0° C. for 2 hours. Then, to the reaction solution, water was added, and the mixture was extracted with ethyl acetate. The extract was combined, dried over sodium sulfate, then concentrated. The residue was dissolved in toluene (5 ml) and heated and refluxed for 18 hours. The solution was concentrated, then the residue was purified by preparative thin layer chromatography (silica gel, hexane/ethyl acetate=3/2) to obtain tert-butyl 4-[(1R)-1-({[(6S)-6-(5-chloro-2-methoxybenzyl)-3,7-dioxo-6,7-dihydro-5H-[1,2,4]oxadiazolo[4,3-a][1,4]diazepin-8(9H)-yl]carbonyl}amino)propyl]-2-nitrobenzoate (compound 94b) (69 mg).

Step (3): To the compound 94b obtained at Step (3) (68 mg), trifluoroacetic acid (2 ml) was added, and the mixture was stirred at room temperature for 1.5 hours. To the reaction solution, zinc powder (0.2 g) was added, the mixture was stirred for 2 hours, then the insolubles were filtered out. The filtrate was concentrated, then the residue was purified by flash column chromatography (silica gel, chloroform/ethyl acetate/methanol/acetic acid=15/15/1/0.1) to obtain the title compound (51 mg).

$^1$H-NMR (DMSO-d$_6$) δ 0.83 (3H, t, J=7.3 Hz), 1.67-1.84 (2H, m), 2.81 (2H, dd, J=9.1, 14.4 Hz), 3.01 (2H, dd, J=4.5, 14.4 Hz), 3.31-3.52 (2H, m), 3.81 (3H, s), 3.96-4.07 (1H, m), 4.56 (1H, dt, J=7.7, 7.7 Hz), 4.85 (1H, d, J=16.6 Hz), 5.51 (1H, d, J=16.6 Hz), 6.44 (2H, dd, J=1.4, 8.1 Hz), 6.59 (1H, d, J=1.4 Hz), 6.63 (2H, br.s), 7.04 (2H, d, J=8.9 Hz), 7.29 (2H, dd, J=2.8, 8.9 Hz), 7.39 (2H, d, J=2.8 Hz), 7.75 (2H, d, J=8.1 Hz), 9.39 (1H, d, J=7.7 Hz)

MS: 544 (M+H)$^+$

Example 95

2-amino-4-[(1R)-1-({[(6S)-6-(5-chloro-2-methoxybenzyl)-2-ethyl-3,7-dioxo-2,6,7,9-tetrahydro-3H-[1,2,4]triazolo[4,3-a][1,4]diazepin-8(5H)-yl]carbonyl}amino)pentyl]benzoic acid (compound 95)

Step (1): Instead of the starting material of Example 87, Step (1), that is, the compound S57, the compound S26 was used, and instead of the reaction agent, that is, acetylhydrazide, methyl carbazate was used for a similar procedure as in Example 87, Step (1) and Step (2) to obtain tert-butyl 4-[(1R)-1-({[(6S)-6-(5-chloro-2-methoxybenzyl)-3-hydroxy-7-oxo-6,7-dihydro-5H-[1,2,4]triazolo[4,3-a][1,4]diazepin-8(9H)-yl]carbonyl}amino)pentyl]-2-nitrobenzoate (compound 95a).

Step (2): Instead of the starting material of Example 91, Step (2), that is, the compound 91a, the compound 95a was used for a similar procedure as in Example 91, Step (2) and Step (3) to obtain the title compound.

$^1$H-NMR (DMSO-$d_6$) δ 0.84 (3H, t, J=7.1 Hz), 1.13 (3H, t, J=7.1 Hz), 1.19-1.34 (4H, m), 1.72 (2H, m), 2.79-2.87 (1H, m), 3.00-3.07 (1H, m), 3.41-3.48 (2H, m), 3.55-3.67 (2H, m), 3.81 (3H, s), 3.97-4.10 (1H, m), 4.61 (1H, dt, J=7.7, 7.7 Hz), 4.81 (1H, d, J=16.6 Hz), 5.40 (1H, d, J=16.6 Hz), 6.42 (1H, d, J=8.1 Hz), 6.59 (1H, s), 7.03 (1H, d, J=8.9 Hz), 7.28 (1H, dd, J=2.4, 8.9 Hz), 7.39 (1H, d, J=2.4 Hz), 7.63 (1H, d, J=8.1 Hz), 9.40 (1H, d, J=7.7 Hz)

MS: 599 (M+H)$^+$

Example 96

2-amino-4-[(1R)-1-({[(6S)-6-(5-chloro-2-methoxybenzyl)-2-ethyl-3,7-dioxo-2,6,7,9-tetrahydro-3H-[1,2,4]triazolo[4,3-a][1,4]diazepin-8(5H)-yl]carbonyl}amino)butyl]benzoic acid (compound 96)

Step (1): Instead of the reaction agent, that is, O-ethyl hydroxylamine hydrochloride, of Example 12, hydroxylamine hydrochloride was used for a similar procedure as in Example 12, Step (1) to obtain tert-butyl 4-[(1R)-1-({[(6S)-6-(5-chloro-2-methoxybenzyl)-3-(hydroxyimino)-7-oxo-1,4-diazepan-1-yl]carbonyl}amino)butyl]-2-nitrobenzoate (compound 96a).

Step (2): To the compound 96a obtained at Step (1) (55 mg) in a methylene chloride (2 ml) solution, triethylamine (37 μl) and bromoacetyl bromide (13 μl) was added, and the mixture was stirred at room temperature for 20 hours. To the reaction solution, saturated aqueous ammonium chloride solution was added, and the mixture was extracted with ethyl acetate. The extract was combined, washed with brine, dried over sodium sulfate, then concentrated. The residue was dissolved in acetonitrile (2 ml), and sodium hydrogencarbonate (7.5 mg) and sodium iodide (13 mg) were added to the solution. The mixture was stirred at room temperature for 3 hours. To the reaction solution, saturated aqueous ammonium chloride solution was added, and the mixture was extracted with ethyl acetate. The extract was combined, washed with brine, dried over sodium sulfate, then concentrated. The residue was purified by preparative thin layer chromatography (silica gel, hexane/ethyl acetate=2/3) to obtain tert-butyl 4-[(1R)-1-({[(6S)-6-(5-chloro-2-methoxybenzyl)-2-ethyl-3,7-dioxo-2,6,7,9-tetrahydro-3H-[1,2,4]triazolo[4,3-a][1,4]diazepin-8(5H)-yl]carbonyl}amino)butyl]-2-nitrobenzoate (compound 96b) (12.5 mg).

Step (3): To the compound 96b obtained at Step (2) (20.8 mg), trifluoroacetic acid (1 ml) was added, and the mixture was stirred at room temperature for 2 hours. To the reaction solution, zinc powder (50 mg) was added, the mixture was stirred for 2 hours, then the insolubles were filtered out. The filtrate was concentrated, then the residue was purified by preparative thin layer chromatography (silica gel, chloroform/ethyl acetate/methanol/acetic acid=20/20/1/0.1) to obtain the title compound (7 mg).

$^1$H-NMR (DMSO-$d_6$) δ 0.87 (3H, t, J=7.3 Hz), 1.13-1.35 (2H, m), 1.59-1.78 (2H, m), 2.77 (1H, dd, J=8.7, 14.4 Hz), 3.04 (1H, dd, J=4.3, 14.4 Hz), 3.46-3.57 (1H, m), 3.80 (3H, s), 3.82-3.92 (2H, m), 4.27 (1H, d, J=15.4 Hz), 4.32 (1H, d, J=15.4 Hz), 4.64 (1H, dt, J=7.3, 7.3 Hz), 4.80 (1H, d, J=16.6 Hz), 5.13 (1H, d, J=16.6 Hz), 6.45 (1H, d, J=8.1 Hz), 6.64 (1H, s), 7.02 (1H, d, J=8.9 Hz), 7.28 (1H, dd, J=2.4, 8.9 Hz), 7.36 (1H, d, J=2.4 Hz), 7.65 (1H, d, J=8.1 Hz), 9.37 (1H, d, J=7.7 Hz)

MS: 572 (M+H)$^+$

Example 97

4-[(1R)-1-({[(6S)-6-(5-chloro-2-methoxybenzyl)-3-(hydroxyimino)-7-oxo-1,4-diazepan-1-yl]carbonyl}amino)butyl]-2-nitrobenzoic acid hydrochloride (compound 97)

Step (1): The compound S30 obtained by the method described in Reference Example 30 (10.13 g) was dissolved in tetrahydrofuran (200 ml) and methanol (200 ml), the mixture was cooled to 0° C., then hydroxylamine hydrochloride (1.32 g), triethylamine (2.65 ml), and mercury acetate (4.85 g) were successively added to the solution. The mixture was stirred at 0° C. for 3 hours. The insolubles were filtered out, then ethyl acetate (200 ml), saturated aqueous ammonium chloride solution (150 ml), and water (50 ml) were added to the filtrate, and the solution was separated. The aqueous layer was extracted with ethyl acetate (100 ml), the extract was combined with the organic layer, and the mixture was washed with an saturated aqueous sodium chloride solution. The obtained organic layer was dried over sodium sulfate, then concentrated to obtain tert-butyl 4-[(1R)-1-({[(6S)-6-(5-chloro-2-methoxybenzyl)-3-(hydroxyimino)-7-oxo-4-(2,4,6-trimethoxybenzyl)-1,4-diazepan-1-yl]carbonyl}amino)butyl]-2-nitrobenzoate (compound 97a) as a crude product (10.7 g).

Step (2): To the compound 97a crude product obtained at Step (1) (10.7 g), a 4M hydrochloric acid in ethyl acetate solution (100 ml) was added, and the mixture was stirred at room temperature for 5.5 hours. The reaction mixture was concentrated until the crystals were precipitated, and the precipitated crystals were collected by filtration to obtain the title compound (1.74 g).

$^1$H-NMR (DMSO-$d_6$) δ 0.90 (3H, t, J=7.3 Hz), 1.20-1.46 (2H, m), 1.66-1.94 (2H, m), 2.70 (1H, dd, J=8.9, 14.5 Hz), 3.01 (1H, dd, J=4.7, 14.5 Hz), 3.19-3.35 (2H, m), 3.81 (3H, s), 3.94-4.06 (1H, m), 4.85-4.94 (2H, m), 5.02 (1H, d, J=17.5 Hz), 7.03 (1H, d, J=8.8 Hz), 7.29 (1H, dd, J=2.7, 8.8 Hz), 7.36 (1H, d, J=2.7 Hz), 7.76 (1H, dd, J=1.2, 7.7 Hz), 7.84 (1H, d, J=7.7 Hz), 7.98 (1H, d, J=1.2 Hz), 9.32 (1H, d, J=7.3 Hz), 10.98 (1H, br.s), 13.80 (1H, br.s)

MS: 562 (M+H)$^+$

Example 98

2-amino-4-[(1R)-1-({[(6S)-6-(5-chloro-2-methoxybenzyl)-3-(hydroxyimino)-7-oxo-1,4-diazepan-1-yl]carbonyl}amino)butyl]benzoic acid bis p-toluenesulfonate (compound 98)

Step (1): To the compound 97 (1.74 g) in an acetic acid (35 ml) suspension, zinc powder (3.5 g) was added, and the mixture was stirred at room temperature for 4 hours. The insolubles were filtered out and the filtrate was concentrated in vacuo. To the residue, acetic acid (20 ml) was added, the mixture was stirred at 60° C. for 1 hour, then the insolubles were filtered out. The filtrate was concentrated in vacuo, the residue was diluted with chloroform-methanol-acetic acid (5:1:0.1) (20 ml), and tha mixture was stirred at room temperature for 1 hour. The insolubles were collected by filtration, then ethyl acetate (105 ml), saturated aqueous ammonium chloride solution (105 ml), and water (53 ml) were added to the obtained crystals, and the mixture was stirred at room temperature for 4 hours. The layers were separated, and the aqueous layer was extracted with ethyl acetate (50 ml×2). The organic layer and the extract were combined, then the mixture was washed with brine, dried over sodium sulfate, then concentrated. The residue was purified by flash column chromatography (silica gel, chloroform/ethyl acetate/methanol=50/50/5 to 50/50/10) to obtain 2-amino-4-[(1R)-1-({[(6S)-6-(5-chloro-2-methoxybenzyl)-3-(hydroxyimino)-7-oxo-1,4-diazepan-1-yl]carbonyl}amino)butyl]benzoic acid (compound 14) (1.07 g).

Step (2): To the compound 14 obtained at Step (1) (50 mg) in a 2-propanol (0.06 ml) and ethyl acetate (0.25 ml) solution, 1M p-toluenesulfonic acid in 2-propanol solution (188 μl) was added at 60° C., then the mixture was slowly cooled down to 0° C. The precipitated crystals were collected by filtration to obtain the title compound (73 mg) as a colorless crystal.

$^1$H-NMR (DMSO-$d_6$) δ 0.88 (3H, t, J=7.3 Hz), 1.20-1.38 (2H, m), 1.58-1.80 (2H, m), 2.29 (6H, s), 2.70 (1H, dd, J=9.1, 14.6 Hz), 3.01 (1H, dd, J=4.7, 14.6 Hz), 3.23-3.31 (1H, m), 3.38 (1H, dd, J=12.8, 12.8 Hz), 3.80 (3H, s), 3.99-4.07 (1H, m), 4.65 (1H, dd, J=7.2 Hz), 4.96 (1H, d, J=17.0 Hz), 5.01 (1H, d, J=17.0 Hz), 6.49 (1H, dd, J=1.4, 8.1 Hz), 6.66 (1H, d, J=1.4 Hz), 7.03 (1H, d, J=8.8 Hz); 7.08-7.14 (4H, m), 7.29 (1H, dd, J=2.7, 8.8 Hz), 7.35 (1H, d, J=2.7 Hz), 7.46-7.50 (4H, m), 7.66 (1H, d, J=8.1 Hz), 9.08 (1H, br.s), 9.25 (1H, d, J=7.2 Hz), 11.02 (1H, br.s)

Example 99

2-amino-4-[(1R)-1-({[(6S)-6-(5-chloro-2-methoxybenzyl)-3-{[($^2$H$_3$)methoxy]imino}-7-oxo-1,4-diazepan-1-yl]carbonyl}amino)butyl]benzoic acid (compound 99)

Step (1): To the compound 97a obtained by the method of Example 97, Step (1) (135 mg) in an N,N-dimethylformamide (0.5 ml) solution, iodo($^2$H$_3$)methane (32 μl) and a 60% dispersion of sodium hydride on mineral oil (6.9 mg) were successively added, and the mixture was stirred at room temperature for 45 minutes. To the reaction solution, saturated aqueous ammonium chloride solution (1 ml), water (2 ml), ethyl acetate (5 ml), and hexane (5 ml) were successively added, then the layers were separated. The aqueous layer was extracted with a mixed solvent, hexane-ethyl acetate (1:1, 5 ml×2). The organic layer and the extract were combined, successively washed with water (2 ml), saturated aqueous sodium thiosulfate solution (1 ml), and brine (2 ml), dried over anhydrous sodium sulfate, then concentrated. The residue was purified by flash column chromatography (silica gel, hexane/ethyl acetate=3/1 to 2/3) to obtain tert-butyl 4-[(1R)-1-({[(6S)-6-(5-chloro-2-methoxybenzyl)-3-{[($^2$H$_3$)methoxy]imino}-7-oxo-4-(2,4,6-trimethoxybenzyl)-1,4-diazepan-1-yl]carbonyl}amino)butyl]-2-nitrobenzoate (compound 99a).

Step (2): Instead of the starting material, that is, the compound 29a, of Example 29, Step (2), the compound 99a was used for a similar procedure as in Example 29, Step (2) to obtain the title compound.

$^1$H-NMR (DMSO-$d_6$) δ 0.87 (3H, t, J=7.3 Hz), 1.14-1.37 (2H, m), 1.57-1.77 (2H, m), 2.67 (1H, dd, J=8.7, 14.3 Hz), 2.96 (1H, dd, J=5.0, 14.3 Hz), 3.07 (1H, dd, J=12.4, 12.4 Hz), 3.11-3.20 (1H, m), 3.80 (3H, s), 3.81-3.89 (1H, m), 4.52 (1H, d, J=16.3 Hz), 4.63 (1H, dt, J=7.8, 7.8 Hz), 4.82 (1H, d, J=16.3 Hz), 6.43 (1H, br.s), 6.45 (1H, dd, J=1.5, 8.3 Hz), 6.65 (1H, d, J=1.5 Hz), 7.00 (1H, d, J=8.8 Hz), 7.27 (1H, dd, J=2.7, 8.8 Hz), 7.31 (1H, d, J=2.7 Hz), 7.65 (1H, d, J=8.3 Hz), 9.43 (1H, d, J=7.8 Hz)

MS: 549 (M+H)$^+$

Example 100

2-amino-4-[(1R)-1-({[(6S)-6-(5-chloro-2-methoxybenzyl)-3-{[($^2$H$_5$)ethoxy]imino}-7-oxo-1,4-diazepan-1-yl]carbonyl}amino)butyl]benzoic acid (compound 100)

Instead of the reaction agent, that is, iodo($^2$H$_3$)methane, of Example 99, Step (1), iodo($^2$H$_5$)etheane was used for a similar procedure as in Example 99, Step (1) and Step (2) to obtain the title compound.

$^1$H-NMR (DMSO-$d_6$) δ 0.87 (3H, t, J=7.3 Hz), 1.14-1.36 (2H, m), 1.55-1.79 (2H, m), 2.66 (1H, dd, J=8.7, 14.4 Hz), 2.96 (1H, dd, J=5.1, 14.4 Hz), 3.04 (1H, dd, J=11.8, 11.8 Hz), 3.09-3.19 (1H, m), 3.80 (3H, s), 3.81-3.90 (1H, m), 4.50 (1H, d, J=16.3 Hz), 4.63 (1H, dt, J=7.7, 7.7 Hz), 4.80 (1H, d, J=16.3 Hz), 6.31 (1H, br.s), 6.45 (1H, dd, J=1.6, 8.3 Hz), 6.65 (1H, d, J=1.6 Hz), 7.00 (1H, d, J=8.8 Hz), 7.26 (1H, dd, J=2.7, 8.8 Hz), 7.31 (1H, d, J=2.7 Hz), 7.66 (1H, d, J=8.3 Hz), 9.44 (1H, d, J=7.7 Hz)

MS: 565 (M+H)$^+$

Reference Example 61 tert-butyl 4-[(1R)-1-({[(6R)-6-(5-chloro-2-methoxybenzyl)-7-oxo-3-thioxo-4-(2,4,6-trimethoxybenzyl)-1,4-diazepan-1-yl]carbonyl}amino)butyl]-2-nitrobenzoate (compound S61)

Step (1): To the compound S25a obtained by the method described at Reference Example 25, Step (1) (2.69 g) and the compound S140C described in WO 06-059801A, that is, (6R)-6-(5-chloro-2-methoxybenzyl)-1-(2,4,6-trimethoxybenzyl)-1,4-diazepane-2,5-dione (3.50 g) in an acetonitrile (60 ml) solution, potassium tert-butoxide in a 1M tetrahydrofuran solution (0.46 ml) was added under ice cooling, and the mixture was stirred at that temperature for 30 minutes. To the reaction solution, saturated aqueous ammonium chloride solution was added and the mixture was extracted with ethyl acetate. The extract was combined, washed with brine, dried over anhydrous sodium sulfate, then concentrated. The residue was purified by flash column chromatography (silica gel, hexane/ethyl acetate=1/1 to 0/1) to obtain tert-butyl 4-[(1R)-1-({[(6R)-6-(5-chloro-2-methoxybenzyl)-3,7-dioxo-1-(2,4,6-trimethoxybenzyl)-1,4-diazepan-1-yl]carbonyl}amino)butyl]-2-nitrobenzoate (compound S61a) (2.49 g).

Step (2): To the compound S61a obtained at Step (1) (4.09 g) in a tetrahydrofuran (21 ml) solution, Lawesson's reagent was added under ice cooling (1.16 g), and the mixture was stirred at that temperature for 16 hours. To the reaction mixture, ethyl acetate and saturated aqueous sodium hydrogencarbonate solution were added, and the layers were separated. The organic layer was successively washed with a sodium hydrogencarbonate aqueous solution and brine, dried over sodium sulfate, then concentrated to obtain the title compound (4.28 g).

$^1$H-NMR (CDCl$_3$) δ 0.94 (3H, t, J=7.3 Hz), 1.29-1.44 (2H, m), 1.56 (9H, s), 1.68-1.89 (2H, m), 2.35 (1H, dd, J=9.7, 13.8 Hz), 3.11 (1H, dd, J=4.5, 13.8 Hz), 3.14-3.27 (2H, m), 3.36-3.47 (1H, m), 3.67 (6H, s), 3.75 (3H, s), 3.86 (3H, s), 4.84 (1H, d, J=16.8 Hz), 4.90-4.99 (2H, m), 5.07 (1H, d, J=14.2 Hz), 5.57 (1H, d, J=16.8 Hz), 6.10 (2H, s), 6.75 (1H, d, J=8.6 Hz), 6.77 (1H, d, J=2.7 Hz), 7.19 (1H, dd, J=2.7, 8.6 Hz), 7.58 (1H, dd, J=1.6, 8.1 Hz), 7.68 (1H, d, J=8.1 Hz), 7.73 (1H, d, J=1.6 Hz), 9.55 (1H, d, J=6.9 Hz)

Example 101

4-[(1R)-1-({[(6R)-6-(5-chloro-2-methoxybenzyl)-3-(ethoxyimino)-7-oxo-1,4-diazepan-1-yl]carbonyl}amino)butyl]-2-nitrobenzoic acid hydrochloride (compound 101)

Step (1): The compound S61 obtained at Reference Example 61 (3.94 g) was dissolved in tetrahydrofuran (40 ml) and methanol (40 ml), the mixture was ice cooled, and then O-ethyl hydroxylamine hydrochloride (1.21 g), triethylamine (1.72 ml), and mercury acetate (3.17 g) were successively added. The mixture was stirred at that temperature for 1 hour. Further, O-ethyl hydroxylamine hydrochloride (0.24 g), triethylamine (0.34 ml), and mercury acetate (0.63 g) were successively added, and the mixture was stirred at 30 minutes. The insolubles were filtered out, then the filtrate was concentrated. To the residue, ethyl acetate (30 ml), saturated aqueous ammonium chloride solution (20 ml), and water (10 ml) were added, and the layers were separated. The organic layer was successively washed with aqueous ammonium chloride solution and brine, dried over anhydrous sodium sulfate, then concentrated to obtain tert-butyl 4-[(1R)-1-({[(6R)-6-(5-chloro-2-methoxybenzyl)-3-(ethoxyimino)-7-oxo-4-(2,4,6-trimethoxybenzyl)-1,4-diazepan-1-yl]carbonyl}amino)butyl]-2-nitrobenzoate (compound 101a) (4.19 g).

Step (2): To the compound 101a obtained at Step (1) (4.18 g), 4M hydrochloric acid in ethyl acetate solution (40 ml) was added, and the mixture was stirred at room temperature for 4 hours. The reaction mixture was ice cooled and stirred for 30 minutes, then diethyl ether (0.5 ml) was added to the solution. The mixture was further stirred for 4.5 hours. The precipitated crystals were collected by filtration to obtain the title compound (2.78 g) as a colorless crystals.

$^1$H-NMR (DMSO-d$_6$) δ 0.89 (3H, t, J=7.3 Hz), 1.16 (3H, t, J=7.0 Hz), 1.21-1.41 (2H, m), 1.69-1.90 (2H, m), 2.70 (1H, dd, J=9.1, 14.3 Hz), 3.00 (1H, dd, J=4.5, 14.3 Hz), 3.13-3.34 (2H, m), 3.80 (3H, s), 3.85-3.95 (1H, m), 3.87 (2H, q, J=7.0 Hz), 4.65-4.90 (3H, m), 7.03 (1H, d, J=8.8 Hz), 7.29 (1H, dd, J=2.7, 8.8 Hz), 7.35 (1H, d, J=2.7 Hz), 7.74 (1H, dd, J=1.6, 8.1 Hz), 7.83 (1H, d, J=8.1 Hz), 7.98 (1H, d, J=1.6 Hz), 9.39 (1H, d, J=6.9 Hz)

Example 102

2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid (compound 102)

To the compound 101 (2.76 g) in an ethyl acetate (32 ml) and acetic acid (16 ml) suspension, zinc powder (2.88 g) was added under ice cooling, and the mixture was stirred at that temperature for 20 minutes and at room temperature for 4 hours. The reaction mixture was filtered by a glass filter spread with Celite®, then the residue was washed with ethyl acetate (50 ml). The filtrate and the washings were combined, then the mixture was successively washed with saturated aqueous ammonium chloride solution and brine, dried over sodium sulfate, then concentrated. The residue was purified by flash column chromatography (silica gel, hexane/ethyl acetate/methanol=6/6/1) to obtain the title compound (2.5 g).

$^1$H-NMR (CD$_3$OD) δ 0.94 (3H, t, J=7.3 Hz), 1.18 (3H, t, J=7.1 Hz), 1.26-1.46 (2H, m), 1.66-1.84 (2H, m), 2.72 (1H, dd, J=8.3, 13.9 Hz), 3.11 (1H, dd, J=5.7, 13.9 Hz), 3.18 (1H, dd, J=12.2, 12.2 Hz), 3.78-3.87 (1H, m), 3.84 (3H, s), 3.88-3.94 (2H, m), 4.36 (1H, d, J=16.4 Hz), 4.72 (1H, dt, J=7.7, 7.7 Hz), 4.99 (1H, d, J=16.4 Hz), 6.48 (1H, dd, J=1.8, 8.5 Hz), 6.64 (1H, d, J=1.8 Hz), 6.93 (1H, d, J=8.5 Hz), 7.20 (1H, dd, J=2.6, 8.5 Hz), 7.24 (1H, d, J=2.6 Hz), 7.76 (1H, d, J=8.5 Hz), 9.68 (1H, d, J=7.7 Hz)

Example 103

2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid di hydrochloride (compound 103)

To the compound 102 (1.10 g) in an acetonitrile (44 ml) solution, a 4M hydrochloric acid in ethyl acetate solution (1.5 ml) was added, and the mixture was stirred at room temperature for 5 hours. The precipitated crystals were collected by filtration to obtain the title compound (1.03 g) as a colorless crystal.

$^1$H-NMR (DMSO-d$_6$) δ 0.88 (3H, t, J=7.0 Hz), 1.17 (3H, t, J=7.0 Hz), 1.19-1.36 (2H, m), 1.59-1.80 (2H, m), 2.69 (1H, dd, J=9.3, 14.2 Hz), 2.98 (1H, dd, J=4.5, 14.2 Hz), 3.14-3.37 (2H, m), 3.80 (3H, s), 3.87-3.96 (1H, m), 3.88 (2H, q, J=7.0 Hz), 4.61 (1H, dt, J=7.7, 7.7 Hz), 4.74 (1H, d, J=16.6 Hz), 4.90 (1H, d, J=16.6 Hz), 6.49 (1H, dd, J=1.6, 8.5 Hz), 6.69 (1H, d, J=1.6 Hz), 7.02 (1H, d, J=8.8 Hz), 7.28 (1H, dd, J=2.7, 8.8 Hz), 7.34 (1H, d, J=2.7 Hz), 7.66 (1H, d, J=8.5 Hz), 9.34 (1H, d, J=7.7 Hz)

MS: 560 (M+H)$^+$

Reference Example 62

6-methylene-1-(2,4,6-trimethoxybenzyl)-1,4-diazepan-2,5-dione (compound S62)

Step (1): To ethyl 2-(bromomethyl)acrylate (104.4 g) in an acetonitrile (900 ml) solution, di-tert-butyl imino dicarboxylate (122.4 g) and potassium carbonate was added, and the mixture was stirred at room temperature for 2 days. The reaction solution was concentrated in vacuo. To the residue, ethyl acetate (1.4 liter) and water (700 ml) were added, and the layers were separated. The organic layer was washed with water (350 ml), dried over sodium sulfate, then concentrated to obtain ethyl 2-{[di(tert-butoxycarbonyl)amino]methyl}acrylate (compound S62a) as a crude product (182.7 g).

Step (2): To the compound S62a crude product obtained at Step (1) (182.0 g) in a methanol (1 liter) solution, 2M aqueous sodium hydroxide solution (552 ml) was slowly added, then the mixture was stirred at room temperature for 1.5 hours. The reaction solution was concentrated in vacuo. To the residue, chloroform (500 ml) and water (500 ml) were added, then saturated aqueous potassium hydrogensulfate solution (280 ml) was slowly added. To the aqueous mixture obtained, chloroform (300 ml) was added, and the layers were separated. The aqueous layer was extracted with chloroform (300 ml). The organic layer and the extract were combined, then the mixture was washed with brine (300 ml), dried over sodium sulfate, and concentrated to obtain 2-{[di(tert-butoxycarbonyl)amino]methyl}acrylic acid (compound S62b) as a crude product (171.8 g).

Step (3): To the compound S62b crude product obtained at Step (2) (171.0 g) in a dichloromethane (1.2 liter) solution, glycine ethylester hydrochloride (94.4 g), 1-hydroxybenzotriazole (94.4 g), 1-(3-dimethylaminopropyl)-3-ethylcarbodiimide hydrochloride (131.9 g), and triethylamine (94.2 ml) were successively added, and the mixture was stirred at room temperature for 4 hours. To the reaction mixture, water (1 liter), saturated aqueous sodium hydrogencarbonate solution (1.29 liter), and chloroform (1 liter) were successively added, and the layers were separated. The organic layer was successively washed with water (1 liter), aqueous potassium hydrogensulfate solution (1 liter), aqueous sodium hydrogencarbonate solution (1.6 liter), and brine (500 ml), dried over sodium sulfate, and then concentrated to obtain ethyl 2-(2-{[di(tert-butoxycarbonyl)amino]methyl}acrylamide)acetate (compound S62c) as a crude product (108.32 g).

Step (4): To the compound S62c crude product obtained at Step (3) (118.0 g) in an ethanol (1015 ml) solution, methanesulfonic acid (60 ml) was added, and the mixture was stirred at 40° C. for 17 hours. The reaction solution was ice cooled, ethanol (252 ml) was added, and further triethylamine (129 ml) was slowly added. Further, to the reaction solution, 2,4,6-trimethoxybenzaldehyde (52.7 g) and sodium triacetoxyborohydride (113.3 g) were successively added under ice cooling, then the mixture was stirred at 40° C. for 1.5 hours. The reaction solution was concentrated in vacuo. To the residue, chloroform (1.4 liter) and water (500 ml) was added, further saturated aqueous sodium hydrogencarbonate solution (1.2 liter) was slowly added. The layers were separated, then the organic layer was successively washed with aqueous sodium hydrogencarbonate solution (600 ml) and brine (500 ml), dried over sodium sulfate, then concentrated. The residue was purified by column chromatography (silica gel, hexane/ethyl acetate=1/0 to 1/1) to obtain ethyl 2-(2-{[(2,4,6-trimethoxybenzyl)amino]methyl}acrylamide) acetate (compound S62d) (50.4 g) as a light yellow crystals.

$^1$H-NMR (CDCl$_3$) δ 1.27 (3H, t, J=7.1 Hz), 3.42 (2H, br.s), 3.79 (2H, s), 3.79 (6H, s), 3.82 (3H, s), 4.09 (2H, d, J=5.3 Hz), 4.19 (2H, q, J=7.1 Hz), 5.34-5.37 (1H, m), 6.13 (2H, s), 6.15 (1H, d, J=2.0 Hz), 9.96 (1H, t, J=5.3 Hz)

Step (5): To the compound S62d obtained at Step (4) (50.0 g) in a methanol (164 ml) solution, 4 M aqueous sodium hydroxide solution (40.5 ml) was added, and the mixture was stirred at room temperature for 14 hours. The reaction solution was ice cooled, saturated aqueous potassium hydrogensulfate solution was slowly added to adjust pH to 4.9, then the mixture was concentrated in vacuo. To the residue, acetonitrile (200 ml) was added and concentrated in vacuo. The operation was repeated four times. To the residue thus obtained, acetonitrile (1 liter), 1-hydroxybenztriazole (18.4 g), and 1-(3-dimethylaminopropyl)-3-ethylcarbodiimide hydrochloride (26.1 g) were successively added, and the mixture was stirred at room temperature for 2 days. The reaction solution was concentrated in vacuo, and chloroform (1 liter) and water (470 ml) were added to the residue, then saturated aqueous sodium hydrogencarbonate solution (600 ml) was slowly added. The layers were separated, then the organic layer was washed with brine, and then concentrated. The residue was purified by column chromatography (silica gel, chloroform/methanol=96/4 to 95/5) to obtain the title compound (28.0 g) as a light yellow crystals.

$^1$H-NMR (DMSO-d$_6$) δ 3.72 (6H, s), 3.78 (3H, s), 3.85 (2H, d, J=5.2 Hz), 3.98 (2H, s), 4.43 (2H, s), 4.87 (1H, m), 5.84 (1H, d, J=2.4 Hz), 6.20 (2H, s), 8.02 (1H, t, J=5.2 Hz)

MS: 321 (M+H)$^+$

Reference Example 63

6-[4-chloro-3-(trifluoromethyl)benzyl]-1-(2,4,6-trimethoxybenzyl)-1,4-diazepan-2,5-dione (compound S63)

To a mixture of the compound S62 (250 mg), hydroxy (cyclooctadiene) rhodium (I) dimer (18 mg), 4-chloro-3-(trifluoromethyl)phenylboronic acid (262 mg), and powdered potassium hydroxide (44 mg), a 1,2-dimethoxymethane-water (6:1) mixed solvent (2.1 ml) was added in an argon atmosphere, and the mixture was stirred at room temperature for 16 hours. The insolubles were filtered out, and the filtrate was diluted with ethyl acetate, then this was successively washed with water, saturated aqueous sodium hydrogencarbonate solution, and brine. The organic layer was dried over sodium sulfate, and then concentrated. The residue was purified by flash column chromatography (silica gel, hexane/ethyl acetate/methanol=4/4/1) to obtain the title compound (94.2 mg) as a light yellow crystals.

$^1$H-NMR (CDCl$_3$) δ 2.23-2.42 (1H, m), 2.50 (1H, dd, J=10.3, 13.9 Hz), 2.94 (1H, dd, J=4.9, 15.3 Hz), 3.22 (1H, dd, J=3.7, 13.9 Hz), 3.41 (1H, dd, J=12.4, 15.3 Hz), 3.63 (6H, s), 3.70 (1H, dd, J=7.7, 15.4 Hz), 3.84 (3H, s), 4.22 (1H, d, J=13.8 Hz), 4.23 (1H, dd, J=3.2, 15.4 Hz), 4.87 (1H, d, J=13.8 Hz), 5.98 (2H, s), 6.03-6.15 (1H, m), 7.03 (1H, dd, J=1.9, 8.2 Hz), 7.32 (1H, d, J=1.9 Hz), 7.35 (1H, d, J=8.2 Hz)

MS: 501 (M+H)$^+$

Reference Example 64

6-(4,5-difluoro-2-methoxybenzyl)-1-(2,4,6-trimethoxybenzyl)-1,4-diazepan-2,5-dione (compound S64)

Instead of the reaction agent, that is, 4-chloro-3-(trifluoromethyl)phenylboronic acid, of Reference Example 63, 4,5-difluoro-2-methoxyphenylboronic acid was used for a similar procedure as in Reference Example 63 to obtain the title compound.

$^1$H-NMR (CDCl$_3$) δ 2.31-2.42 (1H, m), 2.50 (1H, dd, J=10.6, 13.8 Hz), 2.91 (1H, dd, J=4.7, 15.3 Hz), 3.07 (1H, dd, J=3.7, 13.8 Hz), 3.37 (1H, dd, J=12.6, 15.3 Hz), 3.66 (6H, s), 3.67-3.76 (1H, m), 3.71 (3H, s), 3.83 (3H, s), 4.21-4.26 (2H, m), 4.83 (1H, d, J=13.8 Hz), 5.94-6.00 (1H, m), 5.99 (2H, s), 6.59 (1H, dd, J=6.9, 12.2 Hz), 6.68 (1H, dd, J=8.9, 10.6 Hz)

MS: 465 (M+H)$^+$

Reference Example 65

6-(5-fluoro-2-methoxybenzyl)-1-(2,4,6-trimethoxybenzyl)-1,4-diazepan-2,5-dione (compound S65)

Instead of the reaction agent, that is, 4-chloro-3-(trifluoromethyl)phenylboronic acid, of Reference Example 63, 5-fluoro-2-methoxyphenylboronic acid was used for a similar procedure as in Reference Example 63 to obtain the title compound.

$^1$H-NMR (CDCl$_3$) δ 2.36-2.49 (1H, m), 2.58 (1H, dd, J=10.8, 13.8 Hz), 2.95 (1H, dd, J=4.9, 15.4 Hz), 3.08 (1H, dd, J=3.7, 13.8 Hz), 3.38 (1H, dd, J=12.6, 15.4 Hz), 3.64 (6H, s), 3.67-3.75 (1H, m), 3.72 (3H, s), 3.83 (3H, s), 4.25 (1H, dd, J=4.1, 15.4 Hz), 4.26 (1H, d, J=13.4 Hz), 4.82 (1H, d, J=13.4 Hz), 5.90-6.05 (1H, m), 5.99 (2H, s), 6.59 (1H, dd, J=2.9, 8.9 Hz), 6.70 (1H, dd, J=4.5, 8.9 Hz), 6.87 (1H, ddd, J=2.9, 8.9, 8.9 Hz)

MS: 447 (M+H)$^+$

Reference Example 66

6-(5-chloro-2-fluorobenzyl)-1-(2,4,6-trimethoxybenzyl)-1,4-diazepane-2,5-dione (compound S66)

Instead of the reaction agent, that is, 4-chloro-3-(trifluoromethyl)phenylboronic acid, of Reference Example 63, 5-chloro-2-fluorophenylboronic acid was used for a similar procedure as in Reference Example 63 to obtain the title compound.

$^1$H-NMR (CDCl$_3$) δ 2.30-2.45 (1H, m), 2.58 (1H, dd, J=10.3, 14.0 Hz), 3.00 (1H, dd, J=4.9, 15.4 Hz), 3.05-3.14 (1H, m), 3.43 (1H, dd, J=12.6, 15.4 Hz), 3.66 (6H, s), 3.72 (1H, d, J=7.9, 15.8 Hz), 3.84 (3H, s), 4.25 (1H, dd, J=3.7, 15.8 Hz), 4.27 (1H, d, J=13.8 Hz), 4.86 (1H, d, J=13.8 Hz), 5.95-6.01 (1H, m), 6.00 (2H, s), 6.91 (1H, dd, J=8.8, 8.8 Hz), 6.97 (1H, dd, J=2.4, 6.5 Hz), 7.16 (1H, ddd, J=2.4, 4.3, 8.8 Hz)

MS: 451 (M+H)$^+$

Reference Example 67

(6R)-6-(5-chloro-2-hydroxybenzyl)-1-(2,4,6-trimethoxybenzyl)-1,4-diazepane-2,5-dione (compound S67)

Step (1): To (2R)-3-[(tert-butoxycarbonyl)amino]-2-(5-chloro-2-methoxybenzyl)propanoic acid (20.15 g), which can be obtained by the method described in WO 06-059801A, Reference Example 151, Step (1) and Step (2), in a dichloromethane (180 ml) solution, boron tribromide (44.78 g) in a dichloromethane (150 ml) solution was slowly added dropwise under ice cooling, then the mixture was stirred at room temperature for 3 hours. The reaction solution was again ice cooled, then 2M aqueous sodium hydroxide solution (358 ml) was slowly added dropwise. The layers were separated, and the aqueous layer was washed with dichloromethane (90 ml). To the aqueous layer, tetrahydrofuran (200 ml) and ditert-butyl-dicarbonate (28.65 g) were added, and the mixture was stirred at room temperature for 16 hours. To the reaction solution, N,N-dimethylethylenediamine (0.72 g) was added, and the mixture was stirred at 35° C. for 2 hours, then saturated aqueous potassium hydrogensulfate solution (270 ml) was slowly added dropwise. To the mixture, ethyl acetate (225 ml) was added, and the layers were separated, then the aqueous layer was extracted with ethyl acetate (50 ml). The organic layer and the extract were combined and successively washed with water (90 ml) and brine (90 ml), dried over magnesium sulfate, then concentrated to obtain (2R)-3-[(tert-butoxycarbonyl)amino]-2-[2-(tert-butoxycarbonyl)oxy-5-chlorobenzyl]propanoic acid (compound S67a) as a crude product (19.4 g).

Step (2): To the compound S67a crude product obtained at Step (1) (19.4 g) in a dichloromethane (180 ml) solution, glycine ethylester hydrochloride (7.54 g), triethylamine (7.53 ml), 1-hydroxybenzotriazole (6.09 g), and 1-(3-dimethylaminopropyl)-3-ethylcarbodiimide hydrochloride (12.95 g) were successively added, and the mixture was stirred at 35° C. for 1.5 hours. The reaction solution was concentrated, the residue was diluted with ethyl acetate (250 ml) and saturated aqueous sodium hydrogencarbonate solution (100 ml), and the layers were separated. The organic layer was successively washed with water (100 ml), saturated aqueous potassium hydrogensulfate (100 ml), brine (90 ml), saturated aqueous sodium hydrogencarbonate solution (50 ml), and brine (50 ml), dried over magnesium sulfate, then was concentrated. The residue was purified by column chromatography (silica gel, hexane/ethyl acetate=4/1 to 1/1) to obtain ethyl (2R)-2-{3-[(tert-butoxycarbonyl)amino]-2-[5-chloro-2-(tert-butoxycarbonyl)oxybenzyl]propanamide}acetate (15.7 g) (compound S67b) as a colorless solid.

$^1$H-NMR (CDCl$_3$) δ 1.26 (3H, t, J=7.1 Hz), 1.42 (9H, s), 1.57 (9H, s), 2.60-3.03 (3H, m), 3.24-3.47 (2H, m), 3.70-3.82 (1H, m), 3.99 (1H, dd, J=5.7, 18.3 Hz), 4.18 (2H, q, J=7.1 Hz), 5.16 (1H, br.s), 6.13 (1H, br.s), 6.98-7.08 (1H, m), 7.15-7.24 (2H, m)

MS: 415 (M−COO$^t$Bu)$^+$

Step (3): To the compound S67b obtained at Step (2) (15.7 g) in an ethanol (160 ml) solution, methanesulfonic acid (9.6 ml) was added, and the mixture was stirred at 40° C. for 6 hours. The reaction mixture was allowed to cool down to room temperature, then was ice cooled, and triethylamine (15.2 g) was added dropwise. To the reaction solution, 2,4,6-trimethoxybenzaldehyde (5.99 g) and sodium triacetoxyborohydride (9.71 g) were successively added under ice cooling, and the mixture was stirred at room temperature for 3.5 hours. The reaction solution was concentrated, ethyl acetate (240 ml) and saturated aqueous sodium hydrogencarbonate solution (136 ml), were added to the residue, and the layers were separated. The organic layer was washed with brine, then dried over magnesium sulfate, and concentrated to obtain ethyl (2R)-2-{(5-chloro-hydroxybenzyl)-3-[(2,4,6-trimethoxybenzyl)amino]propanamide}acetate (compound S67c) as a crude product (16.6 g) as a yellow crystals.

Step (4): To the compound S67c crude product obtained at Step (3) (15.6 g), 2M aqueous sodium hydroxide solution (38.5 ml) and water (38.5 ml) were added, and the mixture was stirred at room temperature for 4 hours. To the reaction solution, 2M hydrochloric acid (36.5 ml) was added, and the precipitated crystals were collected by filtration and dried to obtain (2R)-2-{(5-chloro-hydroxybenzyl)-3-[(2,4,6-trimethoxybenzyl)amino]propanamide}acetic acid (compound S67d) as a crude product (13.5 g) as a yellow solid.

Step (5): To a mixture of the compound S67d crude product obtained at Step (4) (13.5 g), 1-hydroxybenztriazole (4.7 g), and 1-(3-dimethylaminopropyl)-3-ethylcarbodiimide hydrochloride (8.33 g), N,N-dimethylformamide (350 ml) and acetonitrile (350 ml) were successively added, and the mixture was stirred at 40° C. for 21 hours. The reaction solution was concentrated. To the residue, ethyl acetate (450 ml) and water (300 ml) were added, and the layers were separated. The organic layer was successively washed with aqueous potassium hydrogensulfate solution (150 ml), water (150 ml), saturated aqueous sodium hydrogencarbonate solution (150 ml), and brine (150 ml), dried over magnesium sulfate, then concentrated. The residue was purified by column chromatography (silica gel, dichloromethane/methanol=1/0 to 14/1) to obtain the title compound (5.8 g).

$^1$H-NMR (CDCl$_3$) δ 2.29 (1H, dd, J=4.7, 14.4 Hz), 2.33-2.42 (1H, m), 2.86-2.97 (1H, m), 3.28 (1H, dd, J=4.5, 15.4 Hz), 3.53 (1H, dd, J=11.8, 15.4 Hz), 3.70-3.88 (1H, m), 3.73 (6H, s), 3.78 (3H, s), 4.24 (1H, dd, J=3.7, 15.8 Hz), 4.50 (1H, d, J=13.8 Hz), 4.79 (1H, d, J=13.8 Hz), 6.00 (2H, s), 6.39 (1H, br.s), 6.75 (1H, d, J=2.6 Hz), 6.79 (1H, d, J=8.7 Hz), 7.07 (1H, dd, J=2.6, 8.7 Hz)

MS: 449 (M+H)$^+$

Reference Example 68

(6R)-6-(5-chloro-2-cyanobenzyl)-1-(2,4,6-trimethoxybenzyl)-1,4-diazepane-2,5-dione (compound S68)

Step (1): To the compound S67 obtained in Reference Example 67 (100 mg) in an N,N-dimethylformamide (1 ml)

solution, p-nitrophenyl trifluoromethanesulfonic acid (66 mg) and potassium carbonate (68 mg) were successively added, and the mixture was stirred at room temperature for 2 hours. The reaction solution was diluted with toluene and was successively washed with water, saturated aqueous sodium hydrogencarbonate solution, water, and brine. The organic layer was dried over sodium sulfate, then concentrated to obtain (6R)-6-[5-chloro-2-(trifluoromethanesulfonyl)oxybenzyl]-1-(2,4,6-trimethoxybenzyl)-1,4-diazepane-2,5-dione (compound S68a) as a crude product (135 mg).

Step (2): To a mixture of the compound S68a crude product obtained in Step (1) (135 mg) and zinc cyanide (47 mg), N,N-dimethylformamide (1 ml) was added. After the inside of the reaction system was made an argon atmosphere, tetrakis(triphenylphosphine) palladium (26 mg) was added, and the mixture was stirred at 100° C. for 1 hour. The reaction solution was diluted with toluene, then the insolubles were filtered out. The filtrate was successively washed with saturated aqueous sodium hydrogencarbonate solution, water, and brine, dried over sodium sulfate, then concentrated. The residue was purified by flash column chromatography (silica gel, hexane/ethyl acetate/methanol=6/6/1) to obtain the title compound (17 mg).

$^1$H-NMR (CDCl$_3$) δ 2.39-2.47 (1H, m), 2.77 (1H, dd, J=9.8, 14.1 Hz), 3.03 (1H, dd, J=4.7, 15.3 Hz), 3.32 (1H, dd, J=5.3, 14.1 Hz), 3.52 (1H, dd, J=12.3, 15.3 Hz), 3.68 (6H, s), 3.74 (1H, d, J=7.8, 15.7 Hz), 3.84 (3H, s), 4.22-4.66 (1H, m), 4.25 (1H, d, J=13.7 Hz), 4.88 (1H, d, J=13.7 Hz), 5.95-6.01 (1H, m), 6.00 (2H, s), 7.13 (1H, d, J=2.0 Hz), 7.31 (1H, dd, J=2.0, 8.3 Hz), 7.49 (1H, d, J=8.3 Hz)

MS: 458 (M+H)$^+$

Reference Example 69

(6S)-6-(5-chloro-2-hydroxybenzyl)-1-(2,4,6-trimethoxybenzyl)-1,4-diazepane-2,5-dione (compound S69)

Instead of the starting material, that is, (2R)-3-[(tert-butoxycarbonyl)amino]-2-(5-chloro-2-methoxybenzyl)propanoic acid, of Reference Example 67, Step (1), (2S)-3-[(tert-butoxycarbonyl)amino]-2-(5-chloro-2-methoxybenzyl) propanoic acid, which can be obtained by the method described in WO 06-059801A, Reference Example 152, Step (1) and Step (2), was used for a similar procedure as in Reference Example 67 to obtain the title compound.

$^1$H-NMR (CDCl$_3$) δ 2.29 (1H, dd, J=4.7, 14.4 Hz), 2.33-2.42 (1H, m), 2.86-2.97 (1H, m), 3.28 (1H, dd, J=4.5, 15.4 Hz), 3.53 (1H, dd, J=11.8, 15.4 Hz), 3.70-3.88 (1H, m), 3.73 (6H, s), 3.78 (3H, s), 4.24 (1H, dd, J=3.7, 15.8 Hz), 4.50 (1H, d, J=13.8 Hz), 4.79 (1H, d, J=13.8 Hz), 6.00 (2H, s), 6.39 (1H, br.s), 6.75 (1H, d, J=2.6 Hz), 6.79 (1H, d, J=8.7 Hz), 7.07 (1H, dd, J=2.6, 8.7 Hz)

MS: 449 (M+H)$^+$

Reference Example 70

(6S)-6-(5-chloro-2-cyanobenzyl)-1-(2,4,6-trimethoxybenzyl)-1,4-diazepane-2,5-dione (compound S70)

Instead of the starting material, that is, the compound S67, of Reference Example 68, Step (1), the compound S69 was used for a similar procedure as in Reference Example 68, Step (1) and Step (2) to obtain the title compound.

$^1$H-NMR (CDCl$_3$) δ 2.39-2.47 (1H, m), 2.77 (1H, dd, J=9.8, 14.1 Hz), 3.03 (1H, dd, J=4.7, 15.3 Hz), 3.32 (1H, dd, J=5.3, 14.1 Hz), 3.52 (1H, dd, J=12.3, 15.3 Hz), 3.68 (6H, s), 3.74 (1H, d, J=7.8, 15.7 Hz), 3.84 (3H, s), 4.22-4.66 (1H, m), 4.25 (1H, d, J=13.7 Hz), 4.88 (1H, d, J=13.7 Hz), 5.95-6.01 (1H, m), 6.00 (2H, s), 7.13 (1H, d, J=2.0 Hz), 7.31 (1H, dd, J=2.0, 8.3 Hz), 7.49 (1H, d, J=8.3 Hz)

MS: 458 (M+H)$^+$

Reference Example 71 tert-butyl 4-[(1R)-1-({[(6R)-6-[4-chloro-3-(trifluoromethyl)benzyl]-7-oxo-3-thioxo-4-(2,4,6-trimethoxybenzyl)-1,4-diazepan-1-yl]carbonyl}amino) butyl]-2-nitrobenzoate (compound S71)

Step (1): Instead of the starting material, that is, (6R)-6-(5-chloro-2-methoxybenzyl)-1-(2,4,6-trimethoxybenzyl)-1,4-diazepane-2,5-dione, of Reference Example 20, Step (2), the compound S63 was used, and instead of the reaction agent, that is, the compound S19, the compound S25a was used for a similar procedure as in Reference Example 20, Step (2) to obtain tert-butyl 4-[(1R)-1-({[(6R)-6-[4-chloro-3-(trifluoromethyl)benzyl]-3,7-dioxo-4-(2,4,6-trimethoxybenzyl)-1,4-diazepan-1-yl]carbonyl}amino)butyl]-2-nitrobenzoate (compound S71a) and tert-butyl 4-[(1R)-1-({[(6S)-6-[4-chloro-3-(trifluoromethyl)benzyl]-3,7-dioxo-4-(2,4,6-trimethoxybenzyl)-1,4-diazepan-1-yl]carbonyl}amino)butyl]-2-nitrobenzoate (compound S71b).

Step (2): Instead of the starting material, that is, the compound S21, of Reference Example 22, the compound S71a was used for a similar procedure as in Reference Example 22 to obtain the title compound.

MS: 837 (M+H)$^+$

Example 104

2-amino-4-[(1R)-1-({[(6R)-6-[4-chloro-3-(trifluoromethyl)benzyl]-3-(ethoxyimino)-7-oxo-1,4-diazepan-1-yl]carbonyl}amino)butyl]benzoic acid (compound 104)

Instead of the starting material, that is, the compound S31, of Example 29, the compound S71 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2) to obtain the title compound.

$^1$H-NMR (DMSO-d$_6$) δ 0.87 (3H, t, J=7.3 Hz), 1.12 (3H, t, J=7.0 Hz), 1.16-1.37 (2H, m), 1.57-1.80 (2H, m), 2.71 (1H, dd, J=8.0, 14.2 Hz), 3.02-3.24 (3H, m), 3.77-3.87 (2H, m), 3.88-4.02 (1H, m), 4.50 (1H, d, J=16.2 Hz), 4.60 (1H, dt, J=7.7, 7.7 Hz), 4.78 (1H, d, J=16.2 Hz), 6.28 (1H, br.s), 6.39 (1H, dd, J=1.6, 8.3 Hz), 6.63 (1H, d, J=1.6 Hz), 7.55-7.71 (3H, m), 7.82 (1H, d, J=1.5 Hz), 9.41 (1H, d, J=7.7 Hz)

MS: 598 (M+H)$^+$

Reference Example 72 tert-butyl 4-[(1R)-1-({[(6S)-6-[4-chloro-3-(trifluoromethyl)benzyl]-7-oxo-3-thioxo-4-(2,4,6-trimethoxybenzyl)-1,4-diazepan-1-yl]carbonyl}amino) butyl]-2-nitrobenzoate (compound S72)

Instead of the starting material, that is, the compound S21, of Reference Example 22, the compound S71b was used for a similar procedure as in Reference Example 22 to obtain the title compound.

MS: 837 (M+H)$^+$

Example 105

2-amino-4-[(1R)-1-({[(6S)-6-[4-chloro-3-(trifluoromethyl)benzyl]-3-(ethoxyimino)-7-oxo-1,4-diazepan-1-yl]carbonyl}amino)butyl]benzoic acid (compound 105)

Instead of the starting material, that is, the compound S31, of Example 29, the compound S72 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2) to obtain the title compound.

$^1$H-NMR (DMSO-d$_6$) δ 0.85 (3H, t, J=7.3 Hz), 1.09 (3H, t, J=7.0 Hz), 1.12-1.33 (2H, m), 1.55-1.76 (2H, m), 2.65-2.70 (1H, dd, J=8.4, 14.1 Hz), 3.06 (1H, dd, J=12.5, 12.5 Hz), 3.15 (1H, dd, J=5.6, 14.1 Hz), 3.16-3.25 (1H, m), 3.72-3.86 (2H, m), 3.90-4.05 (1H, m), 4.52 (1H, d, J=16.3 Hz), 4.61 (1H, dt, J=7.4, 7.8 Hz), 4.81 (1H, d, J=16.3 Hz), 6.43 (1H, dd, J=1.6, 8.3 Hz), 6.64 (1H, d, J=1.6 Hz), 7.60-7.73 (3H, m), 7.82 (1H, d, J=1.4 Hz), 9.40 (1H, d, J=7.8 Hz)

MS: 598 (M+H)$^+$

Reference Example 73 tert-butyl 4-[(1R)-1-({[(6R)-6-(4,5-difluoro-2-methoxybenzyl)-7-oxo-3-thioxo-1,4-diazepan-1-yl]carbonyl}amino)butyl]-2-nitrobenzoate (compound S73)

Step (1): Instead of the starting material, (6R)-6-(5-chloro-2-methoxybenzyl)-1-(2,4,6-trimethoxybenzyl)-1,4-diazepane-2,5-dione, of Reference Example 20, Step (2), the compound S64 was used, and instead of the reaction agent, that is, the compound S19, the compound S25a was used for a same procedure as in Reference Example 20, Step (2) to obtain tert-butyl 4-[(1R)-1-({[(6R)-6-(4,5-difluoro-2-methoxybenzyl)-3,7-dioxo-1,4-diazepan-1-yl]carbonyl}amino)butyl]-2-nitrobenzoate (compound S73a) and tert-butyl 4-[(1R)-1-({[(6S)-6-(4,5-difluoro-2-methoxybenzyl)-3,7-dioxo-1,4-diazepan-1-yl]carbonyl}amino)butyl]-2-nitrobenzoate (compound S73b).

Step (2): Instead of the starting material, that is, the compound S21, of Reference Example 22, the compound S73a was used for a similar procedure as in Reference Example 22 to obtain the title compound.

MS: 801 (M+H)$^+$

Example 106

2-amino-4-[(1R)-1-({[(6R)-6-(4,5-difluoro-2-methoxybenzyl)-3-(ethoxyimino)-7-oxo-1,4-diazepan-1-yl]carbonyl}amino)butyl]benzoic acid (compound 106)

Instead of the starting material, that is, the compound S31, of Example 29, the compound S73 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2) to obtain the title compound.

$^1$H-NMR (DMSO-d$_6$) δ 0.87 (3H, t, J=7.3 Hz), 1.12 (3H, t, J=7.0 Hz), 1.15-1.35 (2H, m), 1.58-1.78 (2H, m), 2.65 (1H, dd, J=8.7, 14.5 Hz), 2.92 (1H, dd, J=5.1, 14.5 Hz), 3.06 (1H, dd, J=12.2, 12.2 Hz), 3.11-3.20 (1H, m), 3.73-3.88 (3H, m), 3.79 (3H, s), 4.47 (1H, d, J=16.3 Hz), 4.60 (1H, dt, J=7.2, 7.7 Hz), 4.78 (1H, d, J=16.3 Hz), 6.27 (1H, br.s), 6.42 (1H, dd, J=1.6, 8.4 Hz), 6.64 (1H, d, J=1.6 Hz), 7.13 (1H, dd, J=7.0, 12.9 Hz), 7.35 (1H, dd, J=9.3, 11.4 Hz), 7.64 (1H, d, J=8.4 Hz), 9.42 (1H, d, J=7.7 Hz)

MS: 562 (M+H)$^+$

Reference Example 74 tert-butyl 4-[(1R)-1-({[(6S)-6-(4,5-difluoro-2-methoxybenzyl)-7-oxo-3-thioxo-1,4-diazepan-1-yl]carbonyl}amino)butyl]-2-nitrobenzoate (compound S74)

Instead of the starting material, that is, the compound S21, of Reference Example 22, the compound S73b was used for a similar procedure as in Reference Example 22 to obtain the title compound.

MS: 801 (M+H)$^+$

Example 107

2-amino-4-[(1R)-1-({[(6S)-6-(4,5-difluoro-2-methoxybenzyl)-3-(ethoxyimino)-7-oxo-1,4-diazepan-1-yl]carbonyl}amino)butyl]benzoic acid (compound 107)

Instead of the starting material, that is, the compound S31, of Example 29, the compound S74 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2) to obtain the title compound.

$^1$H-NMR (DMSO-d$_6$) δ 0.86 (3H, t, J=7.2 Hz), 1.09 (3H, t, J=7.0 Hz), 1.14-1.34 (2H, m), 1.57-1.77 (2H, m), 2.64 (1H, dd, 8.9, 14.4 Hz), 2.93 (1H, dd, J=5.2, 14.4 Hz), 3.04 (1H, dd, 12.8, 12.8 Hz), 3.09-3.21 (1H, m), 3.71-3.91 (3H, m), 3.79 (3H, s), 4.49 (1H, d, J=16.4 Hz), 4.62 (1H, dt, J=7.8, 7.8 Hz), 4.80 (1H, d, J=16.4 Hz), 6.44 (1H, dd, J=1.6, 8.3 Hz), 6.64 (1H, d, J=1.6 Hz), 7.13 (1H, dd, J=7.1, 13.0 Hz), 7.35 (1H, dd, J=9.3, 11.5 Hz), 7.65 (1H, d, J=8.3 Hz), 9.42 (1H, d, J=7.8 Hz)

MS: 562 (M+H)$^+$

Reference Example 75 tert-butyl 4-[(1R)-1-({[6R)-6-(5-fluoro-2-methoxybenzyl)-7-oxo-3-thioxo-1,4-diazepan-1-yl]carbonyl}amino)butyl]-2-nitrobenzoate (compound S75)

Step (1): Instead of the starting material, that is, (6R)-6-(5-chloro-2-methoxybenzyl)-1-(2,4,6-trimethoxybenzyl)-1,4-diazepane-2,5-dione, of Reference Example 20, Step (2), the compound S65 was used, and instead of the reaction agent, that is, the compound S19, the compound S25a was used for a similar procedure as in Reference Example 20, Step (2) to obtain tert-butyl 4-[(1R)-1-({[(6R)-3,7-dioxo-6-(5-fluoro-2-methoxybenzyl)-1,4-diazepan-1-yl]carbonyl}amino)butyl]-2-nitrobenzoate (compound S75a) and tert-butyl 4-[(1R)-1-({[(6S)-3,7-dioxo-6-(5-fluoro-2-methoxybenzyl)-1,4-diazepan-1-yl]carbonyl}amino)butyl]-2-nitrobenzoate (compound S75b).

Step (2): Instead of the starting material, that is, the compound S21, of Reference Example 22, the compound S75a was used for a similar procedure as in Reference Example 22 to obtain the title compound.

MS: 783 (M+H)$^+$

Example 108

2-amino-4-[(1R)-1-({[(6R)-3-(ethoxyimino)-6-(5-fluoro-2-methoxybenzyl)-7-oxo-1,4-diazepan-1-yl]carbonyl}amino)butyl]benzoic acid (compound 108)

Instead of the starting material, that is, the compound S31, of Example 29, the compound S75 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2) to obtain the title compound.

$^1$H-NMR (DMSO-d$_6$) δ 0.88 (3H, t, J=7.3 Hz), 1.12 (3H, t, J=7.0 Hz), 1.15-1.37 (2H, m), 1.58-1.78 (2H, m), 2.68 (1H, dd, J=8.9, 14.4 Hz), 2.96 (1H, dd, J=5.0, 14.4 Hz), 3.07 (1H, dd, J=12.7, 12.7 Hz), 3.13-3.21 (1H, m), 3.79 (3H, s), 3.79-3.86 (3H, m), 4.48 (1H, d, J=16.3 Hz), 4.60 (1H, dt, J=7.3, 7.7 Hz), 4.78 (1H, d, J=16.3 Hz), 6.42 (1H, dd, J=1.6, 8.3 Hz), 6.64 (1H, d, J=1.6 Hz), 6.97 (1H, dd, J=4.6, 8.9 Hz), 7.04 (1H, ddd, J=3.0, 8.9, 8.9 Hz), 7.12 (1H, dd, J=3.0, 9.3 Hz), 7.64 (1H, d, J=8.3 Hz), 9.44 (1H, d, J=7.7 Hz)

MS: 544 (M+H)$^+$

Example 109

2-amino-4-[(1R)-1-({[(6R)-3-[(3,5-difluorophenoxy)imino]-6-(5-fluoro-2-methoxybenzyl)-7-oxo-1,4-diazepan-1-yl]carbonyl}amino)butyl]benzoic acid (compound 109)

Instead of the starting material, that is, the compound S31, of Example 29, the compound S75 was used, and instead of the reaction agent, that is, O-(4-fluorophenyl)hydroxylamine hydrochloride, O-(3,5-difluorophenyl)hydroxylamine hydrochloride was used for a similar procedure as in Example 29, Step (1) and Step (2) to obtain the title compound.

$^1$H-NMR (CDCl$_3$) δ 0.93 (3H, t, J=7.3 Hz), 1.27-1.45 (2H, m), 1.59-1.85 (2H, m), 2.68 (1H, dd, J=8.2, 13.9 Hz), 3.21 (1H, dd, J=5.4, 13.9 Hz), 3.33 (1H, dd, J=12.8, 12.8 Hz), 3.44-3.55 (1H, m), 3.82-3.85 (1H, m), 3.83 (3H, s), 4.23 (1H, d, J=16.6 Hz), 4.75 (1H, dt, J=7.4, 7.2 Hz), 5.35 (1H, d, J=16.6 Hz), 5.46 (1H, br.s), 6.34-6.43 (1H, m), 6.57-6.73 (4H, m), 6.80 (1H, dd, J=4.0, 8.8 Hz), 6.89-6.98 (2H, m), 7.85 (1H, d, J=8.0 Hz), 9.52 (1H, d, J=7.2 Hz)

MS: 628 (M+H)$^+$

Reference Example 76 tert-butyl 4-[(1R)-1-({[(6S)-6-(5-fluoro-2-methoxybenzyl)-7-oxo-3-thioxo-1,4-diazepan-1-yl]carbonyl}amino)butyl]-2-nitrobenzoate (compound S76)

Instead of the starting material, that is, the compound S21, of Reference Example 22, the compound S75b was used for a similar procedure as in Reference Example 22 to obtain the title compound.

MS: 783 (M+H)$^+$

Example 110

2-amino-4-[(1R)-1-({[(6S)-3-(ethoxyimino)-6-(5-fluoro-2-methoxybenzyl)-7-oxo-1,4-diazepan-1-yl]carbonyl}amino)butyl]benzoic acid (compound 110)

Instead of the starting material, that is, the compound S31, of Example 29, the compound S76 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2), to obtain the title compound.

$^1$H-NMR (DMSO-d$_6$) δ 0.86 (3H, t, J=7.2 Hz), 1.09 (3H, t, J=7.0 Hz), 1.13-1.36 (2H, m), 1.57-1.77 (2H, m), 2.67 (1H, dd, J=8.3, 14.4 Hz), 2.96 (1H, dd, J=5.1, 14.4 Hz), 3.06 (1H, dd, J=11.7, 11.7 Hz), 3.11-3.20 (1H, m), 3.73-3.91 (3H, m), 3.78 (3H, s), 4.52 (1H, d, J=16.4 Hz), 4.58-4.67 (1H, m), 4.82 (1H, d, J=16.4 Hz), 6.44 (1H, dd, J=1.6, 8.3 Hz), 6.64 (1H, d, J=1.6 Hz), 6.98 (1H, dd, J=5.0, 9.2 Hz), 7.04 (1H, ddd, J=3.6, 9.2, 9.2 Hz), 7.13 (1H, dd, J=3.1, 9.2 Hz), 7.65 (1H, d, J=8.3 Hz), 9.43 (1H, d, J=7.7 Hz)

MS: 544 (M+H)$^+$

Reference Example 77 tert-butyl 4-[(1R)-1-({[(6R)-6-(5-chloro-2-fluorobenzyl)-7-oxo-3-thioxo-1,4-diazepan-1-yl]carbonyl}amino)butyl]-2-nitrobenzoate (compound S77)

Step (1): Instead of the starting material, that is, (6R)-6-(5-chloro-2-methoxybenzyl)-1-(2,4,6-trimethoxybenzyl)-1,4-diazepan-2,5-dione, of Reference Example 20, Step (2), the compound S66 was used, and instead of the reaction agent, that is, the compound S19, the compound S25a was used for a similar procedure as in Reference Example 20, Step (2) to obtain tert-butyl 4-[(1R)-1-({[(6R)-6-(5-chloro-2-fluorobenzyl)-3,7-dioxo-1,4-diazepan-1-yl]carbonyl}amino)butyl]-2-nitrobenzoate (compound S77a) and tert-butyl 4-[(1R)-1-({[(6S)-6-(5-chloro-2-fluorobenzyl)-3,7-dioxo-1,4-diazepan-1-yl]carbonyl}amino)butyl]-2-nitrobenzoate (compound S77b).

Step (2): Instead of the starting material, that is, the compound S21, of Reference Example 22, the compound S77a was used for a similar procedure as in Reference Example 22 to obtain the title compound.

MS: 787 (M+H)$^+$

Example 111

2-amino-4-[(1R)-1-({[(6R)-6-(5-chloro-2-fluorobenzyl)-3-(ethoxyimino)-7-oxo-1,4-diazepan-1-yl]carbonyl}amino)butyl]benzoic acid (compound 111)

Instead of the starting material, that is, the compound S31, of Example 29, the compound S77 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2), to obtain the title compound.

$^1$H-NMR (DMSO-d$_6$) δ 0.87 (3H, t, J=7.3 Hz), 1.12 (3H, t, J=7.0 Hz), 1.16-1.34 (2H, m), 1.58-1.79 (2H, m), 2.70 (1H, dd, J=8.8, 14.5 Hz), 2.99-3.27 (3H, m), 3.80-3.86 (2H, m), 3.87-3.96 (1H, m), 4.53 (1H, d, J=16.3 Hz), 4.60 (1H, dt, J=7.2, 7.5 Hz), 4.79 (1H, d, J=16.3 Hz), 6.42 (1H, dd, J=1.6, 8.4 Hz), 6.64 (1H, d, J=1.6 Hz), 7.24 (1H, t, J=9.1 Hz), 7.35 (1H, ddd, J=2.7, 4.4, 9.1 Hz), 7.53 (1H, dd, J=2.7, 6.5 Hz), 7.64 (1H, d, J=8.4 Hz), 9.39 (1H, d, J=7.5 Hz)

MS: 548 (M+H)$^+$

Example 112

2-amino-4-{(1R)-1-[({(6R)-6-(5-chloro-2-fluorobenzyl)-3-[(3,5-difluorophenoxy)imino]-7-oxo-1,4-diazepan-1-yl}carbonyl)amino]butyl}benzoic acid (compound 112)

Instead of the starting material, that is, the compound S31, of Example 29, the compound S77 was used, and instead of the reaction agent, that is, O-(4-fluorophenyl)hydroxylamine hydrochloride, O-(3,5-difluorophenyl)hydroxylamine hydrochloride was used for a similar procedure as in Example 29, Step (1) and Step (2), to obtain the title compound.
$^1$H-NMR (CDCl$_3$) δ 0.93 (3H, t, J=7.2 Hz), 1.18-1.48 (2H, m), 1.68-1.88 (2H, m), 2.75 (1H, dd, J=7.9, 14.4 Hz), 3.23 (1H, dd, J=5.7, 14.4 Hz), 3.38 (1H, dd, J=12.4, 12.4 Hz), 3.48-3.57 (1H, m), 3.62-3.75 (1H, m), 4.23 (1H, d, J=16.7 Hz), 4.75 (1H, dt, J=7.1, 7.4 Hz), 5.39 (1H, d, J=16.7 Hz), 5.48 (1H, s), 6.39 (1H, dt, J=2.4, 8.9 Hz), 6.55-6.62 (2H, m), 6.64-6.75 (2H, m), 7.02 (1H, dd, J=9.3, 9.3 Hz), 7.20-7.29 (2H, m), 7.86 (1H, d, J=8.2 Hz), 9.43 (1H, d, J=7.4 Hz)
MS: 632 (M+H)$^+$

Reference Example 78 tert-butyl 4-[(1R)-1-({[(6S)-6-(5-chloro-2-fluorobenzyl)-7-oxo-3-thioxo-1,4-diazepan-1-yl]carbonyl}amino)butyl]-2-nitrobenzoate (compound S77)

Instead of the starting material, that is, the compound S21, of Reference Example 22, the compound S77b was used for a similar procedure as in Reference Example 22 to obtain the title compound.
MS: 787 (M+H)$^+$

Example 113

2-amino-4-[(1R)-1-({[(6S)-6-(5-chloro-2-fluorobenzyl)-3-(ethoxyimino)-7-oxo-1,4-diazepan-1-yl]carbonyl}amino)butyl]benzoic acid (compound 113)

Instead of the starting material, that is, the compound S31, of Example 29, the compound S78 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2), to obtain the title compound.
$^1$H-NMR (DMSO-d$_6$) δ 0.86 (3H, t, J=7.3 Hz), 1.09 (3H, t, J=7.0 Hz), 1.15-1.34 (2H, m), 1.57-1.76 (2H, m), 2.68 (1H, dd, J=8.3, 15.1 Hz), 3.00-3.14 (2H, m), 3.15-3.26 (1H, m), 3.75-3.85 (2H, m), 3.86-4.00 (1H, m), 4.55 (1H, d, J=16.4 Hz), 4.62 (1H, dt, J=7.4, 7.8 Hz), 4.81 (1H, d, J=16.4 Hz), 6.44 (1H, dd, J=1.6, 8.3 Hz), 6.64 (1H, d, J=1.6 Hz), 7.24 (1H, dd, J=9.0, 9.0 Hz), 7.35 (1H, ddd, J=2.8, 4.5, 9.0 Hz), 7.54 (1H, dd, J=2.8, 6.5 Hz), 7.65 (1H, d, J=8.3 Hz), 9.38 (1H, d, J=7.8 Hz)
MS: 548 (M+H)$^+$

Reference Example 79 tert-butyl 4-[(1R)-1-({[(6R)-6-(5-chloro-2-cyanobenzyl)-7-oxo-3-thioxo-1,4-diazepan-1-yl]carbonyl}amino)butyl]-2-nitrobenzoate (compound S79)

Step (1): Instead of the starting material, that is, (6R)-6-(5-chloro-2-methoxybenzyl)-1-(2,4,6-trimethoxybenzyl)-1,4-diazepane-2,5-dione, of Reference Example 20, Step (2), the compound S68 was used, and instead of the reaction agent, that is, the compound S19, the compound S25a was used for a similar procedure as in Reference Example 20, Step (2) to obtain tert-butyl 4-[(1R)-1-({[(6R)-6-(5-chloro-2-cyanobenzyl)-3,7-dioxo-1,4-diazepan-1-yl]carbonyl}amino)butyl]-2-nitrobenzoate (compound S79a).
Step (2): Instead of the starting material of Reference Example 22, that is, the compound S21, the compound S79a was used for a similar procedure as in Reference Example 22 to obtain the title compound.
MS: 794 (M+H)$^+$

Example 114

2-amino-4-[(1R)-1-({[(6R)-6-(5-chloro-2-cyanobenzyl)-3-(ethoxyimino)-7-oxo-1,4-diazepan-1-yl]carbonyl}amino)butyl]benzoic acid (compound 114)

Instead of the starting material, that is, the compound S31, of Example 29, the compound S79 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2), to obtain the title compound.
$^1$H-NMR (DMSO-d$_6$) δ 0.87 (3H, t, J=7.3 Hz), 1.13 (3H, t, J=7.0 Hz), 1.16-1.35 (2H, m), 1.56-1.81 (2H, m), 2.87 (1H, dd, J=8.0, 14.8 Hz), 3.15 (1H, dd, J=11.8, 11.8 Hz), 3.22-3.25 (1H, m), 3.27 (1H, dd, J=6.7, 14.8 Hz), 3.76-3.89 (2H, m), 4.01-4.13 (1H, m), 4.55 (1H, d, J=16.4 Hz), 4.60 (1H, dt, J=7.7, 7.7 Hz), 4.79 (1H, d, J=16.4 Hz), 6.40 (1H, dd, J=1.6, 8.4 Hz), 6.63 (1H, d, J=1.6 Hz), 7.54 (1H, dd, J=2.1, 8.4 Hz), 7.63 (1H, d, J=8.4 Hz), 7.77 (1H, d, J=2.1 Hz), 7.86 (1H, d, J=8.4 Hz), 9.34 (1H, d, J=7.7 Hz)
MS: 555 (M+H)$^+$

Example 115

2-amino-4-{(1R)-1-[({(6R)-6-(5-chloro-2-cyanobenzyl)-3-[(3,5-difluorophenoxy)imino]-7-oxo-1,4-diazepan-1-yl}carbonyl)amino]butyl}benzoic acid (compound 115)

Instead of the starting material, that is, the compound S31, of Example 29, the compound S79 was used, and instead of the reaction agent, that is, O-(4-fluorophenyl)hydroxylamine hydrochloride, O-(3,5-difluorophenyl)hydroxylamine hydrochloride was used for a similar procedure as in Example 29, Step (1) and Step (2), to obtain the title compound.
$^1$H-NMR (CDCl$_3$) δ 0.93 (3H, t, J=7.3 Hz), 1.26-1.47 (2H, m), 1.68-1.87 (2H, m), 2.93 (1H, dd, J=6.5, 14.2 Hz), 3.41-3.51 (2H, m), 3.55-3.64 (1H, m), 3.73-3.82 (1H, m), 4.21 (1H, d, J=16.8 Hz), 4.74 (1H, dt, J=7.2, 7.4 Hz), 5.41 (1H, d, J=16.8 Hz), 5.50 (1H, s), 6.40 (1H, dt, J=2.3, 8.4 Hz), 6.53-6.60 (2H, m), 6.71 (2H, dd, J=2.5, 8.4 Hz), 7.39 (1H, dd, J=2.0, 8.4 Hz), 7.47 (1H, d, J=2.0 Hz), 7.62 (1H, d, J=8.4 Hz), 7.85 (1H, d, J=8.7 Hz), 9.34 (1H, d, J=7.4 Hz)
MS: 639 (M+H)$^+$

Reference Example 80 tert-butyl 4-[(1R)-1-({[(6S)-6-(5-chloro-2-cyanobenzyl)-7-oxo-3-thioxo-1,4-diazepan-1-yl]carbonyl}amino)butyl]-2-nitrobenzoate (compound S80)

Step (1): Instead of the starting material, that is, (6R)-6-(5-chloro-2-methoxybenzyl)-1-(2,4,6-trimethoxybenzyl)-1,4- diazepane-2,5-dione, of Reference Example 20, Step (2), the compound S70 was used, and instead of the reaction agent, that is, the compound S19, the compound S25a was used for a similar procedure as in Reference Example 20, Step (2), to obtain tert-butyl 4-[(1R)-1-({[(6S)-6-(5-chloro-2-cyanobenzyl)-3,7-dioxo-1,4-diazepan-1-yl]carbonyl}amino)butyl]-2-nitrobenzoate (compound S80a).

Step (2): Instead of the starting material of Reference Example 22, that is, the compound S21, the compound S80a was used for a similar procedure as in Reference Example 22 to obtain the title compound.

MS: 794 (M+H)$^+$

Example 116

2-amino-4-[(1R)-1-({[(6S)-6-(5-chloro-2-cyanobenzyl)-3-(ethoxyimino)-7-oxo-1,4-diazepan-1-yl]carbonyl}amino)butyl]benzoic acid (compound 116)

Instead of the starting material, that is, the compound S31, of Example 29, the compound S80 was used, and instead of the reaction agent, that is, O-(4-fluorophenyl)hydroxylamine hydrochloride, O-ethyl hydroxylamine hydrochloride was used for a similar procedure as in Example 29, Step (1) and Step (2), to obtain the title compound.

$^1$H-NMR (DMSO-d$_6$) δ 0.85 (3H, t, J=7.2 Hz), 1.10 (3H, t, J=7.0 Hz), 1.13-1.33 (2H, m), 1.55-1.76 (2H, m), 2.87 (1H, dd, J=7.7, 14.8 Hz), 3.15 (1H, dd, J=12.0, 12.0 Hz), 3.18-3.25 (1H, m), 3.29 (1H, dd, J=6.1, 14.8 Hz), 3.74-3.86 (2H, m), 4.03-4.15 (1H, m), 4.55 (1H, d, J=16.3 Hz), 4.60 (1H, dt, J=7.7, 7.7 Hz), 4.83 (1H, d, J=16.3 Hz), 6.44 (1H, dd, J=1.6, 8.3 Hz), 6.64 (1H, d, J=1.6 Hz), 7.54 (1H, dd, J=2.1, 8.3 Hz), 7.65 (1H, d, J=8.3 Hz), 7.78 (1H, d, J=2.1 Hz), 7.87 (1H, d, J=8.3 Hz), 9.34 (1H, d, J=7.7 Hz)

MS: 555 (M+H)$^+$

The chemical structures of the compounds of the Examples are shown in Table I.

TABLE I

| Compound No. | Structure |
|---|---|
| 1 | |
| 2 | |
| 3 | 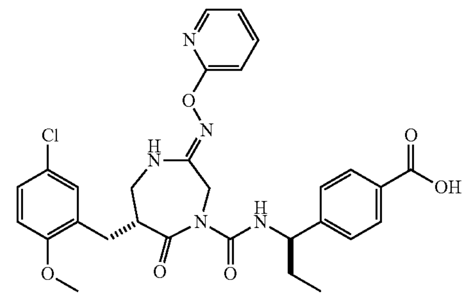 |
| 4 | 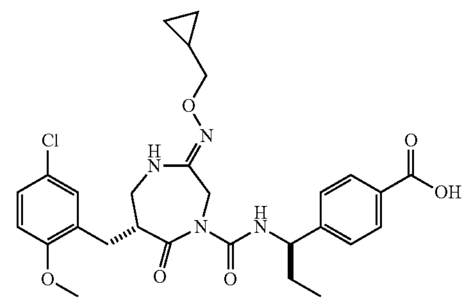 |
| 5 | 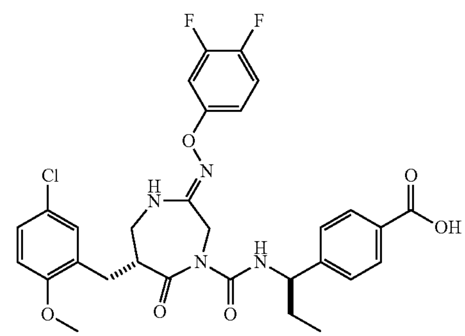 |
| 6 | 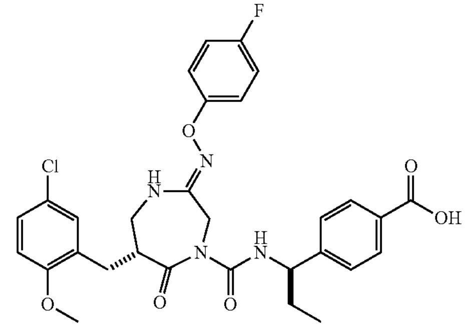 |

TABLE I-continued

| Compound No. | Structure |
|---|---|
| 7 | 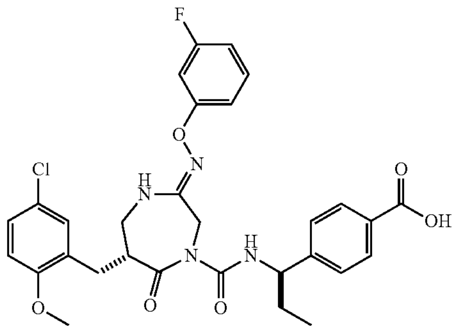 |
| 8 | 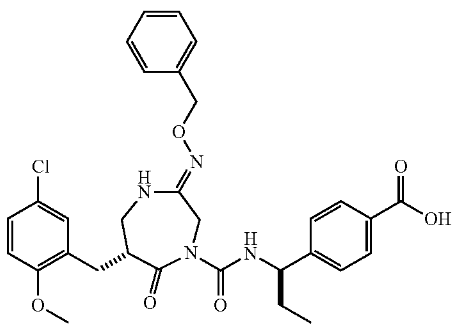 |
| 9 | 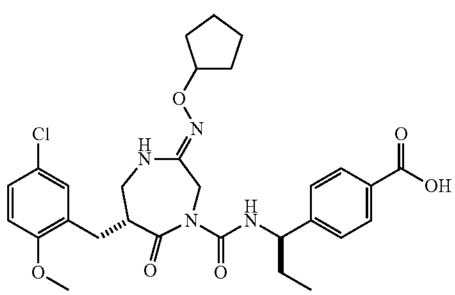 |
| 10 | 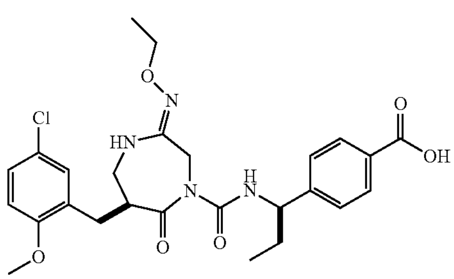 |
| 11 | 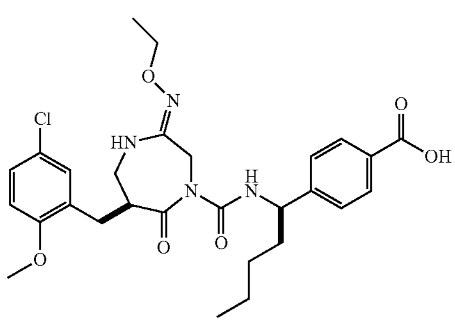 |
| 12 | |
| 13 | |
| 14 | |
| 15 | |
| 16 | |

TABLE I-continued

| Compound No. | Structure |
|---|---|
| 17 | 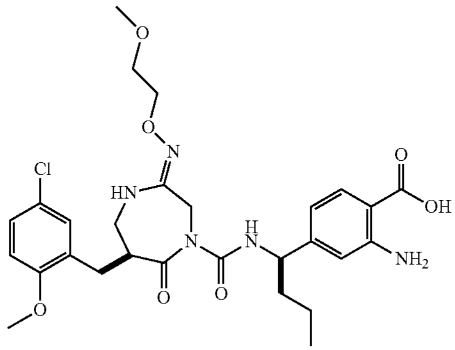 |
| 18 | 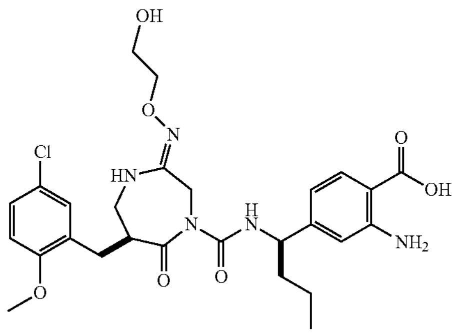 |
| 19 | 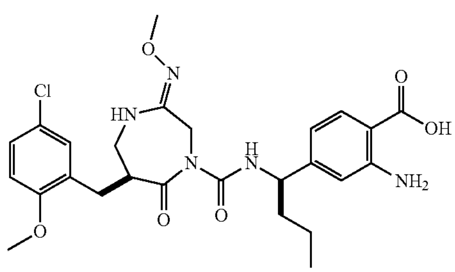 |
| 20 | 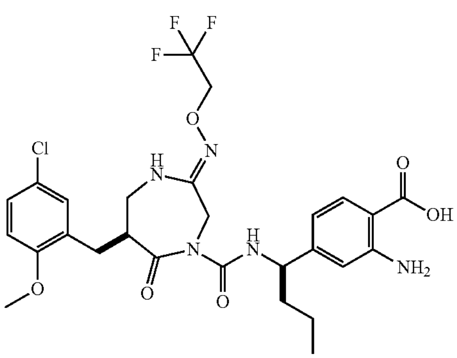 |
| 21 | 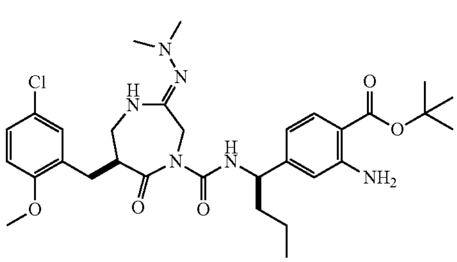 |
| 22 | 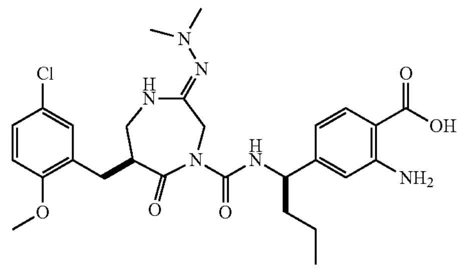 |
| 23 | 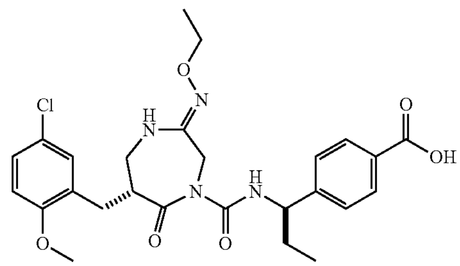 |
| 24 | 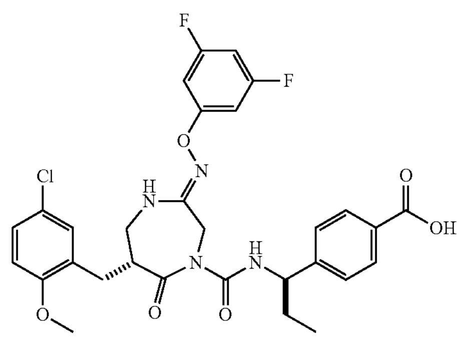 |
| 25 | 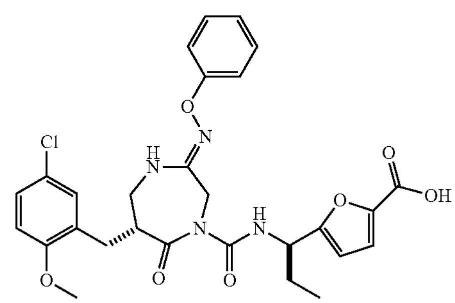 |
| 26 | 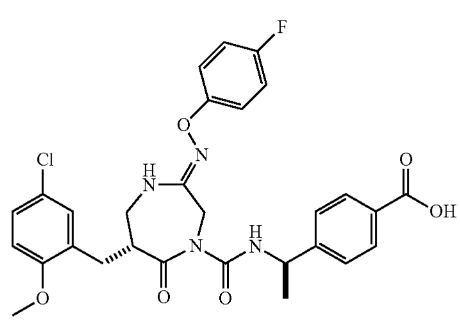 |

TABLE I-continued

| Compound No. | Structure |
|---|---|
| 27 | (structure) |
| 28 | (structure) 3/2TsOH |
| 29 | (structure) |
| 30 | (structure) |
| 31 | (structure) |
| 32 | (structure) |
| 33 | (structure) |
| 34 | (structure) |
| 35 | (structure) H—Cl |
| 36 | (structure) AcOH |

TABLE I-continued

| Compound No. | Structure |
| --- | --- |
| 37 | 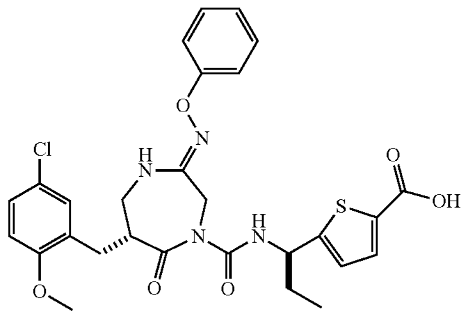 |
| 38 | 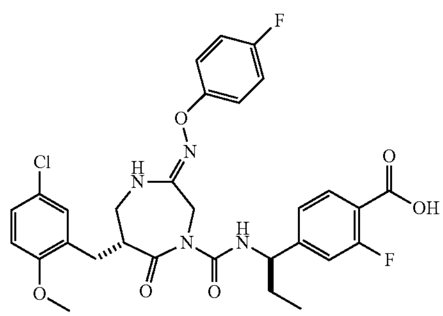 |
| 39 | 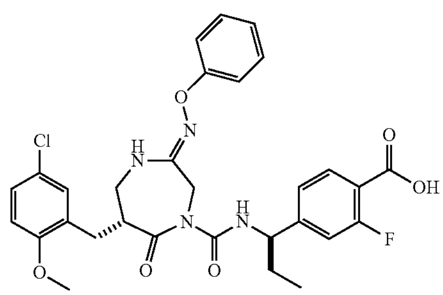 |
| 40 | 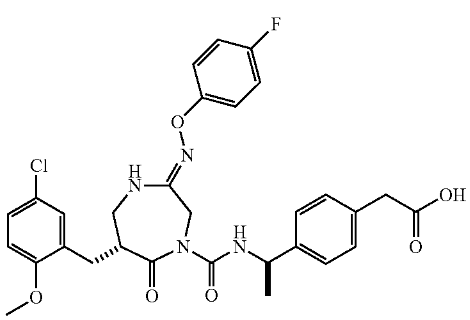 |
| 41 | 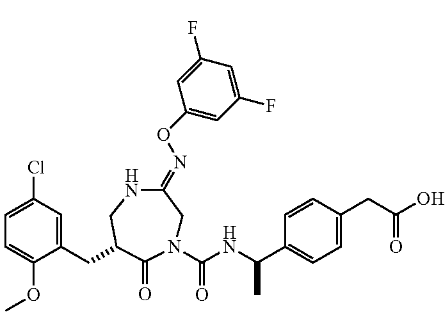 |

TABLE I-continued

| Compound No. | Structure |
| --- | --- |
| 42 | 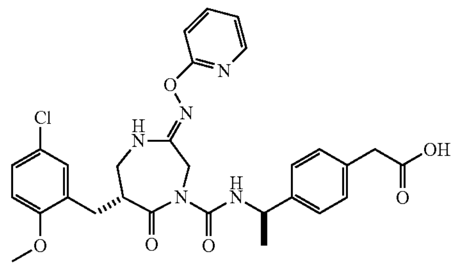 |
| 43 | 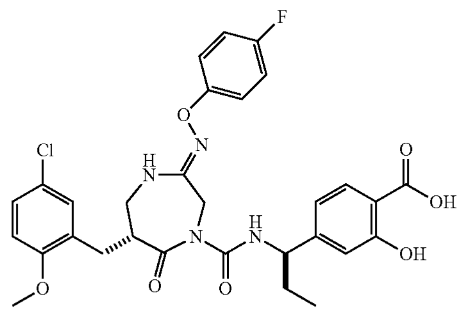 |
| 44 | 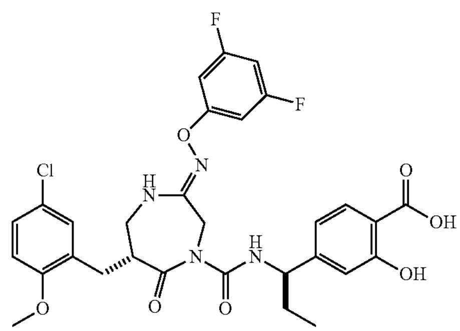 |
| 45 | 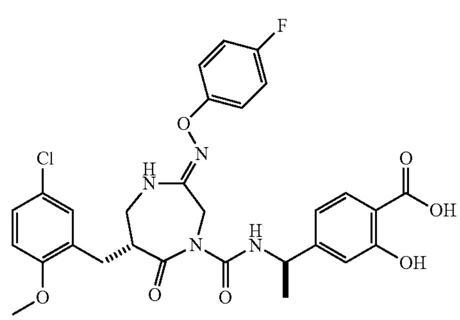 |
| 46 | 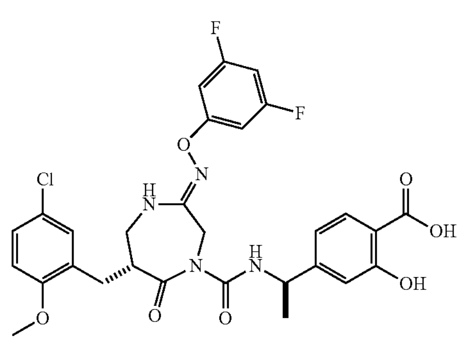 |

TABLE I-continued
| Compound No. | Structure |
|---|---|
| 47 | 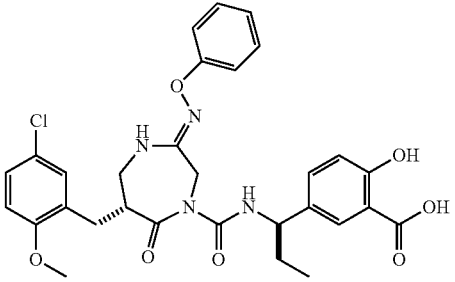 |
| 48 | 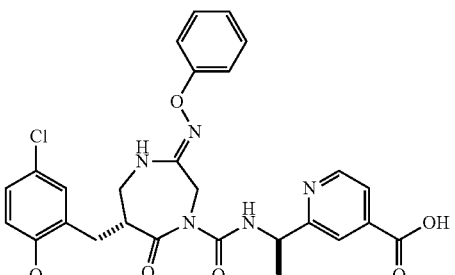 |
| 49 | 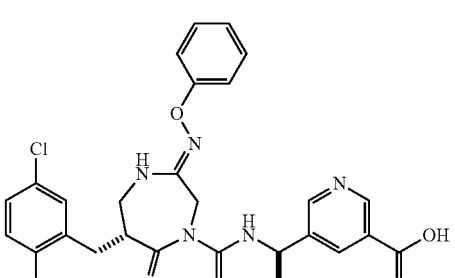 |
| 50 | 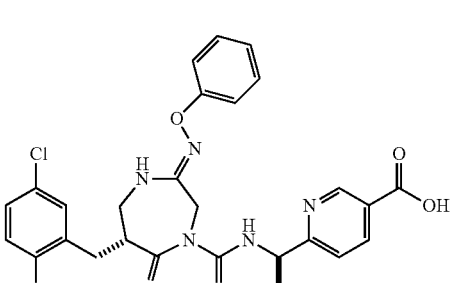 |
| 51 | 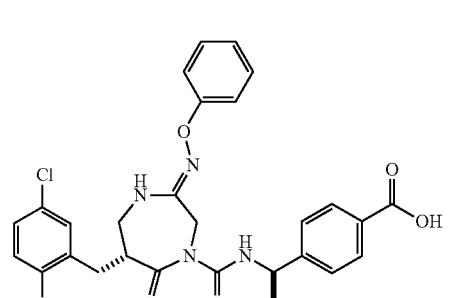 |
| 52 | 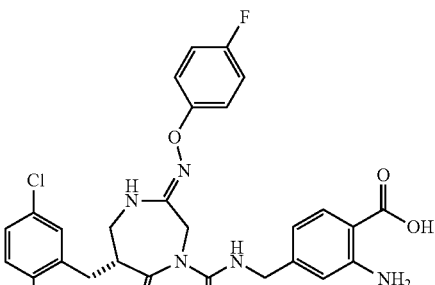 |
| 53 | 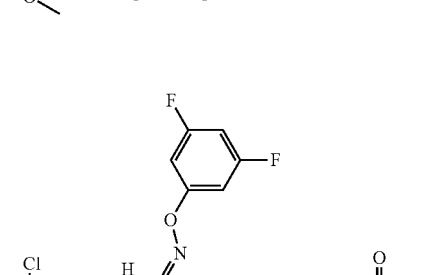 |
| 54 | 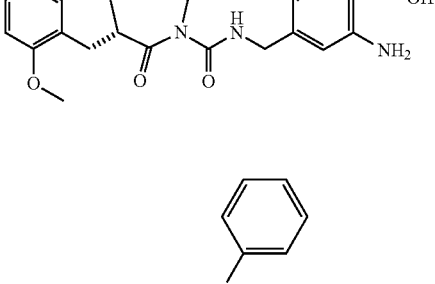 |
| 55 | 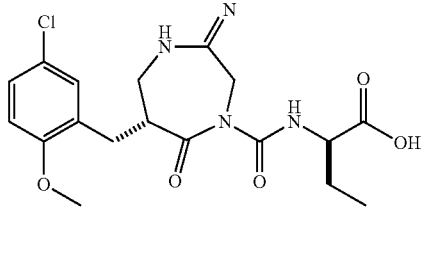 |

TABLE I-continued
| Compound No. | Structure |
|---|---|
| 56 |  |
| 57 | |
| 58 | |
| 59 | |
| 60 | 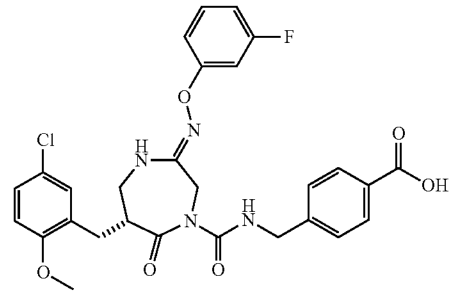 |
| 61 | 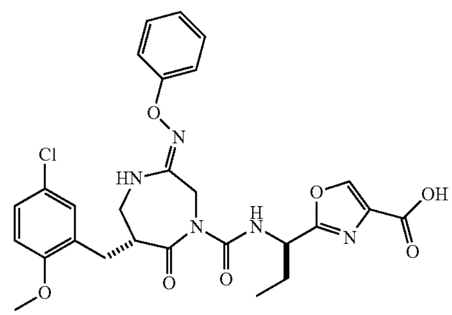 |
| 62 | 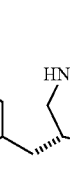 |
| 63 | 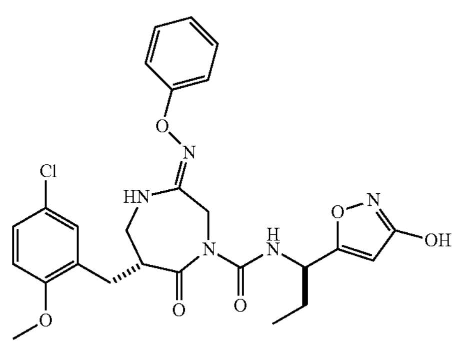 |
| 64 | 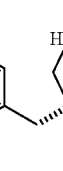 |

TABLE I-continued
| Compound No. | Structure |
|---|---|
| 65 | 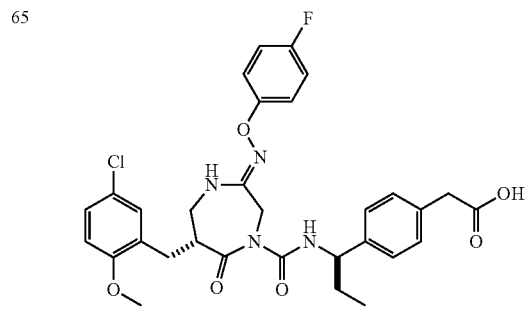 |
| 66 | 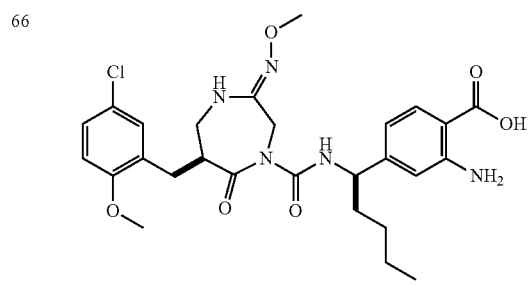 |
| 67 | 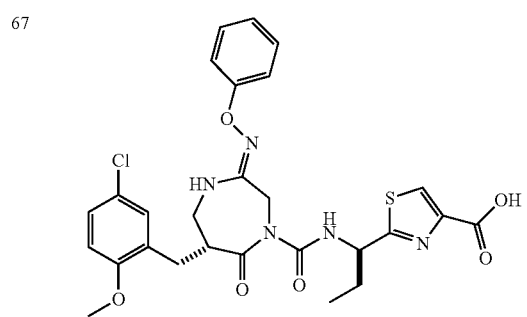 |
| 68 | 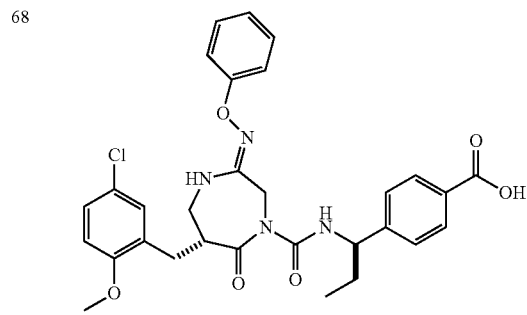 |
| 69 | 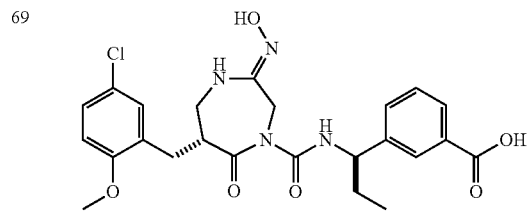 |
TABLE I-continued
| Compound No. | Structure |
|---|---|
| 70 | 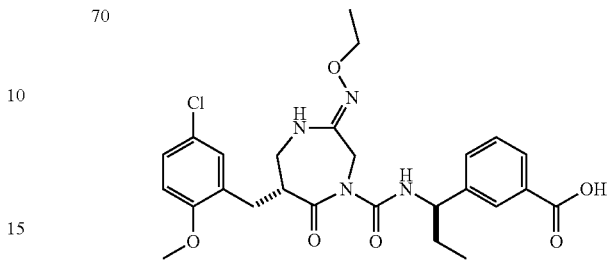 |
| 71 | 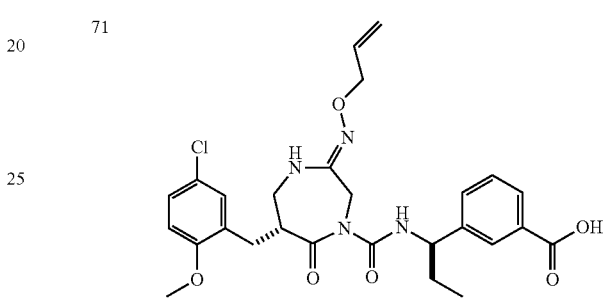 |
| 72 | 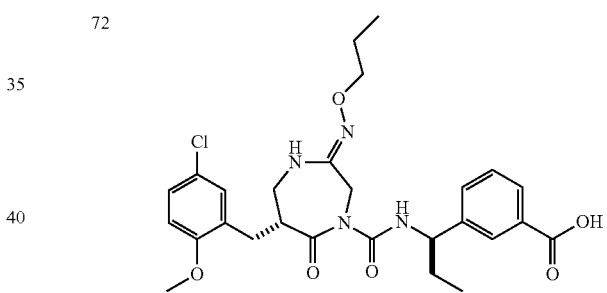 |
| 73 | 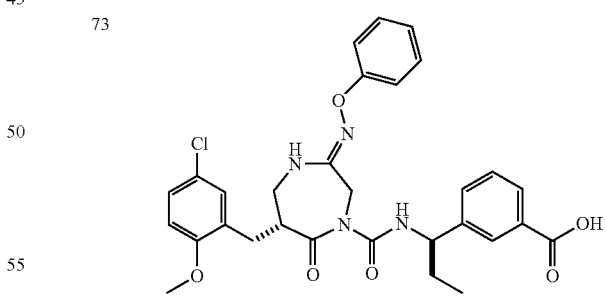 |
| 74 | 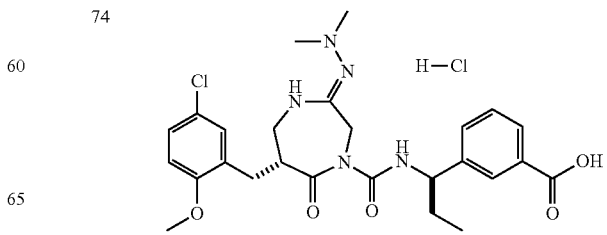 |

TABLE I-continued
| Compound No. | Structure |
|---|---|
| 75 | 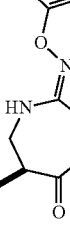 |
| 76 | 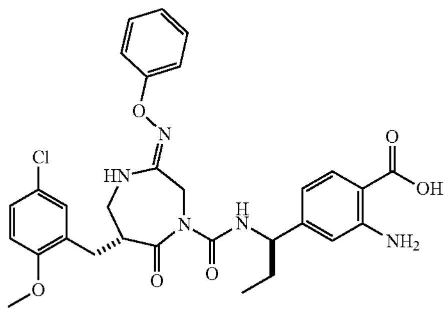 |
| 77 | H—Cl |
| 78 | 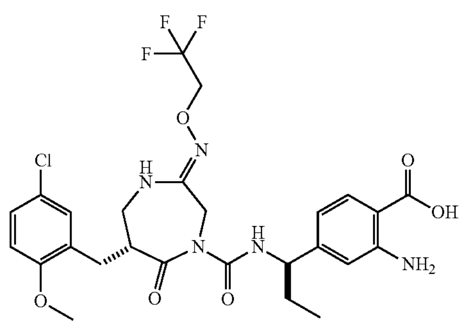 |
| 79 | 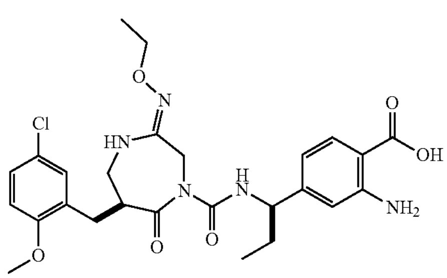 |
| 80 | 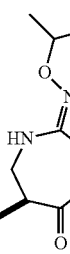 |
| 81 | 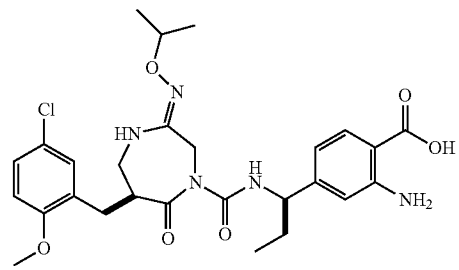 |
| 82 | 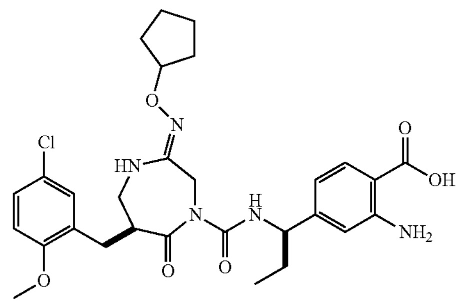 |
| 83 | 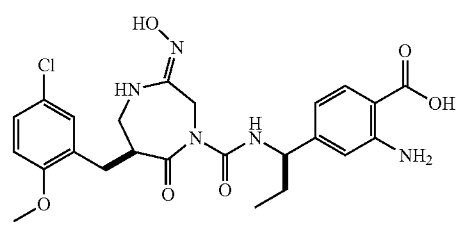 |
| 84 | 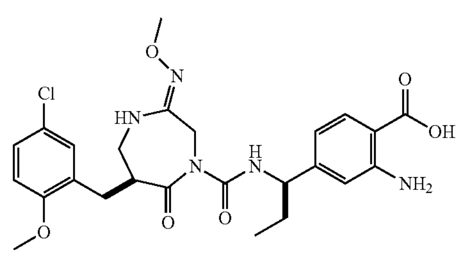 |

TABLE I-continued

| Compound No. | Structure |
|---|---|
| 85 | (structure) |
| 86 | (structure) |
| 87 | (structure) |
| 88 | (structure) |
| 89 | (structure) |
| 90 | (structure) |
| 91 | (structure) |
| 92 | (structure) |
| 93 | (structure) |
| 94 | (structure) |
| 95 | (structure) |
| 96 | (structure) |

TABLE I-continued
| Compound No. | Structure |
|---|---|
| 97 | 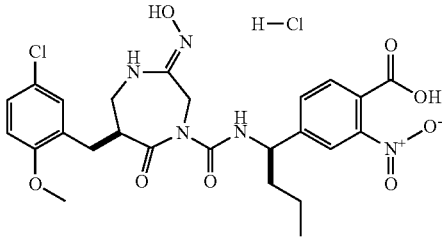 |
| 98 | 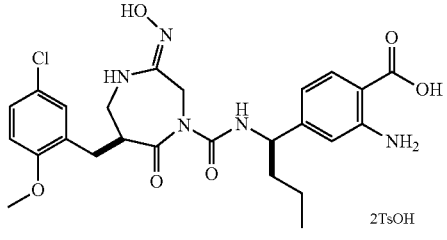 |
| 99 | 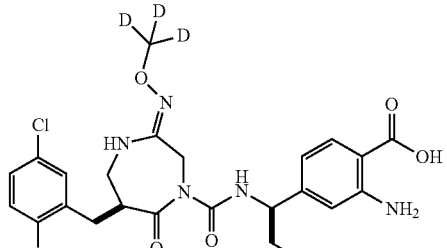 |
| 100 | 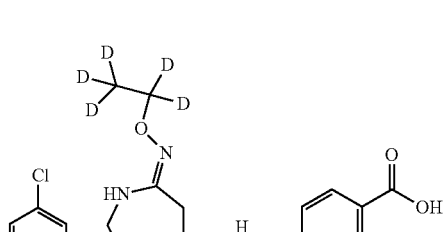 |
| 101 | 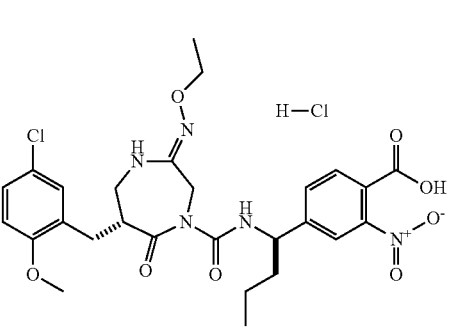 |
| 102 | 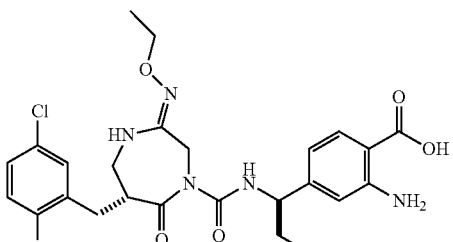 |
| 103 | 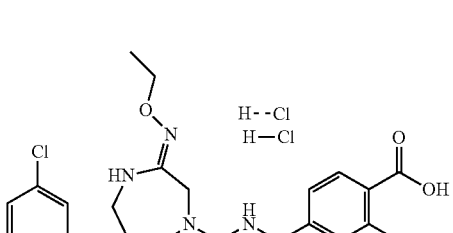 |
| 104 | 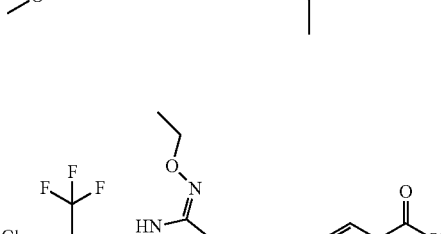 |
| 105 | 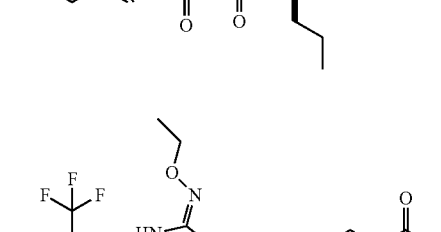 |
| 106 | 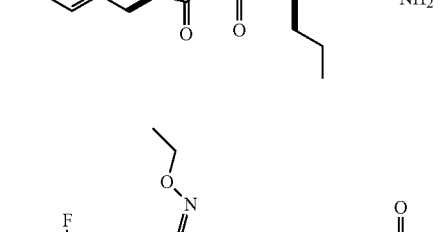 |

TABLE I-continued
| Compound No. | Structure |
|---|---|
| 107 | 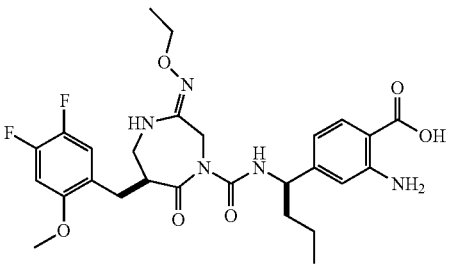 |
| 108 | 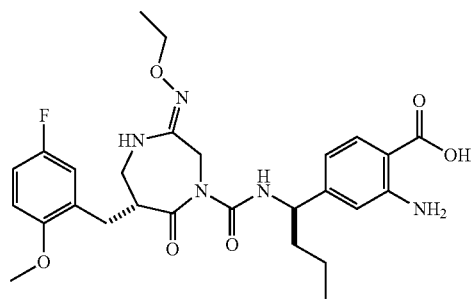 |
| 109 | 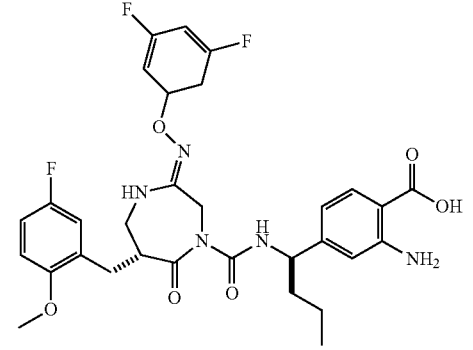 |
| 110 | 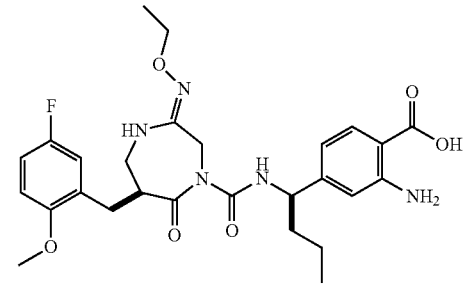 |
| 111 | 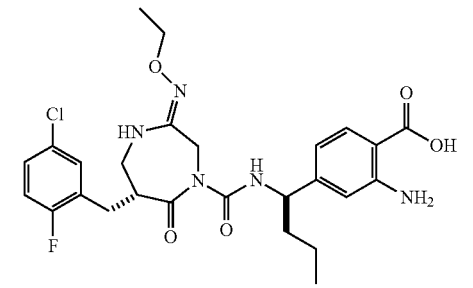 |
| 112 | 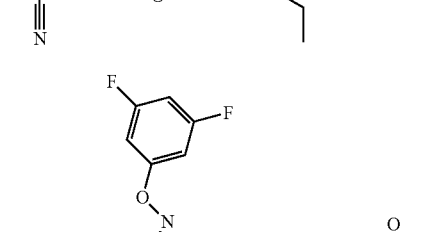 |
| 113 | 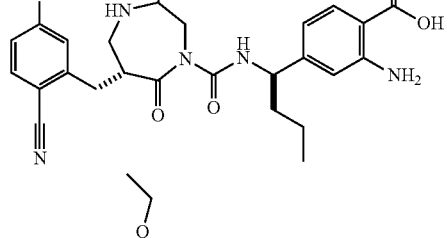 |
| 114 | 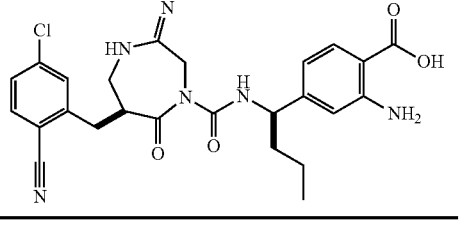 |
| 115 | 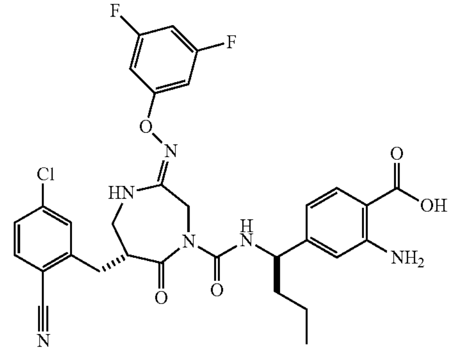 |
| 116 | 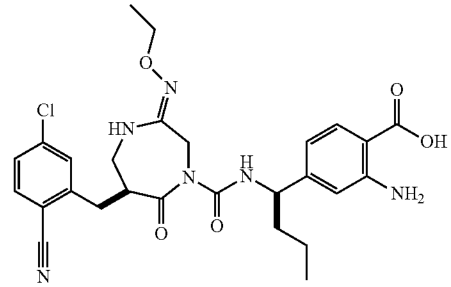 |

Test Example 1

Measurement of Inhibitory Activity of Test Compound for Human Chymase

The inhibitory activity of the compounds of the present invention for recombinant human chymase was measured by the method of Pasztor et al. (Pasztor et al., Acta. Biol. Hung. 42: 285-95, 1991). That is, recombinant human chymase was diluted to an appropriate concentration by a 50 mM tris-hydrochloride buffer (pH 7.5), 1M sodium chloride solution, and 0.01% (v/v) Triton X-100 to obtain an enzyme solution. A 10 mM dimethyl sulfoxide (hereinafter referred to as DMSO) solution of Suc-Ala-Ala-Pro-Phe-MCA (Peptide Institute) was diluted 20-fold at the time of use by 50 mM tris-hydrochloride buffer (pH 7.5), 1M sodium chloride solution and 0.01% (v/v) Triton X-100 to obtain the substrate solution. 75 µl of the enzyme solution was mixed with 5 µl of the test compound in a DMSO solution, and incubated for 10 minutes. Then 20 µl of the substrate solution was added to the mixture and reacted for a further 10 minutes at room temperature. The reaction was stopped by adding 50 µl of 30% (v/v) acetic acid. The intensity of the fluorescence (Ex 380 nm, Em 460 nm) of the fluorescent substance MCA produced by the degradation of the substrate was measured by a fluorescent photometer (Fluoroscan II, Labsystems Japan). Simultaneously, 5 µl of DMSO was added to a reaction instead of the test compound, and was used as a blank. The inhibitory activity for chymase was calculated based on the value of the blank. Further, the ratio of inhibition and the 50% inhibition concentration ($IC_{50}$ value) were calculated. The $IC_{50}$ values of representative compounds are shown in Table II.

TABLE II

| | Tested compound | $IC_{50}$ value (µM) |
|---|---|---|
| 1 | Compound 3 | 0.03 |
| 2 | Compound 12 | 0.02 |
| 3 | Compound 14 | 0.03 |
| 4 | Compound 15 | 0.03 |
| 5 | Compound 18 | 0.02 |
| 6 | Compound 20 | 0.03 |
| 7 | Compound 22 | 0.04 |
| 8 | Compound 26 | 0.05 |
| 9 | Compound 27 | 0.02 |
| 10 | Compound 29 | 0.01 |
| 11 | Compound 30 | 0.004 |
| 12 | Compound 31 | 0.01 |
| 13 | Compound 34 | 0.03 |
| 14 | Compound 37 | 0.05 |
| 15 | Compound 40 | 0.01 |
| 16 | Compound 41 | 0.003 |
| 17 | Compound 42 | 0.02 |
| 18 | Compound 44 | 0.02 |
| 19 | Compound 49 | 0.03 |
| 20 | Compound 53 | 0.04 |
| 21 | Compound 58 | 0.02 |
| 22 | Compound 64 | 0.03 |
| 23 | Compound 67 | 0.05 |
| 24 | Compound 73 | 0.03 |
| 25 | Compound 76 | 0.009 |
| 26 | Compound 88 | 0.06 |
| 27 | Compound 96 | 0.007 |
| 28 | Compound 103 | 0.02 |
| 29 | Compound 108 | 0.03 |
| 30 | Compound 113 | 0.04 |

Test Example 2

Effect of Test Compounds on the Late-Phase Skin Reaction (at 24 Hours after Challenge) of TNCB-Induced Biphasic Dermatitis in Mice Preparation of IgE solution for sensitization containing anti-TNP mouse IgE, sensitization, and induction of dermatitis were performed with reference to the method of Nagai et al (Nagai et al., Biol Pharm Bull. 18: 239-45, 1995). That is, IGELb4 cells (ATCC-TIB141) were suspended in a culture medium (RPMI1640 with 10% FBS) and adjusted to a concentration of $0.5 \times 10^5$ cells/ml. The prepared cells were incubated at 37° C. in 5% $CO_2$ for 72 hours, and the culture supernatant was used as the IgE solution for sensitization. The IgE solution containing anti-TNP mouse IgE was administered in an amount of 1.0 ml to 7-week old female BALB/c mice (Charles River Japan) intravenously for sensitization. Dermatitis was induced after about 24 hours from sensitization by application of 1% TNCB dissolved in acetone/olive oil (1:9) to both sides of the right ear of the mice (10 µl/side, total 20 µl). As a control, acetone/olive oil (1:9) was applied to sensitized mice by a similar method (control group). Further, to consider the effect of application of TNCB, non-sensitized mice were applied with 1% TNCB dissolved in acetone/olive oil (1:9) by a similar method (non-sensitized+TNCB applied group). The test compound was suspended in distilled water containing 0.5% hydroxypropylcellulose (hereinafter abbreviated as "0.5% HPC-distilled water") and orally administered at a dosage of 1 or 0.5 mg/kg at 1 hour before induction of dermatitis (compound group). Further, as a control, instead of the suspension of test compound, 0.5% HPC-distilled water was administered in the same way (vehicle group).

Ear thickness was measured before TNCB application and 24 hours after TNCB application by a microgauge (Mitsutoyo), and the amount of increase of ear thicness was evaluated by subtracting ear thickness before TNCB application from the ear thickness at 24 hours after application with TNCB. The effect of the test compound was judged by calculating the inhibition ratio (%) according to the following calculation formula.

$$\text{Inhibition ratio (\%)} = \frac{\{(\text{Increase of vehicle group}) - (\text{Increase of control group})\} - \{(\text{Increase of compound group}) - (\text{Increase of control group})\}}{\{(\text{Increase of vehicle group}) - (\text{Increase of control group})\} - \left\{(\text{Increase of non-sensitized} + \text{TNCB applied group}) - (\text{Increase of control group})\right\}} \times 100$$

Due to application of TNCB, earedema (late-phase reaction) was observed after 24 hours. As a result of oral administration of the test compounds, each test compound remarkably inhibited the late-phase skin reaction. For example, when the compound 3, compound 12, compound 64, and compound 76 were administered orally by a dosage of 1 mg/kg, the inhibition ratio of the late-phase reaction were respectively 71.0%, 64.0%, 74.2%, and 85.7%, while when the compound 20, compound 34, and compound 53 were administered orally by a dosage of 0.5 mg/kg, the inhibition ratio of the late-phase reaction were respectively 115.0%, 135.0%, and 91.2%.

INDUSTRIAL APPLICABILITY

The compound of formula (I) of the present invention has a chymase inhibitory activity, is superior in stability in blood plasma and in vivo pharmacokinetics, and is useful as a pharmaceutical for the prevention and/or treatment of diseases such as bronchial asthma, chronic obstructive pulmonary disease, urticaria, atopic dermatitis, allergic conjunctivitis, rhinitis, rheumatoid arthritis, food allergies, colitis, allergic enteritis, mastocytosis, scleroderma, heart failure, cardiac hypertrophy, hypertension, arrhythmia, atherosclerosis, abdominal aortic aneurysm, myocardial infarction, restenosis after PTCA, restenosis after bypass graft surgery, ischemic peripheral circulatory disorders, hyperaldosteronism, diabetes, diabetic retinopathy, diabetic nephropathy, nephritis, glomerulosclerosis, renal insufficiency, solid tumor, fibrosis, postoperative adhesion, cicatrix, glaucoma, and ocular hypertension.

The invention claimed is:
1. A compound, or a pharmaceutically acceptable salt or solvate thereof, having a formula (I):

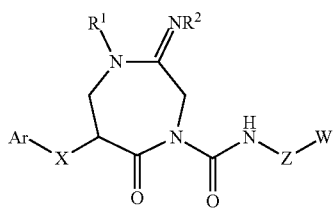

(I)

wherein,

Ar indicates (1) a $C_6$ to $C_{14}$ aromatic hydrocarbon group, (2) a 5 to 8-membered aromatic heterocyclic group having 1 to 4 hetero atoms selected from the group consisting of a nitrogen atom, sulfur atom, and oxygen atom, in place of a carbon atom, or (3) a bicyclic or tricyclic aromatic group formed by condensation of the above aromatic heterocyclic group and a $C_6$ to $C_{14}$ aromatic hydrocarbon ring, where the above groups (1) to (3) of Ar are optionally substituted with 1 to 5 groups selected from the group consisting of:
(i) a halogen atom,
(ii) nitro,
(iii) cyano,
(iv) $C_1$ to $C_6$ alkyl optionally substituted with 1 to 3 halogen atoms,
(v) $C_2$ to $C_6$ alkenyl optionally substituted with 1 to 3 halogen atoms,
(vi) $C_2$ to $C_6$ alkynyl optionally substituted with 1 to 3 halogen atoms,
(vii) $C_3$ to $C_6$ cycloalkyl,
(viii) hydroxyl,
(ix) $C_1$ to $C_6$ alkoxy optionally substituted with 1 to 3 groups selected from the group consisting of a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atom,
(x) $C_1$ to $C_5$ alkylenedioxy,
(xi) $C_1$ to $C_6$ alkylthio optionally substituted with 1 to 3 groups selected from the group consisting of a halogen atom, mono- or di-$C_1$ to $C_6$ alkylamino, $C_1$ to $C_6$ alkoxy, mono- or di-$C_2$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atom,
(xii) amino,
(xiii) mono-$C_1$ to $C_6$ alkylamino,
(xiv) di-$C_1$ to $C_6$ alkylamino,
(xv) 5- to 6-membered cyclic amino,
(xvi) $C_1$ to $C_6$ alkylcarbonyl,
(xvii) carboxyl,
(xviii) $C_1$ to $C_6$ alkoxycarbonyl,
(xix) carbamoyl,
(xx) thiocarbamoyl,
(xxi) mono-$C_1$ to $C_6$ alkylcarbamoyl,
(xxii) di-$C_1$ to $C_6$ alkylcarbamoyl,
(xxiii) 5- to 6-membered cyclic aminocarbonyl,
(xxiv) sulfo,
(xxv) $C_1$ to $C_6$ alkylsulfonyl
(xxvi) $C_1$ to $C_6$ alkoxycarbonylamino,
(xxvii) $C_1$ to $C_6$ alkylcarbonylamino,
(xxviii) mono- or di-$C_1$ to $C_6$ alkylaminocarbonylamino,
(xxix) aminosulfonyl, and
(xxx) mono- or di-$C_1$ to $C_6$ alkylaminosulfonyl, or substituted with 1 to 9 deuterium atoms, X indicates (1) a connecting bond, (2) linear or branched $C_1$ to $C_6$ alkylene optionally substituted with 1 to 12 deuterium atoms, (3) an oxygen atom, (4) $NR^3$, where $R^3$ indicates a hydrogen atom or a $C_1$ to $C_6$ alkyl group, or (5) —$S(O)_m$—, where m indicates an integer of 0 to 2, Z indicates (1) a connecting bond or (2) $CR^4R^5$ where $R^4$ and $R^5$ are, independently,
(A) a hydrogen atom,
(B) a deuterium atom,
(C) $C_1$ to $C_6$ alkyl optionally substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) halogen atom, and (vii) $C_3$ to $C_6$ cycloalkyl, or substituted with 1 to 13 deuterium atoms,
(D) $C_3$ to $C_6$ cycloalkyl optionally substituted with 1 to 5 groups selected from the group consisting of (i) a halogen atom and (ii) an alkyl group optionally substituted with 1 to 3 halogen atoms or optionally substituted, with 1 to 11 deuterium atoms,
(E) $COOR^6$, where $R^6$ indicates a hydrogen atom or $C_1$ to $C_6$ alkyl, or
(F) $CONR^7R^8$, where $R^7$ and $R^8$ are, independently,
(a) hydrogen atom,
(b) $C_1$ to $C_6$ alkyl optionally substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl,
(c) $C_6$ to $C_{14}$ aromatic hydrocarbon group,
(d) a 5- to 8-membered aromatic heterocyclic group having 1 to 4 hetero atoms selected from the group consisting of a nitrogen atom, sulfur atom, and oxygen atom, in place of a carbon atom, or
(e) a bicyclic or tricyclic aromatic group formed by condensation of the above aromatic heterocyclic, group and a $C_6$ to $C_{14}$ aromatic hydrocarbon ring,
where each of the groups (c) to (e) is optionally substituted with 1 to 5 groups selected from the group consisting of (i) a halogen atom, (ii) nitro, (iii) cyano, (iv) $C_1$ to $C_6$ alkyl optionally substituted with 1 to 3 halogen atoms, (v) $C_2$ to $C_6$ alkenyl optionally substituted with 1 to 3 halogen atoms, (vi) $C_2$ to $C_6$ alkynyl optionally substituted with 1 to 3 halogen atoms, (vii) $C_3$ to $C_6$ cycloalkyl, (viii) hydroxyl, (ix) $C_1$ to $C_6$ alkoxy optionally substituted with 1 to 3 halogen atoms, (x) $C_1$ to $C_5$ alkylenedioxy, (xi) $C_1$ to $C_6$ alkylthio optionally substituted with 1 to 3 halogen atoms, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) carbamoyl, (xx) thiocarbamoyl, (xxi) mono-$C_1$ to $C_6$ alkylcarbamoyl, (xxii) di-$C_1$ to $C_6$ alkylcarbamoyl, (xxiii) $C_6$ to $C_{10}$ arylcarbamoyl, (xxiv) $C_1$ to $C_{10}$ heteroarylcarbamoyl, (xxv) sulfo, (xxvi) $C_1$ to $C_6$ alkylsulfonyl, (xxvii) aminosulfonyl, and (xxviii) mono- or di-$C_1$ to $C_6$ alkylaminosulfonylamino, or substituted with 1 to 9 deuterium atoms, W indicates (1) a hydrogen atom, (2) a $C_6$ to $C_{14}$ aromatic hydrocarbon group, (3) a 5- to 8-membered aromatic heterocyclic group having 1 to 4 hetero atoms selected from a nitrogen atom, a sulfur atom, and an oxygen atom, in place of a carbon atom, (4) a bicyclic, or tricyclic aromatic group formed by condensation of the above aromatic heterocyclic group and a $C_6$ to $C_{14}$ aromatic hydrocarbon ring, or a deuterium atom, where, each of the groups (2) to (4) of the above W is optionally substituted with 1 to 5 groups selected from the group consisting of (i) a halogen atom, (ii) nitro, (iii) cyano, (iv) $C_1$ to $C_6$ alkyl optionally substituted with 1 to 3 groups selected from the group consisting of a halogen atom, amino, $C_1$ to $C_6$ alkoxycarbonyl, $C_1$ to $C_6$ alkoxycarbonylamino, and carboxyl, (v) $C_2$ to $C_6$ alkenyl optionally substituted with 1 to 3 halogen atoms, (vi) $C_2$ to $C_6$ alkynyl optionally substituted with 1 to 3 halogen atoms, (vii) $C_3$ to $C_6$ cycloalkyl, (viii) hydroxyl, (ix) $C_1$ to $C_6$ alkoxy optionally substituted with 1 to 3 groups selected from the group consisting of a halogen atom, hydroxyl, $C_1$ to $C_6$ alkoxy, amino and mono- or di-$C_1$ to $C_6$ alkylamino, (x) $C_1$ to $C_5$ alkylenedioxy, (xi) $C_1$ to $C_6$ alkylthio optionally substituted with 1 to 3 groups selected from the group consisting of a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkyl-carbonyl, (xvii) carboxyl, (xviii) $C_1$ to $C_6$ alkoxycarbonyl optionally substituted with a halogen atom, (xix) $C_7$ to $C_{16}$ aralkyloxycarbonyl optionally substituted with a halogen atom, (xx) carbamoyl, (xxi) mono-$C_1$ to $C_6$ alkylcarbamoyl optionally substituted with 1 to 3 groups which are selected from the group consisting of a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl optionally substituted with hydroxyl, (xxiii) 5- to 6-membered cyclic aminocarbonyl optionally substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino optionally substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ aralkyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl, or substituted with 1 to 9 deuterium atoms, $R^1$ indicates
(1) a hydrogen atom,
(2) $C_1$ to $C_6$ alkyl optionally substituted with 1 to 3 of (i) a halogen atom or (ii) $C_3$ to $C_6$ cycloalkyl or substituted with (iii) 1 to 13 deuterium atoms,
(3) $C_2$ to $C_6$ alkenyl optionally substituted with 1 to 3 of (i) a halogen atom or (ii) $C_3$ to $C_6$ cycloalkyl or substituted with (iii) 1 to 11 deuterium atoms,
(4) $C_2$ to $C_6$ alkynyl optionally substituted with 1 to 3 of (i) a halogen atom or (ii) $C_3$ to $C_6$ cycloalkyl, or substituted with (iii) 1 to 9 deuterium atoms, or
(5) $C_3$ to $C_6$ cycloalkyl optionally substituted with 1 to 3 of (i) a halogen atom or (ii) $C_3$ to $C_6$ cycloalkyl, or substituted with (iii) 1 to 11 deuterium atoms, $R^2$ indicates (1) $OR^9$ or (2) $NR^{10}R^{11}$
where, $R^9$, $R^{10}$, and $R^{11}$ independently indicate
(A) a hydrogen atom,
(B) $C_1$ to $C_6$ alkyl,
(C) $C_2$ to $C_6$ alkenyl,
(D) $C_3$ to $C_6$ alkynyl,
(E) $C_3$ to $C_6$ cycloalkyl
(F) $C_6$ to $C_{14}$ aromatic hydrocarbon group,
(G) a 5- to 8-membered aromatic heterocyclic group having 1 to 4 hetero atoms selected from the group consisting of a nitrogen atom, sulfur atom, and oxygen atom, in place of a carbon atom, or
(H) a bicyclic or tricyclic aromatic group formed by condensation of the above aromatic heterocyclic group and a $C_6$ to $C_{14}$ aromatic hydrocarbon ring, where each of the groups of the above (B) to (E) is optionally substituted with 1 to 3 groups selected from the group consisting of (i) a halogen atom, (ii) $C_3$ to $C_6$ cycloalkyl, (iii) hydroxyl, (iv) $C_1$ to $C_6$ alkoxy optionally substituted with 1 to 3 halogen atoms, (v) amino, (vi) mono-$C_1$ to $C_6$ alkylamino, (vii) di-$C_1$ to $C_6$ alkylamino, (viii) 5 to 6-membered cyclic amino, (ix) carboxyl, (x) $C_1$ to $C_6$ alkoxycarbonyl, (xi) $C_1$ to $C_6$ alkylcarbonyl, (xii) carbamoyl, (xiii) mono-$C_1$ to $C_6$ alkylcarbamoyl, (xiv) di-$C_1$ to $C_6$ alkylcarbamoyl, (xv) $C_6$ to $C_{12}$ aryl, and (xvi) $C_1$ to $C_{10}$ heteroaryl, or substituted with 1 to 13 deuterium atoms, further, each of the groups of the above (F) to (H) are optionally substituted with 1 to 5 groups which are selected from the group consisting of (i) a halogen atom, (ii) nitro, (iii) cyano, (iv) $C_1$ to $C_6$ alkyl optionally substituted with 1 to 3 halogen atoms, (v) $C_3$ to $C_6$ cycloalkyl optionally substituted with 1 to 3 halogen atoms, (vi) hydroxyl, (vii) $C_1$ to $C_6$ alkoxy optionally substituted with 1 to 3 halogen atoms, (viii) amino, (ix) mono-$C_1$ to $C_6$ alkylamino, (x) di-$C_1$ to $C_6$ alkylamino, (xi) 5- to 6-membered cyclic amino, (xii) $C_1$ to $C_6$ alkylcarbonyl, (xiii) carboxyl, (xiv) $C_1$ to $C_6$ alkoxycarbonyl, (xv) carbamoyl, (xvi) mono-$C_1$ to $C_6$ alkylcarbamoyl, (xvii) di-$C_1$ to $C_6$ alkylcarbamoyl, (xviii) $C_1$ to $C_6$ alkylsulfonyl, (xix) aminosulfonyl, and (xx) mono- or di-$C_1$ to $C_6$ alkylaminosulfonyl, or substituted with 1 to 9 deuterium atoms, or $R^1$ and $R^2$ may form 5- or 6-member heterocyclic ring together with the atoms they are bonded with, where the above 5- or 6-member heterocyclic ring is optionally substituted with 1 to 3 groups selected from the group consisting of
(A) a halogen atom,
(B) oxo,
(C) hydroxyl (D) $C_1$ to $C_6$ alkyl,
(E) $C_2$ to $C_6$ alkenyl,
(F) $C_2$ to $C_6$ alkynyl,
(G) $C_3$ to $C_6$ cycloalkyl
(H) $C_6$ to $C_{14}$ aromatic hydrocarbon group,
(I) 5- to 8-membered aromatic heterocyclic group having 1 to 4 hetero atoms selected from the group consisting of a nitrogen atom, sulfur atom, and oxygen atom, in place of a carbon atom, and
(J) a bicyclic or tricyclic aromatic group formed by condensation of the above aromatic heterocyclic group and a $C_6$ to $C_{14}$ aromatic hydrocarbon ring, or substituted with
(K) 1 to 6 deuterium atoms,
where each of the groups of the above (D) to (G) is optionally substituted with 1 to 3 groups selected from the group consisting of (i) a halogen atom, (ii) $C_3$ to $C_6$ cycloalkyl, (iii) hydroxyl, (iv) $C_1$ to $C_6$ alkoxy optionally substituted with 1 to 3 halogen atoms, (v) amino, (vi) mono-$C_1$ to $C_6$ alkylamino, (vii) di-$C_1$ to $C_6$ alkylamino, (viii) 5- to 6-membered cyclic amino, (ix) carboxyl, (x) $C_1$ to $C_6$ alkoxycarbonyl, (xi) $C_1$ to $C_6$ alkyl-carbonyl, (xii) carbamoyl, (xiii) mono-$C_1$ to $C_6$ alkylcarbamoyl, (xiv) di-$C_1$ to $C_6$ alkylcarbamoyl, (xv) $C_6$ to $C_{12}$ aryl and (xvi) $C_1$ to $C_{10}$ heteroaryl, or substituted with 1 to 13 deuterium atoms, each of the groups of the above (H) to (J) is optionally substituted with 1 to 5 groups which are selected from the group consisting, of (i) a halogen atom, (ii) nitro, (iii) cyano, (iv) $C_1$ to $C_6$ alkyl optionally substituted with 1 to 3 halogen atoms, (v) $C_3$ to $C_6$ cycloalkyl optionally substituted with 1 to 3 halogen atoms, (vi) hydroxyl, (vii) $C_1$ to $C_6$ alkoxy optionally substituted with 1 to 3 halogen atoms, (viii) amino, (ix) mono-$C_1$ to $C_6$ alkylamino, (x) di-$C_1$ to $C_6$ alkylamino, (xi) 5- to 6-membered cyclic amino, (xii) $C_1$ to $C_6$ alkylcarbonyl, (xiii) carboxyl, (xiv) $C_1$ to $C_6$ alkoxycarbonyl, (xv) carbamoyl, (xvi) mono-$C_1$ to $C_6$ alkylcarbamoyl, (xvii) di-$C_1$ to $C_6$ alkylcarbamoyl, (xviii) $C_1$ to $C_6$ alkylsulfonyl, (xix) aminosulfonyl, and (xx) mono- or di-$C_1$ to $C_6$ alkylaminosulfonyl, or substituted with 1 to 9 deuterium atoms.

2. A compound, or a pharmaceutically acceptable salt or solvate thereof, as claimed in claim 1, wherein, in the formula (I), X indicates a linear or branched $C_1$ to $C_6$ alkylene and Ar is a $C_6$ to $C_{14}$ aromatic hydrocarbon group.

3. A compound, or a pharmaceutically acceptable salt or solvate thereof, as claimed in claim 1, wherein, in the formula (I), Ar is a phenyl group, of which Ar group is optionally substituted with 1 to 5 groups which are selected front the group consisting of (i) a halogen atom, (ii) nitro, (iii) cyano, (iv) $C_1$ to $C_6$ alkyl optionally substituted with 1 to 3 halogen atoms, (viii) hydroxyl, (ix) $C_1$ to $C_6$ alkoxy optionally substituted with 1 to 3 halogen atoms or substituted with 1 to 13 deuterium atoms, and (xxxi) a deuterium atom.

4. A compound, or a pharmaceutically acceptable salt or solvate thereof, as claimed in claim 1, wherein, in the formula (I), W is (1) a $C_6$ to $C_{14}$ aromatic hydrocarbon group or (2) a 5- to 8-membered aromatic heterocyclic group having 1 to 4 hetero atoms selected from the group consisting of a nitrogen atom, sulfur atom, and oxygen atom, the place of a carbon atom.

5. A compound, or a pharmaceutically acceptable salt or solvate thereof, as claimed in claim 4, wherein, in the formula (I), Z is (1) a connecting bond or (2) $CR^4R^5$, wherein $R^4$ and $R^5$ independently are
(A) a hydrogen atom,
(B) a deuterium atom,
(C) $C_1$ to $C_6$ alkyl optionally substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl, or substituted with 1 to 13 deuterium atoms, or (D) $C_3$ to $C_6$ cycloalkyl optionally substituted with 1 to 5 groups selected from the group consisting of (i) a halogen atom and (ii) an alkyl group optionally with 1 to 3 halogen atoms, or substituted with 1 to 11 deuterium atoms.

6. A compound, or a pharmaceutically acceptable salt or solvate thereof, as claimed in claim 1, wherein, in the formula (I), W is a hydrogen atom or deuterium atom.

7. A compound, or a pharmaceutically acceptable salt or solvate thereof, as claimed in claim 6, wherein, in the formula (I), Z is (1) a connecting bond or (2) $CR^4R^5$, where $R^4$ and $R^5$ independently are
(A) a hydrogen atom,
(B) a deuterium atom,
(C) $C_1$ to $C_6$ alkyl optionally substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl, or substituted with 1 to 13 deuterium atoms,
(D) $C_3$ to $C_6$ cycloalkyl optionally substituted with 1 to 5 groups selected from the group consisting of (i) a halogen atom and (ii) an alkyl group optionally substituted with 1 to 3 halogen atoms, or substituted with 1 to 11 deuterium atoms,
(E) $COOR^6$, where $R^6$ indicates a hydrogen atom or $C_1$ to $C_6$ alkyl, or
(F) $CONR^7R^8$, where $R^7$ and $R^8$ respectively independently are
(a) a hydrogen atom,
(b) $C_1$ to $C_6$ alkyl optionally substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl,
(c) a $C_6$ to $C_{14}$ aromatic hydrocarbon cyclic group, or
(d) a 5- to 8-membered aromatic heterocyclic group having 1 to 4 hetero atoms selected from the group consisting of a nitrogen atom, sulfur atom, and oxygen atom, in place of a carbon atom,
where the above groups (c) to (d) are optionally substituted with 1 to 5 groups selected from the group consisting of (i) a halogen atom, (iv) $C_1$ to $C_6$ alkyl optionally substituted with 1 to 3 halogen atoms, (viii) hydroxyl, (ix) $C_1$ to $C_6$ alkoxy optionally substituted with 1 to 3 halogen atoms, (xii) amino, (xiii) mono-$C_1$ to $C_6$ alkylamino, (xiv) di-$C_1$ to $C_6$ alkylamino, (xv) 5 to 6-membered cyclic amino, (xvi) $C_1$ to $C_6$ alkylcarbonyl, (xvii) carboxyl, (xxvii) aminosulfonyl, and (xxviii) mono- or di-$C_1$ to $C_6$ alkylaminosulfonyl, or substituted with 1 to 9 deuterium atoms.

8. A compound, or a pharmaceutically acceptable salt or solvate thereof, as claimed in claim 1, wherein, in the formula (I), $R^1$ is (1) a hydrogen atom or (2) $C_1$ to $C_6$ alkyl optionally substituted with 1 to 3 of (i) a halogen atom or (ii) $C_3$ to $C_6$ cycloalkyl, or substituted with 1 to 13 deuterium atoms, and $R^2$ indicates (1) $OR^9$ or (2) $NR^{10}R^{11}$
where $R^9$, $R^{10}$, and $R^{11}$ independently are
(A) a hydrogen atom,
(B) $C_1$ to $C_6$ alkyl,
(C) $C_2$ to $C_6$ alkenyl, (F) $C_3$ to $C_6$ cycloalkyl (F) $C_6$ to $C_{14}$ aromatic hydrocarbon group, or (G) a 5- to 8-membered aromatic heterocyclic group having 1 to 4 hetero atoms selected from the group consisting of a nitrogen atom, sulfur atom, and oxygen atom, in place of a carbon atom, where each group of the above (B) to (F) is optionally substituted with 1 to 3 groups selected from the group consisting of (i) a halogen atom, (ii) $C_3$ to $C_6$ cycloalkyl, (iii) hydroxyl, (iv) $C_1$ to $C_6$ alkoxy optionally substituted with 1 to 3 halogen atoms, (v) amino (vi) mono-$C_1$ to $C_6$ alkylamino, (vii) di-$C_1$ to $C_6$ alkylamino, (viii) 5- to 6-membered cyclic amino, (ix) carboxyl, and (xv) $C_6$ to $C_{12}$ aryl, or substituted with 1 to 13 deuterium atoms, further, each group of the above (F) to (G) is optionally substituted with 1 to 5 groups selected from the group consisting of (i) a halogen atom, (iv) $C_1$ to $C_6$ alkyl optionally substituted with 1 to 3 halogen atoms, (vi) hydroxyl, (vii) $C_1$ to $C_6$ alkoxy optionally substituted with 1 to 3 halogen atoms, (viii) amino, (ix) mono-$C_1$ to $C_6$ alkylamino, (x) di-$C_1$ to $C_6$ alkylamino, (xi) 5- to 6-membered cyclic amino, and (xiii) carboxyl, or substituted with 1 to 9 deuterium atoms.

9. A compound, or a pharmaceutically acceptable salt or solvate thereof, as claimed in claim 1, wherein, in the formula (I), the heterocyclic ring which is formed by $R^1$ and $R^2$ together with the atoms they are bonded with is (1) imidazole, (2) triazole, (3) oxadiazole, or (4) oxadiazine, or partially saturated heterocyclic rings of the same, where (1) to (4) are optionally substituted with 1 to 3 groups selected from the group consisting of (A) a halogen atom, (B) oxo, (C) hydroxyl, (D) $C_1$ to $C_6$ alkyl and (K) deuterium atoms.

10. A compound or a pharmaceutically acceptable salt or solvate thereof, as claimed in claim 1, wherein the compound is (1) 4-{(1R)-1-[({(6R)-6-(5-chloro-2-methoxybenzyl)-7-oxo-3-[(pyridin-2-yloxy)imino]-1,4-diazepan-1-yl}carbonyl)amino]propyl}benzoic acid, (2) 2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid, (3) 2-amino-4-{(1R)-1-[({(6S)-6-(5-chloro-2-methoxybenzyl)-7-oxo-3-[(2,2,2-trifluoroethoxy)imino]-1,4-diazepan-1-yl}carbonyl)amino]butyl}benzoic acid, (4) 2-amino-4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}benzoic acid, (5) 2-amino-4-[(1R)-1-({[(6S)-6-(5-chloro-2-methoxybenzyl)-3-(methoxyimino)-4-methyl-7-oxo-1,4-diazepan-1-yl]carbonyl}amino)butyl]benzoic acid, (6) (4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}phenyl)acetic acid, (7) 2-amino-4-{[({(6R)-6-(5-chloro-2-methoxybenzyl)-3-[(3,5-difluorophenoxy)imino]-7-oxo-1,4-diazepan-1-yl}carbonyl)amino]methyl}benzoic acid, (8) {4-[(1R)-1-({[(6R)-6-(5-chloro-2-methoxybenzyl)-7-oxo-3-(phenoxyimino)-1,4-diazepan-1-yl]carbonyl}amino)propyl]phenyl}acetic acid, (9) 2-amino-4-[(1R)-1-({[(6R)-6-(5-chloro-2-methoxybenzyl)-7-oxo-3-(phenoxyimino)-1,4-diazepan-1-yl]carbonyl}amino)propyl]benzoic acid, or

(10) 2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid.

11. A pharmaceutical composition comprising a compound according to claim 1, or a pharmaceutically acceptable salt or solvate thereof, and a pharmaceutically acceptable carrier.

12. A method for treating a disease or a disorder in a mammal comprising, administering a compound of formula (I), or a pharmaceutically acceptable salt or solvate thereof, according to claim 1, wherein said disease or said disorder is atopic dermatitis.

13. A method for producing a compound of claim 1 having the formula (I):

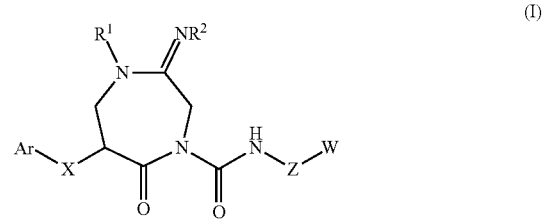

wherein Ar, W, X, Z, $R^1$, and $R^2$ are as defined in claim 1, comprising the steps of 1) reacting a compound (V):

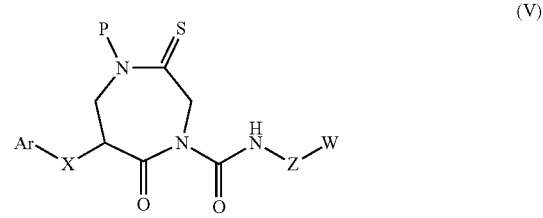

wherein Ar, W, X, and Z are as defined in claim 1,

P indicates a protective group of allyl, allyloxycarbonyl, 9-fluorenylmethylcarbonyl, $C_1$ to $C_6$ alkyloxycarbonyl optionally substituted with 1 to 3 halogen atoms, $C_1$ to $C_6$ alkylcarbonyl optionally substituted with 1 to 3 halogen atoms, $C_7$ to $C_{16}$ aralkyl optionally substituted with 1 to 3 of (i) a halogen atom, (ii) $C_1$ to $C_6$ alkyl, (iii) $C_1$ to $C_6$ alkoxy or (iv) nitro, $C_5$ to $C_{16}$ arylcarbonyl optionally substituted with 1 to 3 of (i) a halogen atom, (ii) $C_1$ to $C_6$ alkyl, (iii) $C_1$ to $C_6$ alkoxy, or (iv) nitro, $C_7$ to $C_{16}$ aralkyloxycarbonyl optionally substituted with 1 to 3 of (i) a halogen atom, (ii) $C_1$ to $C_6$ alkyl, (iii) $C_1$ to $C_6$ alkoxy, or (iv) nitro, or $C_5$ to $C_{16}$ arylsulfonyl optionally substituted with 1 to 3 of (i) a halogen atom, (ii) $C_1$ to $C_6$ alkyl, (iii) $C_1$ to $C_6$ alkoxy, or (iv) nitro, or indicates $R^1$, where $R^1$ is as defined above, with $R^2$—$NH_2$, where $R^2$ is as defined in claim 1, or a pharmaceutically acceptable salt thereof, and optionally, if necessary, performing a deprotection reaction, 2) reacting the above compound (V) with $R^{12}$—$NH_2$, where $R^{12}$ is or $NHR^{11}$ and $R^{11}$ is the same as defined in claim 1, or a pharmaceutically acceptable salt thereof, then subsequently reacting the resulting product with the compound (XI):

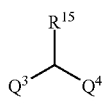

(XI)

wherein $Q^3$ and $Q^4$ independently indicate a halogen atom, $C_6$ to $C_{10}$ arylsulfonyloxy optionally substituted with 1 to 3 halogen atoms, $C_1$ to $C_4$ alkylsulfonyloxy optionally substituted with 1 to 3 halogen atoms, or $C_6$ to $C_{10}$ aryloxy optionally substituted with 1 to 3 halogen atoms or nitro, and $R^{15}$ indicates a hydrogen atom or oxo,
or with the compound (XII):

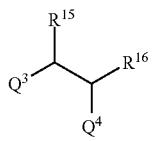

(XII)

wherein $Q^3$ and $Q^4$ are as defined above, and $R^{15}$ and $R^{16}$ independently indicate a hydrogen atom or oxo,
so as to perform a cyclization reaction and, optionally, performing a deprotection reaction, or
3) reacting the above compound (V) with $R^{13}$—$NH_2$, where $R^{13}$ is $OR^{14}$, $NR^{11}R^{14}$ or a $C_2$ to $C_6$ alkyl group substituted with two $C_1$ to $C_6$ alkoxy, $R^{11}$ is as defined in claim 1, and $R^{14}$ is formyl, $C_1$ to $C_6$ alkylcarbonyl, $C_2$ to $C_6$ alkenylcarbonyl, $C_2$ to $C_6$ alkynylcarbonyl, $C_3$ to $C_6$ cyclo alkylcarbonyl, $C_6$ to $C_{14}$ arylcarbonyl, $C_1$ to $C_{10}$ heteroarylcarbonyl, or $C_1$ to $C_6$ alkoxycarbonyl, or a pharmaceutically acceptable salt thereof, then subsequently performing a cyclization reaction and, if necessary, performing a deprotection reaction.

14. A method for producing a compound of claim 1 having the formula (I):

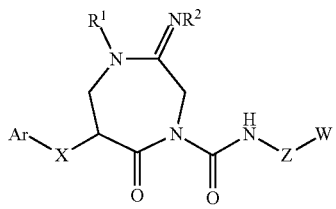

(I)

where Ar, W, X, Z, $R^1$, and $R^2$ are as defined in claim 1, comprising the steps of obtaining from the compound (XIII):

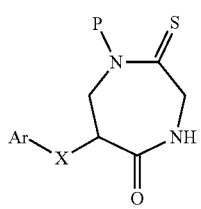

(XIII)

where Ar and are as defined in claim 1, and P indicates a protective group of allyl, allyloxycarbonyl, 9-fluorenylmethylcarbonyl, $C_1$ to $C_6$ alkyloxycarbonyl optionally substituted with 1 to 3 halogen atoms, $C_1$ to $C_6$ alkylcarbonyl optionally substituted with 1 to 3 halogen atoms, $C_7$ to $C_{16}$ aralkyl optionally substituted with 1 to 3 of (i) a halogen atom, (ii) $C_1$ to $C_6$ alkyl, (iii) $C_1$ to $C_6$ alkoxy or (iv) nitro, $C_5$ to $C_{16}$ arylcarbonyl optionally substituted with 1 to 3 of (i) a halogen atom, (ii) $C_1$ to $C_6$ alkyl, (iii) $C_1$ to $C_6$ alkoxy, or (iv) nitro, $C_7$ to $C_{16}$ aralkyloxycarbonyl optionally substituted with 1 to 3 of (i) a halogen atom, (ii) $C_1$ to $C_6$ alkyl, (iii) $C_1$ to $C_6$ alkoxy, or (iv) nitro, or $C_5$ to $C_{16}$ arylsulfonyl optionally substituted with 1 to 3 of (i) a halogen atom, (ii) $C_1$ to $C_6$ alkyl, (iii) $C_1$ to $C_6$ alkoxy, or (iv) nitro, or indicates $R^1$, where $R^1$ is as defined in claim 1, with $R^2$—$NH_2$, where $R^2$ is as defined in claim 1, or a pharmaceutically acceptable salt thereof, the compound (XIV):

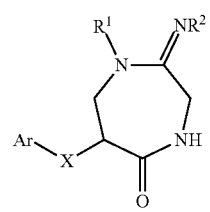

(XIV)

where Ar, X, $R^1$ and $R^2$ are as defined in claim 1, then subsequently
1) reacting the above compound (XIV) and compound (X):

O=C=N—Z—W (X)

where W and Z are as defined in claim 1, and optionally performing a deprotection reaction, or
2) reacting the above compound (XIV) and compound (VIII):

$Q^1Q^2C$=O where $Q^1$ and $Q^2$ independently indicate a halogen atom or $C_6$ to $C_{10}$ aryloxy optionally substituted with 1 to 3 of a halogen atom or nitro,
then reacting the resultant product with the compound (IX):
where, W and Z are as defined above, and, optionally performing a deprotection reaction.

15. A compound or a pharmaceutically acceptable salt thereof, having the formula (V):

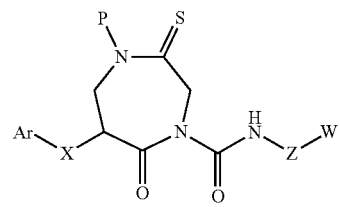

(V)

wherein,
Ar indicates (1) a $C_6$ to $C_{14}$ aromatic hydrocarbon group, (2) a 5- to 8-membered aromatic heterocyclic group having 1 to 4 hetero atoms selected from the group consisting of a nitrogen atom, a sulfur atom, and an oxygen atom, in place of a carbon atom, or (3) a bicyclic or tricyclic aromatic group formed by condensation of the above aromatic heterocyclic group and a $C_6$ to $C_{14}$ aromatic hydrocarbon ring, where the above groups (1) to (3) of Ar are optionally substituted with 1 to 5 groups selected from the group consisting of:
(i) a halogen atom,
(ii) nitro,
(iii) cyano,
(iv) $C_1$ to $C_6$ alkyl optionally substituted with 1 to 3 halogen atoms,
(v) $C_2$ to $C_6$ alkenyl optionally substituted with 1 to 3 halogen atoms,
(vi) $C_2$ to $C_6$ alkynyl optionally substituted with 1 to 3 halogen atoms,
(vii) $C_3$ to $C_6$ cycloalkyl,
(viii) hydroxyl,
(ix) $C_1$ to $C_6$ alkoxy optionally substituted with 1 to 3 groups selected from the group consisting of a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atom,
(x) $C_1$ to $C_5$ alkylenedioxy,
(xi) $C_1$ to $C_6$ alkylthio optionally substituted with 1 to 3 groups selected from the group consisting of a halogen atom, mono- or di-$C_1$ to $C_6$ alkylamino, $C_1$ to $C_6$ alkoxy, mono- or di-$C_1$ to $C_6$ alkylcarbamoyl, mono- or di-$C_7$ to $C_{16}$ aralkylcarbamoyl, mono- or di-$C_1$ to $C_{10}$ heteroaryl-$C_1$ to $C_6$ alkylcarbamoyl, carboxyl, and $C_1$ to $C_6$ alkoxycarbonyl, or substituted with 1 to 13 deuterium atom,
(xii) amino,
(xiii) mono-$C_1$ to $C_6$ alkylamino,
(xiv) di-$C_1$ to $C_6$ alkylamino,
(xv) 5- to 6-membered cyclic amino,
(xvi) $C_1$ to $C_6$ alkylcarbonyl,
(xvii) carboxyl,
(xviii) $C_1$ to $C_6$ alkoxycarbonyl,
(xix) carbamoyl,
(xx) thiocarbamoyl,
(xxi) mono-$C_1$ to $C_6$ alkylcarbamoyl,
(xxii) di-$C_1$ to $C_6$ alkylcarbamoyl,
(xxiii) 5- to 6-membered cyclic aminocarbonyl,
(xxiv) sulfo,
(xxv) $C_1$ to $C_6$ alkylsulfonyl,
(xxvi) $C_1$ to $C_6$ alkoxycarbonylamino,
(xxvii) $C_1$ to $C_6$ alkylcarbonylamino,
(xxviii) mono- or di-$C_1$ to $C_6$ alkylaminocarbonylamino,
(xxix) aminosulfonyl, and
(xxx) mono- or di-$C_1$ to $C_6$ alkylaminosulfonyl, or substituted with 1 to 9 deuterium atoms, X indicates (1) a connecting bond, (2) linear or branched $C_1$ to $C_6$ alkylene optionally substituted with 1 to 12 deuterium atoms, (3) an oxygen atom, (4) $NR^3$, where $R^3$ indicates a hydrogen atom or a $C_1$ to $C_6$ alkyl group, or (5) —$S(O)_m$—, where m indicates an integer of 0 to 2, Z indicates (1) a connecting bond or (2) $CR^4R^5$, where $R^4$ and $R^5$ are, independently,
(A) a hydrogen atom,
(B) a deuterium atom,
(C) $C_1$ to $C_6$ alkyl optionally substituted with 1 to 5 groups selected from the group consisting of (i) carboxyl, (ii) $C_1$ to $C_6$ alkoxycarbonyl, (iii) phenyl, (iv) hydroxyl, (v) $C_1$ to $C_6$ alkoxy, (vi) a halogen atom, and (vii) $C_3$ to $C_6$ cycloalkyl, or substituted with 1 to 13 deuterium atoms,
(D) $C_3$ to $C_6$ cycloalkyl optionally substituted with 1 to 5 groups selected from the group consisting of (i) a halogen atom and (ii) an alkyl group optionally substituted with 1 to 3 halogen atoms or optionally substituted, with 1 to 11 deuterium atoms,
(E) $COOR^6$, where $R^6$ indicates a hydrogen atom or $C_1$ to $C_6$ alkyl, or
(F) $CONR^7R^8$, where $R^7$ and $R^8$ are, independently,
(a) hydrogen atom,
(b) $C_1$ to $C_6$ alkyl optionally substituted with 1 to 3 groups selected from the group consisting of (i) a halogen atom, (ii) $C_3$ to $C_6$ cycloalkyl, (iii) carboxyl, (iv) $C_1$ to $C_6$ alkoxycarbonyl, (v) $C_1$ to $C_6$ alkylcarbonyl, (vi) carbamoyl, (vii) mono-$C_1$ to $C_6$ alkylcarbamoyl, (viii) di-$C_1$ to $C_6$ alkylcarbamoyl, (ix) $C_6$ to $C_{12}$ aryl, and (x) $C_1$ to $C_{10}$ heteroaryl,
(c) $C_6$ to $C_{14}$ aromatic hydrocarbon group,
(d) a 5- to 8-membered aromatic heterocyclic group having 1 to 4 hetero atoms selected from the group consisting of a nitrogen atom, a sulfur atom, and an oxygen atom, in place of a carbon atom, or
(e) a bicyclic or tricyclic aromatic group formed by condensation of the above aromatic heterocyclic group and a $C_6$ to $C_{14}$ aromatic hydrocarbon ring,
where each of the groups (c) to (e) is optionally substituted with 1 to 5 groups selected from the group consisting of (i) a halogen atom, (ii) nitro, (iii) cyano, (iv) $C_1$ to $C_6$ alkyl optionally substituted with 1 to 3 halogen atoms, (v) $C_1$ to $C_6$ alkenyl optionally substituted with 1 to 3 halogen atoms, (vi) $C_2$ to $C_6$ alkynyl optionally substituted with 1 to 3 halogen atoms, (vii) $C_3$ to $C_6$ cycloalkyl, (viii) hydroxyl, (ix) $C_1$ to $C_6$ alkoxy optionally substituted with 1 to 3 halogen atoms, (x) $C_1$ to $C_5$ alkylenedioxy, (xi) $C_1$ to $C_6$ alkylthio optionally substituted with 1 to 3 halogen atoms, (xii) amino, (viii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkylcarbonyl, (xvii) carboxyl, (xviii) $C_1$ to $C_6$ alkoxycarbonyl, (xix) carbamoyl, (xx) thiocarbamoyl, (xxi) mono-$C_1$ to $C_6$ alkylcarbamoyl, (xxii) di-$C_1$ to $C_6$ alkylcarbamoyl, (xxiii) $C_6$ to $C_{10}$ arylcarbamoyl, (xxiv) $C_1$ to $C_{10}$ heteroarylcarbamoyl, (xxv) sulfo, (xxvi) $C_1$ to $C_6$ alkylsulfonyl, (xxvii) aminosulfonyl, and (xxviii) mono- or di-$C_1$ to $C_6$ alkylaminosulfonylamino, or substituted with 1 to 9 deuterium atoms, W indicates (1) a hydrogen atom, (2) a $C_6$ to $C_{14}$ aromatic hydrocarbon group, (3) a 5- to 8-membered aromatic heterocyclic group having 1 to 4 hetero atoms selected from a nitrogen atom, a sulfur atom, and an oxygen atom, in place of a carbon atom, (4) a bicyclic or tricyclic aromatic group formed by condensation of the above aromatic heterocyclic group and a $C_6$ to $C_{14}$ aromatic hydrocarbon ring, or a deuterium atom, where each of the groups (2) to (4) of the above W is optionally substituted with 1 to 5 groups selected from the group consisting of (i) a halogen atom, (ii) nitro, (iii) cyano, (iv) $C_1$ to $C_6$ alkyl optionally substituted with 1 to 3 groups selected from the group consisting of a halogen atom, amino, $C_1$ to $C_6$ alkoxycarbonyl, $C_1$ to $C_6$ alkoxycarbonylamino, and carboxyl, (v) $C_2$ to $C_6$ alkenyl optionally substituted with 1 to 3 halogen atoms, (vi) $C_2$ to $C_6$ alkynyl optionally substituted with 1 to 3 halogen atoms, (vii) $C_3$ to $C_6$ cycloalkyl, (viii) hydroxyl, (ix) $C_1$ to $C_6$ alkoxy optionally substituted with 1 to 3 groups selected from the group consisting of a halogen atom, hydroxyl, $C_1$ to $C_6$ alkoxy, amino and mono- or di-$C_1$ to $C_6$ alkylamino, (x) $C_1$ to $C_5$ alkylenedioxy, (xi) $C_1$ to $C_6$ alkylthio optionally substituted with 1 to 3 groups selected from the group consisting of a halogen atom, hydroxyl, $C_1$ to $C_6$ alkoxy, amino, and mono- or di-$C_1$ to $C_6$ alkylamino, (xii) amino, (xiii) mono-$C_1$ to $C_6$ alkylamino, (xiv) di-$C_1$ to $C_6$ alkylamino, (xv) 5- to 6-membered cyclic amino, (xvi) $C_1$ to $C_6$ alkyl-carbonyl, (xvii) carboxyl, (xviii) $C_1$ to $C_6$ alkoxycarbonyl optionally substituted with a halogen atom, (xix) $C_7$ to $C_{16}$ arakyloxycarbonyl optionally substituted with a halogen atom, (xx) carbamoyl, (xxi) mono-$C_1$ to $C_6$ alkylcarbamoyl optionally substituted with 1 to 3 groups which are selected from the group consisting of a halogen atom, hydroxyl, carboxyl, $C_1$ to $C_6$ alkoxy, amino, and mono- or di-$C_1$ to $C_6$ alkylamino, (xxii) di-$C_1$ to $C_6$ alkylcarbamoyl optionally substituted with hydroxyl, (xxiii) 5- to 6-membered cyclic aminocarbonyl optionally substituted with $C_1$ to $C_6$ alkoxycarbonyl, (xxiv) $C_6$ to $C_{10}$ arylcarbamoyl, (xxv) $C_1$ to $C_{10}$ heteroarylcarbamoyl, (xxvi) $C_7$ to $C_{16}$ aralkylcarbamoyl, (xxvii) $C_1$ to $C_{10}$ heteroaryl-$C_1$ to $C_6$ alkylcarbamoyl, (xxviii) N—$C_1$ to $C_6$ alkyl-N—$C_6$ to $C_{12}$ arylcarbamoyl, (xxix) $C_3$ to $C_6$ cycloalkylcarbamoyl, (xxx) sulfo, (xxxi) $C_1$ to $C_6$ alkylsulfonyl, (xxxii) $C_1$ to $C_6$ alkylsulfonylamino, (xxxiii) $C_6$ to $C_{12}$ arylsulfonylamino optionally substituted with $C_1$ to $C_6$ alkyl, (xxxiv) $C_1$ to $C_{10}$ heteroarylsulfonylamino, (xxxv) $C_1$ to $C_6$ alkoxycarbonylamino, (xxxvi) $C_1$ to $C_6$ alkylcarbonylamino, (xxxvii) mono- or di-$C_1$ to $C_6$ alkylaminocarbonylamino, (xxxviii) $C_6$ to $C_{12}$ aryl, (xxxix) $C_1$ to $C_{10}$ heteroaryl, (xl) $C_6$ to $C_{10}$ aryloxy, (xli) $C_1$ to $C_{10}$ heteroaryloxy, (xlii) $C_7$ to $C_{16}$ arakyloxy, (xliii) $C_1$ to $C_{10}$ heteroaryl-$C_1$ to $C_6$ alkyloxy, (xliv) aminosulfonyl, (xlv) mono- or di-$C_1$ to $C_6$ alkylaminosulfonyl, (xlvi) $C_7$ to $C_{16}$ aralkyloxycarbamoyl, and (xlvii) $C_1$ to $C_{10}$ heteroaryl-$C_1$ to $C_6$ alkyloxycarbamoyl, or substituted with 1 to 9 deuterium atoms, P indicates a protective group of allyl, allyloxycarbonyl, 9-fluorenylmethylcarbonyl, $C_1$ to $C_6$ alkyloxycarbonyl optionally substituted with 1 to 3 halogen atoms, $C_1$ to $C_6$ alkylcarbonyl optionally substituted with 1 to 3 halogen atoms, $C_7$ to $C_{16}$ aralkyl optionally substituted with 1 to 3 of (i) a halogen atom, (ii) $C_1$ to $C_6$ alkyl, (iii) $C_1$ to $C_6$ alkoxy or (iv) nitro, $C_5$ to $C_{16}$ arylcarbonyl, or optionally with 1 to 3 of (i) a halogen atom, (ii) $C_1$ to $C_6$ alkyl, (iii) $C_1$ to $C_6$ alkoxy, or (iv) nitro, $C_7$ to $C_{16}$ aralkyloxycarbonyl optionally substituted with 1 to 3 of (i) a halogen atom, (ii) $C_1$ to $C_6$ alkyl, (iii) $C_1$ to $C_6$ alkoxy, or (iv) nitro, or $C_5$ to $C_{16}$ arylsulfonyl optionally substituted with 1 to 3 of (i) a halogen atom, (ii) $C_1$ to $C_6$ alkyl, (in) $C_1$ to $C_6$ alkoxy, or (iv) nitro, or indicates $R^1$, where $R^1$ is as defined in claim 1, with $R^2$—$NH_2$, where $R^2$ is as defined in claim 1, or a pharmaceutically acceptable salt thereof, or the formula (XIII):

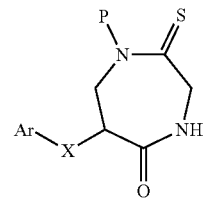

(XIII)

where Ar, X, and P are as defined above, or a pharmaceutically acceptable salt thereof.

16. The method of claim 12, wherein said compound of formula (I) is:
(1) 4-{(1R)-1-[({6R)-6-(5-chloro-2-methoxybenzyl)-7-oxo-3-[(pyridin-2-yloxy)imino]-1,4-diazepan-1-yl}carbonyl)amino]propyl}benzoic acid,
(2) 2-amino-4-[(1R)-1-({[(6S)-6-(5-chloro-2-methoxybenzyl)-3-(ethoxyimino)-7-oxo-1,4-diazepan-1-yl]carbonyl}amino)butyl]benzoic acid,
(3) 2-amino-4-{(1R)-1-[({(6S)-6-(5-chloro-2-methoxybenzyl)-7-oxo-3-[(2,2,2-trifluoroethoxy)imino]-1,4-diazepan-1-yl}carbonyl)amino]butyl}benzoic acid,
(4) 2-amino-4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}benzoic acid,
(5) 2-amino-4-{(1R)-1-({[(6S)-6-(5-chloro-2-methoxybenzyl)-3-(methoxyimino)-4-methyl-7-oxo-1,4-diazepan-1-yl]carbonyl}amino)butyl]benzoic acid,
(6) (4-{(1R)-1-[({(6R)-6-(5-chloro-2-methoxybenzyl)-3-[(3,5-difluorophenoxy)imino]-7-oxo-1,4-diazepan-1-yl}carbonyl)amino]ethyl}phenyl)acetic acid,
(7) 2-amino-4-{[({(6R)-6-(5-chloro-2-methoxybenzyl)-3-[(3,5-difluorophenoxy)imino]-7-oxo-1,4-diazepan-1-yl}carbonyl)amino]methyl}benzoic acid,
(8) {4-[(1R)-1-({[(6R)-6-(5-chloro-2-methoxybenzyl)-7-oxo-3-(phenoxyimino)-1,4-diazepan-1-yl]carbonyl}amino)propyl]phenyl}acetic acid,
(9) 2-amino-4-[(1R)-1-({[(6R)-6-(5-chloro-2-methoxybenzyl)-7-oxo-3-(phenoxyimino)-1,4-diazepan-1-yl]carbonyl}amino)propyl]benzoic acid, or
(10) 2-amino-4-[(1R)-1-({[(6R)-6-(5-chloro-2-methoxybenzyl)-3-(ethoxyimino)-7-oxo-1,4-diazepan-1-yl]carbon}amino)butyl]benzoic acid, or a pharmaceutically acceptable salt or a solvate thereof.

17. The compound, or a pharmaceutically acceptable salt or solvate thereof, of claim 1, wherein the solvate is 2-amino-4-[(1R)-1-({[(3Z,6S)-6-(5-chloro-2-methoxybenzyl)-3-(ethoxyimino)-7-oxo-1,4-diazepan-1-yl]carbonyl}amino)butyl]benzoic acid monoacetic acid solvate.

18. A method for treating a disease or a disorder in a mammal comprising,
administering the solvate of claim 17,
wherein said disease or said disorder is atopic dermatitis.

* * * * *

UNITED STATES PATENT AND TRADEMARK OFFICE
CERTIFICATE OF CORRECTION

PATENT NO. : 8,846,660 B2
APPLICATION NO. : 13/518628
DATED : September 30, 2014
INVENTOR(S) : Tsuyoshi Muto et al.

It is certified that error appears in the above-identified patent and that said Letters Patent is hereby corrected as shown below:

In the claims

Column 141, lines 32-35, "(2) a 5 to 8-membered aromatic heterocyclic group having 1 to 4 hetero atoms selected from the group consisting of a nitrogen atom, sulfur atom, and oxygen atom, in place of a carbon atom" should read -- (2) a 5- to 8-membered aromatic heterocyclic group having 1 to 4 hetero atoms selected from the group consisting of a nitrogen atom, sulfur atom, and oxygen atom, in place of a carbon atom --

Column 142, line 14, "(xxv) $C_1$ to $C_6$ alkylsulfonyl" should read -- (xxv) $C_1$ to $C_6$ alkylsulfonyl, --

Column 142, lines 26-27, "Z indicates (1) a connecting bond or (2) $CR^4R^5$ where $R^4$ and $R^5$ are, independently" should read -- Z indicates (1) a connecting bond or (2) $CR^4R^5$, where $R^4$ and $R^5$ are, independently --

Column 142, line 33, "(vi) halogen atom" should read -- (vi) a halogen atom --

Column 142, lines 56-58, "(e) a bicyclic or tricyclic aromatic group formed by condensation of the above aromatic heterocyclic, group and a $C_6$ to $C_{14}$ aromatic hydrocarbon ring" should read -- (e) a bicyclic or tricyclic aromatic group formed by condensation of the above aromatic heterocyclic group and a C6 to C14 aromatic hydrocarbon ring --

Column 143, lines 17-20, "(4) a bicyclic, or tricyclic aromatic group formed by condensation of the above aromatic heterocyclic group and a $C_6$ to $C_{14}$ aromatic hydrocarbon ring, or a deuterium atom" should read -- (4) a bicyclic or tricyclic aromatic group formed by condensation of the above aromatic heterocyclic group and a $C_6$ to $C_{14}$ aromatic hydrocarbon ring, or a deuterium atom --

Signed and Sealed this
Third Day of November, 2015

Michelle K. Lee
*Director of the United States Patent and Trademark Office*

CERTIFICATE OF CORRECTION (continued)
U.S. Pat. No. 8,846,660 B2

In the claims

Column 143, lines 21-23, "where, each of the groups (2) to (4) of the above W is optionally substituted with 1 to 5 groups selected from the group consisting of (i) a halogen atom" should read -- where each of the groups (2) to (4) of the above W is optionally substituted with 1 to 5 groups selected from the group consisting of (i) a halogen atom --

Column 144, line 22, "(D) $C_3$ to $C_6$ alkynyl" should read -- (D) $C_2$ to $C_6$ alkynyl --

Column 144, line 38, "(viii) 5 to 6-membered cyclic amino" should read -- (viii) 5- to 6-membered cyclic amino --

Column 145, lines 26-29, "each of the groups of the above (H) to (J) is optionally substituted with 1 to 5 groups which are selected from the group consisting, of (i) a halogen atom" should read -- each of the groups of the above (H) to (J) is optionally substituted with 1 to 5 groups which are selected from the group consisting of (i) a halogen atom --

Column 145, lines 48-50, "of which Ar group is optionally substituted with 1 to 5 groups which are selected front the group consisting of (i) a halogen atom" should read -- of which Ar group is optionally substituted with 1 to 5 groups which are selected from the group consisting of (i) a halogen atom --

Column 146, lines 53-54, "(xv) 5 to 6-membered cyclic amino" should read -- (xv) 5- to 6-membered cyclic amino --

Column 147, line 1, "(F) $C_3$ to $C_6$ cycloalkyl" should read -- (E) $C_3$ to $C_6$ cycloalkyl --

Column 147, lines 7-9, "where each group of the above (B) to (F) is optionally substituted with 1 to 3 groups selected from the group consisting of (i) a halogen atom" should read -- where each group of the above (B) to (E) is optionally substituted with 1 to 3 groups selected from the group consisting of (i) a halogen atom --

Column 147, lines 11-12, "(v) amino (vi) mono-$C_1$ to $C_6$ alkylamino" should read -- (v) amino, (vi) mono-$C_1$ to $C_6$ alkylamino --

Column 148, lines 1-3, "(10) 2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid" should read -- (10) 2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid --

Column 148, lines 64-65, "where $R^{12}$ is or $NHR^{11}$ and $R^{11}$ is the same as defined in claim 1" should read -- where $R^{12}$ is OH or $NHR^{11}$ and $R^{11}$ is the same as defined in claim 1 --

Column 150, line 1, "where Ar and are as defined in claim 1" should read -- where Ar and X are as defined in claim 1 --

CERTIFICATE OF CORRECTION (continued)
U.S. Pat. No. 8,846,660 B2

In the claims

Column 150, line 31, "where Ar, X, $R^1$ and $R^2$ are as defined in claim 1" should read -- where Ar, X, $R^1$, and $R^2$ are as defined in claim 1 --

Column 150, lines 45-47, "then reacting the resultant product with the compound (IX):
where, W and Z are as defined above," should read -- then reacting the resultant product with the compound (IX):
$H_2N$-Z-W
where, W and Z are as defined above, --

Column 152, lines 29-30, "(v) $C_1$ to $C_6$ alkenyl optionally substituted with 1 to 3 halogen atoms" should read -- (v) $C_2$ to $C_6$ alkenyl optionally substituted with 1 to 3 halogen atoms --

Column 152, lines 35-36, "(viii) mono-$C_1$ to $C_6$ alkylamino" should read
-- (xiii) mono-$C_1$ to $C_6$ alkylamino --

Column 153, lines 50-51, "(in) $C_1$ to $C_6$ alkoxy" should read -- (iii) $C_1$ to $C_6$ alkoxy --

Column 154, lines 15-17, "(1) 4-{(1R)-1-[({6R)-6-(5-chloro-2-methoxybenzyl)-7-oxo-3-[(pyridin-2-yloxy)imino]-1,4-diazepan-1-yl}carbonyl)amino]propyl}benzoic acid" should read -- (1) 4-{(1R)-1-[({(6R)-6-(5-chloro-2-methoxybenzyl)-7-oxo-3-[(pyridin-2-yloxy)imino]-1,4-diazepan-1-yl}carbonyl)amino]propyl}benzoic acid --

Column 154, lines 27-29, "(5) 2-amino-4-{(1R)-1-({[(6S)-6-(5-chloro-2-methoxybenzyl)-3-(methoxyimino)-4-methyl-7-oxo-1,4-diazepan-1-yl]carbonyl}amino)butyl] benzoic acid" should read -- (5) 2-amino-4-[(1R)-1-({[(6S)-6-(5-chloro-2-methoxybenzyl)-3-(methoxyimino)-4-methyl-7-oxo-1,4-diazepan-1-yl]carbonyl}amino)butyl] benzoic acid --

Column 154, lines 41-43, "(10) 2-amino-4-[(1R)-1-({[(6R)-6-(5-chloro-2-methoxybenzyl)-3-(ethoxyimino)-7-oxo-1,4-diazepan-1-yl]carbon}amino)butyl]benzoic acid" should read -- (10) 2-amino-4-[(1R )-1-({[(6R)-6-(5-chloro-2-methoxybenzyl)-3-(ethoxyimino)-7-oxo-1,4-diazepan-1-yl]carbonyl}amino)butyl]benzoic acid --

Column 154, lines 44-45, "$C_5$ to $C_{16}$ arylcarbonyl, or optionally with 1 to 3 of (i) a halogen atom" should read -- $C_5$ to $C_{16}$ arylcarbonyl optionally substituted with 1 to 3 of (i) a halogen atom --

UNITED STATES PATENT AND TRADEMARK OFFICE
CERTIFICATE OF CORRECTION

PATENT NO. : 8,846,660 B2
APPLICATION NO. : 13/518628
DATED : September 30, 2014
INVENTOR(S) : Tsuyoshi Muto et al.

It is certified that error appears in the above-identified patent and that said Letters Patent is hereby corrected as shown below:

In the claims

Column 141, lines 32-35, "(2) a 5 to 8-membered aromatic heterocyclic group having 1 to 4 hetero atoms selected from the group consisting of a nitrogen atom, sulfur atom, and oxygen atom, in place of a carbon atom" should read -- (2) a 5- to 8-membered aromatic heterocyclic group having 1 to 4 hetero atoms selected from the group consisting of a nitrogen atom, sulfur atom, and oxygen atom, in place of a carbon atom --

Column 142, line 14, "(xxv) $C_1$ to $C_6$ alkylsulfonyl" should read -- (xxv) $C_1$ to $C_6$ alkylsulfonyl, --

Column 142, lines 26-27, "Z indicates (1) a connecting bond or (2) $CR^4R^5$ where $R^4$ and $R^5$ are, independently" should read -- Z indicates (1) a connecting bond or (2) $CR^4R^5$, where $R^4$ and $R^5$ are, independently --

Column 142, line 33, "(vi) halogen atom" should read -- (vi) a halogen atom --

Column 142, lines 56-58, "(e) a bicyclic or tricyclic aromatic group formed by condensation of the above aromatic heterocyclic, group and a $C_6$ to $C_{14}$ aromatic hydrocarbon ring" should read -- (e) a bicyclic or tricyclic aromatic group formed by condensation of the above aromatic heterocyclic group and a C6 to C14 aromatic hydrocarbon ring --

Column 143, lines 17-20, "(4) a bicyclic, or tricyclic aromatic group formed by condensation of the above aromatic heterocyclic group and a $C_6$ to $C_{14}$ aromatic hydrocarbon ring, or a deuterium atom" should read -- (4) a bicyclic or tricyclic aromatic group formed by condensation of the above aromatic heterocyclic group and a $C_6$ to $C_{14}$ aromatic hydrocarbon ring, or a deuterium atom --

This certificate supersedes the Certificate of Correction issued November 3, 2015.

Signed and Sealed this
Seventeenth Day of May, 2016

Michelle K. Lee
*Director of the United States Patent and Trademark Office*

CERTIFICATE OF CORRECTION (continued)
U.S. Pat. No. 8,846,660 B2

In the claims

Column 143, lines 21-23, "where, each of the groups (2) to (4) of the above W is optionally substituted with 1 to 5 groups selected from the group consisting of (i) a halogen atom" should read -- where each of the groups (2) to (4) of the above W is optionally substituted with 1 to 5 groups selected from the group consisting of (i) a halogen atom --

Column 144, line 22, "(D) $C_3$ to $C_6$ alkynyl" should read -- (D) $C_2$ to $C_6$ alkynyl --

Column 144, line 38, "(viii) 5 to 6-membered cyclic amino" should read -- (viii) 5- to 6-membered cyclic amino --

Column 145, lines 26-29, "each of the groups of the above (H) to (J) is optionally substituted with 1 to 5 groups which are selected from the group consisting, of (i) a halogen atom" should read -- each of the groups of the above (H) to (J) is optionally substituted with 1 to 5 groups which are selected from the group consisting of (i) a halogen atom --

Column 145, lines 48-50, "of which Ar group is optionally substituted with 1 to 5 groups which are selected front the group consisting of (i) a halogen atom" should read -- of which Ar group is optionally substituted with 1 to 5 groups which are selected from the group consisting of (i) a halogen atom --

Column 146, lines 53-54, "(xv) 5 to 6-membered cyclic amino" should read -- (xv) 5- to 6-membered cyclic amino --

Column 147, line 1, "(F) $C_3$ to $C_6$ cycloalkyl" should read -- (E) $C_3$ to $C_6$ cycloalkyl --

Column 147, lines 7-9, "where each group of the above (B) to (F) is optionally substituted with 1 to 3 groups selected from the group consisting of (i) a halogen atom" should read -- where each group of the above (B) to (E) is optionally substituted with 1 to 3 groups selected from the group consisting of (i) a halogen atom --

Column 147, lines 11-12, "(v) amino (vi) mono-$C_1$ to $C_6$ alkylamino" should read -- (v) amino, (vi) mono-$C_1$ to $C_6$ alkylamino --

Column 148, lines 1-3, "(10) 2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid" should read -- (10) 2-amino-4-[(1R)-1-({[(6R)-6-(5-chloro-2-methoxybenzyl)-3-(ethoxyimino)-7-oxo-1,4-diazepan-1-yl]carbonyl}amino)butyl]benzoic acid --

Column 148, lines 64-65, "where $R^{12}$ is or $NHR^{11}$ and $R^{11}$ is the same as defined in claim 1" should read -- where $R^{12}$ is OH or $NHR^{11}$ and $R^{11}$ is the same as defined in claim 1 --

Column 150, line 1, "where Ar and are as defined in claim 1" should read -- where Ar and X are as defined in claim 1 --

CERTIFICATE OF CORRECTION (continued)
U.S. Pat. No. 8,846,660 B2

In the claims

Column 150, line 31, "where Ar, X, $R^1$ and $R^2$ are as defined in claim 1" should read -- where Ar, X, $R^1$, and $R^2$ are as defined in claim 1 --

Column 150, lines 45-47, "then reacting the resultant product with the compound (IX):
where, W and Z are as defined above," should read -- then reacting the resultant product with the compound (IX):
$H_2N-Z-W$
where, W and Z are as defined above, --

Column 152, lines 29-30, "(v) $C_1$ to $C_6$ alkenyl optionally substituted with 1 to 3 halogen atoms" should read -- (v) $C_2$ to $C_6$ alkenyl optionally substituted with 1 to 3 halogen atoms --

Column 152, lines 35-36, "(viii) mono-$C_1$ to $C_6$ alkylamino" should read
-- (xiii) mono-$C_1$ to $C_6$ alkylamino --

Column 153, lines 44-45, "$C_5$ to $C_{16}$ arylcarbonyl, or optionally with 1 to 3 of (i) a halogen atom" should read -- $C_5$ to $C_{16}$ arylcarbonyl optionally substituted with 1 to 3 of (i) a halogen atom --

Column 153, lines 50-51, "(in) $C_1$ to $C_6$ alkoxy" should read -- (iii) $C_1$ to $C_6$ alkoxy --

Column 154, lines 15-17, "(1) 4-{(1R)-1-[({6R)-6-(5-chloro-2-methoxybenzyl)-7-oxo-3-[(pyridin-2-yloxy)imino]-1,4-diazepan-1-yl}carbonyl)amino]propyl}benzoic acid" should read -- (1) 4-{(1R)-1-[({(6R)-6-(5-chloro-2-methoxybenzyl)-7-oxo-3-[(pyridin-2-yloxy)imino]-1,4-diazepan-1-yl}carbonyl)amino]propyl}benzoic acid --

Column 154, lines 27-29, "(5) 2-amino-4-{(1R)-1-({[(6S)-6-(5-chloro-2-methoxybenzyl)-3-(methoxyimino)-4-methyl-7-oxo-1,4-diazepan-1-yl]carbonyl}amino)butyl] benzoic acid" should read -- (5) 2-amino-4-[(1R)-1-({[(6S)-6-(5-chloro-2-methoxybenzyl)-3-(methoxyimino)-4-methyl-7-oxo-1,4-diazepan-1-yl]carbonyl}amino)butyl] benzoic acid --

Column 154, lines 41-43, "(10) 2-amino-4-[(1R)-1-({[(6R)-6-(5-chloro-2-methoxybenzyl)-3-(ethoxyimino)-7-oxo-1,4-diazepan-1-yl]carbon}amino)butyl]benzoic acid" should read -- (10) 2-amino-4-[(1R )-1-({[(6R)-6-(5-chloro-2-methoxybenzyl)-3-(ethoxyimino)-7-oxo-1,4-diazepan-1-yl]carbonyl}amino)butyl]benzoic acid --